(12) United States Patent
Zhang et al.

(10) Patent No.: US 12,331,130 B2
(45) Date of Patent: Jun. 17, 2025

(54) DDR1 ANTIBODIES AND USES THEREOF

(71) Applicants: THE BOARD OF REGENTS OF THE UNIVERSITY OF TEXAS SYSTEM, Austin, TX (US); THE GEORGE WASHINGTON UNIVERSITY, Washington, DC (US)

(72) Inventors: Ningyan Zhang, Houston, TX (US); Zhiqiang An, Houston, TX (US); Hui Deng, Houston, TX (US); Xiujie Sun, Washington, DC (US); Rong Li, Washington, DC (US)

(73) Assignees: THE BOARD OF REGENTS OF THE UNIVERSITY OF TEXAS SYSTEM, Austin, TX (US); THE GEORGE WASHINGTON UNIVERSITY, Washington, DC (US)

( * ) Notice: Subject to any disclaimer, the term of this patent is extended or adjusted under 35 U.S.C. 154(b) by 0 days.

(21) Appl. No.: 18/176,072

(22) Filed: Feb. 28, 2023

(65) Prior Publication Data
US 2023/0235078 A1    Jul. 27, 2023

Related U.S. Application Data

(63) Continuation of application No. 17/757,510, filed as application No. PCT/US2020/065618 on Dec. 17, 2020.

(60) Provisional application No. 62/949,300, filed on Dec. 17, 2019.

(51) Int. Cl.
| C07K 16/30 | (2006.01) |
| A61P 35/00 | (2006.01) |
| C07K 16/28 | (2006.01) |
| C12N 15/63 | (2006.01) |

(52) U.S. Cl.
CPC .......... C07K 16/2896 (2013.01); A61P 35/00 (2018.01); C12N 15/63 (2013.01); *C07K 2317/20* (2013.01); *C07K 2317/565* (2013.01)

(58) Field of Classification Search
None
See application file for complete search history.

(56) References Cited

U.S. PATENT DOCUMENTS

| 7,855,076 | B2 | 12/2010 | Yoshimura |
| 8,652,843 | B2 | 2/2014 | Gurney et al. |
| 9,206,256 | B2 | 12/2015 | Gurney et al. |
| 9,550,835 | B2 | 1/2017 | Ono et al. |
| 10,150,817 | B2 | 12/2018 | Dunn et al. |
| 10,849,980 | B2 | 12/2020 | Bradner et al. |
| 11,491,237 | B2 | 11/2022 | Han et al. |
| 11,732,052 | B2 | 8/2023 | Bourquin et al. |
| 2002/0115173 | A1 | 8/2002 | Ben-Sasson |
| 2004/0001841 | A1 | 1/2004 | Nagavarapu et al. |
| 2006/0147372 | A1 | 7/2006 | Ullrich |
| 2007/0025997 | A1 | 2/2007 | Nagavarapu et al. |
| 2010/0166731 | A1 | 7/2010 | Bartz et al. |
| 2012/0316071 | A1 | 12/2012 | Smider et al. |
| 2014/0086913 | A1 | 3/2014 | Smith et al. |
| 2014/0199312 | A1 | 7/2014 | Gurney et al. |
| 2014/0248282 | A1 | 9/2014 | Ono et al. |
| 2015/0064721 | A1 | 3/2015 | Kim et al. |
| 2015/0148345 | A1 | 5/2015 | Lannutti et al. |
| 2016/0251440 | A1 | 9/2016 | Roobrouck et al. |
| 2016/0279135 | A1 | 9/2016 | Lannutti et al. |
| 2017/0158762 | A1 | 6/2017 | Jun et al. |
| 2018/0002446 | A1 | 1/2018 | Adamkewicz et al. |
| 2019/0008835 | A1 | 1/2019 | Sundy |
| 2019/0015379 | A1 | 1/2019 | Bacha et al. |
| 2019/0310250 | A1 | 10/2019 | Okitsu et al. |
| 2020/0069814 | A1 | 3/2020 | Zhao et al. |
| 2020/0157633 | A1 | 5/2020 | Regev et al. |
| 2020/0158716 | A1 | 5/2020 | Shalek et al. |
| 2020/0172480 | A1 | 6/2020 | Zhao et al. |
| 2020/0276261 | A1 | 9/2020 | Zhao et al. |
| 2020/0338074 | A1 | 10/2020 | Hammerman et al. |
| 2021/0169896 | A1 | 6/2021 | Zhao et al. |
| 2021/0244737 | A1 | 8/2021 | Tartare-Deckert et al. |
| 2021/0284731 | A1 | 9/2021 | Ganesan et al. |
| 2021/0318318 | A1 | 10/2021 | Duncan |
| 2021/0332080 | A1 | 10/2021 | Han |
| 2021/0393790 | A1 | 12/2021 | Zhao et al. |
| 2022/0242958 | A1 | 8/2022 | Roobrouck et al. |
| 2022/0249594 | A1 | 8/2022 | Zhao et al. |
| 2022/0306739 | A1 | 9/2022 | Ganesan et al. |
| 2022/0372016 | A1 | 11/2022 | Phillips et al. |
| 2023/0010108 | A1 | 1/2023 | Zhao et al. |
| 2023/0035898 | A1 | 2/2023 | Han et al. |
| 2023/0057350 | A1 | 2/2023 | Zhao et al. |

(Continued)

FOREIGN PATENT DOCUMENTS

| CA | 3160181 A1 * | 6/2021 | .............. A61P 35/00 |
| CN | 106632677 A | 5/2017 | |

(Continued)

OTHER PUBLICATIONS

Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Dubel (Handbook of Therapeutic Antibodies, 2007, p. 100-101) (Year: 2007).*
Johnson and Wu (Methods in Molecular Biology, Antibody Engineering: Methods and Protocols, vol. 248, p. 11-25, 2004) (Year: 2004).*
Paul (Fundamental Immunology, 3rd Edition, 1993, pp. 292-295) (Year: 1993).*
Bayer et al., DDR2 controls breast tumor stiffness and metastasis by regulating integrin mediated mechanotransduction in CAFs. *Elife* 8, doi: 10.7554/eLife.45508 (2019).

(Continued)

*Primary Examiner* — Michael Allen
(74) *Attorney, Agent, or Firm* — Parker Highlander PLLC

(57) ABSTRACT

The present disclosure relates to antibodies binding to tumor discoidin domain receptor 1 (DDR1) and the uses of the antibodies in detecting and treating cancer.

13 Claims, 22 Drawing Sheets

Specification includes a Sequence Listing.

(56) References Cited

U.S. PATENT DOCUMENTS

| | | |
|---|---|---|
| 2023/0093080 A1 | 3/2023 | Ji et al. |
| 2023/0115871 A1 | 4/2023 | Zhao et al. |
| 2023/0165931 A1 | 6/2023 | Zhao et al. |
| 2023/0241241 A1 | 8/2023 | Zhao et al. |
| 2023/0372496 A1 | 11/2023 | Nasveschuk et al. |
| 2023/0391893 A1 | 12/2023 | Lee et al. |

FOREIGN PATENT DOCUMENTS

| | | |
|---|---|---|
| CN | 110381998 A | 10/2019 |
| EP | 0909315 B1 | 5/2005 |
| EP | 1992347 A1 | 11/2008 |
| EP | 2749572 A1 | 7/2014 |
| EP | 2659269 B1 | 10/2016 |
| EP | 2611834 B1 | 3/2018 |
| EP | 3049439 B1 | 12/2019 |
| EP | 2809682 B1 | 4/2020 |
| EP | 4053153 A1 | 9/2022 |
| WO | WO 2010/019702 | 2/2010 |
| WO | WO 2012/135854 | 10/2012 |
| WO | WO 2013/027802 | 2/2013 |
| WO | WO 2013/034933 A1 | 3/2013 |
| WO | WO 2014/047624 | 3/2014 |
| WO | WO 2014/140330 A1 | 9/2014 |
| WO | WO 2018/12659 | 7/2018 |
| WO | WO 2018/162724 | 9/2018 |
| WO | WO 2018/237287 | 12/2018 |
| WO | WO 2021/086159 A1 | 5/2021 |
| WO | WO 2022/078524 A2 | 4/2022 |
| WO | WO 2022/092974 A1 | 5/2022 |
| WO | WO 2022/135332 A1 | 6/2022 |
| WO | WO 2022/156786 A1 | 7/2022 |
| WO | WO 2022/171101 A1 | 8/2022 |
| WO | WO 2022/231424 A1 | 11/2022 |
| WO | WO 2022/235059 A1 | 11/2022 |
| WO | WO 2023/274352 A1 | 1/2023 |
| WO | WO 2023/025248 A1 | 3/2023 |
| WO | WO 2023/040793 A1 | 3/2023 |
| WO | WO 2023/046156 A1 | 3/2023 |
| WO | WO 2023/061478 A1 | 4/2023 |
| WO | WO 2023/078273 A1 | 5/2023 |
| WO | WO 2023/160721 A1 | 8/2023 |
| WO | WO 2023/163873 A1 | 8/2023 |

OTHER PUBLICATIONS

Gao et al., Multi-organ Site Metastatic Reactivation Mediated by Non-canonical Discoidin Domain Receptor 1 Signaling. *Cell* 166, 47-62, doi: 10.1016/j.cell.2016.06.009 (2016).

Hidalgo-Carcedo et al., Collective cell migration requires suppression of actomyosin at cell-cell contacts mediated by DDR1 and the cell polarity regulators Par3 and Par6. *Nature Cell Biol* 13, 49-58, doi: 10.1038/ncb2133 (2011).

International Preliminary Report on Patentability issued in International Application No. PCT/US2020/065618, dated Jun. 30, 2022.

International Search Report and Written Opinion issued in International Application No. PCT/US2020/065618, dated May 19, 2021.

Marcotte et al., Essential gene profiles in breast, pancreatic, and ovarian cancer cells. *Cancer Discov* 2, 172-189, doi:10.1158/2159-8290.CD-11-0224 (2012).

Moll et al., DDR1 role in fibrosis and its pharmacological targeting. *BBA-Molecular Cell Research* 1866, 118474, doi:10.1016/j.bbamcr.2019.04.004 (2019).

Rammal et al., Discoidin Domain Receptors: Potential Actors and Targets in Cancer. *Front Pharmacol* 7, 55, doi:10.3389/fphar.2016.00055 (2016).

Takai et al., Discoidin domain receptor 1 (DDR1) ablation promotes tissue fibrosis and hypoxia to induce aggressive basal-like breast cancers. *Genes Dev* 32, 244-257, doi: 10.1101/gad.301366.117 (2018).

Valiathan et al., Discoidin domain receptor tyrosine kinases: new players in cancer progression. *Cancer Metastasis Rev* 31, 295-321, doi:10.1007/s10555-012-9346-z (2012).

Carafoli, Federico, et al. "Structure of the discoidin domain receptor 1 extracellular region bound to an inhibitory Fab fragment reveals features important for signaling." *Structure* 20.4 (2012): 688-697.

Office Communication issued in Japanese Application No. 2022-537312, dated Feb. 25, 2024. English Translation.

Partial Search Report issued in European Application No. 20903632.6, dated Feb. 28, 2024.

Abhinandan (Molecular Immunology, vol. 45, p. 3832-3839, 2008) (Year: 2008).

Ewert (Methods, vol. 34, p. 184-199, 2004) (Year: 2004).

Office Communication issued in corresponding Chinese Application No. 202080094867.1, dated Feb. 28, 2025. English Translation.

\* cited by examiner

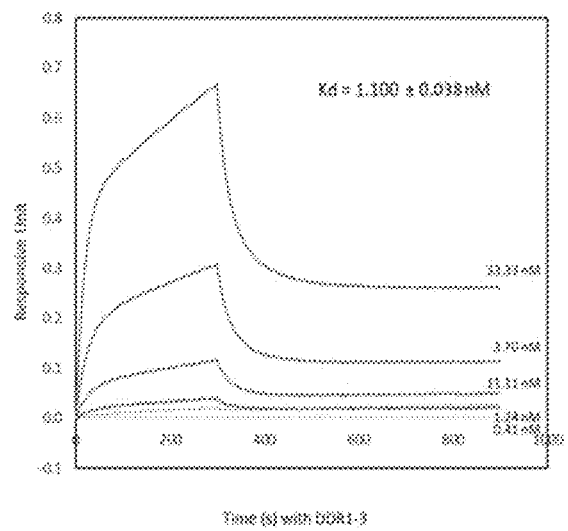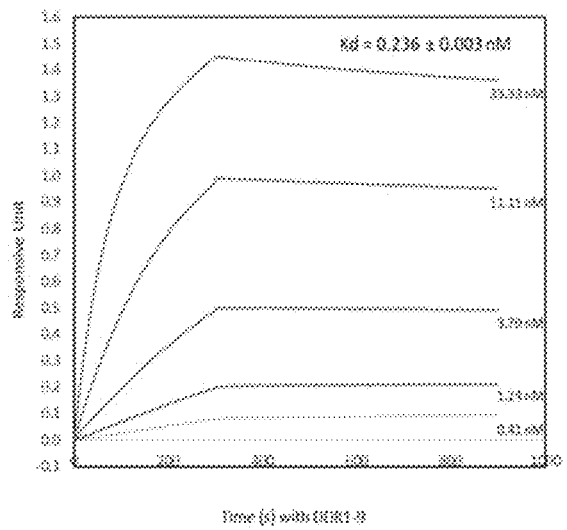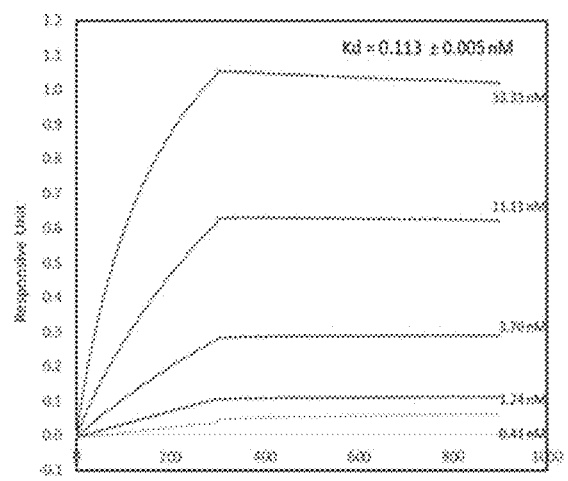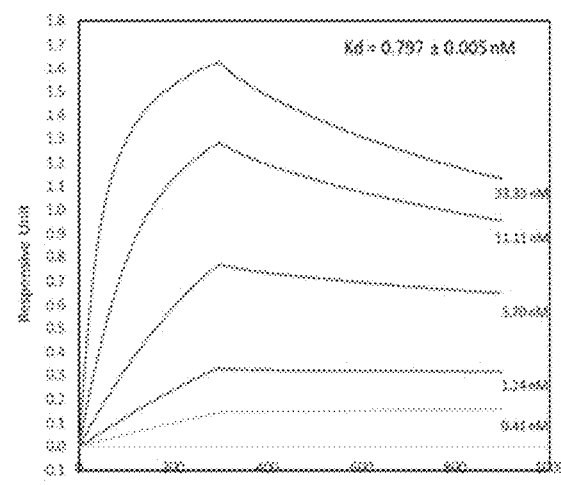
FIG. 11

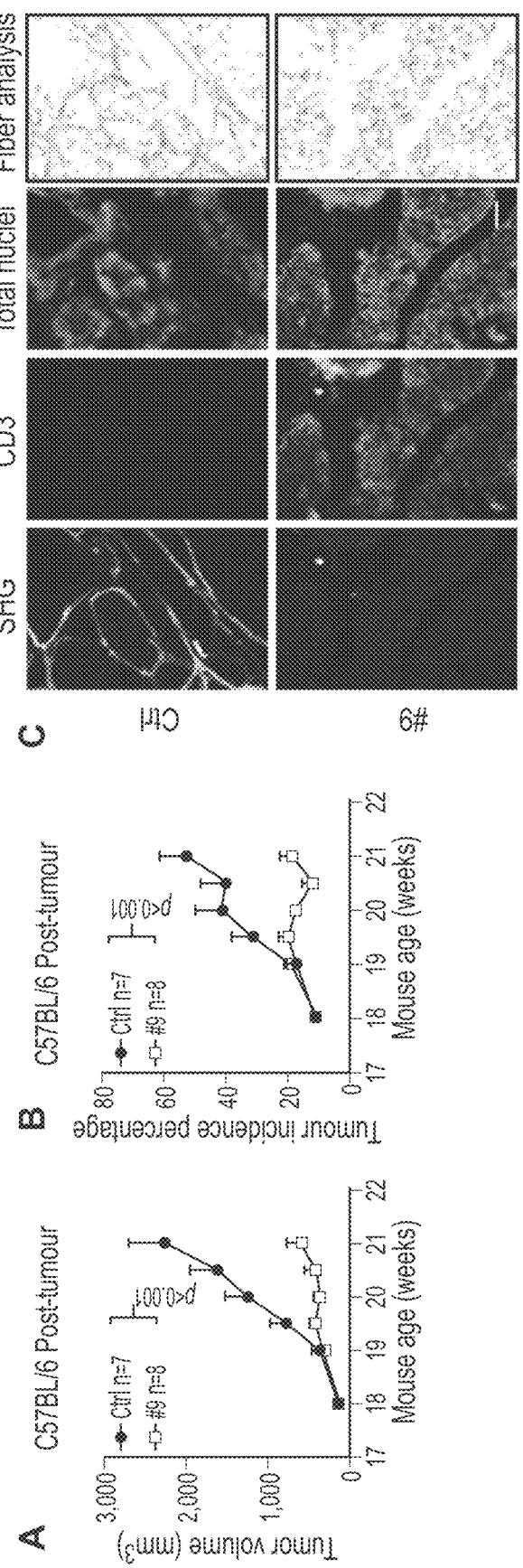
FIGS. 12A-C

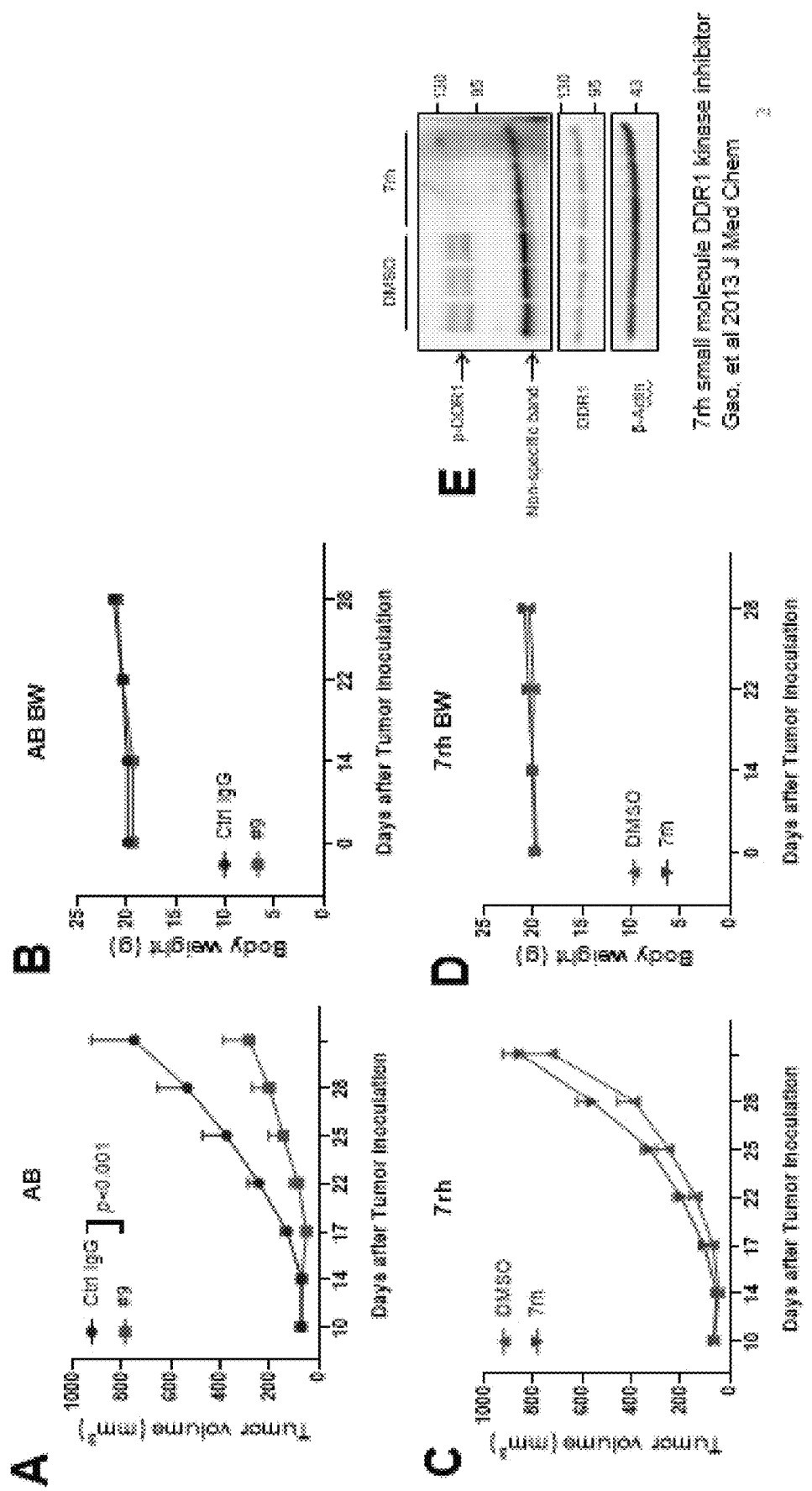
FIGS. 13A-E

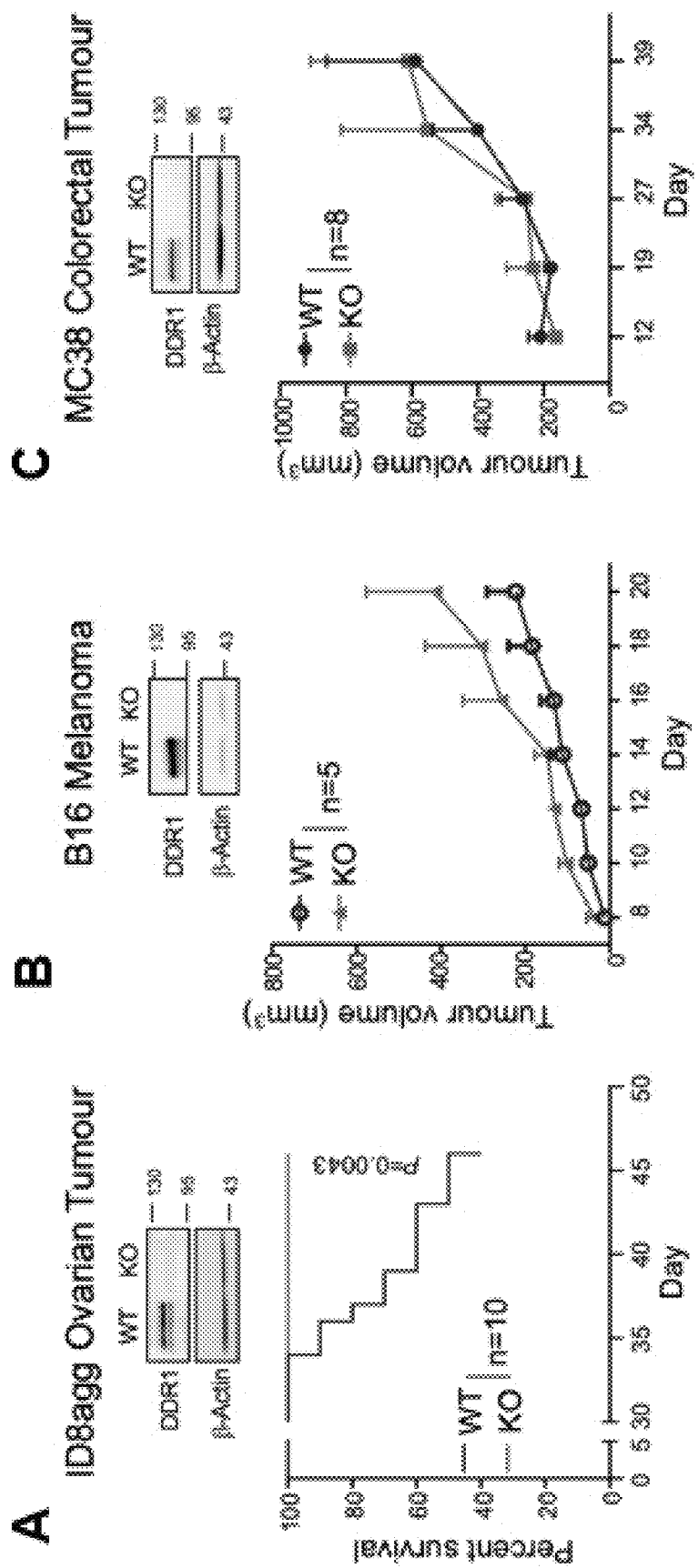
FIGS. 14A-C

DDR1 ANTIBODIES AND USES THEREOF

CROSS-REFERENCES TO RELATED APPLICATIONS

This application is a continuation of U.S. application Ser. No. 17/757,510, filed Jun. 16, 2022, as a national phase application under 35 U.S.C. § 371 of International Application No. PCT/US2020/065618, filed Dec. 17, 2020, which claims benefit of priority to U.S. Provisional Application Ser. No. 62/949,300, filed Dec. 17, 2019, the entire contents of which are hereby incorporated by reference.

STATEMENT REGARDING GOVERNMENT SPONSORED RESEARCH

The invention was made with government support under Grant No. CA220578 awarded by the U.S. National Institutes of Health. The government has certain rights in the invention.

REFERENCE TO A SEQUENCE LISTING

This application contains a Sequence Listing XML, which has been submitted electronically and is hereby incorporated by reference in its entirety. Said XML Sequence Listing, created on Feb. 27, 2023, is named UTSHP0362USC1.xml and is 420,859 bytes in size.

BACKGROUND

1. Field

The present disclosure relates generally to the fields of medicine, oncology, and immunology. More particular, the disclosure relates to antibodies that bind to DDR1 and can treat cancers, including breast cancer.

2. Description of Related Art

Aberrant expression of tumor discoidin domain receptors 1 (DDR1) and 2 (DDR2) proteins is associated with progression of multiple solid cancer types including breast cancer (Valiathan et al., 2012; Rammal et al., 2016; Gao et al., 2016; Bayer et al., 2019). Published data support roles of DDR proteins in promoting tumor progression and metastatic potential (Gao et al., 2016; Bayer et al., 2019, Hidalgo-Carcedo et al., 2011; Marcotte et al., 2012). However, genetic ablation of Ddr1 in MMTV-PyMT mice promotes spontaneous tumorigenesis (Takai et al., 2018), suggesting a stage-dependent tumor DDR1 function in cancer development and progression.

SUMMARY

Thus, in one aspect, the present disclosure provides an isolated monoclonal antibody or an antigen-binding fragment thereof that binds specifically to DDR1. In certain embodiments, the antibody or antigen-binding fragment, when bound to DDR1, modulates the activity of DDR1, i.e., suppresses DDR1. In certain embodiments, the antibody or antigen-binding fragment, when bound to DDR1, specifically blocks binding of ligands to DDR1.

In one aspect, the isolated monoclonal antibody or an antigen-binding fragment thereof comprises a light chain (LC) variable region (VL) and a heavy chain (HC) variable region (VH) comprising clone-paired CDR amino acid sequences as set forth in Table 1 and Table 2, respectively; and variants thereof wherein one or more of the LC-CDRs and/or one or more of the HC-CDRs has one, two, or three amino acid substitutions, additions, deletions, or combinations thereof. In some embodiments, the isolated monoclonal antibody or an antigen binding fragment thereof is a murine, a rodent, a rabbit, a chimeric, humanized, or human antibody. In some embodiments, the isolated monoclonal antibody or an antigen-binding fragment thereof may have VL and VH chains with amino acid sequences at least 90% or 95% identical to clone-paired sequences of Table 3 and Table 4, respectively. In some embodiments, the isolated monoclonal antibody or an antigen-binding fragment thereof may have VL and VH chains encoded by nucleic acid sequences at least 80% or 90% identical to clone-paired sequences of Table 8 and Table 9 respectively. In some embodiments, the isolated monoclonal antibody or an antigen-binding fragment thereof of has VL and VH chains with amino acid sequences identical to clone-paired sequences of Table 3 and Table 4, respectively. In some embodiments, the isolated monoclonal antibody or an antigen binding fragment thereof may have VL and VH chains encoded by nucleic acid sequences identical to clone-paired sequences of Table 8 and Table 9 respectively.

The variants may be those where one or more of the HC-CDRs or LC-CDRs has one, two, or three amino acid substitutions, additions, deletions, or combinations thereof. In certain embodiments, each CDR is defined in accordance with Kabat definition, the Chothia definition, the IMGT definition, the combination of Kabat definition and Chothia definition, the AbM definition, or the contact definition of CDR.

In another aspect, the present disclosure provides an isolated monoclonal antibody or an antigen-binding fragment thereof, which competes for the same epitope with an antibody having clone-paired light and heavy chain CDR amino acid sequences from Table 1 and Table 2 respectively.

In certain embodiments, the isolated monoclonal antibody described herein is a chimeric, humanized, or human antibody. In certain embodiments, isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')$_2$ fragment, or Fv fragment.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody and recovering the antibody.

In another aspect, there is provided a chimeric antigen receptor (CAR) protein comprising an antigen-binding fragment as provided herein.

In another aspect, there is provided an isolated nucleic acid that encodes a CAR protein as provided herein.

In another aspect, there is provided an engineered cell comprising the isolated nucleic acid as provided herein. In certain embodiments, the cell is a T cell, NK cell, or myeloid cell. In another aspect, there is provided a method of treating or ameliorating the effect of a cancer or for treating or ameliorating fibrosis (e.g., organ fibrosis) in a subject, the method comprising administering to the subject a therapeutically effective amount of the antibody or an antigen-binding fragment thereof as defined herein. In the treatment of cancer, the method may reduce or eradicate the tumor burden in the subject, may reduce the number of tumor cells, may reduce tumor size, may eradicate the tumor in the subject. In some embodiments, the cancer treated is breast cancer.

The antibody or an antigen-binding fragment thereof may be administered locally, intravenously, intra-arterially, intra-tumorally, or subcutaneously. In some embodiments, the method may further comprise administering to the subject one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection (VYXEOS®), an azacytidine (VIDAZA®), a decitabine, an all-trans-retinoic acid (ATRA), an arsenic, an arsenic trioxide, a histamine dihydrochloride (CEPLENE®), an interleukin-2, an aldesleukin (PROLEUKIN®), a gemtuzumab ozogamicin (MYLOTARG®), an FLT-3 inhibitor, a midostaurin (RYDAPT®), a clofarabine, a farnesyl transferase inhibitor, a decitabine, an IDH1 inhibitor, an ivosidenib (TIBSOVO®), an IDH2 inhibitor, an enasidenib (IDHIFA®), a smoothened (SMO) inhibitor, a glasdegib, an arginase inhibitor, an IDO inhibitor, an epacadostat, a BCL-2 inihbitor, a venetoclax (VENCLEXTA®), a platinum complex derivative, oxaliplatin, a kinase inhibitor, a tyrosine kinase inhibitor, a PI3 kinase inhibitor, a BTK inhibitor, an ibrutinib (IMBRUVICA®), an acalabrutinib (CALQUENCE®), a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

In some embodiments, the isolated monoclonal antibody or an antigen binding fragment thereof may comprise an antitumor drug linked thereto. The antitumor drug may be linked to said antibody through a photolabile linker. The antitumor drug may be linked to said antibody through an enzymatically-cleaved linker. The antitumor drug may a toxin, a radioisotope, a cytokine, or an enzyme.

In another embodiment, there is provided a method of detecting a cancer cell or fibrotic tissue in a sample or subject comprising (a) contacting a subject or a sample from the subject with the antibody or an antigen-binding fragment thereof as defined herein; and (b) detecting binding of said antibody to a cancer cell or the fibrotic tissue in said subject or sample. The sample may be a body fluid or biopsy, or blood, bone marrow, sputum, tears, saliva, mucous, serum, urine or feces. Detection may comprise immunohistochemistry, flow cytometry, FACS, ELISA, RIA or Western blot. In some embodiments, the method may further comprise performing steps (a) and (b) a second time and determining a change in detection levels as compared to the first time. The isolated monoclonal antibody or an antigen binding fragment thereof may further comprise a label, such as a peptide tag, an enzyme, a magnetic particle, a chromophore, a fluorescent molecule, a chemo-luminescent molecule, or a dye. The isolated monoclonal antibody or an antigen binding fragment thereof may be conjugated to a liposome or nanoparticle.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1a) Immunoblots of DDR1, DDR2 and loading control GAPDH in DDR1 WT/KO mammary tumor E0771 cells. (FIG. 1b) Cell proliferation of WT/KO E0771 cells as measured by MTT assay (n=6). (FIGS. 1c-d) Quantification of DDR1 WT/KO M-Wnt cell migration (c) and invasion (d) (n=6 random fields). (FIG. 1e) Growth of DDR1 WT/KO E0771 tumors in Rag1$^{-/-}$ (n=6, e) hosts. (FIGS. 1f-h) Growth of WT/KO E0771 (n=6, f), M-Wnt (n=7, g) and AT-3 (n=7, h) tumors in C57BL/6 mice. (FIGS. 1i-j) Tumor growth kinetics (i) and weight (j) at the end point of E0771 DDR1 WT/KO tumor transplanted from Rag1$^{-/-}$ to C57BL/6 hosts (n=8). (FIG. 1k) Diagram for tumor re-challenge. Mice were challenged with saline buffer or DDR1 KO E0771 cells on one side of inguinal mammary gland in the first round of inoculation. After 30 days, mice were re-challenged with DDR1 WT E0771 tumor cells on both sides of inguinal mammary gland. L, left; R, right. (FIGS. 1l-m) Tumor curve (FIG. 1l) and weight (FIG. 1m) from re-challenged mice (n=6). Values represent mean±SEM, p value as indicated.

(FIG. 2a) Representative images of CD8$^+$ and CD4$^+$ T cell staining at tumor margin (top panels, denoted by red dash lines) and in the tumor core (bottom panels) (n=3). Scale bar: 50 μm. (FIGS. 2b-g) Tumor infiltrating lymphocytes (TILs) cell number normalized by tumor weight per gram. Cell number of CD8⁺ (FIG. 2b) and CD4⁺ (FIG. 2c) T cells, cytokine IFN-γ⁺ CD8⁺ cells (FIG. 2d) and CD4⁺ (FIG. 2e) T cells, and CD44$^{hi}$ CD62L$^{lo}$-activiated CD8⁺ (FIG. 2f) and CD4⁺ (FIG. 2g) T cells. (FIGS. 2h-j) WT/KO E0771 tumor growth in C57BL/6 host with prior treatment of either anti-IgG or anti-CD8 antibody (n=5). Tumor volumes (FIG. 2h), image (FIG. 2i) and weight (FIG. 2j) at the end point are shown. Scale bar: 1 cm. (FIGS. 2k-m) Adoptive transfer CD8⁺ T cells or media (sham) to Rag1$^{-/-}$ (n=6) mice burdened with DDR1 WT/KO E0771 tumors. Arrow in (FIG. 2k) indicates transfer of CD8⁺ T cells on day 17. Tumor image (FIG. 2l) and weight (FIG. 2m) are shown. Scale bar: 1 cm. Values represent mean±SEM, p value as indicated.

FIGS. 3A-P. DDR1-dependent ECM remodelling deters antitumor immune infiltration. (FIG. 3a) Diagram of full-length DDR1 (top) and tumor curve of DDR1 KO E0771 tumor cells with various DDR1 expression vectors: wild-type (WT), empty vector (EV), deletion of the kinase domain (ΔKD), and extracellular domain (ECD) only. All p-values compared to KO group. TM: transmembrane domain. (FIG. 3b) ECD diagram consisting of DS and DS-like (DSL) domain (top) and crystal structure (bottom) of mouse DDR1 DS domain, generated by Jmol software. Amino acid residues targeted in the mutational analysis are shown. (FIG. 3c) Collagen binding of WT and point mutant ECD expressed in KO E0771 cells, assessed by ELISA (n=4). (FIGS. 3d-k) Individual tumor growth curves of KO E0771 tumor cells with ectopically expressed ECD WT or point mutants. Tumor incidence was shown in parentheses for each panel. (FIG. 3l) Representative SEM images of WT/KO E0771 tumor cells cultured in vitro. (FIG. 3m) Decellularized ECM from E0771 cells inhibits T cell migration in an ECD-dependent manner. Shown on the left is a diagram of the transwell migration assay. (FIG. 3n) WT/KO E0771 tumors transplanted from Rag1$^{-/-}$ to C57BL/6 hosts were analysed by SHG (grey), CD3 staining (green), To-pro-3 staining (red), and collagen fibre individualization (far right panel). Block arrows indicate tumor margins. Scale bar: 50 μm. (FIGS. 3o-p) Quantification of tumor fibre alignment (o) and fibre length (p) by the CT Fire software. Values represent mean±SEM, p value as indicated.

(FIG. 4a) Immunoblots of ectopic human (hu) DDR1 and endogenous mouse DDR1 in cell lysates and media of E0771-derived cells. (FIG. 4n) A model diagram of ECD (red circles)-remodelled collagen fibres (curves) that form barriers to prevent immune cells infiltration. Values represent mean±SEM, p value as indicated.

(FIG. 5a) DDR1 expression in normal (N) tissue and breast tumor (T) samples in TCGA database. P value is analysed using wilcoxon test. (FIG. 5b) DDR1 immunoblots of WT/KO cells derived from murine mammary tumor cells M-Wnt and AT-3. (FIGS. 5c-d) Genomic DNA sequencing of sgRNA targeted sites at the mouse Ddr1 gene locus. Both AT-3 and E0771 KO clones contain one base-pair insertion (FIG. 5c) (CAGAC-CATGCAGTTATCTGAGGTG (SEQ ID NO:312); CAGACCATGCAGTTATTCTGAGGTG (SEQ ID NO:313); CAGACCATGCAGTTATTCTGAGGTG (SEQ ID NO:314).. M-Wnt DDR1 KO clone carries an 8 bp deletion (FIG. 5d) (CCTGTGTTCCCCAAAGAAGAG-GAGTACTTG (SEQ ID NO:315); CCTGTGTTCCC-CAAAGTAC (SEQ ID NO:316)). The cleavage occurred upstream of the PAM sequence. (FIG. 5e) Representative images for migration and invasion of DDR1 WT/KO M-Wnt and AT-3 cells. (FIG. 5f) In vitro cell proliferation of WT/KO M-Wnt tumor cells. (FIG. 5g) M-Wnt tumor growth in nude mice (n=4). (FIG. 5h) Individual tumor growth curves of DDR1 KO E0771 cells inoculated at various numbers in C57BL/6 mice (0.5, 5, 10 and 20×10⁶ per mouse, n=4). (FIGS. 5i-k) Tumor volume (FIG. 5i), image (FIG. 5j) and weight (FIG. 5k) of M-Wnt DDR1 WT, KO, and 1:1 mixture at inoculation (n=8). Values represent mean±SEM, p value as indicated.

(FIGS. 6a-d) Percentages of T cells from KO and parental controls that are positive for Ki67 (CD4⁺ in a and CD8+ in FIG. 6b), IFNγ (CD8⁺ in FIG. 6c) or Gzmb (CD8⁺ in FIG. 6d). (FIGS. 6e-f) Flow cytometry of CD4⁺ and CD8⁺ T cells from splenocytes of anti-IgG 2b treated or anti-CD8 antibody treated C57BL/6 mice (e), and percentage of CD8⁺ in CD3⁺ T cells in blood (f, n=5). (FIG. 6g) CD8⁺ T cell number in TILs normalized by tumor weight in Rag1$^{-/-}$ mice (n=6). (FIGS. 6h-i) RNA-seq heat map for T cell-homing genes and chemokine genes from DDR1 WT/KO E0771 tumors transplanted from Rag1$^{-/-}$ to C57BL/6 host. ***, p<0.001. Values represent mean±SEM, p value as indicated.

(FIGS. 7a-b) Growth curves (FIG. 7a) and tumor weight (FIG. 7b) of E0771 DDR1 KO+ECD, KO, KO+DS, KO+DSL tumors in C57BL/6 hosts (n=10). (FIG. 7c) Co-IP of type I collagen and Flag-tagged ECD WT and mutants. (FIG. 7d) Immunoblots of full-length DDR1 in cells and soluble ECD in conditioned media from murine (left) and various human (right) breast cancer cell lines. (FIG. 7e) Top 10 biological processes (BP) based on gene ontology analysis of RNA-seq data from E0771 DDR1 WT and KO tumors transplanted from Rag1$^{-/-}$ to C57BL/6 host. Values represent mean±SEM, p value as indicated.

(FIG. 8a) Transwell migration assay for purified CD8⁺ T cells in the presence of conditioned media from E0771 cells containing endogenous DDR1 WT, with DDR1 KO, and with DDR1 KO and ectopic expression of huDDR1. (FIG. 8b) Representative neutralizing antibodies screening by the CD8⁺ T cell migration assay, using conditional media from KO or KO+huDDR1 E0771 cells. Control: isotype IgG; anti-huDDR1 antibody: #3, #9, #14, and #33. (FIG. 8c) body weight measurement of mice treated with control (α-IgG) and anti-huDDR1 antibody #9 (n=5). (FIGS. 8d-e)

KO+huDDR1 E0771 tumors in C57BL/6 (FIG. 8d) and Rag1$^{-/-}$ hosts (FIG. 8e) treated with either isotype IgG or anti-huDDR1 #33 antibody. (FIG. 8f) KO+huDDR1 tumors core were analysed by SHG (grey), CD3 staining (green), To-pro-3 staining (red), and collagen fibre individualization (far right panel). Scale bar: 50 µm. (FIGS. 8g-i) Correlation between huDDR1 mRNA levels and immune cytotoxic marker genes IFNG (FIG. 8g), GZMB (FIG. 8h), and PRF1 (FIG. 8i) among 1,093 breast cancer tumors in the TIMER database. Values represent mean±SEM, p value as indicated.

FIG. 11. Kinetic binding curves of anti-DDR1 antibodies measured using Octet instrument.

FIG. 12A-C. Anti-hECD antibody inhibits spontaneous tumor growth. To demonstrate the effect of anti-DDR1 antibody treatment on mammary tumorigenesis at various stages, MMTV-PyMT mice (C57BL/6 strain background) were treated with control IgG or anti-DDR1 antibody for two weeks when average tumor size reached 100 mm$^3$ ("post-tumor"). (FIGS. 12A-B) Tumor growth kinetics (per mouse, FIG. 12A) and tumor incidence (per mouse, FIG. 12B) in MMTV-PyMT spontaneous mammary tumor model of C57BL/6 genetic background, treated in a "post-tumor" scheme with Ctrl (n=7) or humanized anti-DDR1 #9 antibody (n=8). (FIG. 12C) Representative images of tumors from the post-tumor treatment group, analysed by SHG (grey), CD3 staining (green), To-pro-3 staining (red), and collagen fibre individualisation (far right panel). Scale bar: 50 µm.

FIG. 13A-E. Comparison of anti-hECD antibody and DDR1 kinase inhibitor. E0771 mammary tumors were treated with anti-hECD antibody and tumor growth (FIG. 13A) and host body weight (FIG. 13B) were assessed. A previously published small-molecule DDR1 kinase inhibitor, 7rh, did not reduced tumor growth (FIG. 13C). This is consistent with the assertion that DDR1-dependent exclusion of antitumor immunity is independent of its kinase activity. (FIG. 13 D) 7rh did not affect host body weight. (FIG. 13E) tumors treated with 7rh had substantially lower DDR1 autophosphorylation, a marker of DDR1 tyrosine kinase activity (Gao et al., *J Med Chem* 2013).

FIGS. 14A-C. DDR1 is required for growth of some tumor types. (FIG. 14A) CRISPR-based genetic ablation of tumor Ddr1 significantly increased survival of immunocompetent hosts bearing ID8agg ovarian tumors. (FIGS. 14B-C) Ddr1 KO in B16 melanoma or MC38 colorectal tumors did not affect tumor growth in syngeneic immunocompetent hosts.

(FIG. 15A) DDR1 mRNA levels in multiple cancers negatively correlate with cytotoxic immune markers such as Granzyme B (GZMB), suggesting that DDR1 may antagonize anti-tumor immunity in many cancer types. (FIGS. 15B-C) Analysis of the TCGA breast cancer proteome data set (NCI CPTAC) showed that DDR1 protein levels also negatively correlated with CD8 and proteins in the cytolytic effector pathway.

(FIG. 18A) DDR1-9Hu antibody titration was used to determine binding curves and EC$_{50}$s. Deletion of the DS or the DSL domain of DDR1 ECD resulted in reduced binding by humanized DDR1-9hu antibody. The deletion of DS domain alone reduced binding, with an EC50 of 168 ng/ml vs 83 ng/ml, while deletion of the DSL domain totally abolished the DDR1-9 (FIG. 18B) and DDR1-14 antibody binding. (FIG. 18C)

DESCRIPTION OF ILLUSTRATIVE EMBODIMENTS

Figure 1:
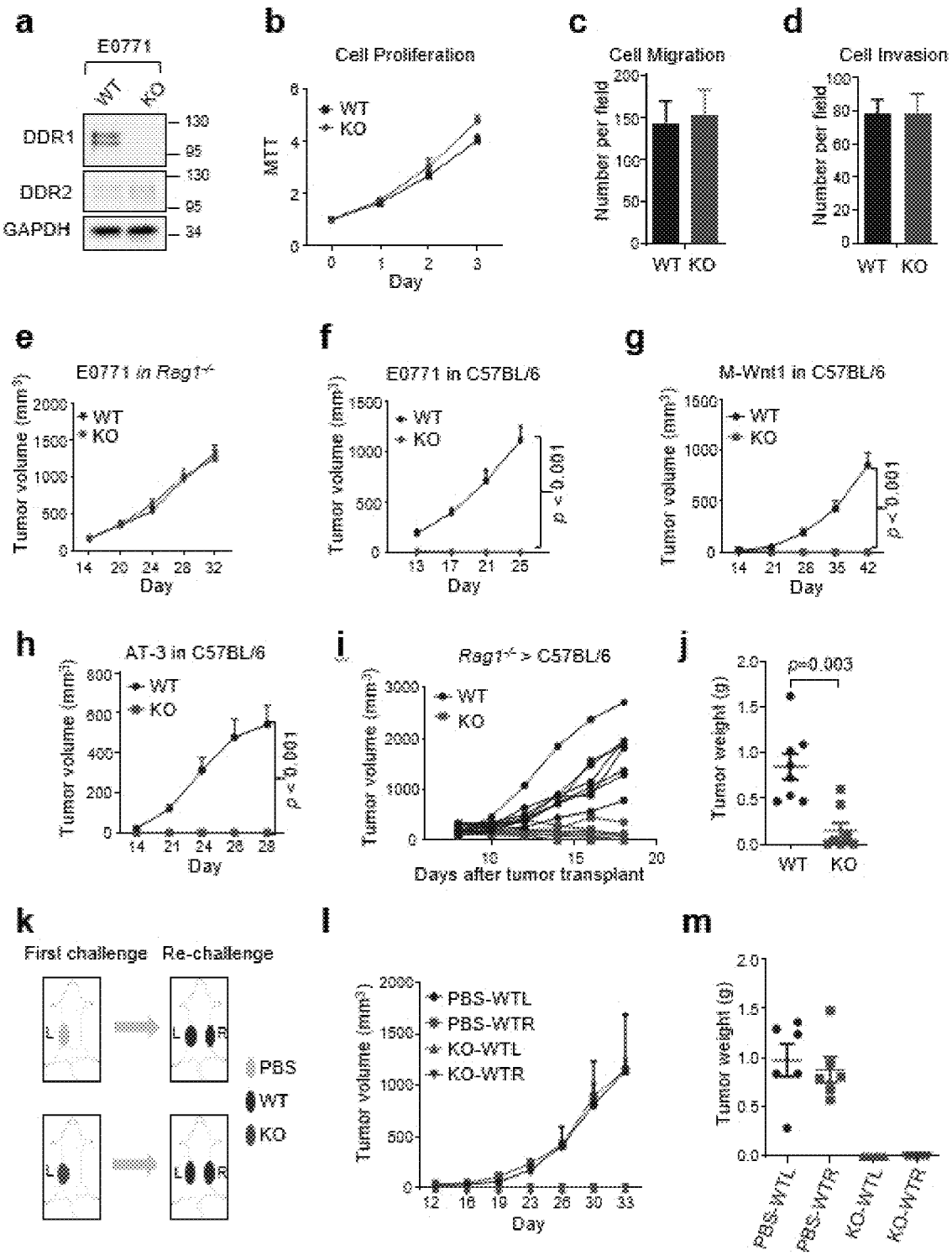
FIGS. 1A-M. DDR1 confers mammary tumor growth in immunocompetent hosts.

The inventors determined that tumor discoidin domain receptor 1 (DDR1) plays a critical role in regulation of host immunity. DDR1 is a collagen receptor with tyrosine kinase activity. The inventors have found that DDR1 induces tumor defense that prevents host immune cells from infiltrating tumor tissue and attacking the tumor itself in a kinase-independent manner. The inventors have isolated a panel of novel monoclonal antibodies recognizing DDR1 protein, which can be used for the treatment of cancer. The anti-human DDR1 antibodies are antagonists of DDR1 function and prevent DDR1's induction of tumor defense.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

I. DEFINITIONS

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition, IMGT definition, and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996). The IMGT definition uses a unique numbering system that combines the definition of framework (FR) and CDR regions, structural data from X-ray diffraction studies, and the characterization of the hypervariable loops, as described in by Lefranc M-P et al., "IMGT unique numbering for immunoglobulin and T cell receptor variable domains and Ig superfamily V-like domains," Dev Comp Immunol 27:55-77 (2003). In one preferred embodiment, the CDR sequences are based on IMGT definition.

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus. In the present disclosure, the CDR regions of the light chain variable region are also denoted as LC-CDR1, LC-CDR2, and LC-CDR3 while the CDR regions of the heavy chain variable region are denoted as HC-CDR1, HC-CDR2, and HC-CDR3.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

The term "antigen binding protein" ("ABP") as used herein means any protein that binds a specified target antigen. In the instant application, the specified target antigen is the DDR1 protein or fragment thereof. "Antigen binding protein" includes but is not limited to antibodies and antigen-binding fragment thereof. Peptibodies are another example of antigen binding proteins.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. In certain embodiments, the antigen-binding fragment is not derived from an antibody but rather is derived from a receptor. Examples of antigen-binding fragment include, without limitation, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies. In certain embodiments, the antigen-binding fragment is derived from a receptor and contains one or more mutations. In certain embodiments, the antigen-binding fragment does not bind to the natural ligand of the receptor from which the antigen-binding fragment is derived.

The term "Fab fragment" comprises one light chain and the CH1 and variable regions of one heavy chain. The heavy chain of a Fab molecule cannot form a disulfide bond with another heavy chain molecule.

The term "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the DDR1 specific antibodies of the present invention are specific to DDR1. In some embodiments, the antibody that binds to DDR1 has a dissociation constant (Kd) of ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$M).

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., DDR1 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, and an alveolar macrophage; a cell from circular system or organ (e.g., myocardiocyte and pericyte); a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, and a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell; a cell from urinary system or organ (e.g., a podocyte, a juxtaglomerular cell, an intraglomerular mesangial cell, an extraglomerular mesangial cell, a kidney proximal tubule brush border cell, and a macula densa cell); and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

The term "chimeric antigen receptor" or "CAR" as used herein refers to an artificially constructed hybrid protein or polypeptide containing an antigen-binding domain of an antibody (e.g., a single chain variable fragment (scFv)) linked to a domain or signaling, e.g., T-cell signaling or T-cell activation domains, that activates an immune cell, e.g., a T cell or a NK cell (see, e.g., Kershaw et al., supra, Eshhar et al., Proc. Natl. Acad. Sci. USA, 90(2): 720-724 (1993), and Sadelain et al., Curr. Opin. Immunol. 21(2): 215-223 (2009)). CARs are capable of redirecting the immune cell specificity and reactivity toward a selected target in a non-MHC-restricted manner, taking advantage of the antigen-binding properties of monoclonal antibodies. The non-MHC-restricted antigen recognition confers immune cells expressing CARs on the ability to recognize an antigen independent of antigen processing, thus bypassing a major mechanism of tumor escape. In addition, when expressed in T-cells, CARs advantageously do not dimerize with endogenous T-cell receptor (TCR) alpha and beta chains.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic makeup to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass DDR1 antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a DDR1-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional nontoxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. DDR1 AND DDR1 ANTIBODIES

A. Ddr1

Receptor tyrosine kinases (RTKs) play a key role in the communication of cells with their microenvironment. These molecules are involved in the regulation of cell growth, differentiation and metabolism. The DDR1 protein encoded by the DDR1 gene is a RTK that is widely expressed in normal and transformed epithelial cells and is activated by various types of collagen. The DDR1 protein belongs to a subfamily of tyrosine kinase receptors with a homology region to the Dictyostelium discoideum protein discoidin I in their extracellular domain. Its autophosphorylation is achieved by all collagens so far tested (type I to type VI). A closely related family member is the DDR2 protein. In situ studies and Northern-blot analysis showed that expression of DDR1 encoded protein is restricted to epithelial cells, particularly in the kidney, lung, gastrointestinal tract, and brain. In addition, the DDR1 protein is significantly over-expressed in several human tumors from breast, ovarian, esophageal, and pediatric brain. This gene is located on chromosome 6p21.3 in proximity to several HLA class I genes. Alternative splicing of this gene results in multiple transcript variants. A representative mRNA sequence for DDR1 is NM_001202521 (SEQ ID NO:1), and a representative amino acid sequence is NP_001189450 (SEQ ID NO:2).

B. Antibodies to DDR1 Protein

Antibodies or antigen-binding fragments thereof according to the present disclosure may be defined, in the first instance, by their binding specificity, which in this case is for DDR1. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to DDR1. In some embodiments, when bound to DDR1, such antibodies modulate the activation of DDR1. In certain embodiments, the antibody or antigen-binding fragment, when bound to DDR1, activates DDR1. In certain embodiments, the antibody or antigen-binding fragment, when bound to DDR1, suppresses activation of DDR1. In certain embodiments, the antibody or antigen-binding fragment, when bound to DDR1, can specifically interfere with, block or reduce the interaction between DDR1 and its binding partners. In certain embodiments, the antibodies or antigen-binding fragments provided herein specifically or selectively bind to human DDR1.

In some embodiments, the antibodies or antigen-binding fragments bind specifically to human DDR1 and/or substantially inhibits binding of human DDR1 to its binding partners by at least about 20%-40%, 40-60%, 60-80%, 80-85%, or more (for example, by an assay as disclosed in the Example). In some embodiments, the antibody or antigen-binding fragment has a Kd of less (binding more tightly) than $10^{-7}$, $10^{-8}$, $10^{-9}$, $10^{-10}$, $10^{-11}$, $10^{-12}$, $10^{-13}$M.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (Clq) of the classical complement system. Thus, the term "antibody" includes intact immunoglobulins of types IgA, IgG, IgE, IgD, IgM (as well as subtypes thereof), wherein the light chains of the immunoglobulin may be of types kappa or lambda. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., $2^{nd}$ ed. Raven Press, N.Y. (1989).

In some embodiments, the present disclosure provides an antibody or an antigen-binding fragment thereof that binds specifically to DDR1 protein, wherein the antibody comprises a LC-CDR1, LC-CDR2 and LC-CDR3 in a light chain variable region sequence presented in Table 3 and a HC-CDR1, HC-CDR2, and HC-CDR3 in a heavy chain variable region sequence presented in Table 4; or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a LC-CDR1, LC-CDR2 and LC-CDR3 in a light chain variable region sequence presented in Table 3 and a HC-CDR1, HC-CDR2, and HC-CDR3 in a heavy chain variable region sequence presented in Table 4; or variants thereof wherein one or more of the LC-CDRs and/or HC-CDRs has one, two, or three amino acid substitutions, additions, deletions or combinations of, wherein the light chain variable region sequence and the heavy chain variable region sequence is a clone-paired (e.g., of the same mAb designation) light chain variable region sequence and heavy chain variable region sequence presented in Table 3 and Table 4, respectively. An exemplary embodiment of a "clone-paired" LC-CDR1, LC-CDR2 and LC-CDR3 of a light chain variable region sequence and a HC-CDR1, HC-CDR2, and HC-CDR3 of a heavy chain variable region sequence is the LC-CDRs and HC-CDRs of the light chain variable region sequence and heavy chain variable region sequence, respectively, of mAb DDR1-1.

In some embodiments, the isolated antibody or an antigen-binding fragment thereof comprises a light chain variable region having a LC-CDR1, LC-CDR2 and LC-CDR3 selected from the LC-CDR1, LC-CDR2 and LC-CDR3 sequences for each mAb set forth in Table 1; and a heavy chain variable region having a HC-CDR1, HC-CDR2, and HC-CDR3 selected from the HC-CDR1, HC-CDR2 and HC-CDR3 sequences for each mAb set forth in Table 2, or variants thereof wherein one or more of the LC-CDRs and/or HC-CDRs has one, two, or three amino acid substitutions, additions, deletions or combinations of. In some embodiments, the isolated antibody or an antigen-binding fragment thereof comprises a light chain variable region having a LC-CDR1, LC-CDR2 and LC-CDR3, and a heavy chain variable region having a HC-CDR1, HC-CDR2, and HC-CDR3 of a clone-paired LC-CDRs and HC-CDRs presented in Table 1 and Table 2, respectively, or variants thereof wherein one or more of the LC-CDRs and/or HC-CDRs has one, two, or three amino acid substitutions, additions, deletions or combinations of.

TABLE 1

CDRs of light chain amino acid variable region sequences of DDR1 antibodies

| mAb Name | CDR1 | SEQ ID NO | CDR2 | CDR3 | SEQ ID NO |
| --- | --- | --- | --- | --- | --- |
| DDR1-1 | QNIYSN | 3 | GAS | QSGYYSSTDIA | 4 |
| DDR1-3 | QTISSW | 5 | YAF | QQGISSSNVDNV | 6 |
| DDR1-5 | QTISSW | 7 | YAF | QCTYGSGSSSYGCA | 8 |
| DDR1-6 | QSVYSNY | 9 | ETS | QGGYSEIIENT | 10 |
| DDR1-9 | QSIGSV | 11 | GVF | QYIPYGSSP | 12 |
| DDR1-11 | QSIGSTY | 13 | KAS | LYGGFGSSTGDA | 14 |
| DDR1-12 | QTIYSN | 15 | QAS | QSYYGADDYT | 16 |
| DDR1-13 | KSVYNNNA | 17 | GVS | AGDYSDISDNN | 18 |
| DDR1-14 | QSISSY | 19 | EAS | QNNGFSGSNFNN | 20 |
| DDR1-15 | QTIYSS | 21 | KAS | QQGSSISNVDKNA | 22 |
| DDR1-17 | QSIGSY | 23 | EAS | QNNGMTVSDFNA | 24 |
| DDR1-20 | QIIDHDH | 25 | RAS | QNNGMTVSDFNA | 26 |
| DDR1-21 | QSVVDKNW | 27 | EAS | AGDFESGVSG | 28 |
| DDR1-22 | KNIYNNNA | 29 | GAS | AADYSDISDNN | 30 |
| DDR1-23 | QSVYSNNY | 31 | AAS | LGGYNDDAN | 32 |
| DDR1-26 | ESVYSNNH | 33 | AAS | LGGYNDDAN | 34 |
| DDR1-28 | QSIDNND | 35 | RTS | QSYCVNTYGYT | 36 |
| DDR1-29 | QSISNH | 37 | RAS | QSYYIINRSNYANS | 38 |
| DDR1-32 | ESINSW | 39 | DAS | QSYYIINRSNYGNS | 40 |
| DDR1-33 | ETISSR | 41 | QAS | QGCYYGGGSFYDSA | 42 |
| DDR1-34 | ENLYKDNY | 43 | GAS | AGGYDSWD | 44 |

TABLE 2

CDRs of heavy chain amino acid variable region sequences of DDR1 antibodies

| mAb Name | CDR1 | SEQ ID NO | CDR2 | SEQ ID NO | CDR3 | SEQ ID NO |
|---|---|---|---|---|---|---|
| DDR1-1 | GFSLSRYA | 45 | IGSSGLT | 46 | ARGMWYDDSDDYEDYFNL | 47 |
| DDR1-3 | GIDLSSYA | 48 | INIGGGT | 49 | ARDVDAHTLTYFTL | 50 |
| DDR1-5 | GFTLSNNA | 51 | IYASGRT | 52 | ARGDTETDYGIPYFDL | 53 |
| DDR1-6 | GFSFSSSYY | 54 | IYASSGST | 55 | AILGADYRLTRLDL | 56 |
| DDR1-9 | GFSLNRYY | 57 | ISYGDTT | 58 | ARADTGDNGYLGLQL | 59 |
| DDR1-11 | GFSFSSGYY | 60 | IYTGRTDFT | 61 | ARGDYSGGVGGNYWLDL | 62 |
| DDR1-12 | GIDLSNTW | 63 | ITDSGTT | 64 | GRDPGDITSGTNDL | 65 |
| DDR1-13 | SGFSLNNY | 66 | IFNNGDI | 67 | ARTGYRTGGWL | 68 |
| DDR1-14 | GIDLSYYA | 69 | INGRGDT | 70 | AREDSAIPFIVGNYYGMDL | 71 |
| DDR1-15 | TFSFNSRYW | 72 | INNGDIS | 73 | AKGGNLAGDCYGL | 74 |
| DDR1-17 | GFSLNRYA | 75 | IGSSGST | 76 | ARDLDDSYGYTYATGMDIRLDL | 77 |
| DDR1-20 | GFSLSDYA | 78 | INSRDDT | 79 | AREDSSIPFIVGNYYGMDL | 80 |
| DDR1-21 | GFSLSSYG | 81 | IYPSGSI | 82 | VRYLTGSSDLHL | 83 |
| DDR1-22 | GFSLSDYA | 84 | INNGDIY | 85 | ARPGYRTGIWL | 86 |
| DDR1-23 | GFDLRSYYY | 87 | IHGGEGNT | 88 | RGGWTNYF | 89 |
| DDR1-26 | GFDLSSNYY | 90 | IYSSNTRT | 91 | RGGWTNYL | 92 |
| DDR1-28 | GFSLSSHD | 93 | IISSGNT | 94 | ARDVYSGASP | 95 |
| DDR1-29 | TFSFNSRYW | 96 | INNGDIT | 97 | AKGGNLAGDCYGL | 98 |
| DDR1-32 | GFSLSSYY | 99 | ITTAGPL | 100 | ARGHAGSIYYSYFDL | 101 |
| DDR1-33 | GFSLSSYD | 102 | SWNSGFV | 103 | ARLGADDIYYFNL | 104 |
| DDR1-34 | GFDLSSYYY | 105 | IYTSSGAT | 106 | RGGWCDFNL | 107 |

In some embodiments, the isolated antibody or an antigen-binding fragment thereof comprises a light chain variable region having a LC-CDR1 comprising the amino acid sequence QNIYSN (SEQ ID NO: 3), a LC-CDR2 comprising the amino acid sequence GAS, and a LC-CDR3 comprising the amino acid sequence QSGYYSSSTDIA (SEQ ID NO: 4), and a heavy chain variable region having a HC-CDR1 comprising the amino acid sequence GFSLSRYA (SEQ ID NO: 45), a HC-CDR2 comprising the amino acid sequence IGSSGLT (SEQ ID NO: 46), and a HC-CDR3 comprising the amino acid sequence ARGMWYDDSD-DYEDYFNL (SEQ ID NO:47) (DDR1-1), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QTISSW (SEQ ID NO: 5), a LC-CDR2 comprising the amino acid sequence YAF, and a LC-CDR3 comprising the amino acid sequence QQGISSSNVDNV (SEQ ID NO: 6), and a heavy chain variable region having a HC-CDR1 comprising the amino acid sequence GIDLSSYA (SEQ ID NO: 48), a HC-CDR2 comprising the amino acid sequence INIGGGT (SEQ ID NO: 49), and a HC-CDR3 comprising the amino acid sequence ARDVDAHTLTYFTL (SEQ ID NO: 50) (DDR1-3), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QTISSW (SEQ ID NO: 7), a LC-CDR2 comprising the amino acid sequence YAF, and a LC-CDR3 comprising the amino acid sequence QCTYGSGSSSSYGCA (SEQ ID NO: 8), and a heavy chain variable region having a HC-CDR1 comprising the amino acid sequence GFTL-SNNA (SEQ ID NO: 51), a HC-CDR2 comprising the amino acid sequence IYASGRT (SEQ ID NO: 52), and a HC-CDR3 comprising the amino acid sequence ARGDTETDY-GIPYFDL (SEQ ID NO: 53) (DDR1-5), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QSVYSNY (SEQ ID NO: 9), a LC-CDR2 comprising the amino acid sequence ETS, and a LC-CDR3 comprising the amino acid sequence QGGYSEIIENT (SEQ ID NO: 10), and a heavy chain variable region having a HC-CDR1 comprising the amino acid sequence GFSFSSSYY (SEQ ID NO: 54), a HC-CDR2 comprising the amino acid sequence IYASSGST (SEQ ID NO: 55), and a HC-CDR3 comprising the amino acid sequence AIL-GADYRLTRLDL (SEQ ID NO: 56) (DDR1-6), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QSIGSV (SEQ ID NO: 11), a LC-CDR2 comprising the amino acid sequence GVF, and a LC-CDR3 comprising the amino acid sequence QYIPYGSSP (SEQ ID NO: 12), and a heavy chain variable region having a HC-CDR1 comprising the amino acid sequence GFSLNRYY (SEQ ID NO: 57), a HC-CDR2 comprising the amino acid sequence ISYGDTT (SEQ ID NO: 58), and a HC-CDR3 comprising the amino acid sequence ARADTGDNGYLGLQL (SEQ ID NO: 59) (DDR1-9), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QSIGSTY (SEQ ID NO: 13), a LC-CDR2 comprising the amino acid sequence KAS, and a LC-CDR3 comprising the amino acid sequence LYGGFGSSTGDA (SEQ ID NO: 14), and a heavy chain variable region having a HC-CDR1 comprising the amino acid sequence GFSFSSGYY (SEQ ID NO: 60), a HC-CDR2 comprising the amino acid sequence IYTGRTDFT (SEQ ID NO: 61), and a HC-CDR3 comprising the amino acid sequence ARGDYSGGVGGNYWLDL (SEQ ID NO: 62) (DDR1-11), or variants thereof wherein one or more of the LC-CDRs and/or HC-CDRs has one, two, or three amino acid substitutions, additions, deletions or combinations of.

In some embodiments, the isolated antibody or an antigen-binding fragment thereof comprises a light chain variable region having a LC-CDR1 comprising the amino acid sequence QTIYSN (SEQ ID NO: 15), a LC-CDR2 comprising the amino acid sequence QAS, and a LC-CDR3 comprising the amino acid sequence QSYYGADDYT (SEQ ID NO: 16), and a heavy chain variable region having a HC-CDR1 comprising the amino acid sequence GIDL-SNTW (SEQ ID NO: 63), a HC-CDR2 comprising the amino acid sequence ITDSGTT (SEQ ID NO: 64), and a HC-CDR3 comprising the amino acid sequence GRDPGDITSGTNDL (SEQ ID NO: 65) (DDR1-12), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence KSVYNNNA (SEQ ID NO: 17), a LC-CDR2 comprising the amino acid sequence GVS, and a LC-CDR3 comprising the amino acid sequence AGDYSDISDNN (SEQ ID NO: 18), and a heavy chain variable region having a HC-CDR1 comprising the amino acid sequence SGFSLNNY (SEQ ID NO: 66), a HC-CDR2 comprising the amino acid sequence IFNNGDI (SEQ ID NO: 67), and a HC-CDR3 comprising the amino acid sequence ARTGYRTGGWL (SEQ ID NO: 68) (DDR1-13), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSISSY (SEQ ID NO: 19), a LC-CDR2 comprising the amino acid sequence EAS, and a LC-CDR3 comprising the amino acid sequence QNNNGFSGSNFNN (SEQ ID NO: 20), and a heavy chain variable region having a HC-CDR1 comprising the amino acid sequence GIDL-SYYA (SEQ ID NO: 69), a HC-CDR2 comprising the amino acid sequence INGRGDT (SEQ ID NO: 70), and a HC-CDR3 comprising the amino acid sequence ARED-SAIPFIVGNYYGMDL (SEQ ID NO: 71) (DDR1-14), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QTIYSS (SEQ ID NO: 21), a LC-CDR2 comprising the amino acid sequence KAS, and a LC-CDR3 comprising the amino acid sequence QQGSSISNVDKNA (SEQ ID NO: 22), and a heavy chain variable region having a HC-CDR1 comprising the amino acid sequence TFSFNSRYW (SEQ ID NO: 72), a HC-CDR2 comprising the amino acid sequence INNGDIS (SEQ ID NO: 73), and a HC-CDR3 comprising the amino acid sequence AKGGNLAGDCYGL (SEQ ID NO: 74) (DDR1-15), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSIGSY (SEQ ID NO: 23), a LC-CDR2 comprising the amino acid sequence EAS, and a LC-CDR3 comprising the amino acid sequence QNNNGMTVSDFNA (SEQ ID NO: 24), and a heavy chain variable region having a HC-CDR1 comprising the amino acid sequence GFSLNRYA (SEQ ID NO: 75), a HC-CDR2 comprising the amino acid sequence IGSSGST (SEQ ID NO: 76), and a HC-CDR3 comprising the amino acid sequence ARDLDDSYGYTYATGMDIRLDL (SEQ ID NO: 77) (DDR1-17), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QIIDHDH (SEQ ID NO: 25), a LC-CDR2 comprising the amino acid sequence RAS, and a LC-CDR3 comprising the amino acid sequence QNNNGMTVSDFNA (SEQ ID NO: 26), and a heavy chain variable region having a HC-CDR1 comprising the amino acid sequence GFSLSDYA (SEQ ID NO: 78), a HC-CDR2 comprising the amino acid sequence INSRDDT (SEQ ID NO: 79), and a HC-CDR3 comprising the amino acid sequence AREDSSIPFIVGNYYGMDL (SEQ ID NO: 80) (DDR1-20), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSVVDKNW (SEQ ID NO: 27), a LC-CDR2 comprising the amino acid sequence EAS, and a LC-CDR3 comprising the amino acid sequence AGDFESGVSG (SEQ ID NO: 28), and a heavy chain variable region having a HC-CDR1 comprising the amino acid sequence GFSLSSYG (SEQ ID NO: 81), a HC-CDR2 comprising the amino acid sequence IYPSGSI (SEQ ID NO: 82), and a HC-CDR3 comprising the amino acid sequence VRYLTGSSDLHL (SEQ ID NO: 83) (DDR1-21), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence KNIYNNNA (SEQ ID NO: 29), a LC-CDR2 comprising the amino acid sequence GAS, and a LC-CDR3 comprising the amino acid sequence AADYSDISDNN (SEQ ID NO: 30), and a heavy chain variable region having a HC-CDR1 comprising the amino acid sequence GFSLSDYA (SEQ ID NO: 84), a HC-CDR2 comprising the amino acid sequence INNGDIY (SEQ ID NO: 85), and a HC-CDR3 comprising the amino acid sequence ARPGYRTGIWL (SEQ ID NO: 86) (DDR1-22), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSVYSNNY (SEQ ID NO: 31), a LC-CDR2 comprising the amino acid sequence AAS, and a LC-CDR3 comprising the amino acid sequence LGGYNDDAN (SEQ ID NO: 32), and a heavy chain variable region having a HC-CDR1 comprising the amino acid sequence GFDLRSYYY (SEQ ID NO: 87), a HC-CDR2 comprising the amino acid sequence IHGGEGNT (SEQ ID NO: 88), and a HC-CDR3 comprising the amino acid sequence RGGWTNYF (SEQ ID NO: 89) (DDR1-23), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence ESVYSNNH (SEQ ID NO: 33), a LC-CDR2 comprising the amino acid sequence AAS, and a LC-CDR3 comprising the amino acid sequence LGGYNDDAN (SEQ ID NO: 34), and a heavy chain variable region having a HC-CDR1 comprising the amino acid sequence GFDLSSNYY (SEQ ID NO: 90), a HC-CDR2 comprising the amino acid sequence IYSSNTRT (SEQ ID NO: 91), and a HC-CDR3 comprising the amino acid sequence RGGWTNYL (SEQ ID NO: 92) (DDR1-26), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSIDNND (SEQ ID NO: 35), a LC-CDR2 comprising the amino acid sequence RTS, and a LC-CDR3 comprising the amino acid sequence QSYCVNTYGYT (SEQ ID NO: 36), and a heavy chain variable region having a HC-CDR1 comprising the amino acid sequence GFSLSSHD (SEQ ID NO: 93), a HC-CDR2 comprising the amino acid sequence IISSGNT (SEQ ID NO: 94), and a HC-CDR3 comprising the amino acid sequence ARDVYSGASP (SEQ ID NO: 95) (DDR1-28), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence QSISNH (SEQ ID NO: 37), a LC-CDR2 comprising the amino acid sequence RAS, and a LC-CDR3 comprising the amino acid sequence QSYYIINRSNYANS (SEQ ID NO: 38), and a heavy chain variable region having a HC-CDR1 comprising the amino acid sequence TFSFNSRYW (SEQ ID NO: 96), a HC-CDR2 comprising the amino acid sequence INNGDIT (SEQ ID NO: 97), and a HC-CDR3 comprising the amino acid sequence AKGGNLAGDCYGL (SEQ ID NO: 98) (DDR1-29), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence ESINSW (SEQ ID NO: 39), a LC-CDR2 comprising the amino acid sequence DAS, and a LC-CDR3 comprising the amino acid sequence QSYYIINRSNYGNS (SEQ ID NO: 40), and a heavy chain variable region having a HC-CDR1 comprising the amino acid sequence GFSLSSYY (SEQ ID NO: 99), a HC-CDR2 comprising the amino acid sequence ITTAGPL (SEQ ID NO: 100), and a HC-CDR3 comprising the amino acid sequence ARGHAGSIYYSYFDL (SEQ ID NO: 101) (DDR1-32), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence ETISSR (SEQ ID NO: 41), a LC-CDR2 comprising the amino acid sequence QAS, and a LC-CDR3 comprising the amino acid sequence QGCYYGGGSFYDSA (SEQ ID NO: 42), and a heavy chain variable region having a HC-CDR1 comprising the amino acid sequence GFSLSSYD (SEQ ID NO: 102), a HC-CDR2 comprising the amino acid sequence SWNSGFV (SEQ ID NO: 103), and a HC-CDR3 comprising the amino acid sequence ARLGADDIYYFNL (SEQ ID NO: 104) (DDR1-33), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence ETISSR (SEQ ID NO: 41), a LC-CDR2 comprising the amino acid sequence QAS, and a LC-CDR3 comprising the amino acid sequence QGCYYGGGSFYDSA (SEQ ID NO: 42), and a heavy chain variable region having a HC-CDR1 comprising the amino acid sequence GFSLSSYD (SEQ ID NO: 102), a HC-CDR2 comprising the amino acid sequence SWNSGFV (SEQ ID NO: 103), and a HC-CDR3 comprising the amino acid sequence ARLGADDIYYFNL (SEQ ID NO: 104) (DDR1-33), or variants thereof wherein one or more of the LC-CDRs and/or HC-CDRs has one, two, or three amino acid substitutions, additions, deletions, or combinations of.

In some embodiments, the isolated antibody or an antigen-binding fragment thereof comprises a light chain variable region having a LC-CDR1 comprising the amino acid sequence ENLYKDNY (SEQ ID NO: 43), a LC-CDR2 comprising the amino acid sequence GAS, and a LC-CDR3 comprising the amino acid sequence AGGYDSVVD (SEQ ID NO: 44), and a heavy chain variable region having a HC-CDR1 comprising the amino acid sequence GFDLSSYYY (SEQ ID NO:105), a HC-CDR2 comprising the amino acid sequence SIYTSSGAT (SEQ ID NO: 106), and a HC-CDR3 comprising the amino acid sequence RGGWCDFNL (SEQ ID NO: 107) (DDR1-34), or variants thereof wherein one or more of the LC-CDRs and/or HC-CDRs has one, two, or three amino acid substitutions, additions, deletions, or combinations of.

In some embodiments, the LC-CDRs in Table 1 and the HC-CDRs in Table 2 are encoded by the polynucleotides in Table 6 and Table 7, respectively, as further discussed below.

In some embodiments, the LC-CDRs and the HC-CDRs are placed in suitable context of framework region (FR) sequences to form the light chain variable region and the heavy chain variable region that define the binding specificity of the antibody. In some embodiment, the framework region sequences of the antibody with the identified LC-CDRs and the HC-CDRs are the framework sequences of the original antibody isolate. In some embodiments, the LC-CDRs and the HC-CDRs are used with framework region sequences from a different mammalian species, for example a primate. In some embodiments, the framework sequences are humanized or human framework sequences to form the antibody that bind specifically to DDR1 protein. In some embodiments, the light chain variable region comprises four light chain framework regions, e.g., designated as $FR_{LC}1$, $FR_{LC}2$, $FR_{LC}3$, and $FR_{LC}4$ and the LC-CDRs according to the following organization from $NH_2$ to the COOH direction: $FR_{LC}1$-LC-CDR1-$FR_{LC}2$-LC-CDR2-$FR_{LC}3$,-LC-CDR3-$FR_{LC}4$. In some embodiments, the heavy chain variable region comprises four heavy chain framework regions, e.g., designated as $FR_{HC}1$, $FR_{HC}2$, $FR_{HC}3$, and $FR_{HC}4$ and the HC-CDRs according to the following organization from $NH_2$ to the COOH direction: $FR_{HC}1$-HC-CDR1-$FR_{HC}2$-HC-CDR2-$FR_{HC}3$,-HC-CDR3-$FR_{HC}4$. In some embodiments, the framework regions of a parent light chain variable region are replaced with framework regions of human light chain variable regions to form humanized light chain variable regions. In some embodiments, the framework regions of a parent heavy chain variable region is replaced with framework regions of human heavy chain variable regions to form humanized heavy chain variable regions.

In some embodiments, an isolated antibody or an antigen-binding fragment thereof that binds specifically to DDR1 protein comprises a light chain variable region having a light chain variable region amino acid sequence selected from the sequences presented in Table 3, i.e., SEQ ID NOs: 108-128. In some embodiments, an isolated antibody or antigen-binding fragment thereof that binds specifically to DDR1 protein comprises a heavy chain variable region have a heavy chain variable region amino acid sequence selected from the sequences presented in Table 4, i.e., SEQ ID Nos: 129-149.

In some embodiments, the isolated antibody or an antigen-binding fragment thereof comprises a light chain variable region having a light chain variable region amino acid sequence selected from SEQ ID NOs: 108-128, and a heavy chain variable region having a heavy chain variable region amino acid sequence selected from SEQ ID NOs: 129-149. In various embodiments, any one of the variable light chain amino acid sequence corresponding to SEQ ID NOs: 108-128 can be used with any one of the variable heavy chain amino acid sequence corresponding to SEQ ID NOs: 129-149.

In some embodiments, the isolated antibody or an antigen-binding fragment thereof comprises a light chain variable region having a light chain variable region amino acid sequence selected from SEQ ID NOs: 108-128, and a heavy chain variable region having a heavy chain variable region amino acid sequence selected from SEQ ID NOs: 129-149. In various embodiments, any one of the variable light chain amino acid sequence corresponding to SEQ ID NOs: 108-128 can be used with any one of the variable heavy chain amino acid sequence corresponding to SEQ ID NOs: 129-149. In some embodiments, the antibody or antigen-binding fragments thereof that specifically bind to DDR1 protein comprises a light chain variable region and a heavy chain variable region of a clone-paired light chain variable region amino acid sequence and a heavy chain variable region amino acid sequence presented in Table 3 and Table 4, respectively.

TABLE 3

Light chain variable region amino acid sequences of anti-DDR1 antibodies

| mAb Name | Light chain variable amino acid sequences | SEQ ID NO. |
|---|---|---|
| DDR1-1K | ELVLTQTPASVSAAVGGTVTINCQASQNIYSNLAWYQQKPGQPPKLLIYGASNLESGVPSRFKGSGSGTQFTLTISDLECDDAATYYCQSGYYSSSTDIAFGGGTEVVVK | 108 |
| DDR1-3K | ELVLTQTPASVSEPVGGTVTIKCQASQTISSWLSWYQQKPGQPPKLLIYYAFNLASGVPSRFKGSGSGTEFTLTISDLECADAATYYCQQGISSSNVDNVFGGGTEVVVK | 109 |
| DDR1-5K | ELVLTQTPASVSEPVGGTVTIKCQASQTISSWLSWYQQKPGQPPKLLIYYAFNLASGVPSRFKGSGSGTEYTLTISDLECADAATYYCQCTYGSGSSSSYGCAFGGGTELEIK | 110 |
| DDR1-6K | ELVMTQTPSPVSAAVGGTVTISCQSSQSVYSNYLSWYQQKPGQPPKLLIYETSTLASGVPSRFKGSGSGTQFTLTISDVQCDDAATYYCQGGYSEIIENTFGGGTEVEIK | 111 |
| DDR1-9K | ELVMTQTPASVEAAVGGTVTIKCQASQSIGSVLAWYQQKPGQRPKLLISGVFDLASGVPSRFKGSGSGTEFTLTISDLECADAATYYCQYIPYGSSPFGGGTEVVVK | 112 |
| DDR1-11K | ELVMTQTASPVSAAVGGTVTINCQASQSIGSTYLSWYQQKPGQPPKLLIYKASILASGVPSRFSGSGSGTEYTLTISGVQCDDAATYYCLYGGFGSSTGDAFGGGTVLWK | 113 |
| DDR1-12K | ELVLTQTPASVSEPVGGTVTIKCQASQTIYSNLAWYQQKPGQRPKLLIYQASKLASGVPSRFKGSGSGTEYTLTISDLECADAATYYCQSYYGADDYTFGGGTEVVVK | 114 |
| DDR1-13K | ELVMTQTPSPVSAAVGGTVSISCQSSKSVYNNNALSWFQQKPGQPPKVLIYGVSTLDSGVSSRFSGSGYGTEFTLTISDVQCDDAATYYCAGDYSDISDNNFGGGTELEIK | 115 |
| DDR1-14K | ELDMTQTPASVSEPVGGTVTIKCQASQSISSYLAWYQQKPGQPPKRLIFEASTLASGVPSRFSGSGSGTDFTLTISDLECADAATYYCQNNNGFSGSNFNNFGGGTEVEIK | 116 |
| DDR1-15K | ELVMTQTPASVEVAVGGTVTIKCQASQTIYSSLAWYQQKPGQPPKLLIYKASTLASGVPSRFSGSGSGTQFTLTISGVQCDDAATYYCQQGSSISNVDKNAFGGGTEVEIK | 117 |
| DDR1-17K | ELVMTQTPASVSEPVGGTVTIKCQASQSIGSYLSWYQQKAGQPPKRLIYEASTLASGVPSRFSGSGSGTDFTLTISDLECADVATYYCQNNNGMTVSDFNAFGGGTEVEIK | 118 |
| DDR1-20K | ELDLTQTPASVSAAVGGTVTINCQSSQIIDHDHLSWYQQKPGQRPKLLIYRASTLTSGVPSRFKGSGSGTDFTLTISDLECADVATYYCQNNNGMTVSDFNAFGGGTEVEIK | 119 |
| DDR1-21K | ELVLTQTPSSTSAAVGGTVTISCQSSQSVVDKNWLAWYQQKPGQPPKLLIYEASKLASGVPPRFSGSGSGTQFTLTISGVQCDDAATYYCAGDFESGVSGFGGGTEVEIK | 120 |
| DDR1-22K | ELVLTQTPSPVSAAVGGTVTINCQSSKNIYNNNALSWFQQKPGQPPKLLIYGASTLASGVPSRFKGSGSGTQFTLTISDVQCDDAATYYCAADYSDISDNNFGGGTEVVVK | 121 |
| DDR1-23K | ELVLTQTPSSVSAAVGGTVTISCQSSQSVYSNNYLAWYQQKPGQPPKLLIYAASTLASGVPSRFKGSGSGTQFTLTISGVQCDDAAVYYCLGGYNDDANFGGGTEVEIK | 122 |
| DDR1-26K | ELDLTQTPSSVSAAVGGTVTISCQSSESVYSNNHLAWYQQKPGQPPKLLIYAASTLASGVPSRFSGSGSGTQFTLTISGVQCDDAAVYYCLGGYNDDANFGGGTEVVVK | 123 |
| DDR1-28K | ELDLTQTPASVEAAVGGTVTIKCQASQSIDNNDLAWYQQKPGQPPNLLISRTSTLASGVSSRFKGSGSGTEFTLTISDLECADAATYYCQSYCVNTYGYTFGGGTEVVVK | 124 |
| DDR1-29K | ELVMTQTPASVEAAVGGTVTIKCQASQSISNHLGWYQQKPGQPPKLLIYRASTLESGVSSRFKGSGSGSEFTLTISDLECADAATYYCQSYYIINRSNYANSFGGGTEVEIK | 125 |
| DDR1-32K | ELVMTQTPASVEAAVGGTVTIKCQASESINSWLAWYQQKPGQRPKLLIYDASKLASGVPSRFKGSGSGTQFTLTISDLECADAATYYCQSYYIINRSNYGNSFGGGTEVEIK | 126 |

TABLE 3-continued

Light chain variable region amino acid sequences of anti-DDR1 antibodies

| mAb Name | Light chain variable amino acid sequences | SEQ ID NO. |
|---|---|---|
| DDR1-33K | ELVMTQTPASVEAAVGGTVTIKCQASETISSRLAWYQQKPGQPPKLLIYQASKL PSGVPSRFKGTGSGTEYTLTISDLECADAATYYCQGCYYGGGSFYDSAFGGGTE VVVK | 127 |
| DDR1-34K | ELDLTQTPASVSAAVGGTVTISCQSSENLYKDNYLAWYQQKPGQPPKLLIYGAS NLASGVPSRFKGSGSGTQFTLTISDLECDDAATYYCAGGYDSVVDFGGGTEVVV K | 128 |

TABLE 4

Heavy chain variable region amino acid sequences of anti-DDR1 antibodies

| mAb Name | Heavy chain variable amino acid sequences | SEQ ID NO: |
|---|---|---|
| DDR1-1H | QSVEESGGRLVTPGTPLTLTCTVSGFSLSRYAMTWVRQAPGKGLEWIGIIGSSG LTYFATWAKGRFTISKTSTTVDLKITSPTTEDTATYFCARGMWYDDSDDYEDYF NLWGPGTLVTISS | 129 |
| DDR1-3H | QSVKESGGRLVTPGTPLTLTCTVSGIDLSSYAMSWVRQAPGKGLEWIGTINIGG GTWDATWARGRFTISRTSTTVDLKITSPTIGDTATYFCARDVDAHTLTYFTLWG PGTLVTISS | 130 |
| DDR1-5H | QSVKESGGRLVTPGTPLTLTCTVSGFTLSNNAISWVRQAPGKGLEWIGIIYASG RTYYATWAKGRFTISKTSTTVDLKMTSPTTEDTATYFCARGDTETDYGIPYFDL WGPGTLVTISS | 131 |
| DDR1-6H | SQSLKESGGDLVKPGASRTLTCIAPGFSFSSSYYMCWVRQAPGKGLEWIACIYA SSGSTYYASWAKGRFTISKTSSTTVTLQMTTLTAADTATYFCAAILGADYRLTR LDLWGQGTLVTVSS | 132 |
| DDR1-9H | QSLEESGGRLVTPGTPLTLTCTASGFSLNRYYMLWVRQAPGEGLEWIGTISYGD TTYYASWAKGRFTISKTSTTVDLKMTSPTTEDTATYFCARADTGDNGYLGLQLW GPGTLVTVSS | 133 |
| DDR1-11H | QSLEESGGDLVKPGASLTLTCTASGFSFSSGYYMCWVRQAPGKGLEWIACIYTG RTDFTDYASWAKGRFTISKTSSTTVTLQLTTLTAADTATYFCARGDYSGGVGGN YWLDLWGQGTLVTISS | 134 |
| DDR1-12H | QSLEESGGRLVTPGTPLTLTCTVSGIDLSNTWMNWVRQAPGKGLEWIGVITDSG TTYYANWAKGRFTISRTSTTVDLKMPSLTTEDTATYFCGRDPGDITSGTNDLWG PGTLVTISS | 135 |
| DDR1-13H | EQSVEESGGRLVTPGGSLTLTCTASGFSLNNYAIIWVRQAPGKGLEYIGIFNNG DIYYANWAKGRFTISKTSTTVGLKIVSPTTEDTATYFCARTGYRTGGWLWGPGT LVTISS | 136 |
| DDR1-14H | QSVKESGGRLVTPGTPLTLTCTVSGIDLSYYAMSWVRQAPGKGLEYIGIINGRG DTGYATWAKGRFTISKTSTTVDLRITSPTIEDTATYFCAREDSAIPFIVGNYYG MDLWGPGTLVTVSS | 137 |
| DDR1-15H | SQSLEESGGDLVKPGASLTLTCTASTFSFNSRYWTCWVRQAPGKGLEWIGCINN GDISTYYASWATGRFTISKSSSTTVTLHMTSLTAADTATYFCAKGGNLAGDCYG LWGPGTLVTISS | 138 |
| DDR1-17H | SSVEESGGRLVAPGTPLTLTCTVSGFSLNRYAMSWVRQAPGKGLEWIGIIGSSG STYYASWAKGRFTISKTSTTVDLKITSPTTEDTATYFCARDLDDSYGYTYATGM DIRLDLWGQGTLVTVSS | 139 |
| DDR1-20H | QSVKESGGGLFKPMDTLTLTCTVSGFSLSDYAMSWVRQAPGKGLEWIGIINSRD DTGYASWAKGRFTISKTSTTVDLRITSPTTEDTATYFCAREDSSIPFIVGNYY GMDLWGPGTLVTVSS | 140 |
| DDR1-21H | QSLEESGGRLVTPGTPLTLTCTVSGFSLSSYGVHWVRQAPGKGLDWIGKIYPSG SIYYSSWAKGRFTISKTSTTVDLKMTSLTTEDTATYFCVRYLTGSSDLHLWGPG TLVTISS | 141 |
| DDR1-22H | QSVKESGGRLVTPGGSLTLTCTVSGFSLSDYAMIWVRQAPGKGLEYIGIINNGD IYYATWAKGRFTISETSSTTMGLNIISPTTEDTATYFCARPGYRTGIWLWGPGT LVTISS | 142 |

TABLE 4-continued

Heavy chain variable region amino acid sequences of anti-DDR1 antibodies

| mAb Name | Heavy chain variable amino acid sequences | SEQ ID NO: |
|---|---|---|
| DDR1-23H | SQSVKESGGDLVKPGASLTLTCKASGFDLRSYYYMCWVRQAPGKGLEWIACIHG GEGNTYYASWAKGRFTISKTSSTAVTLQMTSLTAADTATYFCARGGWTNYFWGP GTLVTVSS | 143 |
| DDR1-26H | EQSLKESGGDLVKPGASLTLTCTASGFDLSSNYYMCWVRQAPGKGPEWIACIYS SNTRTWYARWAKGRFTISKTSSTAVTLQMTSLTAADTATYFCARGGWTNYLWGP GTLVTISS | 144 |
| DDR1-28H | QSVEESGGRLVTPGTPLTLTCTVSGFSLSSHDMIWVRQAAGKGLEWIGLIISSG NTWYASWAKGRFTISKTSTTVDLKMTSLTTEDTATYFCARDVYSGASPWGPGTL VTISS | 145 |
| DDR1-29H | QSVKSGGGLVKPGASLTLTCKASTFSFNSRYWTCWVRQAPGKGLEWIGCINNGD ITTYYTNWATGRFTISKSSSTTVTLQMTSLTAADTATYFCAKGGNLAGDCYGLW GPGTLVTISG | 146 |
| DDR1-32H | QSLEESGGRLVTPGTPLTLTCTASGFSLSSYYMSWVRQAPGEGLEWIGTITTAG PLYYATWAKGRFTISKTSTTVDLKMTGPTTEDTATYFCARGHAGSIYYSYFDLW GPGTLVTVSS | 147 |
| DDR1-33H | QSVEESGGRLVTPGGSLTLTCTVSGFSLSSYDMSWVRQAPGKGLEWIGISWNSG FVDYASWAKGRFSISKTSTTVDLKITSPTTEDTATYFCARLGADDIYYFNLWGP GTLVTISS | 148 |
| DDR1-34H | QSVKESGGGLVKPEGSLTLTCKASGFDLSSYYYMCWVRQAPGKGLEWIACIYTS SGATWYANWAKGRFTISKTSSTTVTLQMTALTAADTATYFCARGGWCDFNLWGP GTLVTISS | 149 |

In some embodiments, the antibody or antigen-binding fragments thereof comprises a light chain variable region having an amino acid sequence of SEQ ID NO: 108 (DDR1-1K) and a heavy chain variable region having an amino acid sequence of SEQ ID NO: 129 (DDR1-1H).

In some embodiments, the antibody or antigen-binding fragments thereof comprises a light chain variable region having an amino acid sequence of SEQ ID NO: 109 (DDR1-3K) and a heavy chain variable region having an amino acid sequence of SEQ ID NO: 130 (DDR1-3H).

In some embodiments, the antibody or antigen-binding fragments thereof comprises a light chain variable region having an amino acid sequence of SEQ ID NO: 110 (DDR1-5K) and a heavy chain variable region having an amino acid sequence of SEQ ID NO: 131 (DDR1-5H).

In some embodiments, the antibody or antigen-binding fragments thereof comprises a light chain variable region having an amino acid sequence of SEQ ID NO: 111 (DDR1-6K) and a heavy chain variable region having an amino acid sequence of SEQ ID NO: 132 (DDR1-6H).

In some embodiments, the antibody or antigen-binding fragments thereof comprises a light chain variable region having an amino acid sequence of SEQ ID NO: 112 (DDR1-9K) and a heavy chain variable region having an amino acid sequence of SEQ ID NO: 133 (DDR1-9H).

In some embodiments, the antibody or antigen-binding fragments thereof comprises a light chain variable region having an amino acid sequence of SEQ ID NO: 113 (DDR1-11K) and a heavy chain variable region having an amino acid sequence of SEQ ID NO: 134 (DDR1-11H).

In some embodiments, the antibody or antigen-binding fragments thereof comprises a light chain variable region having an amino acid sequence of SEQ ID NO: 114 (DDR1-12K) and a heavy chain variable region having an amino acid sequence of SEQ ID NO: 135 (DDR1-12H).

In some embodiments, the antibody or antigen-binding fragments thereof comprises a light chain variable region having an amino acid sequence of SEQ ID NO: 115 (DDR1-13K) and a heavy chain variable region having an amino acid sequence of SEQ ID NO: 136 (DDR1-13H).

In some embodiments, the antibody or antigen-binding fragments thereof comprises a light chain variable region having an amino acid sequence of SEQ ID NO: 116 (DDR1-14K) and a heavy chain variable region having an amino acid sequence of SEQ ID NO: 137 (DDR1-14H).

In some embodiments, the antibody or antigen-binding fragments thereof comprises a light chain variable region having an amino acid sequence of SEQ ID NO: 117 (DDR1-15K) and a heavy chain variable region having an amino acid sequence of SEQ ID NO: 138 (DDR1-15H).

In some embodiments, the antibody or antigen-binding fragments thereof comprises a light chain variable region having an amino acid sequence of SEQ ID NO: 118 (DDR1-17K) and a heavy chain variable region having an amino acid sequence of SEQ ID NO: 139 (DDR1-17H).

In some embodiments, the antibody or antigen-binding fragments thereof comprises a light chain variable region having an amino acid sequence of SEQ ID NO: 119 (DDR1-20K) and a heavy chain variable region having an amino acid sequence of SEQ ID NO: 140 (DDR1-20H).

In some embodiments, the antibody or antigen-binding fragments thereof comprises a light chain variable region having an amino acid sequence of SEQ ID NO: 120 (DDR1-21K) and a heavy chain variable region having an amino acid sequence of SEQ ID NO: 141 (DDR1-21H).

In some embodiments, the antibody or antigen-binding fragments thereof comprises a light chain variable region having an amino acid sequence of SEQ ID NO: 121 (DDR1-22K) and a heavy chain variable region having an amino acid sequence of SEQ ID NO: 142 (DDR1-22H).

In some embodiments, the antibody or antigen-binding fragments thereof comprises a light chain variable region having an amino acid sequence of SEQ ID NO: 122 (DDR1-

23K) and a heavy chain variable region having an amino acid sequence of SEQ ID NO: 143 (DDR1-23H).

In some embodiments, the antibody or antigen-binding fragments thereof comprises a light chain variable region having an amino acid sequence of SEQ ID NO: 123 (DDR1-26K) and a heavy chain variable region having an amino acid sequence of SEQ ID NO: 144 (DDR1-26H).

In some embodiments, the antibody or antigen-binding fragments thereof comprises a light chain variable region having an amino acid sequence of SEQ ID NO: 124 (DDR1-28K) and a heavy chain variable region having an amino acid sequence of SEQ ID NO: 145 (DDR1-28H).

In some embodiments, the antibody or antigen-binding fragments thereof comprises a light chain variable region having an amino acid sequence of SEQ ID NO: 125 (DDR1-29K) and a heavy chain variable region having an amino acid sequence of SEQ ID NO: 146 (DDR1-29H).

In some embodiments, the antibody or antigen-binding fragments thereof comprises a light chain variable region having an amino acid sequence of SEQ ID NO: 126 (DDR1-32K) and a heavy chain variable region having an amino acid sequence of SEQ ID NO: 147 (DDR1-32H).

In some embodiments, the antibody or antigen-binding fragments thereof comprises a light chain variable region having an amino acid sequence of SEQ ID NO: 127 (DDR1-33K) and a heavy chain variable region having an amino acid sequence of SEQ ID NO: 148 (DDR1-33H).

In some embodiments, the antibody or antigen-binding fragments thereof comprises a light chain variable region having an amino acid sequence of SEQ ID NO: 128 (DDR1-34K) and a heavy chain variable region having an amino acid sequence of SEQ ID NO: 149 (DDR1-34H).

In some embodiments, the antibody or antigen-binding fragments thereof is a humanized antibody of parent antibody DDR1-9, as described in the Examples. The light chain variable region and the heavy chain variable region are provided in Table 5. Polynucleotide sequences encoding the humanized variable regions is provided in Table 10 below.

TABLE 5

Humanized DDR1-9hu antibody amino acid sequences

| mAb | Amino Acid Sequence | SEQ ID NO. |
| --- | --- | --- |
| DDR1-9hu_Lv1 | DIQMTQSPSSVSASVGDRVTITCQASQSIGSVLAWYQQKPGKAPKLLISGVFDLASGVPSRFSGSGSGTDFTLTISSLQPEDFATYYCQYIPYGSSPFGGGTKVEIK | 150 |
| DDR1-9hu_Lv2 | DIQMTQSPSSVSASVGDRVTITCRASQSIGSVLAWYQQKPGKAPKLLIYGVFSLQSGVPSRFSGSGSGTDFTLTISSLQPEDFATYYCQYIPYGSSPFGGGTKVEIK | 151 |
| DDR1-9hu_Hv | QVQLVESGGRVVQPGRSLRLSCTASGFSLNRYYMLWVRQAPGKGLEWIGTISYGDTTYYASWAKGRFTISRDNSKNTLYLQMNSLRAEDTAVYYCARADTGDNGYLGLQLWGQGTLVTSS | 152 |

In some embodiments, the antibody or antigen-binding fragments thereof comprises a light chain variable region having a LC-CDR1, LC-CDR2, and LC-CDR3 in the light chain variable region amino acid sequence of SEQ ID NO: 150 (DDR1-9hu_Lv1). In some embodiments, the antibody or antigen-binding fragments thereof comprises a light chain variable region having a LC-CDR1, LC-CDR2, and LC-CDR3 in the light chain variable region amino acid sequence of SEQ ID NO: 151 (DDR1-9hu_Lc2). In some embodiments, the antibody or antigen-binding fragments thereof comprises a heavy chain variable region having a HC-CDR1, HC-CDR2, and HC-CDR3 in the heavy chain variable region amino acid sequence of SEQ ID NO: 151 (DDR1-9hu_Lc2). In some embodiments, the antibody or antigen-binding fragments thereof comprises a light chain variable region having a LC-CDR1, LC-CDR2, and LC-CDR3 in the light chain variable region amino acid sequence of SEQ ID NO: 150 (DDR1-9hu_Lv1) or SEQ ID NO: 151 (DDR1-9hu_Lc2), and a heavy chain variable region having a HC-CDR1, HC-CDR2, and HC-CDR3 in the heavy chain variable region amino acid sequence of SEQ ID NO: 151 (DDR1-9hu_Lc2).

In some embodiments, the antibody or antigen-binding fragments thereof comprises a light chain variable region having an amino acid sequence of SEQ ID NO: 150 (DDR1-9hu_Lv1) or SEQ ID NO: 151 (DDR1-9hu_Lc2), and a heavy chain variable region having an amino acid sequence of SEQ ID NO: 152 (DDR1-9hu_Hv). In some embodiments, the antibody or antigen-binding fragments thereof comprises a light chain variable region having an amino acid sequence of SEQ ID NO: 150 (DDR1-9hu_Lv1), and a heavy chain variable region having an amino acid sequence of SEQ ID NO: 152 (DDR1-9hu_Hv). In some embodiments, the antibody or antigen-binding fragments thereof comprises a light chain variable region having an amino acid sequence of SEQ ID NO: 151 (DDR1-9hu_Lc2), and a heavy chain variable region having an amino acid sequence of SEQ ID NO: 152 (DDR1-9hu_Hv).

In some embodiments, the antibody or antigen-binding fragments thereof is a variant, wherein the light chain variable region sequence and/or the heavy chain variable region sequence of the variant has 1, 2, 3, 4, 5, 6, 7, 8, 9, 10 or more amino acid substitutions, additions, deletions, or combinations of compared to the parent light chain variable region sequence or the heavy chain variable region sequence, wherein the variant retains the binding specificity to the DDR1 protein and/or other functional properties. In some embodiments, the light chain variable region sequence and/or the heavy chain variable region sequence of the variant has 1, 2, 3, 4, 5, 6, 7, 8, 9, 10 or more conservative or non-conservative amino acid substitutions. In some embodiments, the variant has 1, 2 or 3 amino acid substitutions, additions, deletions, or combinations of in one or more of the LC-CDRs and/or HC-CDRs of the variant light chain variable region or the variant heavy chain variable region as compared to the parent LC-CDRs or HC-CDRs. In some embodiments, the variant antibody or antigen-binding fragment thereof has 1, 2, 3, 4, 5, 6, 7, 8, 9, or 10 amino acid substitutions, additions, deletions, or combinations of, in the framework region sequences of the light chain variable region and/or heavy chain variable region compared to the parent light chain variable region sequence or the heavy chain variable region sequence. In some embodiments, the antibody or antigen-binding fragment thereof has 1, 2, 3, 4, 5, 6, 7, 8, 9, 10 or more conservative or non-conservative amino acid substitutions in the framework region sequences of the light chain variable region and/or heavy chain variable region. The foregoing variations apply to each of the light chain variable regions in Table 3 and Table 5, and each of the heavy chain variable regions in Table 4 and Table 5.

In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to any one of the light chain variable region amino acid sequences selected from SEQ ID NOs: 108-128 in Table 3 and SEQ ID NOs: 150 and 151 in Table 5: In some embodiments the antibody or antigen-binding fragments thereof comprises a heavy chain variable region amino acid sequence having 80%, 85%, 90%, 91%, 92%, 93%, 94%, 95%, 96%, 97%, 98% or 99% sequence identity to any one of the heavy chain variable region amino acid sequence selected from SEQ ID NOs: 129-149 in Table 4 or SEQ ID NO: 152 in Table 5. In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to any one of the light chain variable region amino acid sequences selected from SEQ ID NOs: 108-128 in Table 3 and SEQ ID NOs: 150 and 151 in Table 5, and a heavy chain variable region amino acid sequence having 80%, 85%, 90%, 91%, 92%, 93%, 94%, 95%, 96%, 97%, 98% or 99% sequence identity to any one of the heavy chain variable region amino acid sequence selected from SEQ ID NOs: 129-149 in Table 4 and SEQ ID NO: 152 in Table 5.

In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to the light chain variable region amino acid sequence of SEQ ID NO: 112. In some embodiments, the antibody or antigen-binding fragments thereof comprises a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 133. In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to the light chain variable region amino acid sequence of SEQ ID NO: 112, and a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 133.

In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to the light chain variable region amino acid sequence of SEQ ID NO: 127. In some embodiments, the antibody or antigen-binding fragments thereof comprises a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 148. In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to the light chain variable region amino acid sequence of SEQ ID NO: 127, and a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 148.

In some embodiments, the antibody or antigen-binding fragments thereof comprises a light chain variable region amino acid sequence having 80%, 85%, 90%, 91%, 92%, 93%, 94%, 95%, 96%, 97%, 98% or 99% identity to the light chain variable region amino acid sequence of SEQ ID NO: 150 or 151. In some embodiments, the antibody or antigen-binding fragments thereof comprises a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 152. In some embodiments, the antibody or antigen-binding fragments thereof comprises a light chain variable region amino acid sequence having 80%, 85%, 90%, 91%, 92%, 93%, 94%, 95%, 96%, 97%, 98% or 99% sequence identity to the light chain variable region amino acid sequence of SEQ ID NO: 150 or 151, and a heavy chain variable region amino acid sequence having 80%, 85%, 90%, 91%, 92%, 93%, 94%, 95%, 96%, 97%, 98% or 99% sequence identity to the heavy chain variable region amino acid sequence of SEQ ID NO: 152.

In some embodiments, the light chain variable region comprising the LC-CDR1, LC-CDR2, and LC-CDR3 described herein (e.g., Table 1) or the specified light chain variable regions (e.g., Table 3 and Table 5), and present in the antibody or antigen binding fragment thereof has appended or linked to it all or portion of a light chain constant region to form a light chain of the antibody or antigen-binding fragment thereof. In some embodiments, the light chain constant region is of the species from which an antibody was isolated, for example, a rabbit light chain constant region. In some embodiments, the light chain constant region that is appended or linked to the light chain variable region is a kappa (κ) or lambda (λ) constant region, as described herein. In some embodiments, the light chain constant region, when present, can be any one of the known λ subtypes, e.g., $\lambda_1$, $\lambda_2$, $\lambda_3$, or $\lambda_4$. In some embodiments, the light chain constant region is a lambda light chain constant region sequence. In some embodiments, the light chain constant region is a kappa light chain constant region sequence. In a preferred embodiment, the lambda or kappa constant region is that of a human lambda or human kappa constant region sequence.

In some embodiments, each of the heavy chain variable regions comprising the HC-CDR1, HC-CDR2, and HC-CDR3 described herein (e.g., Table 2) or each of the specified heavy chain variable regions described herein (e.g., Table 4 and Table 5), and present in the antibody or antigen binding fragment thereof, has appended or linked to it all or portion of a heavy chain constant region to form a heavy chain of the antibody or antigen-binding fragment thereof. In some embodiments, the heavy chain constant domain is that a rodent, primate, or other mammalian heavy chain constant region. In some embodiments, the heavy chain constant region linked or appended to the heavy chain variable region is a human heavy chain constant region. In some embodiments, the human heavy chain constant region comprises at least one or all of the following: a human CH1, human Hinge, human CH2 and human CH3 domain. In some embodiments, the heavy chain constant region comprises an Fc portion, where the Fc portion is a human IgG1, IgG2, IgG3, IgG4 or IgM isotype. In some embodiments, the human heavy chain constant region can have one or more mutations to alter the properties of the Fc constant region, such as stability, glycosylation, and Fc receptor binding, as further discussed below. In some embodiments, the in some embodiments, an anti-DDR1 antibody may be modified to reduce at least one constant region-mediated biological effector function relative to the unmodified antibody, e.g., reduced binding to one or more of the Fc receptors (FcγR) such as FcγRI, FcγRIIA, FcγRIIB, FcγRIIIA and/or FcγRIIIB. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

In some embodiments, the antibody or antigen-binding fragment thereof described herein include antibodies that have been modified to acquire or improve at least one constant region-mediated biological effector function relative to an unmodified antibody, e.g., to enhance FcγR interactions (See, e.g., US Publication No. 2006/0134709). For example, an antibody of the disclosure can have a constant region that binds FcγRI, FcγRIIA, FcγRIIB, FcγRIIIA and/or FcγRIIIB with greater affinity than the corresponding wild type constant region.

Thus, antibodies of the present disclosure may have alterations in biological activity that result in increased or decreased opsonization, phagocytosis, or ADCC. For example, modifications in antibodies that reduce ADCC activity are described in U.S. Pat. No. 5,834,597. An exemplary ADCC lowering variant corresponds to "mutant 3" (also known as "MY") in U.S. Pat. No. 5,834,597 in which residues 234 and 237 (using EU numbering) are substituted with alanines. A mutant 3 (also known as "M3") variation may be used in a number of antibody isotypes, e.g., $IgG_2$. Additional substitutions that can modify FcγR binding and/or ADCC effector function include the K322A substitution or the L234A and L235A double substitution in the Fc region (see, e.g., Hezareh, et al. J. Virol., 2001, 75 (24): 12161-12168. In some embodiments, the antibodies of the disclosure have low levels of, or lack, fucose. Antibodies lacking fucose have been correlated with enhanced ADCC activity, especially at low doses of antibody (see, e.g., Shields et al., J. Biol. Chem., 2002, 277:26733-26740; Shinkawa et al., J. Biol. Chem., 2003, 278:3466-73. Methods of preparing fucose-less antibodies include growth in rat myeloma YB2/0.

In some embodiments, the antibodies of the disclosure can comprise modified (or variant) CH2 domains or entire Fc domains that include amino acid substitutions that increase binding to FcγRIIB and/or reduced binding to FcγRIIIA as compared to the binding of a corresponding wild-type CH2 or Fc region. Variant CH2 or variant Fc domains have been described in U.S. Patent Publication 2014/0377253, which is incorporated herein in its entirety. A variant CH2 or variant Fc domain typically includes one or more substitutions at position 263, position 266, position 273, and position 305, wherein the numbering of the residues in the Fc domain is that of the EU index as in Kabat. In some embodiments, the anti-DDR1 antibodies comprise one or more substitutions selected from V263L, V266L, V273C, V273E, V273F, V273L, V273M, V273S, V273Y, V305K, and V305W, relative to the wild-type CH2 domain. In specific embodiments, the one or more substitutions of the CH2 domain are selected from V263L, V273E, V273F, V273M, V273S, and V273Y, relative to the CH2 domain of a human $IgG_1$. For example, the one or more substitutions of a CH2 domain can be V273E. In another specific embodiment, the anti-DDR1 antibody of the disclosure comprises a variant CH2 domain comprising the amino acid substitution V263L. Other examples of variant CH2 or variant Fc domains that can afford increased binding to FcγRIIB and/or reduced binding to FcγRIIIA as compared to the binding of a corresponding wild-type CH2 or Fc region include those found in Vonderheide, et al. Clin. Cancer Res., 19(5), 1035-1043 (2013), such as S267E or S267E/L328F in human IgG$_1$.

In some embodiments, the anti-DDR1 antibodies include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-DDR1 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Specific combinations of suitable amino acid substitutions are identified in Table 1 of U.S. Pat. No. 7,217,797, which is incorporated herein by reference. Such mutations increase binding to FcRn, which protects the antibody from degradation and increases its half-life.

In some embodiments, the antibody or antigen binding fragment thereof is a single chain antibody comprising the LC-CDRs and HC-CDRs disclosed herein. In some embodiments, the antibody or antigen binding fragment thereof is a single chain antibody comprising the light chain variable region and the heavy chain variable region disclosed herein. In particular embodiments, the single chain antibody comprises the clone-paired light chain variable region and the heavy chain variable region disclosed herein.

In some embodiments, the antigen-binding fragment comprising the LC-CDRs and HC-CDRs, or the light chain variable region and the heavy chain variable region of the present disclosure is a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, or a bivalent domain antibody, as described herein.

In some embodiment, the antibody or antigen-binding fragment thereof is a chimeric antibody comprising the LC-CDRs and HC-CDRs, or the light chain variable region and heavy chain variable region disclosed herein, wherein the Fc heavy chain constant region is from a different species than the origin of the LC-CDRs and HC-CDRs, or the light chain variable region and heavy chain variable region disclosed herein. In some embodiments, the chimeric antibody comprises a human Fc region.

In some embodiments, the antibody or antigen-binding fragment thereof is a humanized antibody or an antigen-binding fragment thereof, wherein the framework regions of the light chain variable region comprising the LC-CDRs and the heavy chain variable region comprising the HC-CDRs of the present disclosure are replaced with human framework sequences. In some embodiments, the antibody or antigen-binding fragment thereof is a humanized antibody or an antigen-binding fragment thereof, wherein the framework regions of a light chain variable region selected from SEQ ID NOs: 108-128 and SEQ ID NOs: 150 and 151 are replaced with human light chain variable region framework sequences. In some embodiments, the antibody or antigen-binding fragment thereof is a humanized antibody or an antigen-binding fragment thereof, wherein the framework regions of a heavy chain variable region selected from SEQ ID NOs: 129-140 and SEQ ID NO: 152 are replaced with human heavy chain variable region framework sequences. In some embodiments, the antibody or antigen-binding fragment thereof is a humanized antibody or an antigen-binding fragment thereof, wherein the framework regions of a light chain variable region selected from SEQ ID NOs: 108-128 and SEQ ID NOs: 150 and 151 are replaced with human light chain variable region framework sequences, and the framework regions of a heavy chain variable region selected from SEQ ID NOs: 129-140 and SEQ ID NO: 152 are replaced with human heavy chain variable region framework sequences.

C. Exemplary Epitopes and Competing Antigen Binding Proteins

In another aspect, the present disclosure provides epitopes to which anti-DDR1 antibodies bind. In some embodiments, epitopes that are bound by the antibodies described herein are useful. In certain embodiments, an epitope provided herein can be utilized to isolate antibodies or antigen binding proteins that bind to DDR1. In certain embodiments, an epitope provided herein can be utilized to generate antibodies or antigen binding proteins which bind to DDR1. In certain embodiments, an epitope or a sequence comprising an epitope provided herein can be utilized as an immunogen to generate antibodies or antigen binding proteins that bind to DDR1. In certain embodiments, an epitope described herein or a sequence comprising an epitope described herein can be utilized to interfere with biological activity of DDR1.

In some embodiments, antibodies or antigen-binding fragments thereof that bind to any of the epitopes are particularly useful. In some embodiments, an epitope provided herein, when bound by an antibody, interferes with or inhibits the biological activity of DDR1. In some embodiments, an epitope provided herein, when bound by an antibody, block the interaction between DDR1 and its binding partners.

In some embodiments, the domain(s)/region(s) containing residues that are in contact with or are buried by an antibody can be identified by mutating specific residues in DDR1 and determining whether the antibody can bind the mutated DDR1 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In another aspect, the present disclosure provides antigen-binding proteins that compete with one of the exemplified antibodies or antigen-binding fragment binding to the epitope described herein for specific binding to DDR1. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the light and heavy chain variable region CDRs presented in Table 1 and Table 2, respectively, light and heavy chain variable regions as shown in Table 3 and Table 4, and light and heavy chain coding regions as shown in Table 8 and Table 9.

III. POLYNUCLEOTIDES, VECTORS, AND HOST CELLS

In another aspect, the present disclosure provides polynucleotides that encode an antibody and antigen-binding fragments thereof that specifically bind DDR1 protein, as disclosed herein; vectors including expression vectors comprising the polynucleotides; and host cells comprising the polynucleotides, for example for expression of the antibody or antigen-binding fragments thereof.

In particular, the polynucleotides are isolated polynucleotides. The polynucleotides may be operatively linked to one or more heterologous control sequences that control gene expression to create a recombinant polynucleotide capable of expressing the polypeptide of interest. Expression constructs containing a heterologous polynucleotide encoding the relevant polypeptide or protein can be introduced into appropriate host cells to express the corresponding polypeptide.

As should be apparent to the skilled artisan, the knowledge of a protein sequence provides a description of all the polynucleotides capable of encoding the subject protein sequence because of the knowledge of the all possible codons corresponding to the various amino acids. An extremely large number of nucleic acids encoding the forgoing polypeptides can be made by selecting combinations based on the possible codon choices, and all such variations are to be considered specifically disclosed for any and all of polypeptides described herein.

In some embodiments, the polynucleotide encodes the LC-CDR1, LC-CDR2, and/or LC-CDR3 of the light chain variable region disclosed herein, including the LC-CDRs described in Table 1. In some embodiments, the polynucleotide encodes a variant of the LC-CDR1, LC-CDR2, and/or LC-CDR3 of the light chain variable region disclosed herein, including the LC-CDRs described in Table 1, wherein one or more of the LC-CDRs of the variant has one, two, or three amino acid substitutions, additions, deletions, or combinations of, as compared to the parent LC-CDRs.

In some embodiments, the polynucleotide encodes the HC-CDR1, HC-CDR2, and/or HC-CDR3 of the heavy chain variable region disclosed herein, including the HC-CDRs described in Table 2. In some embodiments, the polynucleotide encodes a variant of the HC-CDR1, HC-CDR2, and/or HC-CDR3 of the heavy chain variable region disclosed herein, including the LC-CDRs described in Table 2, wherein one or more of the HC-CDRs of the variant has one, two, or three amino acid substitutions, additions, deletions, or combinations of, as compared to the parent HC-CDRs.

In some embodiments, the polynucleotide encoding the LC-CDR1, LC-CDR2, and/or LC-CDR3 of the light chain variable region are selected from the polynucleotides presented in Table 6.

TABLE 6

DNA sequences encoding CDRs of light chain variable regions of DDR1 antibodies

| mAb Name | CDR1 | SEQ ID NO. | CDR2 | CDR3 | SEQ ID NO. |
|---|---|---|---|---|---|
| DDR1-1 | CAGAACATTTAC AGCAAT | 153 | GGTGCATCC | CAAAGTGGTTATTAT AGTAGTAGTACTGAT ATTGCT | 154 |
| DDR1-3 | CAGACCATTAGC AGTTGG | 155 | TATGCATTC | CAACAGGGTATTAGT AGTAGTAATGTTGAT AATGTT | 156 |
| DDR1-5 | CAGACCATTAGC AGTTGG | 157 | TATGCATTC | CAATGCACTTATGGT AGTGGTAGTAGTAGT AGTTATGGTTGTGCT | 158 |
| DDR1-6 | CAGAGTGTTTAT AGTAACTAC | 159 | GAAACATCC | CAAGGCGGTTATAGT GAGATTATTGAAAAT ACT | 160 |
| DDR1-9 | CAGAGCATTGGT AGTGTT | 161 | GGTGTATTT | CAATATATTCCTTAT GGTAGTAGTCCT | 162 |
| DDR1-11 | CAGAGTATTGGT AGTACCTAC | 163 | AAGGCTTCC | CTATACGGTGGTTTT GGTAGTAGTACTGGT GATGCT | 164 |
| DDR1-12 | CAGACCATTTAT AGTAAT | 165 | CAGGCATCC | CAAAGCTATTATGGT GCTGATGATTATACT | 166 |

TABLE 6-continued

DNA sequences encoding CDRs of light chain variable regions of DDR1 antibodies

| mAb Name | CDR1 | SEQ ID NO. | CDR2 | CDR3 | SEQ ID NO. |
|---|---|---|---|---|---|
| DDR1-13 | AAGAGTGTTTAT AATAACAATGCC | 167 | GGTGTATCC | GCAGGCGATTATAGT GATATTAGTGATAAT AAT | 168 |
| DDR1-14 | CAGAGCATTAGT AGCTAC | 169 | GAGGCATCC | CAAAACAATAATGGT TTTAGTGGTAGTAAT TTCAATAAT | 170 |
| DDR1-15 | CAGACCATTTAC AGCTCT | 171 | AAGGCTTCC | CAACAGGGTTCCAGT ATTAGTAATGTTGAT AAAAATGCT | 172 |
| DDR1-17 | CAGAGCATTGGT AGTTAC | 173 | GAGGCATCC | CAAAATAATAATGGT ATGACTGTCAGCGAT TTCAATGCT | 174 |
| DDR1-20 | CAGATTATTGAT CACGACCAC | 175 | CGGGCATCC | CAAAATAATAATGGT ATGACTGTCAGCGAT TTCAATGCT | 176 |
| DDR1-21 | CAGAGTGTTGTT GATAAGAACTGG | 177 | GAAGCATCC | GCAGGCGATTTTGAG AGTGGTGTTAGTGGT | 178 |
| DDR1-22 | AAGAATATTTAT AATAATAATGCC | 179 | GGTGCATCC | GCAGCAGATTATAGT GATATTAGTGATAAT AAT | 180 |
| DDR1-23 | CAGAGTGTTTAT AGTAACAACTAC | 181 | GCTGCATCC | CTAGGCGGGTATAAT GATGATGCTAAT | 182 |
| DDR1-26 | GAGAGTGTTTAT AGTAACAACCAC | 183 | GCTGCATCC | CTAGGCGGTTATAAT GATGATGCTAAT | 184 |
| DDR1-28 | CAGAGTATTGAT AACAACGAC | 185 | AGGACATCC | CAAAGCTATTGCGTT AATACTTATGGTTAT ACT | 186 |
| DDR1-29 | CAGAGCATTAGT AATCAC | 187 | AGGGCATCC | CAAAGCTATTATATT ATTAATAGGAGTAAT TATGCTAATTCT | 188 |
| DDR1-32 | GAGAGCATTAAT AGTTGG | 189 | GATGCATCC | CAAAGCTATTATATT ATTAATAGGAGTAAT TATGGTAATTCT | 190 |
| DDR1-33 | GAGACCATTAGT AGTAGA | 191 | CAGGCATCC | CAAGGCTGTTATTAT GGTGGGGGTAGTTTT TATGATTCTGCT | 192 |
| DDR1-34 | GAGAATCTTTAT AAGGACAACTAC | 193 | GGTGCATCC | GCAGGCGGTTATGAT AGTGTTGTTGAT | 194 |

In some embodiments, the polynucleotide encoding the HC-CDR1, HC-CDR2, and/or HC-CDR3 of the heavy chain variable region are selected from the polynucleotides presented in Table 7.

TABLE 7

DNA Sequences encoding CDRs of heavy chain variable region of DDR1 antibodies

| mAb Name | CDR1 | SEQ ID NO. | CDR2 | SEQ ID NO. | CDR3 | SEQ ID NO. |
|---|---|---|---|---|---|---|
| DDR1-1 | GGATTCTCCCTC AGTAGATATGCA | 195 | ATTGGTAGTA GTGGTCTCAC A | 196 | GCCAGAGGGATGTGG TACGATGACTCCGAT GATTACGAGGACTAC TTTAACTTG | 197 |

TABLE 7-continued

DNA Sequences encoding CDRs of heavy chain variable region of DDR1 antibodies

| mAb Name | CDR1 | SEQ ID NO. | CDR2 | SEQ ID NO. | CDR3 | SEQ ID NO. |
|---|---|---|---|---|---|---|
| DDR1-3 | GGAATCGACCTCAGTAGCTATGCA | 198 | ATTAATATTGGTGGTGGCACA | 199 | GCCAGAGATGTTGATGCCCATACCCTCACATACTTTACCTTG | 200 |
| DDR1-5 | GGATTCACCCTCAGTAATAATGCA | 201 | ATTTATGCTAGTGGTAGGACA | 202 | GCCAGAGGAGATACTGAGACTGATTATGGTATTCCTTACTTTGACTTG | 203 |
| DDR1-6 | GGATTCTCCTTCAGTAGCAGTTACTAC | 204 | ATTTATGCTAGTAGTGGTAGCACT | 205 | GCAATTCTTGGTGCTGATTATAGGTTGACTCGATTGGATCTC | 206 |
| DDR1-9 | GGATTCTCCCTCAATCGCTACTAC | 207 | ATTAGTTATGGTGATACCACA | 208 | GCCAGAGCAGATACTGGTGATAATGGTTATTTAGGCCTTCAGTTG | 209 |
| DDR1-11 | GGATTCTCCTTCAGTAGCGGCTACTAC | 210 | ATTTATACTGGTCGCACTGATTTCACT | 211 | GCGAGAGGGGATTATTCTGGTGGTGTTGGTGGTAATTATTGGTTGGATCTC | 212 |
| DDR1-12 | GGAATCGACCTCAGTAACACCTGG | 213 | ATTACTGATAGTGGTACCACA | 214 | GGCCGAGATCCTGGTGATATTACTAGTGGTACGAATGATTTG | 215 |
| DDR1-13 | TCTGGATTCTCCCTCAATAACTAT | 216 | ATTTTTAATAATGGTGATATA | 217 | GCCAGAACTGGCTATAGGACTGGTGGCTGGTTG | 218 |
| DDR1-14 | GGAATCGACCTCAGTTACTATGCA | 219 | ATTAATGGTCGTGGTGACACA | 220 | GCCCGAGAAGACAGTGCTATTCCTTTCATAGTAGGAAACTATTACGGCATGGACCTC | 221 |
| DDR1-15 | ACATTCTCCTTCAATAGCCGCTACTGG | 222 | ATTAATAACGGTGACATTAGC | 223 | GCGAAAGGGGGTAATCTTGCTGGTGATTGTTATGGGTTG | 224 |
| DDR1-17 | GGATTCTCCCTCAATCGCTATGCA | 225 | ATTGGTAGTAGTGGTAGTACA | 226 | GCCAGAGATTTGGACGATAGTTATGGTTATACTTATGCTACGGGGATGGACATTCGGTTGGATCTC | 227 |
| DDR1-20 | GGATTCTCCCTCAGTGACTATGCA | 228 | ATTAATAGTCGTGATGACACA | 229 | GCCAGAGAAGACAGTAGTATTCCTTTTATAGTAGGAAATTACTACGGCATGGACCTC | 230 |
| DDR1-21 | GGATTCTCCCTCAGTAGTTATGGA | 231 | ATTTATCCTAGTGGTAGTATA | 232 | GTCAGATATCTTACTGGTAGCAGTGATTTGCATTTG | 233 |
| DDR1-22 | GGATTCTCCCTCAGTGACTATGCA | 234 | ATCAATAATGGTGATATATAC | 235 | GCCAGACCTGGTTATAGGACTGGTATATGGTTG | 236 |
| DDR1-23 | GGATTCGACCTCAGGAGCTACTACTAC | 237 | ATTCATGGTGGTGAGGGTAACACT | 238 | AGAGGTGGCTGGACTAATTACTTT | 239 |
| DDR1-26 | GGATTCGACCTCAGTAGCAACTACTAC | 240 | ATTTATAGTAGTAATACTAGAACA | 241 | AGAGGTGGCTGGACTAATTACTTG | 242 |
| DDR1-28 | GGATTCTCCCTCAGTAGCCACGAC | 243 | ATTATTAGTAGTGGTAACACA | 244 | GCCAGAGATGTTTATAGTGGTGCGAGTCCT | 245 |
| DDR1-29 | ACATTCTCCTTCAATAGCCGCTACTGG | 246 | ATTAATAACGGTGACATTACC | 247 | GCGAAAGGGGGTAATCTTGCTGGTGATTGTTATGGGTTG | 248 |

TABLE 7-continued

DNA Sequences encoding CDRs of heavy chain variable region of DDR1 antibodies

| mAb Name | CDR1 | SEQ ID NO. | CDR2 | SEQ ID NO. | CDR3 | SEQ ID NO. |
|---|---|---|---|---|---|---|
| DDR1-32 | GGATTCTCCCTC AGTAGTTACTAC | 249 | ATTACTACTG CTGGTCCACT A | 250 | GCCAGAGGGCATGCT GGTAGTATTTATTAT TCATACTTTGACTTG | 251 |
| DDR1-33 | GGATTCTCCCTC AGCAGCTACGAC | 252 | AGTTGGAATA GTGGCTTTGT T | 253 | GCCAGACTTGGTGCT GATGACATCTACTAT TTTAACTTG | 254 |
| DDR1-34 | GGATTCGACCTC AGTAGCTACTAC TAC | 255 | ATTTATACTA GTAGTGGTGC CACA | 256 | AGAGGAGGTTGGTGC GACTTTAACTTG | 257 |

In some embodiments, the polynucleotide encodes at least 1, 2, or 3 of the LC-CDRs in the light chain variable region of amino acid sequence of SEQ ID NOS: 108-128 or SEQ NOs: 150 or 151. In some embodiments, the polynucleotide encodes at least 1, 2, or 3 of the HC-CDRs in the heavy chain variable region of amino acid sequence of SEQ ID NOS: 129-149 or SEQ NOs: 153.

In some embodiments, the polynucleotide encodes at least 1, 2, or 3 of the LC-CDRs and in the light chain variable region of amino acid sequence of SEQ ID NOS: 108-128 or SEQ NOs: 150 or 151, and at least 1, 2, or 3 of the HC-CDRs in the heavy chain variable region of amino acid sequence of SEQ ID NOS: 129-149 or SEQ NOs: 153. In some embodiments, the LC-CDRs and HC-CDRs selected are those of clone-paired LC-CDRs and HC-CDRs.

In some embodiments, the polynucleotide comprises at least 1, 2 or 3 of the polynucleotide sequences of the LC-CDRs of each mAb presented in Table 6.

In some embodiments, the polynucleotide comprises at least 1, 2 or 3 of the polynucleotide sequences of the HC-CDRs of each mAb presented in Table 7.

In some embodiments, the polynucleotide comprises at least 1, 2, or 3 of the polynucleotide sequences of the LC-CDRs of each mAb presented in Table 6, at least 1, 2 or 3 of the polynucleotide sequences of the HC-CDRs of each mAb designated in Table 7, where the LC-CDRs and HC-CDRs selected are those of clone-paired LC-CDRs and HC-CDRs presented in Table 6 and Table 7, respectively.

In some embodiments, the polynucleotide encodes a light chain variable region having at least 80%, 85%, 90%, 91%, 92%, 93%, 94%, 95%, 96%, 97%, 98%, 99% or greater sequence identity to the light chain variable region amino acid sequence selected from SEQ ID NOs: 108-128 of Table 3 and SEQ ID NOs: 150 and 151 of Table 5.

In some embodiments, the polynucleotide encodes a heavy chain variable region having at least 80%, 85%, 90%, 91%, 92%, 93%, 94%, 95%, 96%, 97%, 98%, 99% or greater sequence identity to the heavy chain variable region amino acid sequence selected from SEQ ID NOs: 129-149 of Table 4 and SEQ ID NO: 153 of Table 5.

In some embodiments, the polynucleotide encodes a light chain variable region having at least 80%, 85%, 90%, 91%, 92%, 93%, 94%, 95%, 96%, 97%, 98%, 99% or greater sequence identity to the light chain variable region amino acid sequence selected from SEQ ID NOs: 108-128 of Table 3 or SEQ ID NOs: 150 and 151 of Table 5, and a heavy chain variable region having at least 80%, 85%, 90%, 91%, 92%, 93%, 94%, 95%, 96%, 97%, 98%, 99% or greater sequence identity to the heavy chain variable region amino acid sequence selected from SEQ ID NOs: 129-149 of Table 4 and SEQ ID NO: 153 of Table 5.

In some embodiments, the polynucleotide encodes an antibody or antigen-binding fragments thereof comprising a light chain variable region and a heavy chain variable region pairs selected from:

- a light chain variable region having an amino acid sequence of SEQ ID NO: 108 (DDR1-1K) and a heavy chain variable region having an amino acid sequence of SEQ ID NO: 129 (DDR1-1H);
- a light chain variable region having an amino acid sequence of SEQ ID NO: 109 (DDR1-3K) and a heavy chain variable region having an amino acid sequence of SEQ ID NO: 130 (DDR1-3H);
- a light chain variable region having an amino acid sequence of SEQ ID NO: 110 (DDR1-5K) and a heavy chain variable region having an amino acid sequence of SEQ ID NO: 131 (DDR1-5H);
- a light chain variable region having an amino acid sequence of SEQ ID NO: 111 (DDR1-6K) and a heavy chain variable region having an amino acid sequence of SEQ ID NO: 132 (DDR1-6H);
- a light chain variable region having an amino acid sequence of SEQ ID NO: 112 (DDR1-9K) and a heavy chain variable region having an amino acid sequence of SEQ ID NO: 133 (DDR1-9H);
- a light chain variable region having an amino acid sequence of SEQ ID NO: 113 (DDR1-11K) and a heavy chain variable region having an amino acid sequence of SEQ ID NO: 134 (DDR1-11H);
- a light chain variable region having an amino acid sequence of SEQ ID NO: 114 (DDR1-12K) and a heavy chain variable region having an amino acid sequence of SEQ ID NO: 135 (DDR1-12H);
- a light chain variable region having an amino acid sequence of SEQ ID NO: 115 (DDR1-13K) and a heavy chain variable region having an amino acid sequence of SEQ ID NO: 136 (DDR1-13H);
- a light chain variable region having an amino acid sequence of SEQ ID NO: 116 (DDR1-14K) and a heavy chain variable region having an amino acid sequence of SEQ ID NO: 137 (DDR1-14H);
- a light chain variable region having an amino acid sequence of SEQ ID NO: 117 (DDR1-15K) and a heavy chain variable region having an amino acid sequence of SEQ ID NO: 138 (DDR1-15H);

a light chain variable region having an amino acid sequence of SEQ ID NO: 118 (DDR1-17K) and a heavy chain variable region having an amino acid sequence of SEQ ID NO: 139 (DDR1-17H);

a light chain variable region having an amino acid sequence of SEQ ID NO: 119 (DDR1-20K) and a heavy chain variable region having an amino acid sequence of SEQ ID NO: 140 (DDR1-20H);

a light chain variable region having an amino acid sequence of SEQ ID NO: 120 (DDR1-21K) and a heavy chain variable region having an amino acid sequence of SEQ ID NO: 141 (DDR1-21H);

a light chain variable region having an amino acid sequence of SEQ ID NO: 121 (DDR1-22K) and a heavy chain variable region having an amino acid sequence of SEQ ID NO: 142 (DDR1-22H);

a light chain variable region having an amino acid sequence of SEQ ID NO: 122 (DDR1-23K) and a heavy chain variable region having an amino acid sequence of SEQ ID NO: 143 (DDR1-23H);

a light chain variable region having an amino acid sequence of SEQ ID NO: 123 (DDR1-26K) and a heavy chain variable region having an amino acid sequence of SEQ ID NO: 144 (DDR1-26H);

a light chain variable region having an amino acid sequence of SEQ ID NO: 124 (DDR1-28K) and a heavy chain variable region having an amino acid sequence of SEQ ID NO: 145 (DDR1-28H);

a light chain variable region having an amino acid sequence of SEQ ID NO: 125 (DDR1-29K) and a heavy chain variable region having an amino acid sequence of SEQ ID NO: 146 (DDR1-29H);

a light chain variable region having an amino acid sequence of SEQ ID NO: 126 (DDR1-32K) and a heavy chain variable region having an amino acid sequence of SEQ ID NO: 147 (DDR1-32H);

a light chain variable region having an amino acid sequence of SEQ ID NO: 127 (DDR1-33K) and a heavy chain variable region having an amino acid sequence of SEQ ID NO: 148 (DDR1-33H);

a light chain variable region having an amino acid sequence of SEQ ID NO: 128 (DDR1-34K) and a heavy chain variable region having an amino acid sequence of SEQ ID NO: 149 (DDR1-34H);

a light chain variable region having an amino acid sequence of SEQ ID NO: 150 (DDR1-9hu_Lv), and a heavy chain variable region having an amino acid sequence of SEQ ID NO: 153 (DDR1-9hu_Hv); and a light chain variable region having an amino acid sequence of SEQ ID NO: 151 (DDR1-9hu_Lc2), and a heavy chain variable region having an amino acid sequence of SEQ ID NO: 153 (DDR1-9hu_Hv).

In some embodiments, the polynucleotide encoding a light chain variable region is selected from the polynucleotides presented in Table 8:

TABLE 8

| mAb name | Polynucleotide light chain variable region | SEQ ID NO. |
|---|---|---|
| DDR1-1K | GAGCTCGTGCTGACCCAGACACCAGCCTCCGTGTCTGCAGCTGTGGGAGG CACAGTCACCATCAATTGCCAGGCCAGTCAGAACATTTACAGCAATTTAG CCTGGTATCAGCAGAAACCAGGACAGCCTCCCAAGCTCCTGATCTATGT GCATCCAATCTGGAATCTGGGGTCCCATCGCGGTTCAAAGGCAGTGGATC TGGGACACAGTTCACTCTCACCATCAGCGACCTGGAGTGTGACGATGCTG CCACTTACTACTGTCAAAGTGGTTATTATAGTAGTAGTACTGATATTGCT TTCGGCGGAGGGACCGAGGTGGTGGTCAAA | 258 |
| DDR1-3K | GAGCTCGTGCTGACCCAGACACCAGCCTCCGTGTCTGAACCTGTGGGA GGCACAGTCACCATCAAGTGTCAGGCCAGTCAGACCATTAGCAGTTGGTT ATCCTGGTATCAGCAGAAACCAGGGCAGCCTCCCAAGCTCCTGATCTATT ATGCATTCAATCTGGCATCTGGGGTCCCATCGCGGTTCAAAGGCAGTGGA TCTGGGACAGAGTTCACTCTCACCATCAGCGACCTGGAGTGTGCCGATGC TGCCACTTACTACTGTCAACAGGGTATTAGTAGTAGTAATGTTGATAATG TTTTCGGCGGAGGGACCGAGGTGGTGGTCAAA | 259 |
| DDR1-5K | GAGCTCGTGCTGACCCAGACACCAGCCTCCGTGTCTGAACCTGTGGGAGG CACAGTCACCATCAAGTGTCAGGCCAGTCAGACCATTAGCAGTTGGTTAT CCTGGTATCAGCAGAAACCAGGGCAGCCTCCCAAGCTCCTGATCTATTAT GCATTCAATCTGGCATCTGGGGTCCCATCGCGGTTCAAAGGCAGTGGATC TGGGACAGAGTACACTCTCACCATCAGCGACCTGGAGTGTGCCGATGCTG CCACTTATTATTGTCAATGCACTTATGGTAGTGGTAGTAGTAGTAGTTAT GGTTGTGCTTTCGGCGGAGGGACCGAGCTGGAAATCAAA | 260 |
| DDR1-6K | GAGCTCGTGATGACCCAGACACCATCTCCCGTGTCTGCAGCTGTGGGAGG CACAGTCACCATCAGTTGCCAGTCCAGTCAGAGTGTTTATAGTAACTACT TATCCTGGTATCAGCAGAAACCAGGGCAGCCTCCCAAGCTCCTGATCTAC GAAACATCCACTCTGGCATCTGGGGTCCCATCGCGGTTCAAAGGCAGTGG ATCGGGACACAGTTCACTCTCACCATCAGCGACGTGCAGTGTGACGATG CTGCCACTTACTACTGTCAAGGCGGTTATAGTGAGATTATTGAAAATACT TTCGGCGGAGGGACCGAGGTGGAAATCAAA | 261 |
| DDR1-9K | GAGCTCGTGATGACCCAGACACCAGCCTCCGTGGAGGCAGCTGTGGGAGG CACAGTCACCATCAAGTGCCAGGCCAGTCAGAGCATTGGTAGTGTTTTGG CCTGGTATCAGCAGAAACCAGGGCAGCGTCCCAAGCTCCTGATCTCTGGT GTATTTGATCTGGCATCTGGGGTCCCGTCGCGGTTCAAAGGCAGTGGATC TGGGACAGAGTTCACTCTCACCATCAGCGACCTGGAGTGTGCCGATGCTG CCACTTACTACTGTCAATATATTCCTTATGGTAGTAGTCCTTTCGGCGGA GGGACCGAGGTGGTGGTCAAA | 262 |

TABLE 8-continued

DNA sequences encoding light chain variable regions of anti-DDR1 antibodies

| mAb name | Polynucleotide light chain variable region | SEQ ID NO. |
|---|---|---|
| DDR1-11K | GAGCTCGTGATGACCCAGACTGCATCCCCCGTGTCTGCAGCTGTGGGAGG CACAGTCACCATCAATTGCCAGGCCAGTCAGAGTATTGGTAGTACCTACT TATCCTGGTATCAGCAGAAACCAGGGCAGCCTCCCAAACTCCTGATCTAC AAGGCTTCCATTCTGGCGTCTGGGGTCCCATCGCGGTTCAGCGGCAGTGG ATCTGGGACAGAGTACACTCTCACCATCAGCGGCGTGCAGTGTGACGATG CTGCCACTTATTACTGTCTATACGGTGGTTTTGGTAGTAGTACTGGTGAT GCTTTCGGCGGAGGGACCGTGCTGGTGGTCAAA | 263 |
| DDR1-12K | GAGCTCGTGCTGACCCAGACACCAGCCTCCGTGTCTGAACCTGTGGGAGG CACAGTCACCATCAAGTGCCAGGCCAGTCAGACCATTTATAGTAATTTAG CCTGGTATCAGCAGAAACCAGGGCAGCGTCCCAAGCTCCTGATCTACCAG GCATCCAAACTGGCATCTGGGGTCCCATCGCGGTTCAAAGGCAGTGGATC TGGGACAGAGTATACTCTCACCATCAGCGACCTGGAGTGTGCCGATGCTG CCACTTACTACTGTCAAAGCTATTATGGTGCTGATGATTATACTTTCGGC GGAGGGACCGAGGTGGTGGTCAAA | 264 |
| DDR1-13K | GAGCTCGTGATGACCCAGACACCATCTCCCGTGTCTGCAGCTGTGGGAGG CACAGTCAGCATCAGTTGCCAGTCCAGTAAGAGTGTTTATAATAACAATG CCTTATCCTGGTTTCAACAGAAACCAGGGCAGCCTCCCAAGGTCCTGATC TATGGTGTATCCACTCTGGATTCTGGGGTCTCATCGCGGTTCAGCGGCAG TGGATATGGGACAGAGTTCACTCTCACCATCAGCGACGTGCAGTGTGACG ATGCTGCCACTTACTACTGTGCAGGCGATTATAGTGATATTAGTGATAAT AATTTCGGCGGAGGGACCGAGCTGGAAATCAAA | 265 |
| DDR1-14K | GAGCTCGATATGACCCAGACACCAGCCTCCGTGTCTGAACCTGTGGGAGG CACAGTCACCATCAAGTGCCAGGCCAGTCAGAGCATTAGTAGCTACTTAG CCTGGTATCAGCAGAAACCAGGGCAGCCTCCCAAGCGCCTGATCTTTGAG GCATCCCACTCTGGCCTCTGGGGTCCCCTCGCGGTTCAGCGGCAGTGGATC TGGGACAGATTTCACTCTCACCATCAGCGACCTGGAGTGTGCCGATGCTG CCACTTACTACTGTCAAAACAATAATGGTTTTAGTGGTAGTAATTTCAAT AATTTCGGCGGAGGGACCGAGGTGGAAATCAAA | 266 |
| DDR1-15K | GAGCTCGTGATGACCCAGACACCAGCCTCTGTGGAGGTAGCTGTGGGAGG CACAGTCACCATCAAGTGCCAGGCCAGTCAGACCATTTACAGCTCTTTAG CCTGGTATCAGCAGAAACCAGGGCAGCCTCCCAAGCTCCTGATCTACAAG GCTTCCACTCTGGCATCTGGGGTCCCATCGCGGTTCAAAGGCAGTGGATC TGGGACACAGTTCACTCTCACCATCAGTGGCGTGCAGTGTGACGATGCTG CCACTTACTACTGTAACAGGGTTCCAGTATTAGTAATGTTGATAAAAAT GCTTTCGGCGGAGGGACCGAGGTGGAAATCAAA | 267 |
| DDR1-17K | GAGCTCGTGCTGACCCAGACACCAGCCTCCGTGTCTGAACCTGTGGGAGG CACAGTCACCATCAAGTGCCAGGCCAGTCAGAGCATTGGTAGTTACTTAT CCTGGTATCAACAGAAAGCAGGGCAGCCTCCCAAGCGCCTGATCTATGAG GCATCCCACTCTGGCCTCTGGGGTCCCATCGCGGTTCAGCGGCAGTGGATC TGGGACAGATTTCACTCTCACCATCAGCGACCTGGAGTGTGCCGATGTTG CCACTTATTACTGTCAAAATAATAATGGTATGACTGTCAGCGATTTCAAT GCTTTCGGCGGAGGGACCGAGGTGGAAATCAAA | 268 |
| DDR1-20K | GAGCTCGATCTGACCCAGACACCAGCCTCCGTGTCTGCAGCTGTAGGAGG CACAGTCACCATCAATTGCCAGTCCAGTCAGATTATTGATCACGACCACT TATCCTGGTATCAGCAGAAACCAGGGCAGCGTCCCAAGCTCCTAATCTAC CGGGCATCCACTCTGACATCTGGGTCCCCTCGCGGTTCAAAGGCAGTGG ATCTGGGACAGATTTCACTCTCACCATCAGCGACCTGGAGTGTGCCGATG TTGCCACTTATTACTGTCAAAATAATAATGGTATGACTGTCAGCGATTTC AATGCTTTCGGCGGAGGGACCGAGGTGGAAATCAAA | 269 |
| DDR1-21K | GAGCTCGTGCTGACCCAGACACCATCTTCCACGTCTGCAGCTGTGGGAGG CACAGTCACCATCAGTTGCCAGTCCAGTCAGAGTGTTGTTGATAAGAACT GGTTAGCCTGGTATCAGCAGAAACCAGGGCAGCCTCCCAAGCTCTTGATC TACGAAGCATCCAAACTGGCATCTGGGGTCCCGCCGCGGTTCAGCGGCAG TGGATCTGGGACACAGTTCACTCTCACCATCAGCGGCGTGCAGTGTGACG ATGCTGCCACTTACTACTGTCAGGCGATTTTGAGAGTGGTGTTAGTGGT TTCGGCGGAGGGACCGAGGTGGAAATCAAA | 270 |
| DDR1-22K | GAGCTCGTGCTGACCCAGACACCATCACCCGTGTCTGCAGCTGTGGGAGG CACAGTCACCATCAATTGCCAGTCCAGTAAGAATATTTATAATAATAATG CCTTATCCTGGTTTCAACAGAAACCAGGGCAGCCTCCCAAGCTCCTGATC TATGGTGCATCCACTCTGGCATCTGGGGTCCCATCGCGGTTCAAAGGCAG TGGATCTGGGACACAGTTCACTCTCACCATCAGCGACGTGCAGTGTGACG ATGCTGCCACTTACTACTGTCAGCAGATTATAGTGATATTAGTGATAAT AATTTCGGCGGAGGGACCGAGGTGGTGGTCAAA | 271 |
| DDR1-23K | GAGCTCGTGCTGACCCAGACACCATCCTCCGTGTCTGCAGCTGTGGGAGG CACAGTCACCATCAGTTGCCAGTCCAGTCAGAGTGTTTATAGTAACAACT | 272 |

TABLE 8-continued

DNA sequences encoding light chain variable regions of anti-DDR1 antibodies

| mAb name | Polynucleotide light chain variable region | SEQ ID NO. |
|---|---|---|
| | ACTTAGCCTGGTATCAGCAGAAACCAGGGCAGCCTCCCAAGCTCCTGATC<br>TATGCTGCATCCACTCTGGCATCTGGGGTCCCATCGCGGTTCAAAGGCAG<br>TGGATCTGGGACACAGTTCACTCTCACCATCAGCGGCGTGCAGTGTGACG<br>ATGCTGCCGTTTACTACTGTCTAGGCGGGTATAATGATGATGCTAATTTC<br>GGCGGAGGGACCGAGGTGGAAATCAAA | |
| DDR1-26K | GAGCTCGATCTGACCCAGACACCATCCTCCGTGTCTGCAGCTGTGGGAGG<br>CACAGTCACCATCAGTTGCCAGTCCAGTGAGAGTGTTTATAGTAACAACC<br>ACTTAGCCTGGTATCAGCAGAAACCAGGGCAGCCTCCCAAGCTCCTGATC<br>TATGCTGCATCCACTCTGGCATCTGGGGTCCCATCGCGGTTCAGTGGCAG<br>TGGATCTGGGACACAGTTCACTCTCACCATCAGCGGCGTGCAGTGTGACG<br>ATGCTGCCGTTTACTACTGTCTAGGCGGTTATAATGATGATGCTAATTTC<br>GGCGGAGGGACCGAGGTGGTGGTCAAA | 273 |
| DDR1-28K | GAGCTCGATCTGACCCAGACACCAGCCTCCGTGGAGGCAGCTGTGGGAGG<br>CACAGTCACCATCAAGTGCCAGGCCAGTCAGAGTATTGATAACAACGACT<br>TAGCCTGGTATCAGCAGAAACCAGGGCAGCCTCCCAACCTCCTGATCTCC<br>AGGACATCCACTCTGGCATCTGGGGTCTCATCGCGGTTCAAAGGCAGTGG<br>ATCTGGGACAGAGTTCACTCTCACCATCAGCGACCTGGAGTGTGCCGATG<br>CTGCCACTTACTACTGTCAAAGCTATTGCGTTAATACTTATGGTTATACT<br>TTCGGCGGAGGGACCGAGGTGGTGGTCAAA | 274 |
| DDR1-29K | GAGCTCGTGATGACCCAGACACCAGCCTCCGTGGAGGCAGCTGTGGGAGG<br>CACAGTCACCATCAAGTGCCAGGCCAGTCAGAGCATTAGTAATCACTTAG<br>GCTGGTATCAGCAGAAACCAGGGCAGCCTCCCAAGCTCCTGATCTACAGG<br>GCATCCACTCTGGAATCTGGGGTCTCATCGCGGTTCAAAGGCAGTGGATC<br>TGGGTCAGAGTTCACTCTCACCATCAGCGACCTGGAGTGTGCCGATGCTG<br>CCACTTACTACTGTCAAAGCTATTATATTATTAATAGGAGTAATTATGCT<br>AATTCTTTCGGCGGAGGGACCGAGGTGGAAATCAAA | 275 |
| DDR1-32K | GAGCTCGTGATGACCCAGACACCAGCCTCCGTGGAGGCAGCTGTGGGAGG<br>CACAGTCACCATCAAGTGCCAAGCCAGTGAGAGCATTAATAGTTGGTTAG<br>CCTGGTATCAGCAGAAACCAGGGCAGCGTCCCAAGCTCCTGATCTATGAT<br>GCATCCAAACTGGCATCTGGGGTCCCATCGCGGTTCAAAGGCAGTGGATC<br>TGGGACACAGTTCACTCTCACCATCAGCGACCTGGAGTGTGCCGATGCTG<br>CCACTTACTACTGTCAAAGCTATTATATTATTAATAGGAGTAATTATGGT<br>AATTCTTTCGGCGGAGGGACCGAGGTGGAAATCAAA | 276 |
| DDR1-33K | GAGCTCGTGATGACCCAGACACCAGCCTCCGTGGAGGCAGCTGTGGGAGG<br>CACAGTCACCATCAAGTGCCAGGCCAGTGAGACCATTAGTAGTAGATTAG<br>CCTGGTATCAGCAGAAACCAGGGCAGCCTCCCAAGCTCCTGATCTACCAG<br>GCATCCAAACTGCCATCTGGGGTCCCATCGCGGTTCAAAGGCACTGGATC<br>TGGGACAGAGTACACTCTCACCATCAGCGACCTGGAGTGTGCCGATGCTG<br>CCACTTACTACTGTCAAGGCTGTTATTATGGTGGGGTAGTTTTTATGAT<br>TCTGCTTTCGGCGGAGGGACCGAGGTGGTGGTCAAA | 277 |
| DDR1-34K | GAGCTCGATCTGACCCAGACACCAGCCTCCGTGTCTGCAGCTGTGGGAGG<br>CACAGTCACCATCAGTTGCCAGTCCAGTGAGAATCTTTATAAGGACAACT<br>ACTTAGCCTGGTATCAGCAGAAACCAGGGCAGCCTCCCAAGCTCCTGATC<br>TATGGTGCATCCAATCTGGCATCTGGGGTCCCATCGCGGTTCAAAGGCAG<br>TGGATCTGGGACACAGTTCACTCTCACCATCAGCGACCTGGAGTGTGACG<br>ATGCTGCCACTTACTACTGCGCAGGCGGTTATGATAGTGTTGTTGATTTC<br>GGCGGAGGGACCGAGGTGGTGGTCAAA | 278 |

In some embodiments, the polynucleotide encoding a heavy chain variable region is selected from the polynucleotides presented in Table 9.

TABLE 9

DNA sequences encoding heavy chain variable regions of anti-DDR1 antibodies

| mAb name | Polynucleotide heavy chain variable region | SEQ ID NO. |
|---|---|---|
| DDR1-1H | CAGTCGGTGGAGGAGTCCGGGGGTCGCCTGGTCACGCCTGGGACACCCCT<br>GACACTCACCTGCACAGTCTCTGGATTCTCCCTCAGTAGATATGCAATGA<br>CCTGGGTCCGCCAGGCTCCAGGGAAGGGGCTGGAATGGATCGGAATCATT<br>GGTAGTAGTGGTCTCACATACTTCGCGACCTGGGCGAAAGGCCGATTCAC<br>CATCTCCAAAACCTCGACCACGGTAGATCTGAAAATCACCAGTCCGACAA<br>CCGAGGACACGGCCACCTACTTCTGTGCCAGAGGGATGTGGTACGATGAC | 279 |

TABLE 9-continued

DNA sequences encoding heavy chain variable regions of anti-DDR1 antibodies

| mAb name | Polynucleotide heavy chain variable region | SEQ ID NO. |
|---|---|---|
| | TCCGATGATTACGAGGACTACTTTAACTTGTGGGGCCCAGGCACCCTGGT CACCATCTCTTCA | |
| DDR1-3H | CAGTCGGTGAAGGAGTCCGGGGGTCGCCTGGTCACGCCTGGGACACCCCT GACACTCACCTGCACAGTCTCTGGAATCGACCTCAGTAGCTATGCAATGA GCTGGGTCCGCCAGGCTCCAGGGAAGGGGCTGGAATGGATCGGAACCATT AATATTGGTGGTGGCACATGGGACGCGACCTGGGCGAGAGGCCGATTCAC CATCTCCAGAACCTCGACCACGGTGGATCTGAAAATCACCAGTCCGACAA TCGGGGACACGGCCACCTATTTCTGTGCCAGAGATGTTGATGCCCATACC CTCACATACTTTACCTTGTGGGGCCCAGGCACCCTGGTCACCATCTCCTC A | 280 |
| DDR1-5H | CAGTCGGTGAAGGAGTCCGGGGGTCGCCTGGTCACGCCTGGGACACCCCT GACACTCACCTGCACCGTCTCTGGATTCACCCTCAGTAATAATGCAATAA GCTGGGTCCGCCAGGCTCCAGGGAAGGGGCTGGAATGGATCGGAATCATT TATGCTAGTGGTAGGACATACTACGCGACCTGGGCGAAAGGCCGATTCAC CATCTCCAAAACCTCGACCACGGTGGATCTGAAAATGACCAGTCCGACAA CCGAGGACACGGCCACCTATTTCTGTGCCAGAGGAGATACTGAGACTGAT TATGGTATTCCTTACTTTGACTTGTGGGGCCCAGGCACCCTGGTCACCAT CTCCTCA | 281 |
| DDR1-6H | CAGTCGTTGAAGGAGTCCGGGGGAGACCTGGTCAAGCCTGGGGCATCCCGGACACT CACCTGTATAGCCCCTGGATTCTCCTTCAGTAGCAGTTACTACA TGTGCTGGGTCCGCCAGGCTCCAGGGAAGGGGCTGGAGTGGATCGCATGC ATTTATGCTAGTAGTGGTAGCACTTACTACGCGAGCTGGGCGAAAGGCCG ATTCACCATCTCCAAAACCTCGTCGACCACGGTGACTCTGCAAATGACCA CTCTGACAGCCGCGGACACGGCCACCTATTTCTGTGCGGCAATTCTTGGT GCTGATTATAGGTTGACTCGATTGGATCTCTGGGGCCAGGGCACCCTGGT CACCGTCTCCTCA | 282 |
| DDR1-9H | CAGTCGTTGGAGGAGTCCGGGGGTCGCCTGGTCACGCCTGGGACACCCCT GACACTCACCTGCACAGCCTCTGGATTCTCCCTCAATCGCTACTACATGC TCTGGGTCCGCCAGGCTCCAGGGGAGGGCCTGGAATGGATCGGAACCATT AGTTATGGTGATACCACATACTACGCGAGCTGGGCGAAAGGCCGATTCAC CATCTCCAAAACCTCGACCACGGTGGATCTGAAAATGACCAGTCCGACAA CCGAGGACACGGCCACTTATTTCTGTGCCAGAGCAGATACTGGTGATAAT GGTTATTTAGGCCTTCAGTTGTGGGGCCCAGGCACCCTGGTCACCGTCTC TTCA | 283 |
| DDR1-11H | CAGTCGTTGGAGGAGTCCGGGGGAGACCTGGTCAAGCCTGGGGCATCCCT GACACTCACCTGCACAGCCTCTGGATTCTCCTTCAGTAGCGGCTACTACA TGTGCTGGGTCCGCCAGGCTCCAGGGAAGGGGCTGGAGTGGATCGCATGC ATTTATACTGGTCGCACTGATTTCACTGATTACGCGAGCTGGGCGAAAGG CCGATTCACCATCTCCAAAACCTCGTCGACCACGGTGACTCTGCAACTGA CCACTCTGACAGCCGCGGACACGGCCACCTATTTCTGTGCGAGAGGGGAT TATTCTGGTGGTGTTGGTGGTAATTATTGGTTGGATCTCTGGGGCCAGGG CACCCTGGTCACCATCTCCTCA | 284 |
| DDR1-12H | CAGTCGTTGGAGGAGTCCGGGGGTCGCCTGGTCACGCCTGGGACACCCCT GACACTCACCTGCACAGTCTCTGGAATCGACCTCAGTAACACCTGGATGA ACTGGGTCCGCCAGGCTCCAGGGAAGGGGCTGGAATGGATCGGAGTCATT ACTGATAGTGGTACCACATACTACGCGAACTGGGCGAAAGGCCGATTCAC CATCTCCAGAACCTCGACCACGGTGGATCTGAAAATGCCCAGTCTGACAA CCGAGGACACGGCCACCTATTTCTGTGGCCGAGATCCTGGTGATATTACT AGTGGTACGAATGATTTGTGGGGCCCAGGCACCCTGGTCACCATCTCCTCA | 285 |
| DDR1-13H | GAGCAGTCGGTGGAGGAGTCCGGCGGTCGCCTGGTCACGCCTGGAGGATC CCTGACACTCACCTGCACAGCCTCTGGATTCTCCCTCAATAACTATGCAA TCATCTGGGTCCGCCAGGCTCCAGGGAAGGGTCTGGAATATATCGGAATT TTTAATAATGGTGATATATACTATGCGAACTGGGCGAAAGGCCGATTCAC CATCTCCAAAACCTCGACCACGGTGGGTCTGAAAATCGTCAGTCCGACAA CCGAGGACACGGCCACCTATTTCTGTGCCAGAACTGGCTATAGGACTGGT GGCTGGTTGTGGGGCCCAGGCACCCTGGTCACCATCTCCTCA | 286 |
| DDR1-14H | CAGTCGGTGAAGGAGTCCGGGGGTCGCCTGGTCACGCCTGGGACACCCCT GACACTCACCTGCACAGTCTCTGGAATCGACCTCAGTTACTATGCAATGA GCTGGGTCCGCCAGGCTCCAGGGAAGGGGCTGGAATACATCGGAATCATT AATGGTCGTGGTGACACAGGCTACGCGACCTGGGCGAAAGGCCGCTTCAC TATCTCCAAAACCTCGACCACGGTGGATCTGAGGATCACCAGTCCGACAA TCGAGGACACGGCCACCTATTTCTGTGCCCGAGAAGACAGTGCTATTCCT TTCATAGTAGGAAACTATTACGGCATGGACCTCTGGGGCCCAGGGACCCT CGTCACCGTCTCCTCA | 287 |

TABLE 9-continued

DNA sequences encoding heavy chain variable regions of anti-DDR1 antibodies

| mAb name | Polynucleotide heavy chain variable region | SEQ ID NO. |
|---|---|---|
| DDR1-15H | TCGCAGTCGTTGGAGGAGTCCGGGGGAGACCTGGTCAAGCCTGGGGCATCCCTGAC ACTCACCTGCACAGCCTCTACATTCTCCTTCAATAGCCGCTACTGGA CATGCTGGGTCCGCCAGGCTCCAGGGAAGGGACTGGAGTGGATCGGATGT ATTAATAACGGTGACATTAGCACTTACTACGCGAGCTGGGCGACCGGCCG ATTCACCATCTCCAAGTCCTCGTCGACCACGGTGACTCTGCATATGACCA GTCTGACAGCCGCGGACACGGCCACCTATTTCTGTGCGAAAGGGGGTAAT CTTGCTGGTGATTGTTATGGGTTGTGGGGCCCAGGCACCCTGGTCACCAT CTCTTCA | 288 |
| DDR1-17H | AGTTCGGTGGAGGAGTCCGGGGGTCGCCTGGTCGCGCCTGGGACAC CCCTGACACTCACCTGCACAGTCTCTGGATTCTCCCTCAATCGCTATGCA ATGAGCTGGGTCCGCCAGGCTCCAGGGAAGGGGCTGGAGTGGATCGGAAT CATTGGTAGTAGTGGTAGTACATACTACGCGAGCTGGGCGAAAGGCCGAT TCACCATCTCCAAAACCTCGACCACGGTGGATCTGAAAATCACCAGTCCG ACAACCGAGGACACGGCCACCTATTTCTGTGCCAGAGATTTGGACGATAG TTATGGTTATACTTATGCTACGGGGATGGACATTCGGTTGGATCTCTGGG GCCAGGGCACCCTGGTCACCGTCTCCTCA | 289 |
| DDR1-20H | CAGTCGGTGAAGGAGTCCGGGGGAGGCCTCTTCAAGCCAATGGATACCCT GACACTCACCTGCACCGTCTCTGGATTCTCCCTCAGTGACTATGCAATGA GCTGGGTCCGCCAGGCTCCAGGGAAGGGGCTGGAGTGGATCGGAATCATT AATAGTCGTGATGACACAGGCTACGCGAGCTGGGCGAAAGGCCGATTCAC CATCTCCAAAACCTCGTCGACCACGGTGGATCTGAGGATCACCAGTCCGA CAACCGAGGACACGGCCACCTATTTCTGTGCCAGAGAAGACAGTAGTATT CCTTTTATAGTAGGAAATTACTACGGCATGGACCTCTGGGGCCCAGGGAC CCTCGTCACCGTCTCCTCA | 290 |
| DDR1-21H | CAGTCGTTGGAGGAGTCCGGGGGTCGCCTGGTCACGCCTGGGACACCCT GACACTCACCTGCACAGTCTCTGGATTCTCCCTCAGTAGTTATGGAGTGC ACTGGGTCCGCCAGGCTCCAGGGAAGGGGCTGGACTGGATCGGAAAGATT TATCCTAGTGGTAGTATATACTACTCGAGCTGGGCGAAAGGCCGATTCAC CATCTCCAAAACCTCGACCACGGTGGATCTGAAAATGACCAGTCTGACAA CCGAGGACACGGCCACCTATTTCTGTGTCAGATATCTTACTGGTAGCAGT GATTTGCATTTGTGGGGCCCAGGCACCCTGGTCACCATCTCCTCA | 291 |
| DDR1-22H | CAGTCGGTGAAGGAGTCCGGGGGTCGCCTGGTAACGCCTGGAGGATCCCT GACACTCACCTGCACAGTCTCTGGATTCTCCCTCAGTGACTATGCAATGA TCTGGGTCCGCCAGGCTCCAGGGAAGGGGCTGGAATATATCGGCATTATC AATAATGGTGATATATACTACGCAACCTGGGCGAAAGGCCGATTCACCAT CTCCGAAACCTCGTCGACCACGATGGGTCTCAATATCATCAGTCCGACGA CCGAGGACACGGCCACCTATTTCTGTGCCAGACCTGGTTATAGGACTGGT ATATGGTTGTGGGGCCCAGGCACCCTGGTCACCATCTCCTCA | 292 |
| DDR1-23H | TCGCAGTCGGTGAAGGAGTCCGGGGGAGACCTGGTCAAGCCTGGGGCATC CCTGACACTCACCTGCAAAGCCTCTGGATTCGACCTCAGGAGCTACTACT ACATGTGCTGGGTCCGCCAGGCTCCAGGGAAGGGGCTGGAGTGGATCGCA TGCATTCATGGTGGTGAGGGTAACACTTACTACGCGAGCTGGGCGAAAGG CCGATTCACCATCTCCAAGACCTCGTCGACCGCGGTGACTCTACAAATGA CCAGTCTGACAGCCGCGGACACGGCCACCTATTTCTGTGCGAGAGGTGGC TGGACTAATTACTTTTGGGGCCCAGGCACCCTGGTCACCGTCTCTTCA | 293 |
| DDR1-26H | GAGCAGTCGTTGAAGGAGTCCGGGGGAGACCTGGTCAAGCCTGGGGCATC CCTGACACTCACCTGCACAGCCTCTGGATTCGACCTCAGTAGCAACTACT ACATGTGCTGGGTCCGCCAGGCTCCAGGGAAGGGGCCTGAGTGGATCGCA TGCATTTATAGTAGTAATACTAGAACATGGTACGCGCGCTGGGCGAAAGG CCGATTCACCATCTCCAAGACCTCGTCGACCGCGGTGACTCTACAAATGA CCAGTCTGACAGCCGCGGACACGGCCACCTATTTCTGTGCGAGAGGTGGC TGGACTAATTACTTGTGGGGCCCAGGCACCCTAGTCACCATCTCCTCA | 294 |
| DDR1-28H | CAGTCGGTGGAGGAGTCCGGGGGTCGCCTGGTCACGCCTGGGACACCCCT GACACTCACCTGCACAGTCTCTGGATTCTCCCTCAGTAGCCACGACATGA TCTGGGTCCGCCAGGCTGCAGGGAAGGGGCTGGAATGGATCGGACTTATT ATTAGTAGTGGTAACACATGGTACGCGAGCTGGGCGAAAGGCCGATTCAC CATCTCCAAAACCTCGACCACGGTGGATCTGAAAATGACCAGTCTGACAA CCGAGGACACGGCCACCTATTTCTGTGCCAGAGATGTTTATAGTGGTGCG AGTCCTTGGGGCCCAGGCACCCTGGTCACCATCTCCTCA | 295 |
| DDR1-29H | CAGTCGGTGAAGTCCGGGGGAGGCCTGGTCAAGCCTGGGGCATCCCTGAC ACTCACCTGCAAAGCCTCTACATTCTCCTTCAATAGCCGCTACTGGACAT GCTGGGTCCGCCAGGCTCCAGGGAAGGGACTGGAGTGGATCGGATGTATT AATAACGGTGACATTACCACTTACACACGAACTGGGCGACCGGCCGATT | 296 |

TABLE 9-continued

DNA sequences encoding heavy chain variable regions of anti-DDR1 antibodies

| mAb name | Polynucleotide heavy chain variable region | SEQ ID NO. |
|---|---|---|
| | CACCATCTCCAAGTCCTCGTCGACCACGGTGACTCTGCAAATGACCAGTC TGACAGCCGCGGACACGGCCACCTATTTCTGTGCGAAAGGGGGTAATCTT GCTGGTGATTGTTATGGGTTGTGGGGCCCAGGCACCCTGGTCACCATCTCA | |
| DDR1-32H | CAGTCGTTGGAGGAGTCCGGGGGTCGCCTGGTCACGCCTGGGACACCCCT GACACTCACCTGCACAGCCTCTGGATTCTCCCTCAGTAGTTACTACATGA GCTGGGTCCGCCAGGCTCCAGGGGAGGGGCTGGAATGGATCGGAACCATT ACTACTGCTGGTCCACTATATTACGCGACCTGGGCGAAAGGCCGATTCAC CATCTCCAAAACCTCGACCACGGTGGATCTGAAAATGACCGGTCCGACAA CCGAGGACACGGCCACCTATTTCTGTGCCAGAGGGCATGCTGGTAGTATT TATTATTCATACTTTGACTTGTGGGGCCCAGGCACCCTGGTCACCGTCTC TTCA | 297 |
| DDR1-33H | CAGTCGGTGGAGGAGTCCGGGGGTCGCCTGGTCACGCCTGGAGGATCCCT GACACTCACCTGCACAGTCTCTGGATTCTCCCTCAGCAGCTACGACATGA GCTGGGTCCGCCAGGCTCCAGGGAAGGGGCTGGAGTGGATCGGAATCAGT TGGAATAGTGGCTTTGTTGACTACGCGAGCTGGGCGAAAGGCCGATTCAG CATCTCCAAAACCTCGACCACGGTGGATCTGAAAATCACCAGTCCGACAA CCGAGGACACGGCCACCTATTTCTGTGCCAGACTTGGTGCTGATGACATC TACTATTTTAACTTGTGGGGCCCAGGCACCCTGGTCACCATCTCCTCA | 298 |
| DDR1-34H | CAGTCGGTGAAGGAGTCCGGGGGAGGCCTGGTCAAGCCTGAGGGATCCCT GACACTCACCTGCAAAGCCTCTGGATTCGACCTCAGTAGCTACTACTACA TGTGCTGGGTCCGCCAGGCTCCAGGGAAGGGGCTGGAGTGGATCGCATGC ATTTATACTAGTAGTGGTGCCACATGGTACGCGAACTGGGCGAAAGGCCG ATTCACCATTTCCAAAACCTCGTCGACCACGGTGACTCTGCAGATGACCG CTCTGACAGCCGCGGACACGGCCACCTATTTCTGTGCGAGAGGAGGTTGG TGCGACTTTAACTTGTGGGGCCCAGGCACCCTGGTCACCATCTCCTCA | 299 |

In some embodiments, a polynucleotide encoding a humanized light chain variable region and/or humanized heavy chain variable region of antibody DDR1-9 (DDR1-9hu) is selected from the polynucleotides presented in Table 10.

TABLE 10

Humanized DDR1-9hu antibody sequences - nucleic acids

| mAb | Polynucleotide Sequence | SEQ ID NO. |
|---|---|---|
| DDR1-9hu_Hv | CAAGTGCAGCTGGTGGAGAGCGGAGGCAGAGTGGTGCAGCCCGGCAGA TCTCTGAGACTGAGCTGTACCGCCAGCGGCTTCTCTCTGAATAGATAC TACATGCTGTGGGTGAGACAAGCCCCCGGCAAGGGACTGGAGTGGATC GGCACCATCAGCTACGGCGATACCACCTACTACGCCAGCTGGGCCAAG GGAAGATTCACCATCTCTAGAGACAACTCCAAGAACACACTGTATCTG CAGATGAACTCTCTGAGAGCCGAGGACACCGCCGTGTACTACTGCGCC AGAGCCGATACCGGCGACAACGGCTATCTGGGACTGCAGCTGTGGGGA CAAGGCACACTGGTGACCGTGAGCAGC | 300 |
| DDR1-9hu_Lv1 | GACATCCAGATGACCCAGAGCCCTAGCAGCGTGAGCGCTAGCGTGGGA GACAGAGTGACCATCACATGCCAAGCCAGCCAGAGCATTGGCAGCGTG CTGGCTTGGTACCAGCAGAAGCCCGGCAAGGCCCCCAAGCTGCTGATC AGCGGCGTGTTTGATCTGGCCAGCGGCGTGCCCTCCAGATTTAGCGGC AGCGGCAGCGGAACCGATTTCACACTGACCATCAGCTCTCTGCAGCCC GAGGACTTCGCCACCTACTACTGCCAGTACATCCCTTACGGCAGCTCC CCCTTTGGCGGAGGCACCAAGGTGGAAATCAAG | 301 |
| DDR1-9hu_Lv2 | GATATCCAGATGACCCAGAGCCCTAGCAGCGTGAGCGCTAGCGTGGGA GACAGAGTGACCATCACATGCAGAGCCTCCCAGAGCATTGGCAGCGTG CTGGCTTGGTACCAGCAGAAGCCCGGCAAGGCCCCCAAGCTGCTGATC TACGGAGTGTTCTCTCTGCAGAGCGGCGTGCCCTCCAGATTTTCCGGC AGCGGCTCCGGCACAGACTTCACACTGACCATCAGCTCTCTGCAGCCC GAGGACTTCGCCACCTACTACTGCCAGTACATCCCTTACGGCAGCTCC CCCTTTGGAGGCGGCACCAAAGTGGAGATCAAG | 302 |

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide sequence selected from SEQ ID NOs: 258-278 and SEQ ID NOs: 301 and 302, and encodes the corresponding light chain variable region selected from SEQ ID NO: 108-128 or SEQ ID NOs: 150-151.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide sequence selected from SEQ ID NOs: 279-299 and SEQ ID NO: 300, and encodes the corresponding heavy chain variable region selected from SEQ ID NO: 129-149 or SEQ ID NO: 152.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to the reference polynucleotide sequence of SEQ ID NO: 262 or 276, and encodes the corresponding light chain variable region of SEQ ID NO:112 or 126.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to the reference polynucleotide sequence of SEQ ID NO: 283 or 297, and encodes the corresponding heavy chain variable region of SEQ ID NO:133 or 147.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to the reference polynucleotide sequence of SEQ ID NO: 301 or 302, and encodes the corresponding light chain variable region of SEQ ID NO:150 or 151.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to the reference polynucleotide sequence of SEQ ID NO: 300, and encodes the corresponding heavy chain variable region of SEQ ID NO:152.

In further embodiments, the nucleic acids of the present disclosure comprise polynucleotides that hybridize to polynucleotides encoding the antibodies disclosed herein. In some embodiments, the polynucleotides hybridize to a polynucleotide selected from SEQ ID NOs: 258-278 and SEQ ID NOs: 301 and 302 and encode a light chain variable region of an antibody that specifically binds to DDR1 protein. In some embodiments, the polynucleotides hybridize to a polynucleotide selected from SEQ ID NOs: 279-299 and SEQ ID NO: 300 and encode a heavy chain variable region of an antibody that specifically binds to DDR1 protein.

In general, the nucleic acids hybridize under moderate or high stringency conditions to nucleic acids that encode antibodies disclosed herein and also encode antibodies that maintain the ability to specifically bind to a DDR1 protein. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., MOLECULAR CLONING: A LABORATORY MANUAL, 3$^{rd}$ ed., Cold Spring Harbor Press, Cold Spring Harbor, N.Y. 2001). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

In some embodiments, the polynucleotides herein may be manipulated in a variety of ways to provide for expression of the encoded polypeptide such as a light chain variable region or heavy variable region disclosed herein. In some embodiments, the polynucleotide is operably linked to control sequences, including among others, transcription promoters, leader sequences, transcription enhancers, ribosome binding or entry sites, termination sequences, and polyadenylation sequences for expression of the polynucleotide and/or corresponding polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., Molecular Cloning: A Laboratory Manual, 3rd Ed., Cold Spring Harbor Laboratory Press, New York (2001); and Current Protocols in Molecular Biology, Ausubel. F. ed., Greene Pub. Associates (1998), updates to 2020.

In some embodiments, the polynucleotides can be part of an expression vector, where the vector and polynucleotide includes one or more operably linked control sequences for controlling expression of the polynucleotide and/or expression of the encoded polypeptide. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids. Exemplary expression vectors include, among others, vectors based on T7 or T7lac promoters (pACY: Novagen; pET); vectors based on Baculovirus promoters (e.g., pBAC); vectors based on Ef1-α and HTLV promoters (e.g., pFUSE2; Invitrogen, CA, USA); vectors based on CMV enhancer and human ferritin light chain gene promoters (e.g., pFUSE: Invitrogen, CA, USA); vectors based on CMV promoters (e.g, pFLAG: Sigma, USA); and vectors based on dihydrofolate reductase promoters (e.g., pEASE: Amgen, USA). Various vectors can be used for transient or stable expression of the polypeptides of interest.

In another aspect, the polynucleotide encoding a polypeptide is operatively linked to one or more control sequences for expression of the polypeptide in a host cell.

Host cells for use in expressing the polypeptides are well known in the art and include, but are not limited to, bacterial cells, such as *E. coli*, yeast cells; insect cells such as *Drosophila* S2 and *Spodoptera* Sf9 cells; animal cells such as Chinese Hamster Ovary (CHO), African Green Monkey kidney (COS), baby hamster kidney (BHK), mouse myelomas (e.g., NS0 and Sp2/0), and human embryo kidney (HEK); and plant cells. Appropriate culture mediums and growth conditions for the above-described host cells are well known in the art. In some embodiments, the host cells and the expression vectors are used to express the polypeptides of interest.

In some embodiments, the host cells comprising the expression vectors and polynucleotides described herein are cultured in suitable media and under culture conditions appropriate for expression of the encoded polypeptide, for example the polypeptides comprising the amino acid sequences selected from SEQ ID NOs: 108-128; SEQ ID NOs: 150 and 151; SEQ ID NOs: 129-149; and SEQ ID NO:152. In some embodiments, an in vitro expression system can be used with the expression vectors to express the polypeptide. In vitro expression systems include those based on *E. coli*., rabbit reticulocyte, wheat germ, insect cells, and human cells. Whether expressed in a host cell or in vitro, the expressed polypeptides can be isolated or purified, as further described herein.

IV. METHODS FOR PREPARATION OF ANTIBODIES AND MODIFICATIONS THEREOF

In some embodiments, the monoclonal antibodies described herein can be prepared using standard methods, followed by screening, characterization and functional assessment. For example, variable regions can be sequenced and then subcloned into a human expression vector to produce the chimeric antibody genes, which are then expressed and purified. These chimeric antibodies can be tested for antigen binding, signaling blocking, and in xenograft experiments.

A. General Methods

It will be understood that monoclonal antibodies binding to DDR1 will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

In some embodiments, the preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 10 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full-length IgG antibodies may be generated by subcloning heavy and light chain Fv DNAs from the cloning vector into an IgG plasmid vector, transfected into 293 Freestyle cells or CHO cells, and antibodies collected a purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules can comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

As discussed above, the antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In some embodiments, the hinge region of CH1 is modified such that the number of cysteine residues in the hinge region is increased or decreased. A exemplary approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328. In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714, 350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (See for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3GlcNAc2; GalGlcNAc2Man3GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man5GlcNAc2(Fuc), GlcNAcMan5GlcNAc2(Fuc), Man3GlcNAc2(Fuc), GlcNAcMan3GlcNAc2(Fuc), GlcNAc2Man3GlcNAc2(Fuc), GalGlcNAc2Man3GlcNAc2(Fuc), Gal2GlcNAc2Man3GlcNAc2(Fuc), NANAGal2GlcNAc2Man3GlcNAc2(Fuc), and NANA2Gal2GlcNAc2Man3GlcNAc2(Fuc); in an α1,3-linkage or α1,4-linkage fucose to produce a glycoform selected from the group consisting of GlcNAc(Fuc)Man5GlcNAc2, GlcNAc(Fuc)Man3GlcNAc2, GlcNAc2(Fuc1-2)Man3GlcNAc2, GalGlcNAc2(Fuc1-2)Man3GlcNAc2, Gal2GlcNAc2(Fuc1-2)Man3GlcNAc2, NANAGal2GlcNAc2(Fuc1-2)Man3GlcNAc2, and NANA2Gal2GlcNAc2(Fuc1-2)Man3GlcNAc2; or in an α1,2-linkage fucose to produce a glycoform selected from the group consisting of Gal(Fuc)GlcNAc2Man3GlcNAc2, Gal2(Fuc1-2)GlcNAc2Man3GlcNAc2, NANAGal2(Fuc1-2)GlcNAc2Man3GlcNAc2, and NANA2Gal2(Fuc1-2)GlcNAc2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated bisected and multiantennary species. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein.

C. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

D. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

V. USES AND COMPOSITIONS OF THE ANTI-DDR1 ANTIBODIES

A. Therapeutic Methods and Uses

1. Treatment of Cancer

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In the present disclosure, anti-DDR1 antibodies or antigen-binding fragments thereof described herein may be used to decrease cancer cell counts and as such can potentially be used to treat a variety of types of cancer lines. In some aspects, the antibodies or antigen-binding fragments thereof of the present disclosure may be used to treat cancers, including solid tumors, particularly cancers that secrete DDR1 protein or portions thereof (such as the DDR1 extracellular domain) and/or have DDR1 present on the surface of the cancer cell or cancer stem cell. In some embodiments, a cancer or cancer cells that overexpress DDR1 protein are selected for treatment with the antibodies of the present disclosure.

In some embodiments, cancer and cancer cell types that may be treated according to the present disclosure include, but are not limited to cancer or cancer cells of the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

In some embodiments, the antibodies or antigen-binding fragments are used for treating pancreatic cancer; lung cancer, including small cell lung cancer and non-small cell lung cancer; colon and colorectal cancer; head and neck cancer, stomach (gastric) cancer; ovarian cancer; breast cancer; kidney cancer; liver cancer; prostate cancer, cervical cancer, brain cancer; skin cancer, including melanoma; or bone cancer. In some embodiments, the cancer selected for treatment is breast cancer, including various breast cancer subtypes, as further discussed below.

In some embodiments, the subject selected for treatment with the antibodies or antigen-binding fragments thereof has a cancer that secretes DDR1 protein or portion thereof, and/or has DDR1 protein present on the cell surface of the cancer cell. In some embodiments, a method for treating cancer includes a step of determining whether the cancer for treatment secretes DDR1 protein and/or has DDR1 protein on expressed on the surface of the cancer cells.

In some embodiments, the antibodies or antigen-binding fragments thereof are used for treating a hematological or blood cancer, including but not limited to, malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the subject selected for treatment with the antibodies or antigen-binding fragments thereof has a cancer that secretes DDR1 protein or portion thereof, and/or has DDR1 protein present on the cell surface of the cancer cells. In some embodiments, a method for treating cancer includes a step of determining whether the cancer for treatment secretes DDR1 protein and/or has DDR1 protein on expressed on the surface of the cancer cells. Accordingly, in some embodiments, a method of treating cancer in a subject comprises determining the presence of secreted DDR1 protein or presence of DDR1 protein on the surface of cancer cells in the subject, and if the cancer cells are determined to have secreted DDR1 protein or have DDR1 present on surface of cancer cells, treating the cancer in the subject by administering a therapeutically effective amount of the antibody or antigen-binding fragments disclosed herein.

2. Treatment of Breast Cancer

In some embodiments, the cancer for treatment is breast cancer, which typically originates in the breast, usually in the inner lining of the milk ducts or lobules. There are different types of breast cancer, with different stages (spread), aggressiveness, and genetic makeup. With best treatment, 10-year disease-free survival varies from 98% to 10%. Treatment is selected from surgery, drugs (chemotherapy), and radiation. In the United States, there were 216,000 cases of invasive breast cancer and 40,000 deaths in 2004. Worldwide, breast cancer is the second most common type of cancer after lung cancer (10.4% of all cancer incidence, both sexes counted) and the fifth most common cause of cancer death. In 2004, breast cancer caused 519,000 deaths worldwide (7% of cancer deaths; almost 1% of all deaths). Breast cancer is about 100 times as frequent among women as among men, but survival rates are equal in both sexes.

The first symptom, or subjective sign, of breast cancer is typically a lump that feels different from the surrounding breast tissue. According to the Merck Manual, more than 80% of breast cancer cases are discovered when the woman feels a lump. According to the American Cancer Society, the first medical sign, or objective indication of breast cancer as detected by a physician, is discovered by mammogram. Lumps found in lymph nodes located in the armpits can also indicate breast cancer. Indications of breast cancer other than a lump may include changes in breast size or shape, skin dimpling, nipple inversion, or spontaneous single-nipple discharge. Pain ("mastodynia") is an unreliable tool in determining the presence or absence of breast cancer but may be indicative of other breast health issues.

When breast cancer cells invade the dermal lymphatics-small lymph vessels in the skin of the breast-its presentation can resemble skin inflammation and thus is known as inflammatory breast cancer (IBC). Symptoms of inflammatory breast cancer include pain, swelling, warmth and redness throughout the breast, as well as an orange-peel texture to the skin referred to as "peau d'orange." Another reported symptom complex of breast cancer is Paget's disease of the breast. This syndrome presents as eczematoid skin changes such as redness and mild flaking of the nipple skin. As Paget's advances, symptoms may include tingling, itching, increased sensitivity, burning, and pain. There may also be discharge from the nipple. Approximately half of women diagnosed with Paget's also have a lump in the breast.

Occasionally, breast cancer presents as metastatic disease, that is, cancer that has spread beyond the original organ. Metastatic breast cancer will cause symptoms that depend on the location of metastasis. Common sites of metastasis include bone, liver, lung and brain. Unexplained weight loss can occasionally herald an occult breast cancer, as can symptoms of fevers or chills. Bone or joint pains can sometimes be manifestations of metastatic breast cancer, as can jaundice or neurological symptoms. These symptoms are "non-specific," meaning they can also be manifestations of many other illnesses.

The primary risk factors that have been identified are sex, age, childbearing, hormones, a high-fat diet, alcohol intake, obesity, and environmental factors such as tobacco use, radiation and shiftwork. No etiology is known for 95% of breast cancer cases, while approximately 5% of new breast cancers are attributable to hereditary syndromes. In particular, carriers of the breast cancer susceptibility genes, BRCA1 and BRCA2, are at a 30-40% increased risk for breast and ovarian cancer, depending on in which portion of the protein the mutation occurs. Experts believe that 95% of inherited breast cancer can be traced to one of these two genes. Hereditary breast cancers can take the form of a site-specific hereditary breast cancer—cancers affecting the breast only—or breast-ovarian and other cancer syndromes. Breast cancer can be inherited both from female and male relatives.

Breast cancer subtypes are typically categorized on an immunohistochemical basis. Subtype definitions are generally as follows:
 normal (ER+, PR+, HER2+, cytokeratin 5/6+, and HER1+)
 luminal A (ER+ and/or PR+, HER2−)
 luminal B (ER+ and/or PR+, HER2+)
 triple-negative (ER−, PR−, HER2−)
 HER2+/ER−(ER−, PR−, and HER2+)
 unclassified (ER−, PR−, HER2−, cytokeratin 5/6−, and HER1−)

In the case of triple-negative breast cancer cells, the cancer's growth is not driven by estrogen or progesterone, or by growth signals coming from the HER2 protein. By the same token, such cancer cells do not respond to hormonal therapy, such as tamoxifen or aromatase inhibitors, or therapies that target HER2 receptors, such as HERCEPTIN® (trastuzumab). About 10-20% of breast cancers are found to be triple-negative. It is important to identify these types of cancer so that one can avoid costly and toxic effects of therapies that are unlike to succeed, and to focus on treatments that can be used to treat triple-negative breast cancer. Like other forms of breast cancer, triple-negative breast cancer can be treated with surgery, radiation therapy, and/or chemotherapy. One particularly promising approach is "neo-adjuvant" therapy, where chemo- and/or radiotherapy is provided prior to surgery. Another drug therapy is the use of poly (ADP-ribose) polymerase, or PARP inhibitors.

While screening techniques discussed above are useful in determining the possibility of cancer, a further testing is necessary to confirm whether a lump detected on screening is cancer, as opposed to a benign alternative such as a simple cyst. In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), performed as an outpatient procedure using local anaesthetic, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

Breast cancer screening is an attempt to find cancer in otherwise healthy individuals. The most common screening method for women is a combination of x-ray mammography and clinical breast exam. In women at higher than normal risk, such as those with a strong family history of cancer, additional tools may include genetic testing or breast Magnetic Resonance Imaging.

Breast self-examination was a form of screening that was heavily advocated in the past, but has since fallen into disfavour since several large studies have shown that it does not have a survival benefit for women and often causes considerably anxiety. This is thought to be because cancers that could be detected tended to be at a relatively advanced stage already, whereas other methods push to identify the cancer at an earlier stage where curative treatment is more often possible.

X-ray mammography uses x-rays to examine the breast for any uncharacteristic masses or lumps. Regular mammograms are recommended in several countries in women over a certain age as a screening tool.

Genetic testing for breast cancer typically involves testing for mutations in the BRCA genes. This is not generally a recommended technique except for those at elevated risk for breast cancer.

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided into high risk and low risk cases, with each risk category following different rules for therapy. Treatment possibilities include radiation therapy, chemotherapy, hormone therapy, and immune therapy.

Targeted cancer therapies are treatments that target specific characteristics of cancer cells, such as a protein that allows the cancer cells to grow in a rapid or abnormal way. Targeted therapies are generally less likely than chemotherapy to harm normal, healthy cells. Some targeted therapies are antibodies that work like the antibodies made naturally by one's immune system. These types of targeted therapies are sometimes called immune-targeted therapies.

There are currently 3 targeted therapies doctors use to treat breast cancer. HERCEPTIN® (trastuzumab) works against HER2-positive breast cancers by blocking the ability of the cancer cells to receive chemical signals that tell the cells to grow. TYKERB® (lapatinib) works against HER2-positive breast cancers by blocking certain proteins that can cause uncontrolled cell growth. AVASTIN® (bevacizumab) works by blocking the growth of new blood vessels that cancer cells depend on to grow and function.

Hormonal (anti-estrogen) therapy works against hormone-receptor-positive breast cancer in two ways: first, by lowering the amount of the hormone estrogen in the body, and second, by blocking the action of estrogen in the body. Most of the estrogen in women's bodies is made by the ovaries. Estrogen makes hormone-receptor-positive breast cancers grow. So reducing the amount of estrogen or blocking its action can help shrink hormone-receptor-positive breast cancers and reduce the risk of hormone-receptor-positive breast cancers coming back (recurring). Hormonal therapy medicines are not effective against hormone-receptor-negative breast cancers.

There are several types of hormonal therapy medicines, including aromatase inhibitors, selective estrogen receptor modulators, and estrogen receptor down regulators. In some cases, the ovaries and fallopian tubes may be surgically removed to treat hormone-receptor-positive breast cancer or as a preventive measure for women at very high risk of breast cancer. The ovaries also may be shut down temporarily using medication.

In planning treatment, doctors can also use PCR tests like Oncotype DX or microarray tests that predict breast cancer recurrence risk based on gene expression. In February 2007, the first breast cancer predictor test won formal approval from the Food and Drug Administration. This is a new gene test to help predict whether women with early-stage breast cancer will relapse in 5 or 10 years, this could help influence how aggressively the initial tumor is treated.

Radiation therapy is also used to help destroy cancer cells that may linger after surgery. Radiation can reduce the risk of recurrence by 50-66% when delivered in the correct dose.

Accordingly, in some embodiments, the antibodies or antigen-binding fragments thereof are used to treat breast cancer, including each of the subtypes of breast cancer described above. In some embodiments, the antibodies or antigen-binding fragments thereof of the present disclosure are used in combination with a second therapeutic agent, where the second therapeutic agent includes one or more agents described herein (e.g., radiation, chemotherapeutic agents, hormones, and immunotherapeutic agents). In some embodiments, the breast cancer or subtype thereof that is determined to have DDR protein on the cell surface or secrets DDR1 protein, is treated with the antibodies or antigen-binding fragments.

3. Treatment of Fibrotic Disorders

In addition to expression in cancers, DDR1 protein is also expressed in the kidney, lung, gastrointestinal tract, skin, and brain, among other organs and has been implicated in fibrosis of the skin, lung and liver (Moll, et al. 2019, incorporated herein by reference). Therefore, in some embodiments, the anti-DDR1 antibodies or antigen-binding fragments thereof of the present disclosure can be used, alone or in combination with other therapies, to treat fibrotic disorders. In some embodiments, the fibrotic disorder is organ fibrosis. In some embodiments, the fibrotic disorder is fibrosis of the skin, kidney, liver, lung, or heart. In some embodiments, the fibrotic disorder treated is, but not limited to, skin hypertrophic scars, idiopathic pulmonary fibrosis, cirrhotic liver and renal fibrosis.

In some embodiments, the fibrotic disorder for treatment is fibrosis of the lung. In some embodiments, the subject treated has interstitial lung disease. In some embodiments, the subject treated has Idiopathic Pulmonary Fibrosis (IPF) or lung scarring.

B. Formulations and Administration

In another aspect, the present disclosure provides pharmaceutical compositions comprising anti-DDR1 antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In some embodiments, the compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In some embodiments, the antibody or antigen-binding fragment thereof is administered in an effective amount to treat a disease or disorder, in particular a cancer, such as breast cancer. The amount of anti-DDR1 antibody administered will depend upon a variety of factors, including but not limited to, the particular type of cancer treated, the stage of the cancer being treated, the mode of administration, the frequency of administration, the desired therapeutic benefit, and other parameters such as the age, weight and other characteristics of the patient, etc.

Dosages effective to provide therapeutic benefit may be estimated initially from in vivo animal models or clinical trials. Suitable animal models for various diseases are known in the art, and determination of dosages effective to provide therapeutic benefit for specific modes and frequency of administration is within the capabilities of those skilled in the art.

In some embodiments, the anti-DDR1 antibody or antigen binding fragment thereof can be administered can be in the range of 0.0001-100 mg/kg body weight. Wide variations in the dosages administered are to be expected in view of the variety of antibody compositions available and the differing efficiencies of various routes of administration. Variations in these dosage levels can be adjusted using standard empirical routines for optimization as is well understood in the art. In some embodiments, for treatment of indications described herein, the effective dose of an antibody of the disclosure can range from about 0.001 to about 75 mg/kg body weight; 0.005 mg/kg to about 50 mg/kg body weight; about 0.01 mg/kg to about 30 mg/kg body weight; or about 0.01 to 5 mg/kg body weight.

C. Cell Therapies

In another aspect, the present disclosure provides immune cells which express a chimeric antigen receptor (CAR). In some embodiment, The CAR comprises an antigen-binding fragment provided herein. In some embodiments, the CAR protein includes from the N-terminus to the C-terminus: a leader peptide, an anti-DDR1 heavy chain variable domain, a linker domain, an anti-DDR1 light chain variable domain, a human IgG1-CH2-CH3 domain, a spacer region, a CD28 transmembrane domain, a anti-DDR1 intracellular co-stimulatory signaling and a CD3 (intracellular T cell signaling domain.

Also provided are methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy.

The immune cells may be T cells (e.g., regulatory T cells, CD4+ T cells, CD8+ T cells, or gamma-delta T cells), NK cells, invariant NK cells, NKT cells, or macrophages. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from healthy human subjects, healthy volunteers, or healthy donors. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible. To be rendered subject-compatible, allogeneic cells can be treated to reduce immunogenicity.

The immune cells can be genetically engineered to express antigen receptors such as engineered TCRs and/or chimeric antigen receptors (CARs). For example, the host cells (e.g., autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook et al., supra; and Ausubel et al., CURRENT PROTOCOLS IN MOLECULAR BIOLOGY, Greene Publishing Associates and John Wiley & Sons, NY, 1994. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

D. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-DDR1 antibody or the other therapy will be desired. Various combinations may be employed, where the antibody is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (CEPLENE®) and interleukin 2 (PROLEUKIN®) after the completion of consolidation therapy, gemtuzumab ozogamicin (MYLOTARG®) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection (VYXEOS®), an azacytidine (VIDAZA®), a decitabine, an all-trans-retinoic acid (ATRA), an arsenic, an arsenic trioxide, a histamine dihydrochloride (CEPLENE®), an interleukin-2, an aldesleukin (PROLEUKIN®), a gemtuzumab ozogamicin (MYLOTARG®), an FLT-3 inhibitor, a midostaurin (RYDAPT®), a clofarabine, a farnesyl transferase inhibitor, a decitabine, an IDH1 inhibitor, an ivosidenib (TIBSOVO®), an IDH2 inhibitor, an enasidenib (IDHIFA®), a smoothened (SMO) inhibitor, a glasdegib, an arginase inhibitor, an IDO inhibitor, an epacadostat, a BCL-2 inihbitor, a venetoclax (VENCLEXTA®), a platinum complex derivative, oxaliplatin, a kinase inhibitor, a tyrosine kinase inhibitor, a PI3 kinase inhibitor, a BTK inhibitor, an ibrutinib (IMBRUVICA®), an acalabrutinib (CALQUENCE®), a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor. In some embodiments, the agent used in a combination therapy is an agent that has been previously used as therapy for a specified indication, such as a specific type of cancer. In some embodiments, a specific indication is breast cancer, and the agent used in combination with the antibodies or antigen-binding agents thereof is an agent that is accepted treatment for breast cancer.

VI. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Antibody conjugates are also preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In some embodiments, the moiety attached to the antibody or antigen-binding fragments thereof is a paramagnetic ion, which can be selected from, among others, chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, the isotope may be selected from astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include ALEXA FLUOR®350, ALEXA FLUOR®430, AMCA, BODIPY 630/650, BODIPY 650/665, BODIPY-FL, BODIPY-R6G, BODIPY-TMR, BODIPY-TRX, CASCADE BLUE®, Cy3, Cy5,6-FAM, Fluorescein Isothiocyanate, HEX, 6-JOE, OREGON GREEN® 488, OREGON GREEN® 500, OREGON GREEN® 514, PACIFIC BLUE®, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VII. IMMUNODETECTION METHODS

In still further embodiments, the present disclosure concerns immunodetection methods for binding, purifying, removing, quantifying and otherwise generally detecting DDR1-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of DDR1s also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing DDR1-related cancers and contacting the sample with a first antibody in accordance with the present disclosure, as the case may be, under conditions effective to allow the formation of immunocomplexes.

These methods include methods for detecting or purifying DDR1s or DDR1-related cancer cells from a sample. The antibody will preferably be linked to a solid support, such as in the form of a column matrix, and the sample suspected of containing the DDR1-related cancer cells will be applied to the immobilized antibody. The unwanted components will be washed from the column, leaving the DDR1-expressing cells immunocomplexed to the immobilized antibody, which is then collected by removing the organism or antigen from the column.

The immunobinding methods also include methods for detecting and quantifying the amount of DDR1-related cancer cells or related components in a sample and the detection and quantification of any immune complexes formed during the binding process. Here, one would obtain a sample suspected of containing DDR1-related cancer cells and contact the sample with an antibody that binds DDR1s or components thereof, followed by detecting and quantifying the amounts of immune complexes formed under the specific conditions. In terms of antigen detection, the biological sample analyzed may be any sample that is suspected of containing DDR1-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to DDR1s. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the DDR1-related cancer cells is added to the wells. After binding and washing to remove non-specifically bound immune complexes, the bound antigen may be detected. Detection may be achieved by the addition of another anti-DDR1 antibody that is linked to a detectable label. This type of ELISA is a simple "sandwich ELISA." Detection may also be achieved by the addition of a second anti-DDR1 antibody, followed by the addition of a third antibody that has binding affinity for the second antibody, with the third antibody being linked to a detectable label.

In another exemplary ELISA, the samples suspected of containing the DDR1-related cancer cells are immobilized onto the well surface and then contacted with the anti-DDR1 antibodies of the disclosure. After binding and washing to remove non-specifically bound immune complexes, the bound anti-DDR1 antibodies are detected. Where the initial anti-DDR1 antibodies are linked to a detectable label, the immune complexes may be detected directly. Again, the immune complexes may be detected using a second antibody that has binding affinity for the first anti-DDR1 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

In some embodiments, the antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect DDR1-related cancer cells, the antibodies may be included in the kit. The immunodetection kits will thus comprise, in suitable container means, a first antibody that binds to an DDR1, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of DDR1s, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

CRISPR KO. DDR1 was knocked out in M-WNT, AT-3 and E0771 by using DDR1 sgRNA CRISPR/Cas9 All-in-One Lentivector set (ABM; Cat: #K4331005) following the manufacturer's instruction. Briefly, lentivirus packaging was carried out by co-transfecting HEK293T cells with DDR1 KO vector and two helper vectors (psPAX2 and pMD2.G) via Lipofectamine 2000 (Life Technologies, Cat: #11668027). Two days later, lentivirus-containing supernatant was harvested and used to infect target tumor cells. Single clones were picked and expanded following antibiotic selection. Genomic DNA of all selected KO clones were extracted and sequenced to verify desired mutations. sgRNA sequences are as follows: sgRNA1, AAGCAGTGATGGAGATG (SEQ ID NO: 303); sgRNA2, TGTGTTCCCCAAAGAAG (SEQ ID NO: 304); sgRNA3, GACCATGCAGTTATCTG (SEQ ID NO: 305). Scrambled sgRNA sequence was used as a control.

Western Blotting. For cell lysate preparation, cells were lysed with Laemmli buffer. Protein concentration was evaluated by BCA Protein Assay Kit (Pierce, 23225). Protein were then run by SDS-PAGE and transferred to membrane following established protocols. Primary antibodies are: anti-DDR1 (dilution: 1:1000; CST, 5583S) and anti-GAPDH (dilution:1:5000; CST, 2118S).

For harvesting protein in conditioned media, media were harvested and centrifuged at 6,000 rpm followed by passing through filters with a 0.45 um pore size to remove any cell debris. Media were run on SDS-PAGE followed by immunoblotting with anti-DDR1 ECD antibody (dilution: 1:1000; R&D, AF2396).

qRT-PCR. RNA extraction and RT-qPCR were done as previously described (Sun et al., 2018). Briefly, ImProm-II reverse transcription system (Promega, A3800) was used to reverse-transcribe RNA and Luminaris Color HiGreen qPCR Master Mix (Thermo Fisher Scientific, K0364) was used to set up real-time PCR. Relevant Primers were made through Primer Premier software. Primer sequences are as follows:

```
Col1a2-F    GGTGAGCCTGGTCAAACGG (SEQ ID NO: 306)
Col1a2-R    ACTGTGTCCTTTCACGCCTTT (SEQ ID NO: 307)
Col12a1-F   AGGCAGAAGTTGACCCACCT (SEQ ID NO: 308)
Col12a1-R   CAGTGGTACTAGCTGCAAGGG (SEQ ID NO: 309)
mActin-F    CAACGAGCGGTTCCGATG (SEQ ID NO: 310)
mActin-R    GCCACAGGATTCCATACCCA (SEQ ID NO: 311)
```

MTT. Tumor cells were seeded in 96-well plates and cultured for indicated time period before analysis. On the day of harvest, MTT solution (3 mg/ml) was added into individual wells and the plates were incubated for 1 hour. medium was subsequently removed and purple precipitation was dissolved by 100 µl DMSO. Absorbance at 570 nm was measured for individual wells.

Tumor cells migration and invasion. For cell migration, tumor cells were suspended in culture medium without serum and then seeded on top of the transwell chamber. Medium with 10% FBS was placed at the bottom of the chamber. Cells were cultured for 12 hours before analysis.

For cell invasion, matrigel matrix (Corning, 354483) was loaded on the inserts following the manufacturer's instruction and incubated at 37° C. for 30 minutes. Tumor cells were seeded on the top chamber of the inserts with 10% FBS-containing medium in the bottom chamber. Cells were then incubated at 37° C. for 20 hours. Cells on the upper side of the top chamber were gently removed and cells on the bottom side of the top chamber were stained with crystal violet and six random fields were counted by standard microscope.

Mice treatment and tumor study. All animal experiments were approved by the Institutional Animal Care and Use Committee at the George Washington University. 8-week-old WT C57BL/6 (Jackson Lab, 000664), Rag1$^{-/-}$ (Jackson Lab, 002216) or Nude (Jackson Lab, 002019) mice were used for tumor study. E0771, AT-3 and M-Wnt cells were injected in the mouse mammary gland fat pad at a dose of $5\times10^5$, $2\times10^5$, and $2\times10^5$ cells per inoculate, respectively, in a volume of 100 µl. Tumor volumes (0.5×length×width$^2$) were measured with caliper on the indicated days. Upon tumor harvest, tumors were weighed and samples were used for immunophenotyping and IHC.

For tumor transplant assay, tumor cells were firstly inoculated in Rag1$^{-/-}$ mice. When tumor volume reached approximately 200~300 mm$^3$ (usually 20 days after inoculation), 60 mg of tumor organoid were transplanted to WT C57BL/6 mice. Tumor samples were collected on day 12 for immunostaining.

For the tumor re-challenge experiment, WT C57BL/6 mice were firstly inoculated with 0.5 million DDR1 KO E0771 or PBS alone in one side of the inguinal mammary gland fat pad. After 30 days, the same mice were inoculated with 0.5 million DDR1 WT E0771 tumor cells on both sides of the mammary gland fat pad. Tumor volumes were measured as mentioned above.

For DDR1 antibody in vivo treatment, both home-made control IgG and anti-huDDR1 ECD antibodies were locally injected into tumor at 10 mg/kg every other day after the size is larger than 100 mm$^3$, until the end of experiment.

Decellularization. E0771 cells were seeded in inserts with 5 µm pore size (Costar, Corning Inc., 3422) at 2,000 cells per insert and cultured in DMEM+10% FBS+1% PS media for 2 days. The resulting ECM from DDR1 WT or KO cells was washed with PBS and decellularized by incubation for 5 min at 37° C. in PBS containing 0.5% Triton X-100 and 20 mM NH$_4$OH. Decellularized ECM was washed 3 times with PBS, followed by 3× rinse with distilled water, and used in the T cell migration experiments immediately.

In vitro CD8$^+$ T cell isolation and migration assay. CD8$^+$ T cells were isolated from splenocytes of C57BL/6 naïve mouse by EasySep™ mouse CD8$^+$ negative isolation kit (Stemcell, 19853) followed by manufacturer's manual. CD8$^+$ T cell migration assay was performed with 6.5 mm polycarbonate membranes and inserts of 5 µm pore size (Costar, Corning Inc., 3422). 0.5 million purified CD8$^+$ T cells were added to the upper chamber and allowed to migrate at 37° C. for 2 hours in the presence of recombinant CCL21 (100 ng/ml, R&D systems, 4576C025CF) together with tumor-conditioned media in the bottom chamber. CD8$^+$ T cells that migrated to the bottom chamber were quantified by flow cytometry. For huDDR1 antibody neutralization, antibody was first co-incubated with conditioned media at 37° C. for 1 hour, and then followed by the procedure described as above.

Second harmonic generation and immunofluorescence. Mouse mammary tumor tissue was embedded and preserved in Optimal Cutting Temperature (OCT) compound at −80° C. Before cutting, samples were brought to −20° C. for at least 2 h and 20 µm thick section was cut using a cryostat. Slides were thawed and incubated at 37° C. for 30 min and then transferred to boiling antigen unmasking solution (Vector labs, H-3300) for 10 min. Samples were incubated with CD3e (BD, 553057) primary and Alexa-488 (Life Technologies) secondary antibodies. Each tumor section was mounted with fluoromount-G media (VWR) onto a microscope coverslip (No 1.5).

All samples were imaged using Leica TCS SP8 multiphoton confocal microscope and a 20×, HC PL Apo, NA 0.7 oil-immersion objective was used throughout the experiments.

The excitation wavelength to 840 nm (Erikson et al., 2007) was tuned, and a 420±5 nm narrow bandpass emission filter was used for detecting the SHG signal of collagen. SHG signal is generated when two photons of incident light interact with the noncentrosymmetric structure of collagen fibers, which leads to the resulting photons being half the wavelength of the incident photons. Images of 1024×1024 pixels were acquired using LAS X software. The collagen measurement was performed using CT Fire software (freely available at loci.wisc.edu/software/ctfire). For collagen from tumor margin analysis, 60 µm area from the boundary of tumor was taken.

Immunohistochemistry staining (IHC). Mouse mammary tumor tissues were fixed with 10% buffered formalin (Fisher Scientific, 23-427098) at 4° C. overnight. Fixed tumor samples were paraffin embedded and cut into 4 µm sections for staining. Samples were deparaffinized and rehydrated in PBS. Sections were boiled with antigen unmasking solution (Vector labs, H-3300) for 20 min, and then blocked with 10% normal groat serum in PBS at room temperature for 1 h. CD8 (Biorbyt, orb10325) and CD4 (Sino Biological Inc., 50134-R001) primary antibodies were incubated at 4° C. overnight. For detection of primary antibody, the ABC Peroxidase Detection System (Vector labs, PK-6105) was used with DAB (Vector labs, SK-4105) as substrate according to the manufacture's instruction.

CD8+ T cell depletion and adoptive transfer. For CD8+ T cells depletion, C57BL/6 mice were administered intraperitoneally with 200 µg/mouse anti-mouse CD8 (clone 2.43, BioxCell, BE0061) or IgG2b isotype control (clone LTF-2, BioxCell, BE0090) two days before tumor inoculation, and then twice per week.

For CD8+ T cells adoptive transfer, purified CD8+ T cells (>90%) were transferred to $Rag1^{-/-}$ mice bearing E0771 mammary tumor after 17 days of tumor inoculation at a concentration of $5 \times 10^6$ cells/mouse.

Picrosirius Red staining. Fixed mammary tumor samples were prepared and sectioned as described previously (Sun et al., 2018). Briefly, paraffin embedded tumor tissues were cut into 4 µm slides and stained with Picro Sirius Red Stain Kit (Abcam, Cat: #ab150681). Sections were deparaffinized and hydrated in distilled water, Picro-Sirius Red Solution were applied to the slides for 1 hour. Then the slides were rinsed in Acetic Acid Solution and dehydrated in absolute alcohol. Mounted slides were then examined under standard microscope and positive collagen fiber signals were quantified by Image J software.

ELISA. Type I collagen was diluted in PBS to a concentration of 50 µg/ml and added to 96-well microtiter plates (50 µl/well). Plates were sealed and incubated for overnight at room temperature and washed three times with Wash Buffer (R&D, WA126), and then blocked by 200 µl Reagent Diluent (R&D, DY995) for 1 hour. After washing three times, 100 µl of conditional media or recombinant ECD (used as standards, Sino Biological, 10730-H08H) was added to the plate for 2 hours at room temperature. Followed by three times of wash, 100 µl of diluted anti-DDR1 N-terminal antibody (1:500, R&D, AF2396) was added and incubated for 2 hours. After reaction with biotin-conjugated antibody for 1 hour, streptavidin-HRP at dilution 1:2000 (R&D, 893975) was added to each well and incubated for 20 minutes in dark. 100 µl substrate solution (R&D, DY999) was added and incubated for another 20 minutes. After adding 50 µl stop solution (R&D, DY994), plate was analyzed in an ELISA reader at 450 nm.

Flow cytometry. Cells were stained for viability using Ghost Dye™ Violet 450 (Tonbo Biosciences, 13-0863-T100) at 1:1000 dilution in PBS for 20 min at 4° C. in the dark, followed by washing with PBS. Samples were blocked with anti-CD16/32 at 1:100 dilution (clone 2.4G2, Tonbo Biosciences, 70-0161-U100). Antibodies were incubated for 30 min at 4° C. in the dark. The following commercial antibodies were used: CD45-BV 645 (Invitrogen, 64-0451-82), CD3-eflour 660 (eBiosciences, 50-0032-82), CD4-FITC (eBiosciences, 35-0042-U500), CD8-APC-Cy™7 (BD, 557654), CD44-BV 786 (Biolegend, 103059), CD62L-Pacific Blue (Biolegend, 104424). Data were acquired on BD FACSCelesta flow cytometers and analyzed by FACS-Diva or FlowJo software (BD).

Scanning electron microscopy. E0771 cells, both WT and DDR1 KO, were plated at a density of $0.1 \times 10^6$ and cultured for two days in DMEM (10% FBS) to adhere evenly on the surfaces of glass coverslips. Cells were then fixed with 2.5% glutaraldehyde and 1% paraformaldehyde solution, followed by $OsO_4$ and water rinses. Samples were then sequentially dehydrated with alcohol gradient and dried at the critical point. Upon mounting on SEM-stubs, the coverslips were coated with iridium and observed under a scanning electron microscope (Model FEI) with an ETD detector, at a dwelling time of 10 ms and a magnification of 12,000.

Screening and generation of anti-DDR1 monoclonal antibodies (mAbs). Human DDR1 extracellular domain (ECD) protein (Sino Biological, 10730-H08H) was used to immunize rabbits and to generate anti-huDDR1 monoclonal antibodies using a method previously described (Gui et al., 2019b). Briefly, New Zealand white rabbits were administered by intraperitoneal (ip) injection of 0.5 mg recombinant human DDR1 ECD protein for priming and a series of 3-4 boosters after the priming immunization in a 3-week interval. Memory B cells were isolated from PBMCs and single B cells were cultured for 10 to 14 days in 96-well cell culture plates for antibody production. Cell culture supernatants were analyzed for DDR1 binding using ELISA and positive hits were selected for antibody gene cloning and sequence analysis.

Cells from the positives B cell culture wells were lysed, total RNA was isolated, and cDNA was synthesized using a superscript reverse transcriptase II (Invitrogen) according to manufacturer's suggestion. DNA sequences of antibody variable regions from both heavy chains and light chains were amplified by polymerase chain reaction (PCR) using a set of designed primers and cloned into a vector for sequencing variable regions of each antibodies. The cloned antibody variable sequences of both heavy and light chains were constructed into a mammalian expression vector in fusion with the constant region of IgG1 heavy and kappa light chain, respectively, for full length recombinant antibody expression in human embryonic kidney (HEK) 293 (HEK293F) cells (Life science Technologies). Monoclonal antibodies were purified from HEK293 cell culture media using protein-A affinity resin to purity >95% using a method as described previously (O'Donnell et al., 2019). The purified antibodies were screened for neutralizing function in cell culture assays and antitumor activities in mouse tumor models.

Statistics. Student t test was used to compare mean differences between two groups. One-way ANOVA and post hoc multiple comparison were used to compare mean differences between multiple groups. Survival curves were analyzed by Log-rank (Mantel-Cox) analysis. Pearson correlation analysis and all the other statistics were done in Graphpad Prism. $P<0.05$ was considered significant. Data are presented as mean±SEM.

Example 2—Results

Figure 5:
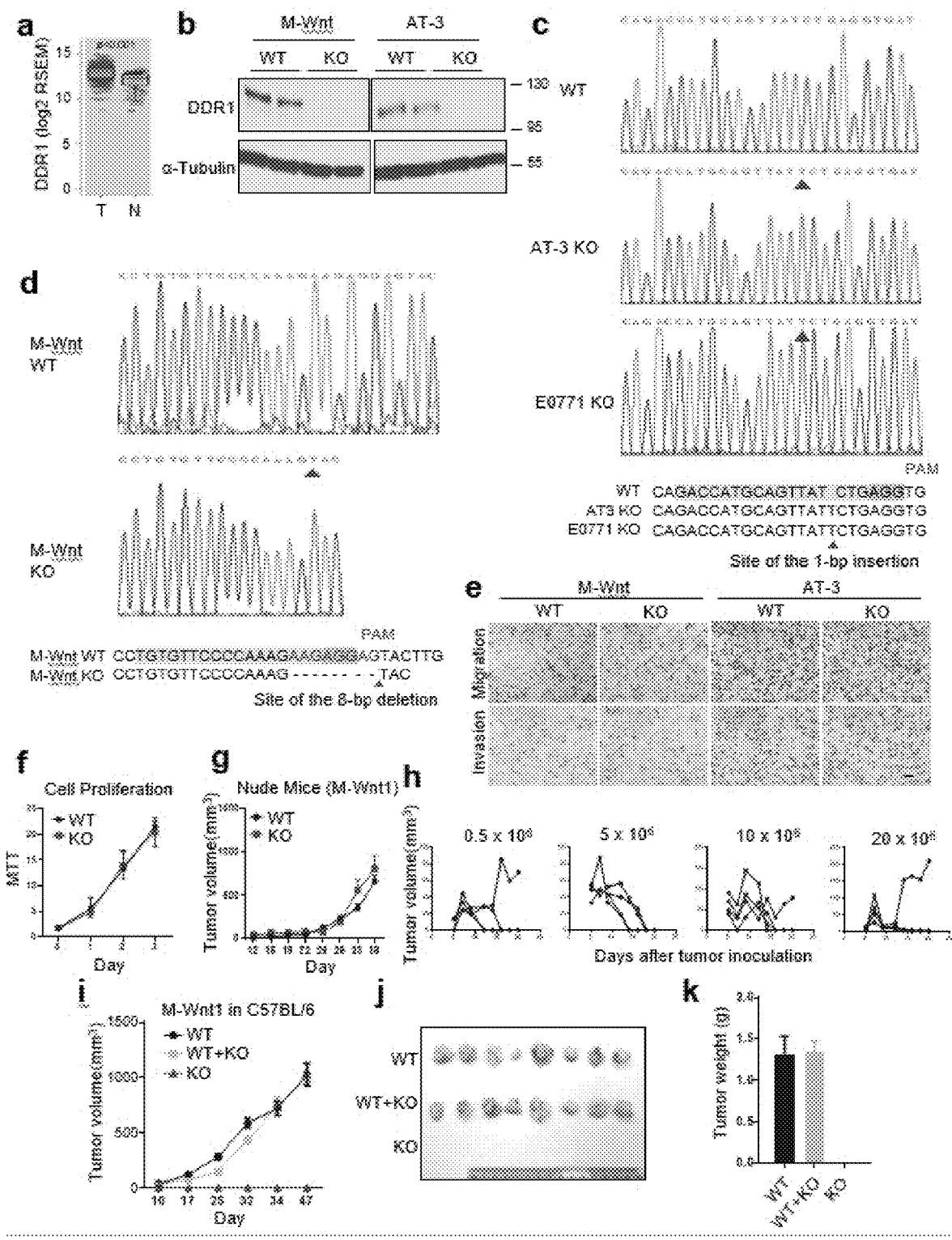
FIGS. 5A-K. Tumor DDR1 ablation inhibits tumor growth in immunocompetent hosts.

The inventors specifically deleted Ddr1 in multiple murine mammary tumor cells with basal like/TNBC characteristic (E0771, AT-3, and M-Wnt; FIG. 1a, FIGS. 5b-d). Knockout (KO) tumor cells did not exhibit any appreciable defects in cell proliferation, migration, or invasion in vitro (FIGS. 1b-d, FIGS. 5e-f). In addition, Ddr1-KO tumors in immunodeficient hosts grew at the same rate as wild-type (WT) control mice (FIG. 1e and FIG. 5g). In stark contrast, Ddr1-KO tumors in an immunocompetent host (C57BL/6) regressed completely 2 weeks post-inoculation in all three mammary tumor models tested (FIGS. 1f-h). This growth defect of KO tumors in immunocompetent hosts was not substantially alleviated by transplantation of increasing numbers of KO tumor cells ($0.5$-$20 \times 10^6$ cells per inoculum, FIG. 5h), nor was growth incompetence rescued by initial growth in immunodeficient hosts ($Rag1^{-/-}$) and subsequent re-transplantation into naïve, immunocompetent mice (FIGS. 1i-j). Furthermore, co-transplantation using mixtures of equal numbers of parental WT and KO tumor cells gave rise to robust tumor growth in immunocompetent hosts (FIGS. 5i-k), indicating a dominant action of tumor DDR1. When WT tumor cells were injected into immunocompetent mice that were previously challenged with KO tumor cells, either at the same or contralateral mammary gland, no appreciable growth of re-challenged parental tumors was observed (FIGS. 1k-m). This indicates that KO tumor cells can vaccinate hosts against WT tumors. Taken together, these data strongly suggest that tumor DDR1 plays a distinctive role in tumor growth in an immunocompetent host.

Figure 2:
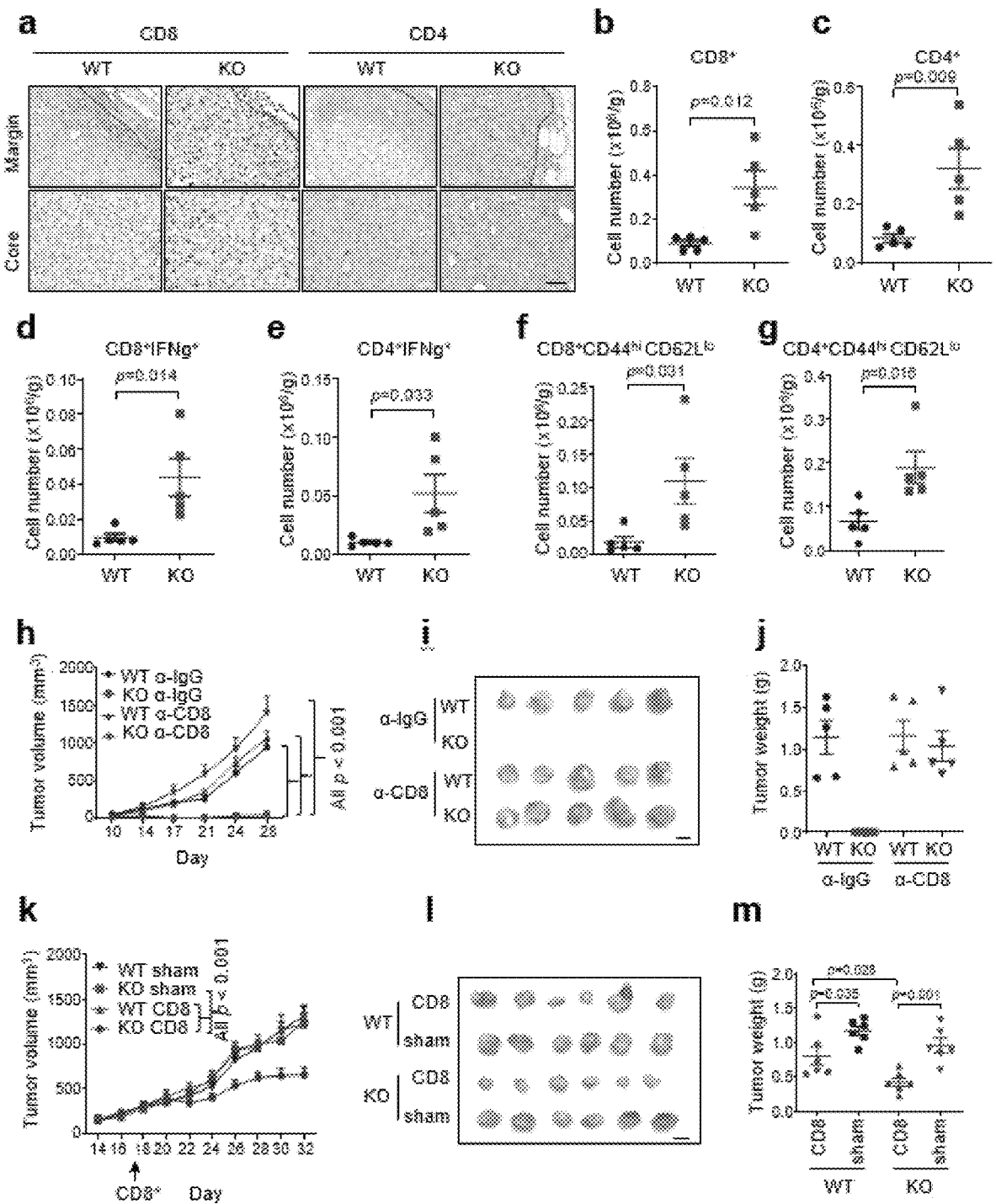
FIGS. 2A-M. DDR1 excludes antitumor immune cell infiltration.

Immunohistochemistry (IHC) showed that CD4+ and CD8+ T cells were limited to the peripheral area of parental tumors after re-grafting from immunodeficient to immunocompetent hosts (FIG. 2a). In contrast, these lymphocytes were abundantly present at both the margin and core of Ddr1-KO tumors (FIG. 2a). In support, flow cytometry showed that total numbers of tumor-infiltrating CD8+ and CD4+ T cells (normalized with tumor weight) were substantially elevated in the KO tumor group versus parental controls (FIGS. 2b-c). Interferon (IFN)-γ-producing CD8+ and CD4+ cells were also more abundant in KO tumors versus WT counterparts (FIGS. 2d-e). Furthermore, effector and helper T cells were more potently activated (CD44$^{hi}$CD62$^{lo}$) in KO tumors versus their parental controls (FIGS. 2f-g). However, when normalized with the corresponding total T cell numbers, KO and parental controls exhibited no difference in the percentage of CD4+ or CD8+ T cells that are positive for Ki67 (FIGS. 6a-b), IFNγ, or Gzmb (FIGS. 2c-d). This indicates that tumor DDR1 likely confers tumor exclusion of T cells without attenuation of their proliferation or antitumor activity per se.

To ascertain a role for tumor DDR1 to antagonize antitumor immunity, the inventors depleted immunocompetent mice of CD8+ T cells by antibody neutralization. Ddr1-KO tumors grew as robustly as their isogenic WT controls in CD8+-cell-depleted hosts (FIGS. 2h-j, FIGS. 2e-f), similar to the inventors' finding in immunodeficient hosts (FIG. 1e). In a reciprocal experiment, the inventors adoptively transferred purified CD8+ T cells into immunodeficient mice and compared growth of parental and KO tumors. Unlike sham-treated immunodeficient hosts, mice with transferred CD8+ T cells yielded significantly smaller KO tumors than parental tumors (FIGS. 2k-m, FIG. 6g). Collectively, these results corroborate the notion that, while dispensable for intrinsic growth of mammary tumors, tumor DDR1 plays an important role in deterrence of T cell infiltration.

Figure 3:
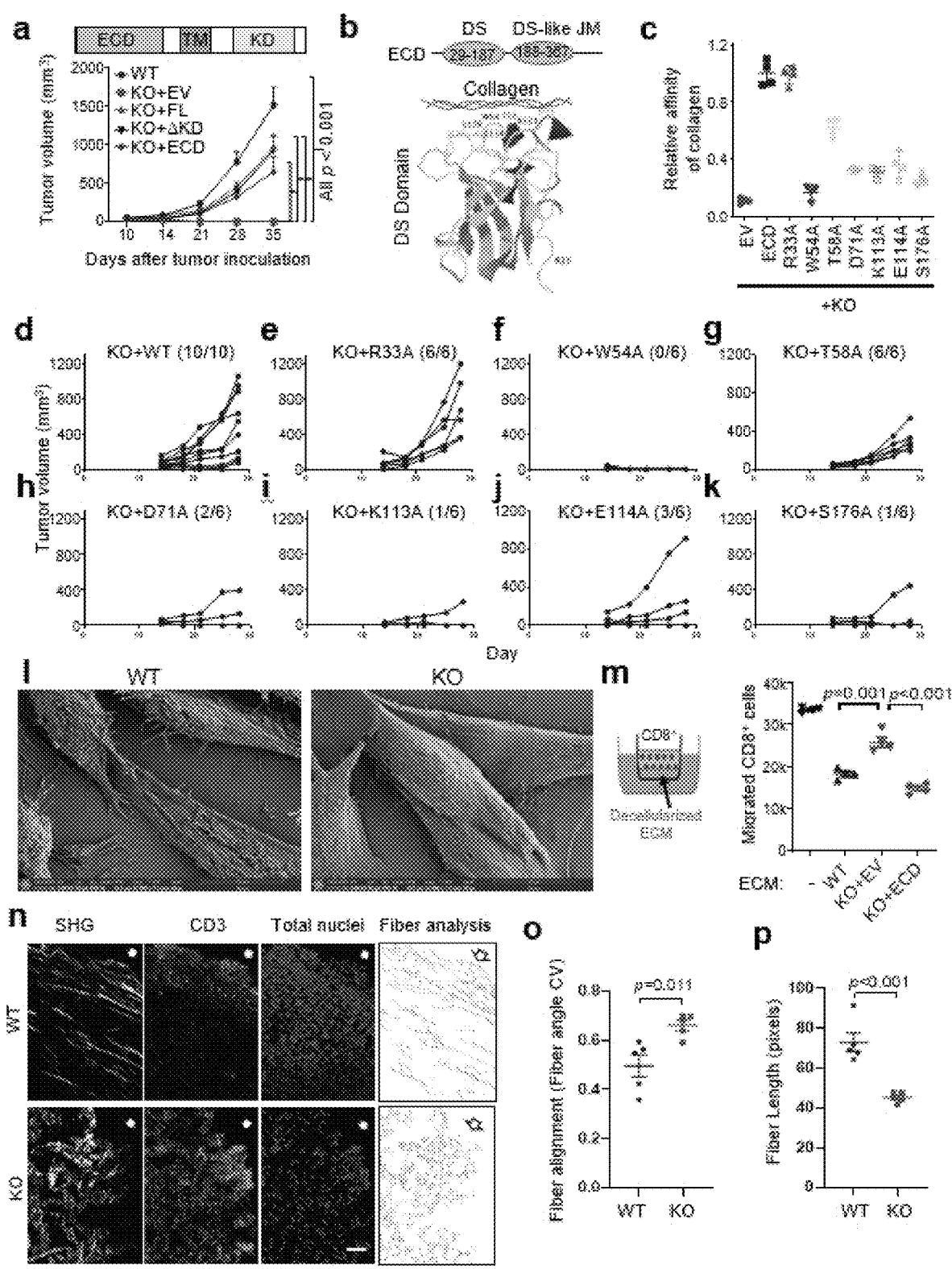
Figure 6:
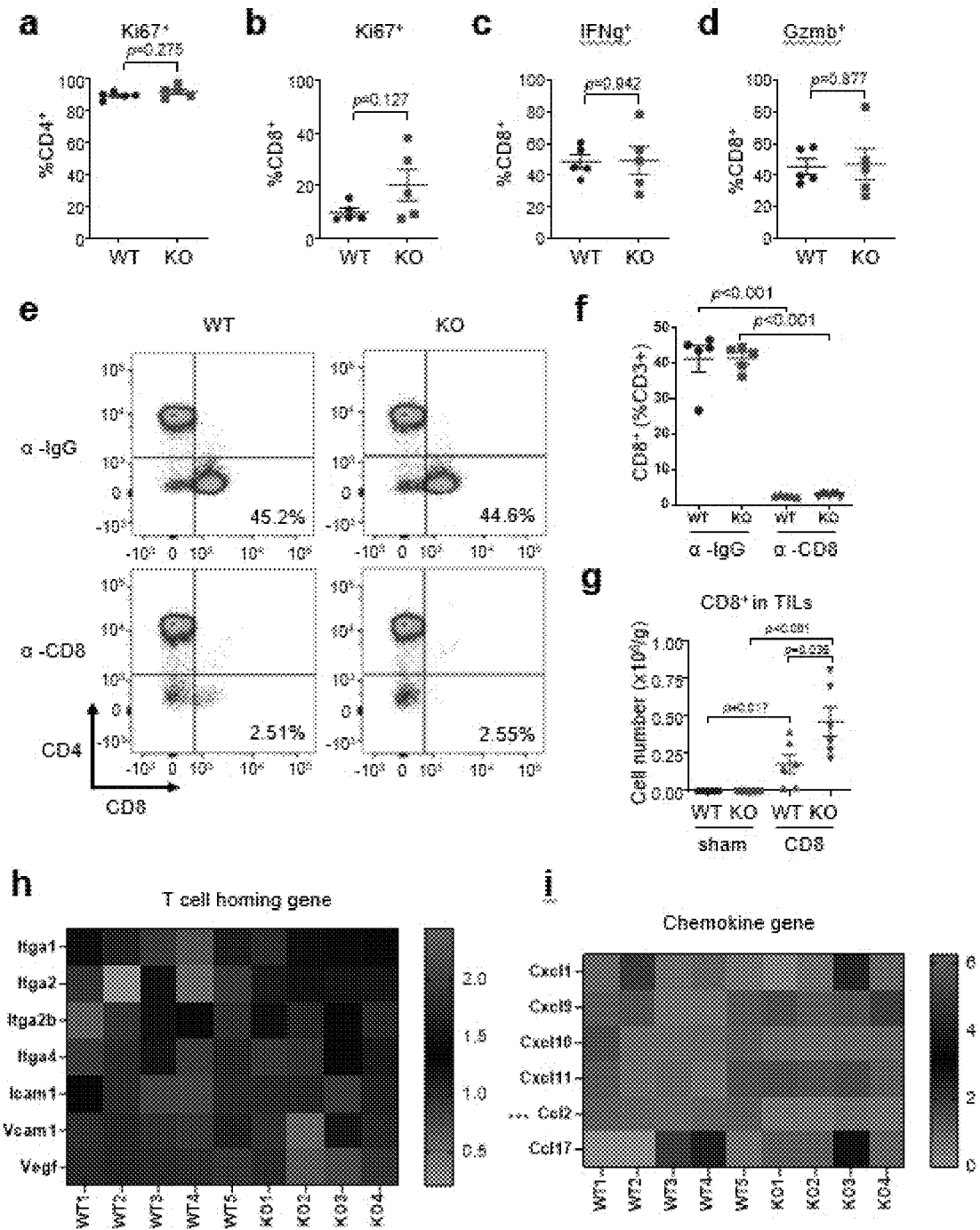
FIGS. 6A-I. Immuno-depletion and adoptive transfer of CD8⁺ cells.
Figure 7:
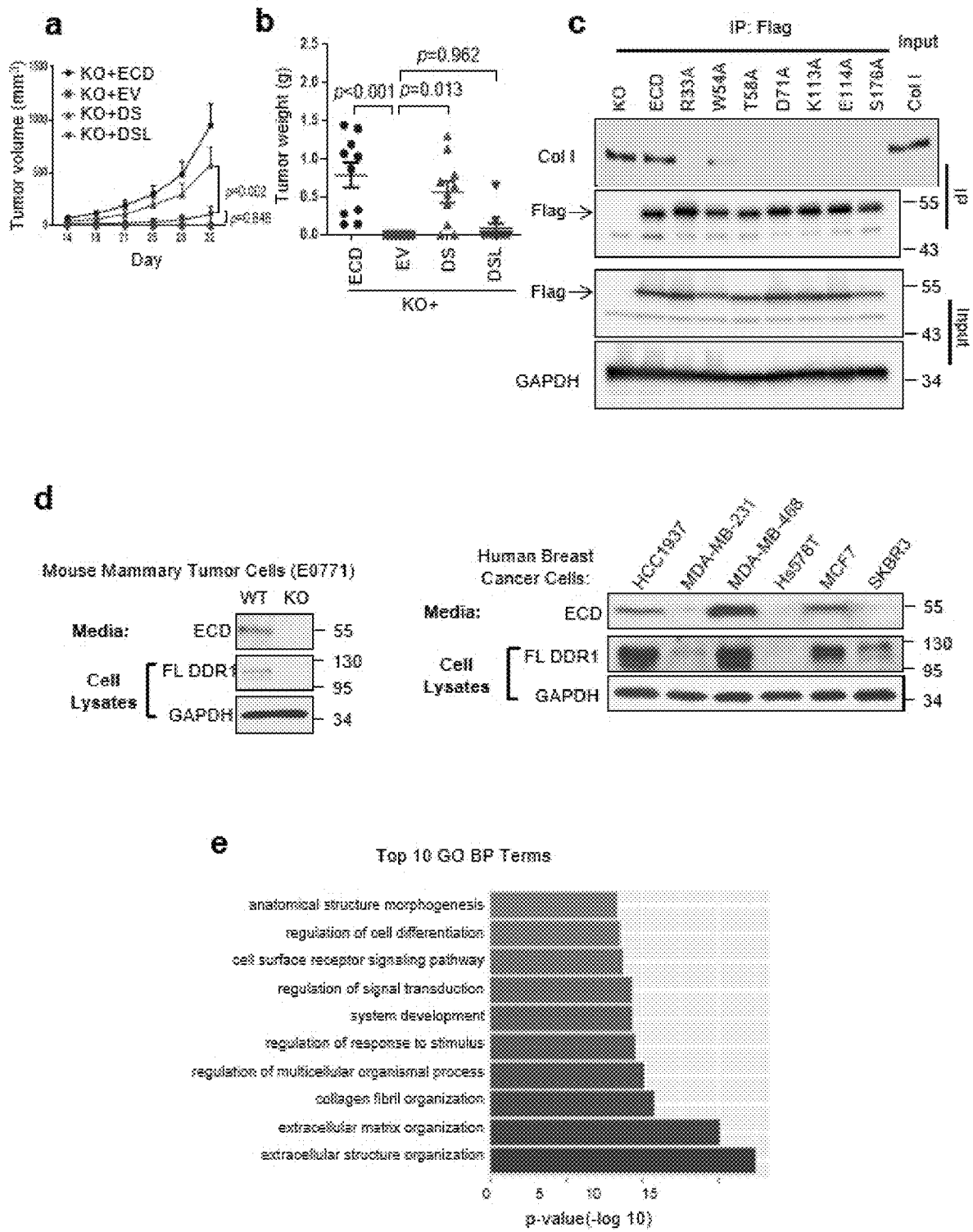
FIGS. 7A-E. DDR1-mediated collagen remodelling is required for immune exclusion.

Intratumoral trafficking of T cells is a highly dynamic multistep process that includes extravasation through blood vessels, tumor-induced chemotaxis, and traversing through the ECM-based physical barrier (Slaney et al, 2014; Sackstein et al, 2017; Ager et al, 2016). CD31-based histologic analysis did not reveal any significant immune-vascular changes between WT and KO tumors (data not shown), nor did RNA-seq show any differences in the mRNA levels of T cell-homing genes or chemokine-encoding genes that could explain enhanced immune infiltration in the Ddr1-KO group (FIGS. 6h-i). Given the affinity of DDR1 for collagen, the inventors sought to test an alternative model whereby tumor DDR1-collagen interaction renders tumors less penetrable by immune cells. To this end, the inventors first determined whether the immune-modulating function of DDR1 depends on its kinase activity by introducing the following constructs into Ddr1-KO tumor cells (FIG. 3a): (1) empty vector (EV), (2) full-length mouse DDR1 (FL), (3) ΔKD, a truncated DDR1 lacking the intracellular kinase domain KD but retaining its transmembrane (TM) domain, and (4) ECD only. Growth deficiency of KO tumors in immunocompetent hosts was rescued to a similar extent by ectopically expressed FL DDR1 and the two truncation mutants, ΔKD and ECD (FIG. 3a). Further deletion analysis shows that the N-terminal discoidin homology domain (DS, FIG. 3b), which is responsible for collagen binding, fully rescued tumor growth of DDR1 KO cells (FIGS. 7a-b). Taken together, these data clearly indicate that tumor DDR1 suppresses antitumor immunity in a kinase-independent manner.

Based on the collagen-DS domain crystal structure (Leitinger, 2014; Carafoli et al., 2012; Carafoli & Hohenester, 2013), the inventors mutated a number of key collagen-binding amino acid residues (W54, T58, D71, K113, E114 and S176 in mouse DDR1 corresponding to W53, T57, D70, K112, E113 and S175 in human DDR1, respectively; FIG. 3b). The inventors also mutated R33, a residue distal to the collagen-binding pocket and responsible for DDR1 transmembrane signalling. The collagen binding affinity of WT and mutant ECD was validated by ELISA and co-IP in vitro (FIG. 3c, FIG. 7c), and their ability to rescue KO tumor growth was assessed in vivo (FIGS. 3d-k). As expected, R33A, which is located outside the collagen binding region of ECD, retained its ability to bind to collagen and support tumor growth (10/10 tumors for WT ECD and 6/6 for R33A, FIGS. 3c-e). In contrast, W54A completely lost collagen binding in vitro and the ability to support tumor growth (0/6 sites, FIG. 3f). Mutants D71A, K113A, E114A and S176A retained modest collagen binding activity of WT ECD (FIG. 3c) and gave rise to tumor growth in a fraction of hosts (2/6, 1/6, 3/6 and 1/6 tumors, respectively, FIGS. 3h-k). On the other hand, T58A retained approximately 50% of WT collagen binding affinity (FIG. 3c) and 100% tumor incidence (6/6) but exhibited slower tumor growth rate than WT (FIG. 3g). In light of the strong correlation of collagen binding affinity and tumor-rescuing ability of ECD mutants, the inventors conclude that collagen binding is required for ECD to impede antitumor immunity.

The fact that ectopic DDR1 ECD alone is sufficient to support tumor growth in immunocompetent hosts is reminiscent of earlier reports of ECD shedding from full-length DDR1 (Vogel, 2020; Flynn et al., 2010; Shitomi et al., 2015), although the biological significance of shed ECD was not known. In support, the inventors detected ECD in media conditioned with parental murine mammary tumor cells and a subset of human breast cancer cell lines (FIG. 7d). Published in vitro biochemical study shows that recombinant DDR1 ECD can remodel collagen fibre structure (Flynn et al., 2010; Agarwal et al., 2007). In support, scanning electron microscopy (SEM) showed that DDR1-WT tumor cells cultured in vitro were associated with more prominent ECM network versus their KO counterparts (FIG. 3l). To determine functionality of tumor cell-associated ECM, the inventors decellularized parental and KO tumor cells (Chen et al., 2007) (Chen et al., 2007) and assessed penetrance of purified CD8+ T cells through decellularized ECM in a Transwell assay (FIG. 3m). Parental tumor-derived ECM significantly reduced T cell migration, which was mitigated in ECM decellularized from Ddr1-KO tumors (FIG. 3m). The T cell-impeding effect was restored to parental levels in ECM derived from ECD-expressing KO tumors (FIG. 3m). To corroborate the in vitro finding, the inventors used second harmonic generation (SHG) microscopy to directly visualize collagen fibres in parental and Ddr1-KO tumors re-grafted from immunodeficient to immunocompetent hosts. Collagen fibres at the margin of parental tumors tended to orient in parallel to the tumor margin (denoted by block arrows, top panels in FIG. 3n), reminiscent of a defensive line against invading tumor cells. As expected, CD3+ T cells from the same parental tumors were limited to the tumor margin (FIG. 3n). In stark contrast, collagen fibres in KO tumors were relatively short and disordered (FIG. 3n). Concordantly, immune cells penetrated deeper into KO tumors versus WT tumors (FIG. 3n). As a measurement for fibre alignment, coefficient of variation of the angle for collagen fibres was significantly larger for KO tumors versus parental ones (FIG. 3o). In addition, average collagen fibre length in KO tumors was substantially shorter than their parental counterparts (FIG. 3p). In support of DDR1-dependent collagen fibre remodelling, pathway analysis of RNA-seq data from primary Ddr1-WT and KO tumors indicates that genes involved in extracellular matrix and collagen fibril organization are most affected ($p<1\times10^{12}$, FIG. 7e). Together, these data strongly suggest that DDR1 ECD helps fortify a collagen-based physical barrier to impede penetration of antitumor immune cells into the tumor microenvironment.

Figure 4:
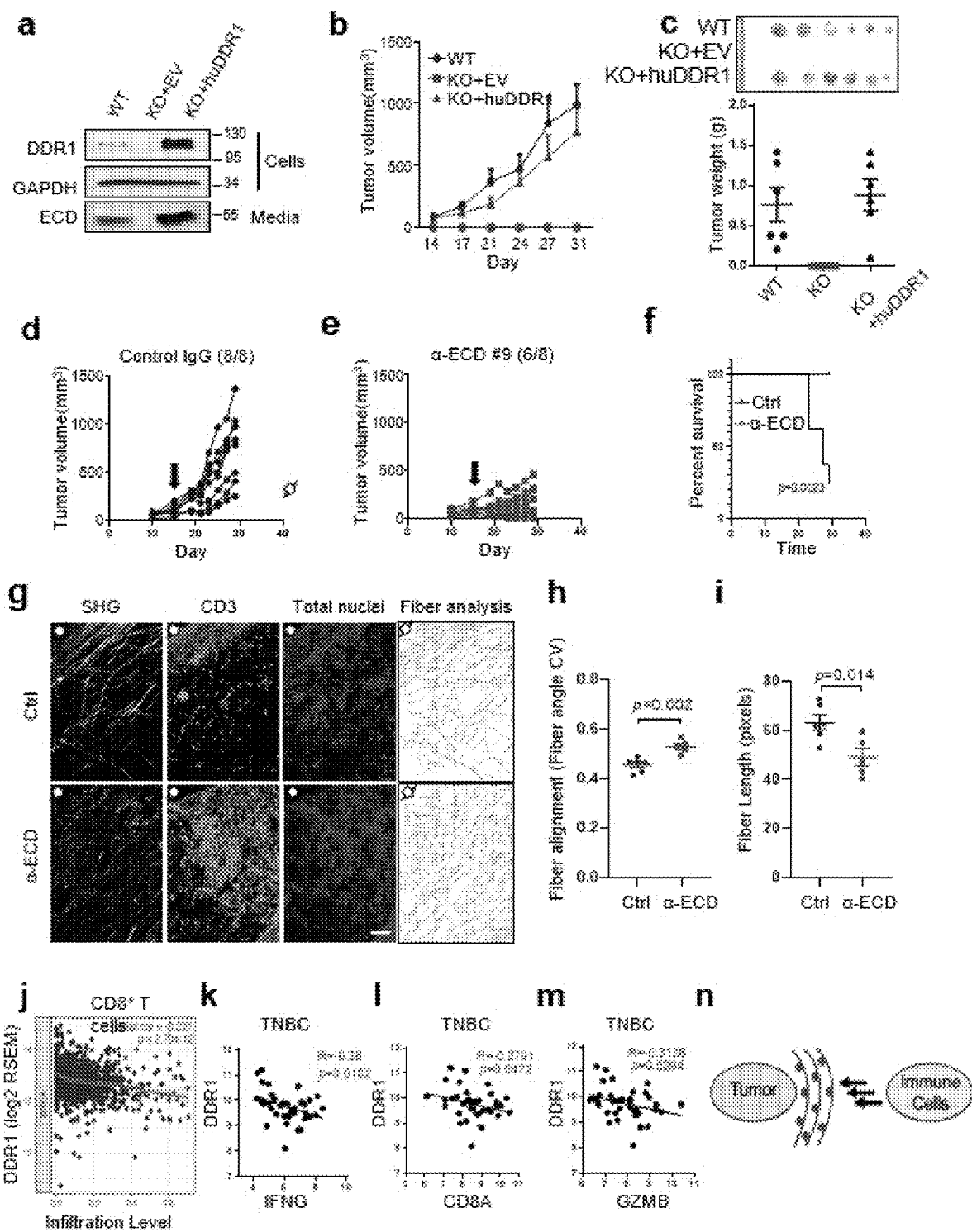
FIGS. 4A-N. DDR1 as a potential therapeutic target for boosting antitumor immunity.
(FIGS. 4b-c) Tumor growth curve (FIG. 4b) and weight (FIG. 4c) of E0771-derived DDR1 WT, KO, KO+huDDR1 cells (n=6). Tumor image is shown on top.
(FIGS. 4d-e) Growth curves of individual KO+huDDR1 tumors in C57BL/6 hosts treated with isotype IgG (FIG. 4d) or anti-huDDR1 antibody #9 (FIG. 4e). Arrows denote the starting date of antibody administration.
(FIG. 4f) Survival curve of isotype IgG and anti-huDDR1 treatment groups.
(FIG. 4g) KO+huDDR1 tumors were analysed by SHG (grey), CD3 staining (green), To-pro-3 staining (red), and collagen fiber individualization (far right panel). Block arrows indicate tumor margins. Scale bar: 50 μm.
(FIGS. 4h-i) Quantification of tumor fiber parameters. Fiber alignment (angle of coefficiency variation, FIG. 4h), fiber length (FIG. 4i).
(FIG. 4j) Correlation between huDDR1 mRNA and abundance of tumor-infiltrating CD8⁺ T among 1,093 breast cancer patient samples (TIMER).
(FIGS. 4k-m) Correlation of DDR1 mRNA levels and antitumor immune markers IFNG (FIG. 4k), CD8A (FIG. 4l), and GZMB (FIG. 4m) among 37 TNBC patient samples (GSE88847).
Figure 8:
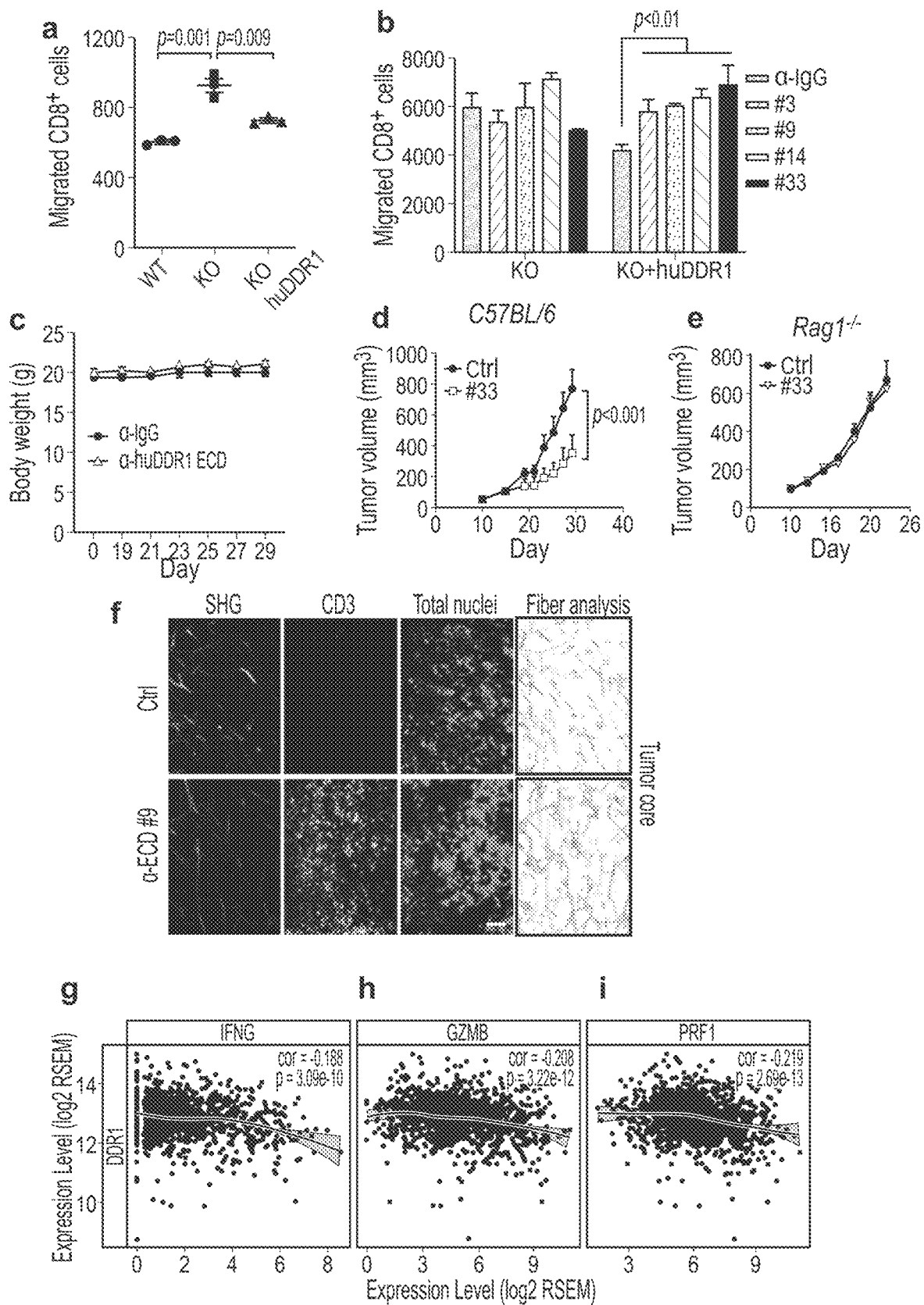
FIGS. 8A-I. Screening for huDDR1-neutralizing antibodies.
Figure 9:
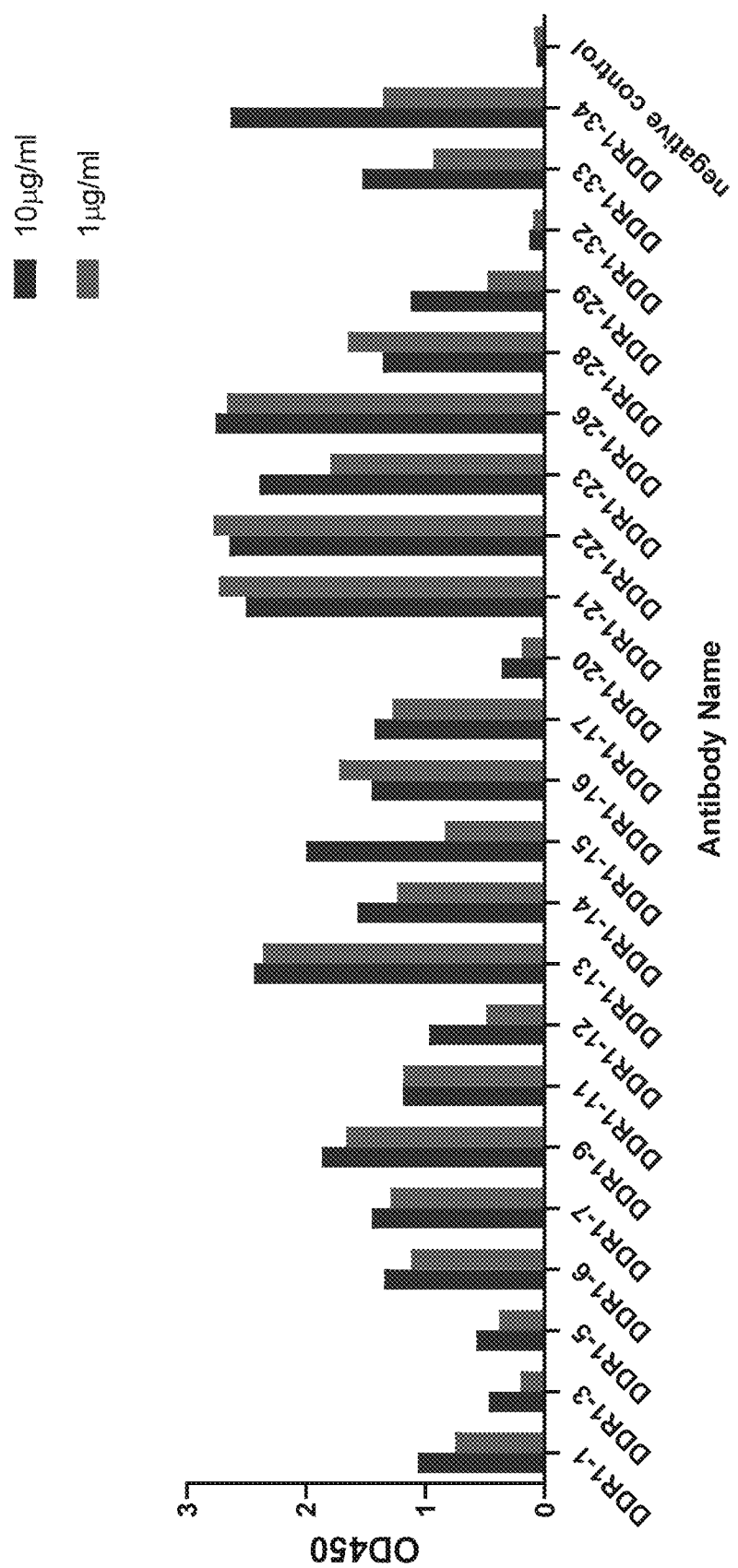
FIG. 9. DDR1-mAb binding to DDR1 assayed by ELISA.

All current small-molecule inhibitors of DDR1 examined for their therapeutic potentials target the intracellular kinase domain (Kothiwale et al., 2015; Li et al., 2015). To effectively neutralize the kinase-independent ECD activity in blocking immune cell infiltration, the inventors generated a series of monoclonal antibody clones by immunization of rabbits with recombinant human DDR1 (huDDR1) ECD and subsequent antibody memory B-cell isolation, as described previously (Meng et al., 2015; Gui et al., 2019a). For screening huDDR1-specific neutralizing antibodies, the inventors ectopically expressed huDDR1 in murine Ddr1-KO mammary tumor cells (FIG. 4a). huDDR1 completely rescued the growth defect of KO murine tumors in immunocompetent hosts (FIG. 4b, c). Using an in vitro co-culture assay that assesses effects of tumor cells on T cell migration (FIG. 8a), the inventors screened anti-huDDR1 antibodies that can effectively neutralize huDDR1-dependent interference of T cell migration (FIG. 8b). Several top neutralizing antibodies were further examined for its tumor-inhibiting potential in vivo. Compared to IgG isotype control, administration of the anti-huDDR1 antibodies gave rise to significantly slower growth of huDDR1-expressing tumors, lower tumor incidence and longer host survival without any appreciable effect on host weight (FIGS. 4d-f, FIGS. 8c-d). Of note, the same antibody administration in immunodeficient hosts did not result in any appreciable tumor inhibition (FIG. 8e), suggesting that the treatment primarily neutralizing the immune-excluding function of DDR1. SHG microscopy shows that anti-huDDR1 antibody-treated tumors in immunocompetent hosts were associated with less aligned, shorter collagen fibres, and significantly enhanced antitumor immune infiltration (FIGS. 4g-i, FIG. 8f). Taken together, the inventors' findings provide proof-of-principle for the anti-hDDR1 antibody approach as a potential anti-tumor therapy.

Using TCGA RNA-seq data sets and TIMER (Li et al., 2018), a public bioinformatics resource for estimating clinical impact of tumor-immune correlations, the inventors found that breast cancer exhibit an inverse correlation between DDR1 mRNA levels and various antitumor immunity signature genes including CD8, IFNG, GZMB, and PRF1 (FIG. 4j; FIGS. 8g-i). Of note, the degree of negative correlation observed for DDR1 is comparable to other recently identified tumor-associated genes with immune modulatory functions (Pan et al., 2018). The same correlation was observed in a separate cohort of samples from treatment-naïve TNBC patients (n=37; FIGS. 4k-m), which were used to stratify TNBC based on immune-excluded phenotype (Grusso et al., 2019). Together, these clinical correlations strongly suggest that high DDR1 expression is associated with low tumor infiltration and low cytotoxic activity of CD8+ T cells. By elucidating a previously unexplored, kinase-independent DDR1 function in instigating a defence line for immune exclusion (FIG. 4n), this study informs development of new stand-alone therapeutics that target DDR1 activity in ECM remodelling and blockade of antitumor immunity. The inventors also envision that their work could help improve clinical outcomes and efficacy of current immunotherapy for breast cancer and other fibrotic cancer types such as pancreatic cancer.

Generation and cloning monoclonal antibodies targeting human DDR1. Monoclonal antibodies (mAbs) against DDR1 were generated by immunization of rabbits and isolation of antibodies from single B cells. Human DDR1 protein was used for antibody generation and was expressed in HEK293 cells. The protein has a 6XHIS-tag and is purified to >95% purity using Ni-NTA resin (Sino Biologicals). Rabbits (NZW, Charles River) were immunized with the recombinantly produced DDR1 using a standard immunization procedure with 3 boost injections after primary priming immunization. Titer of anti-DDR1 sera was determined by series of dilutions of serum in ELISA for binding on DDR1 protein coated on 96-well plates (max-sorb plates, Nunc). When serum titer reached >$10^6$ and peripheral blood samples were collected from the immunized rabbits for B cell isolation from the freshly prepared peripheral blood mononuclear cells (PBMCs) using a fluorescence assisted cell sorting (FACS) instrument (BD FACSAria™ III, BD Biosciences). The sorted single B cells were collected in 96-well cell culture plates (Fisher Scientific) and were cultured for 7-10 days in a cell culture incubator with 5% $CO_2$ and 95% humidity in RPMI culture media with 10% FBS and added cytokines. The antibodies in the culture supernatants were assayed for DDR1 bindings. Cells from the positives wells were lysed, total RNA was isolated, and cDNA was synthesized using a superscript reverse transcriptase II (Invitrogen) according to manufacturer's suggestion. DNA sequences of antibody variable regions from both heavy chains and light chains were amplified by polymerase chain reaction (PCR) using a set of designed primers and cloned into a vector for sequencing variable regions of each antibodies. Amino acid and DNA sequences of antibody variable regions are listed in the Tables 3 and 4, and Tables 8 and 9, respectively. Amino acid sequences for light and heavy chain CDRs of the anti-DDR1 monoclonal antibodies are listed in Tables 1 and 2, respectively.

Selected DDR1 binding hits were expressed as full-length human IgG or rabbit/human chimeric IgGs using a mammalian expression vector system in human embryonic kidney (HEK293) cells (Invitrogen). Antibodies were purified using protein-A affinity resin by a fast protein liquid chromatography (FPLC). Purified DDR1 binding antibodies were characterized for their biological properties.

Figure 10A:
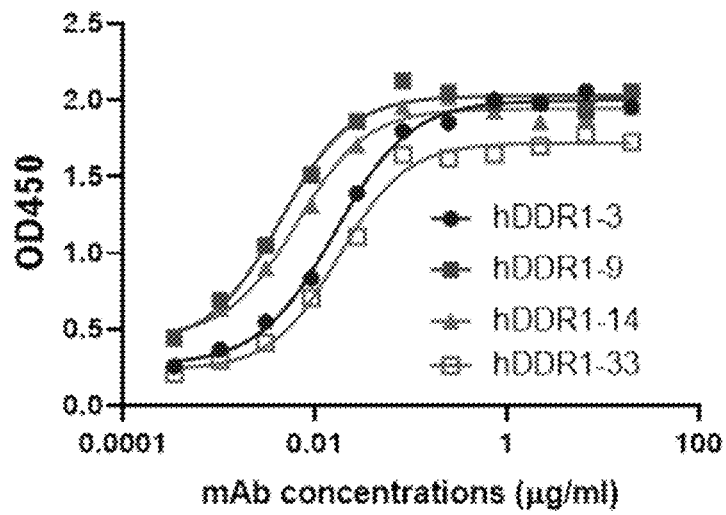
FIGS. 10A-B. Determination of antibody binding affinity to human DDR1 and mouse DDR1 using a titration ELISA.
Figure 10B:
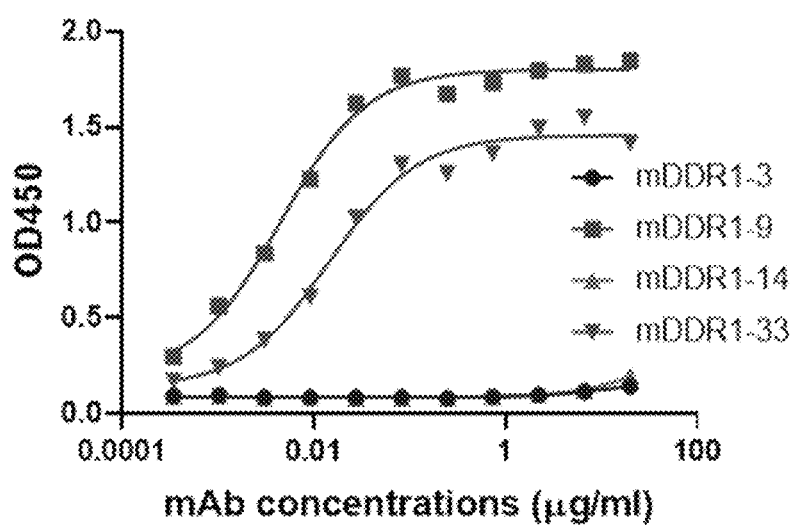

Binding affinity of anti-DDR1 monoclonal antibodies determined using Bio-layer interferometry (BLI) sensor-based Octet instrument. For antibody affinity measurement, antibody (30 µg/mL) was loaded onto the protein A biosensors for 4 min. Following a short baseline in kinetics buffer, the loaded biosensors were exposed to a series of recombinant DDR1 protein at 0.1-200 nM and background subtraction was used to correct for sensor drifting. All experiments were performed with shaking at 1,000 rpm. Background wavelength shifts were measured from reference biosensors that were loaded only with antibody. Kinetic sensorgrams for each antibody are shown in FIGS. 10A-B. ForteBio's data analysis software was used to fit the data to a 1:1 binding model to extract an association rate and dissociation rate. The $K_D$ was calculated using the ratio of $k_{off}/k_{on}$ and the estimated values of $K_D$ for DDR1 mAbs in Table 13.

Epitope binning of DDR1 mAbs. Pairwise binding competition among anti-DDR1 mAbs was used to determine the binding epitopes of each mAbs using Octet instrument and protein A biosensors. The epitope bins are summarized in Table 14.

Anti-hECD Antibody Inhibits Spontaneous Tumor Growth: To demonstrate the effect of anti-DDR1 antibody treatment on mammary tumorigenesis at various stages, MMTV-PyMT mice (C57BL/6 strain background) were treated with control IgG or anti-DDR1 antibody for two weeks when average tumor size reached 100 mm³ ("post-tumor"). DDR1 #9 humanized antibody was selected for this study due to its high affinity for both mouse and human ECD (data not shown). Antibody treatment did not affect host body weight. However, it significantly reduced tumor volume (FIG. 12a) and tumor incidence (FIG. 12b). Concordantly, antibody treatment significantly disrupted collagen alignment and promoted massive immune cell infiltration (FIG. 12c). Similar results were also obtained using anti-DDR1 antibody treatment and mammary tumorigenesis at various stages in MMTV-PyMT mice of a different background strain (FVB).

Comparison of Anti-hECD Antibody and DDR1 Kinase Inhibitor: In the same mammary tumor model where anti-hECD antibody showed significant tumor inhibitory activity, a previously published small-molecule DDR1 kinase inhibitor, 7rh, inhibited tyrosine kinase activity of DDR1 in tumors but did not reduced tumor growth. This is consistent with the assertion that DDR1-dependent exclusion of anti-tumor immunity is independent of its kinase activity (FIGS. 13a-e).

DDR1 is required for growth in some tumor types: Utilizing CRISPR-based genetic ablation of tumor Ddr1 significantly increased survival of immunocompetent hosts bearing ID8agg ovarian tumors. However, Ddr1 KO in B16 melanoma or MC38 colorectal tumors did not affect tumor growth in syngeneic immunocompetent hosts (see FIGS. 14b-c). Combined with the findings obtained with mammary tumors, this study indicates that targeting DDR1 can result in tumor inhibition in multiple types of cancer.

Figure 15A:
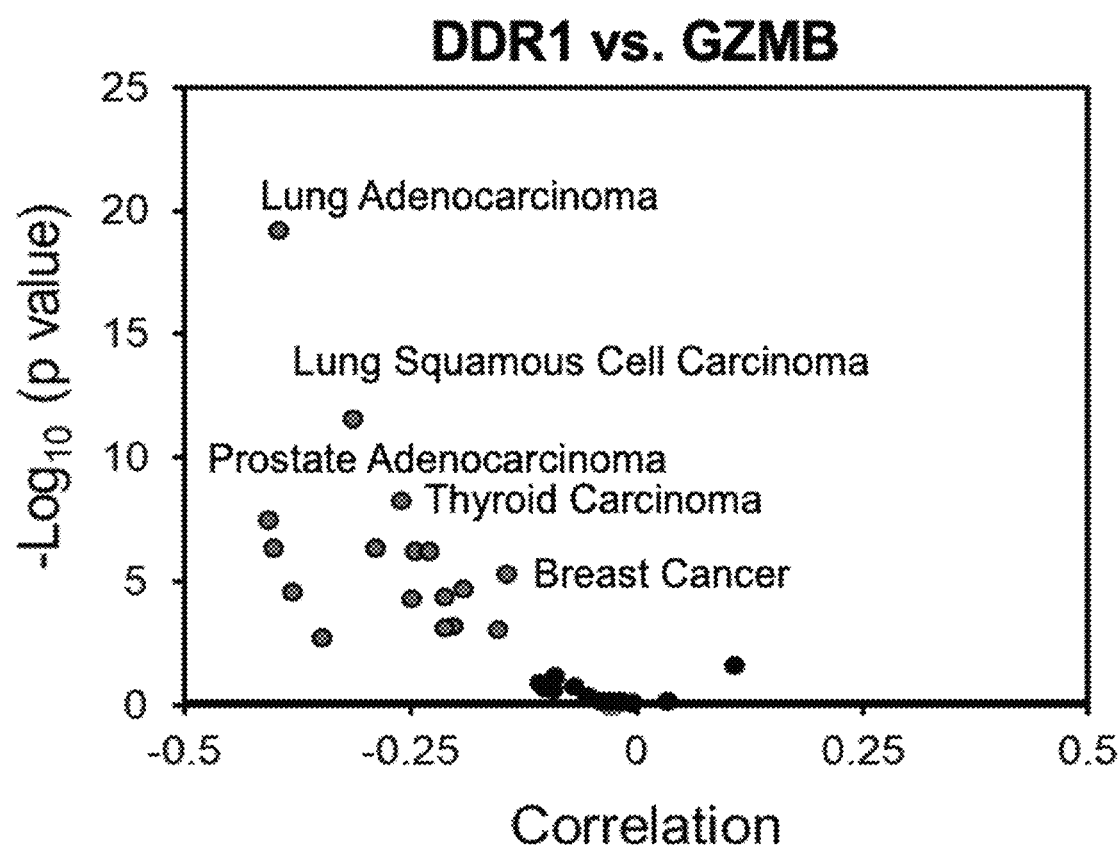
FIGS. 15A-C. Correlation of DDR1 and antitumor immune markers.
Figure 15B:
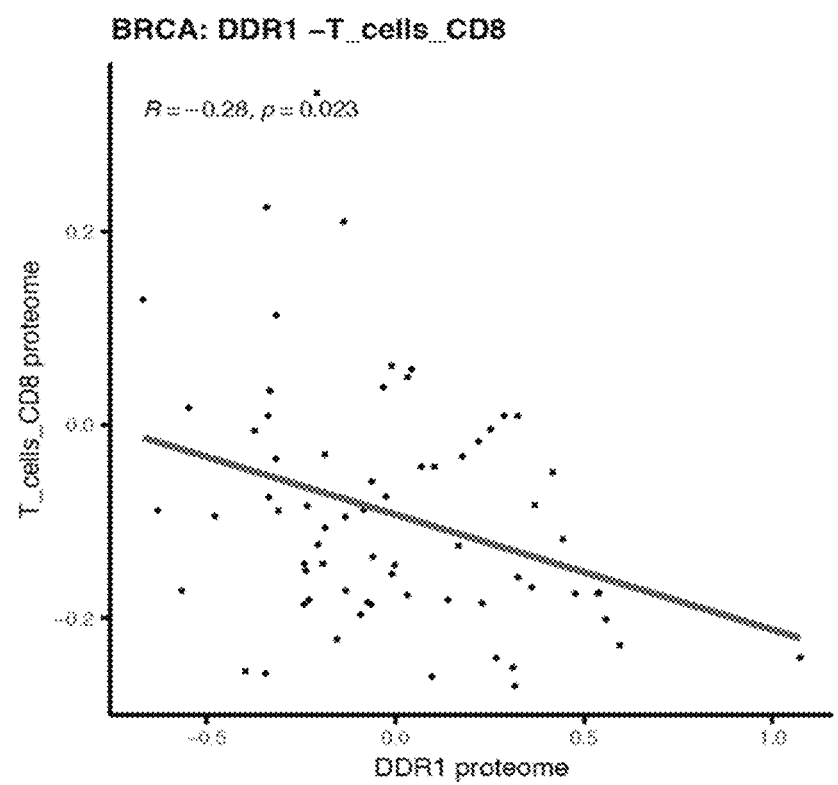
Figure 15C:
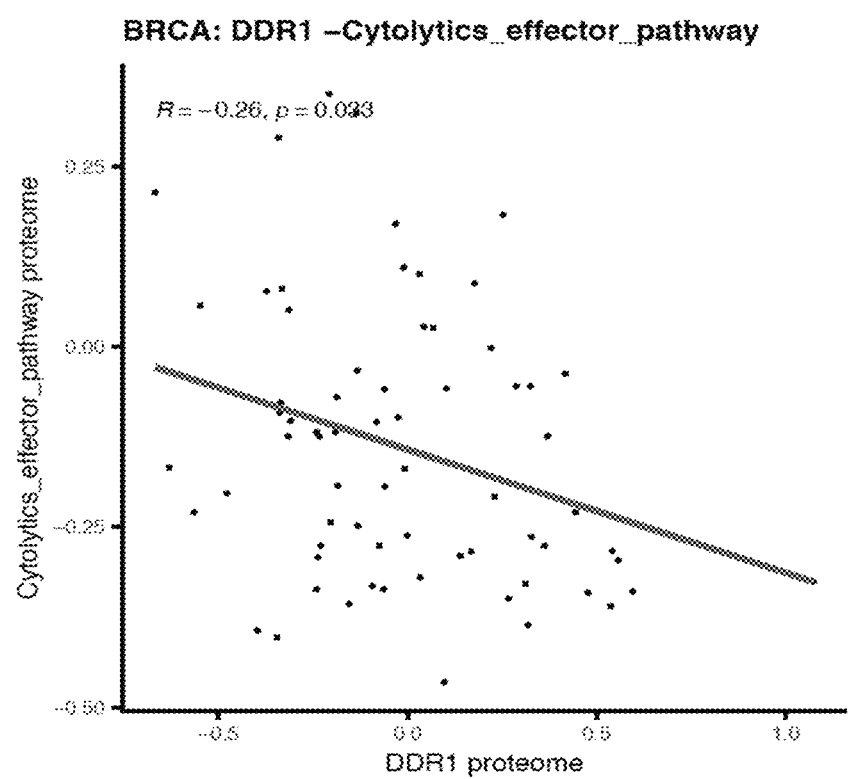

Correlation of DDR1 and antitumor immune markers: Mining of the TCGA transcriptome dataset indicated the unusually high expression of DDR1 in multiple human cancers as compared to corresponding normal tissue (data not shown). Furthermore, DDR1 mRNA levels in multiple cancers negatively correlated with cytotoxic immune markers, such as Granzyme B (GZMB, see FIG. 15a), suggesting that DDR1 may function to antagonize anti-tumor immunity in multiple cancers types. Furthermore, analysis of a TCGA proteome dataset led to the negative correlation between DDR1 protein and CD8 (FIG. 15b), as well as between DDR1 and proteins involved in cytolytic effector pathway of antitumor immunity (FIG. 15c). Thus, at both mRNA and protein levels, high expression of DDR1 correlates with low levels of antitumor immune marker expression. DDR1 appears to function as an antagonist of anti-tumor immunity, thus the inhibition of this antagonist, for example using DDR1 antibody, could increase anti-tumor immunity in multiple cancers types.

Figure 16:
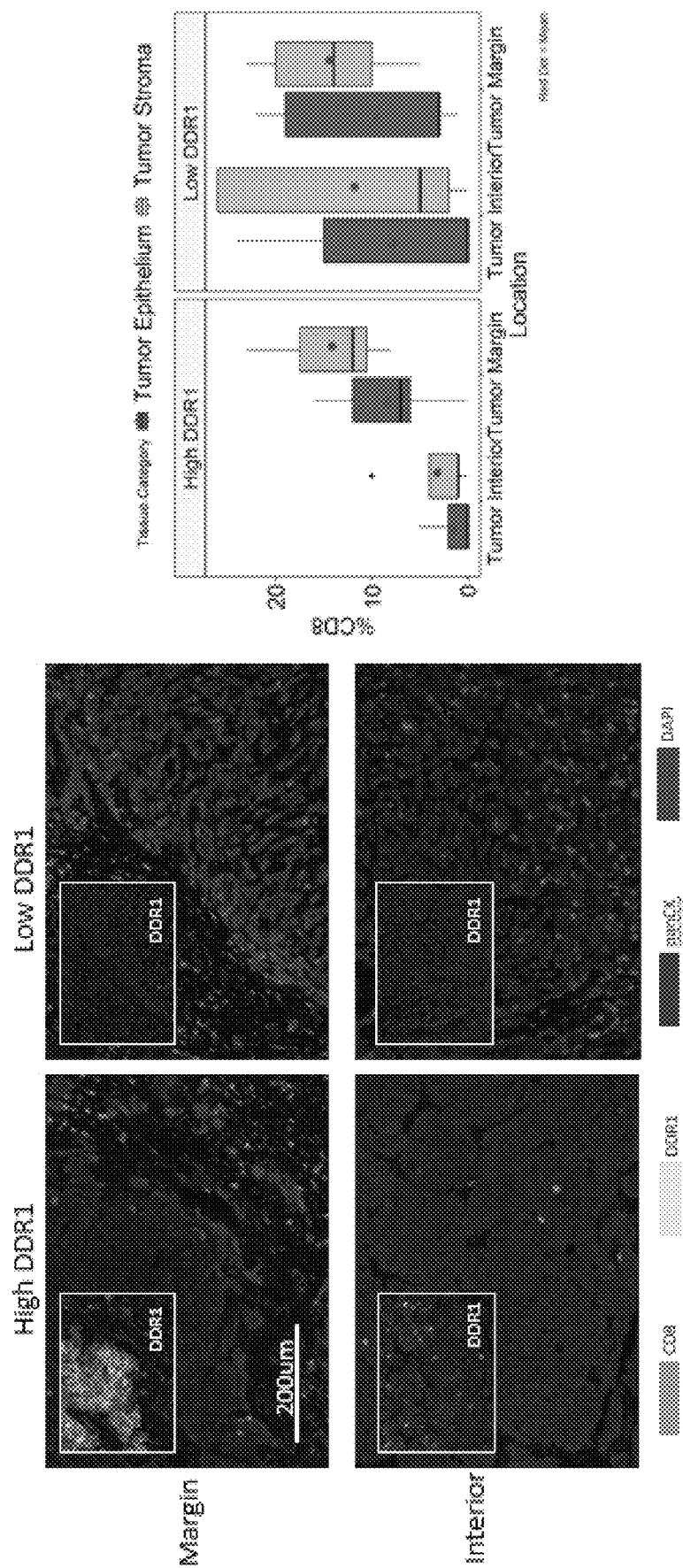
FIG. 16. High Tumor DDR1 Protein Correlates with Immune Exclusion in TNBC. (Left) Images of multiplex IHC of DDR1, CD8, and tumor-specific panCK using treatment-naïve DDR1$^{high}$ (n=7) and DDR1$^{low}$ (n=5) TNBC tumor samples. Scale bar: 200 mm. Using a treatment-naïve TNBC cohort in multiplex IHC, it was shown that DDR1$^{high}$ tumors demonstrate a reduced percentage of CD8$^+$ T cells present within the tumor and a greater percentage of CD8$^+$ T cells present at the tumor margin, as compared to DDR1$^{low}$ tumors which had higher percentages of CD8$^+$ T cells distributed throughout the tumor (right).
Figure 17:
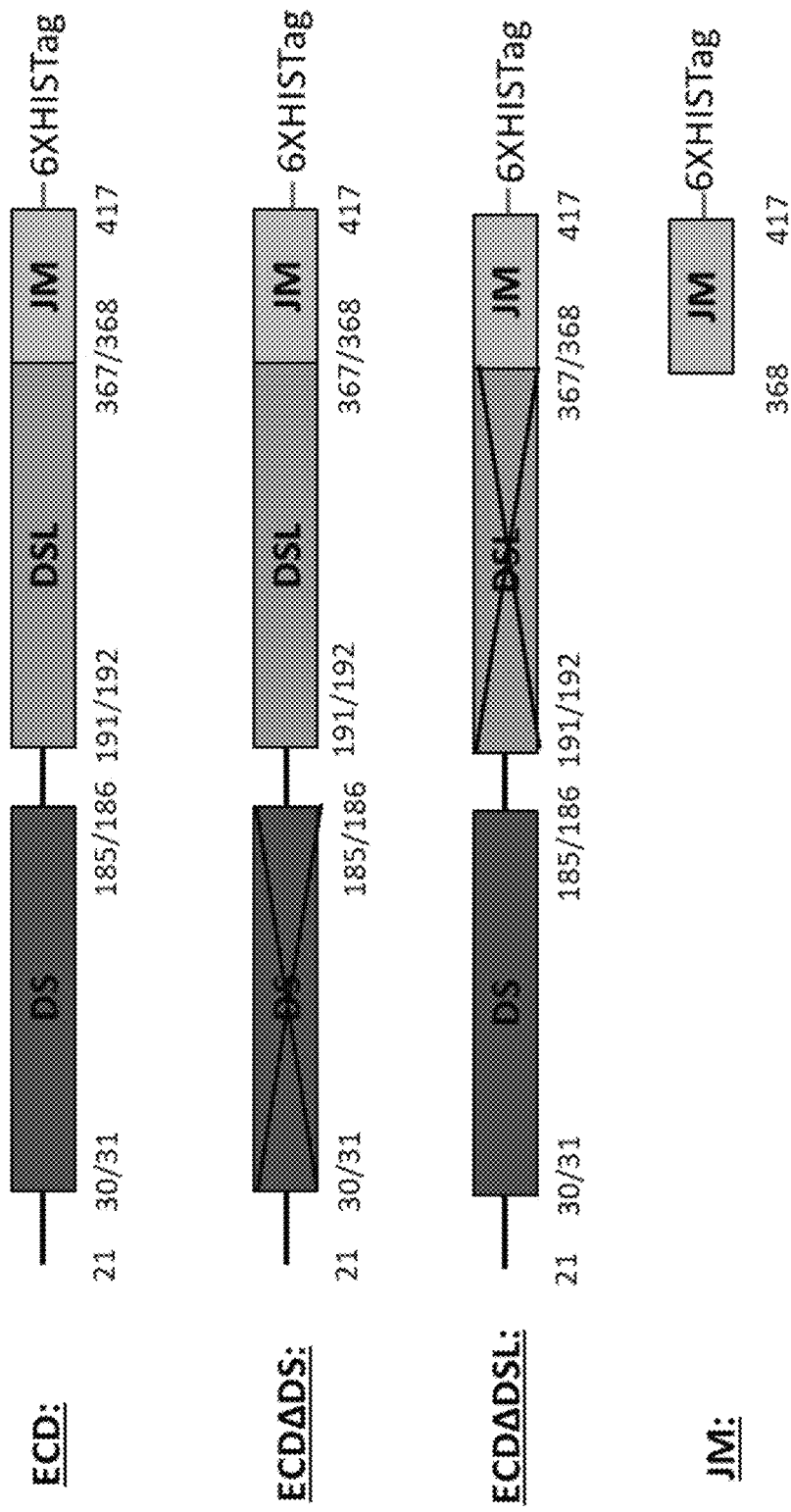
FIG. 17. Recombinant construction schematic of the domains of DDR1 extracellular (ECD) protein for expression in HEK293 cells. DS: N-terminal discoidin domain; DSL: DS-like domain; JM: juxtamembrane domain.

High Tumor DDR1 Protein Correlates with Immune Exclusion. As shown in FIG. 16 using a treatment-naïve triple negative breast cancer (TNBC) cohort in multiplex IHC imagery, DDR1$^{high}$ tumors, demonstrated a reduced percentage of CD8$^+$ T cells present within the tumor and a greater percentage of CD8$^+$ T cells present at the tumor margin, as opposed to DDR1$^{low}$ tumors in which a greater percentage of CD8$^+$ T cells were present both within the tumor and at the tumor margins. Such clinical correlations strongly suggest that tumor DDR1 is associated with reduced levels of cytotoxic activity by CD8$^+$ T cells and low tumor infiltration by such cells.

Figure 18A:
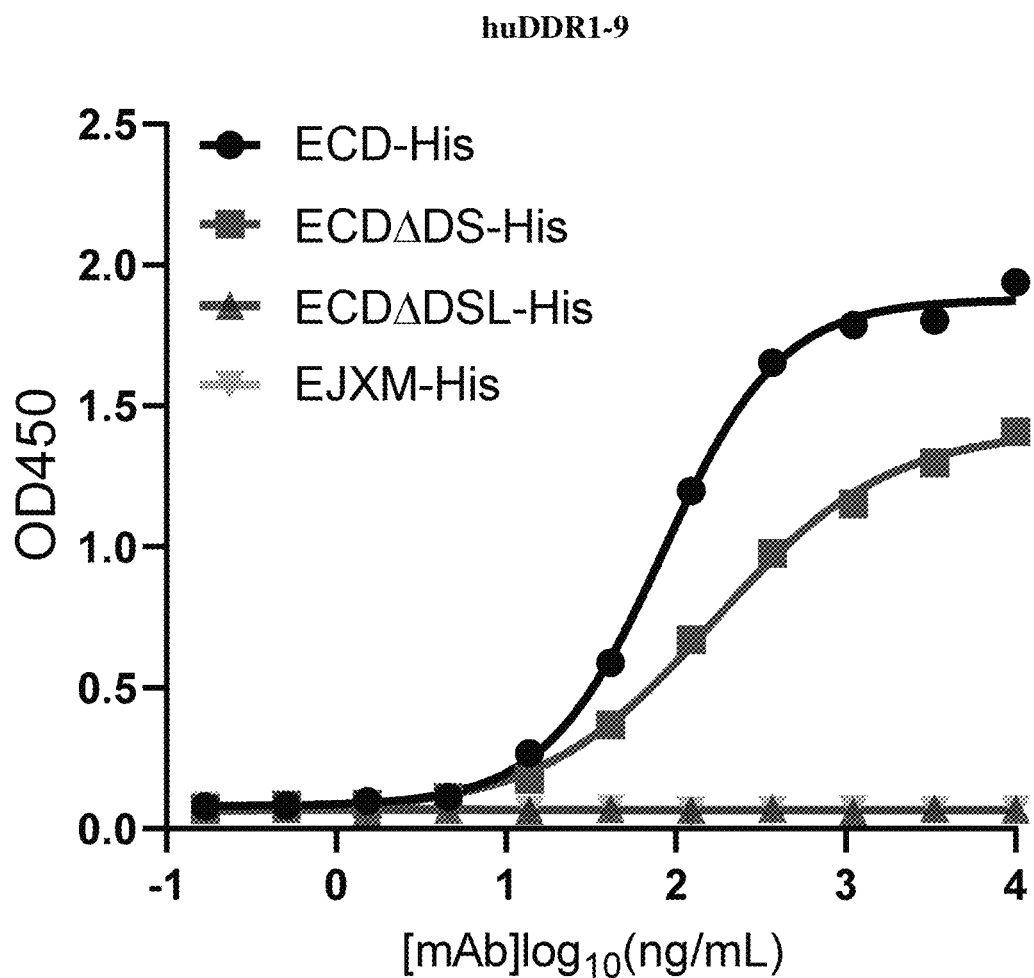
FIG. 18A-C. Determination of DDR1 antibody binding to ECD and DS or DSL domains using ELISA method. Recombinant DDR1 extracellular (ECD) protein and domain proteins were coated on a high binding 96-well plates at concentration at 2 µg/ml.
Figure 18B:
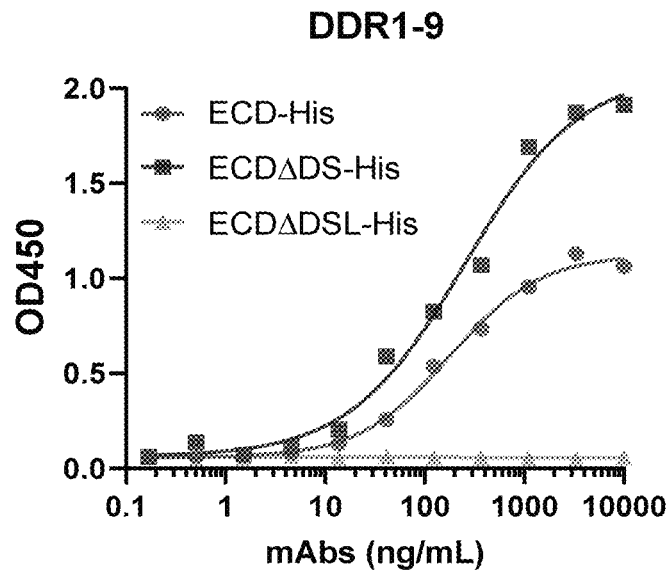
Figure 18C:
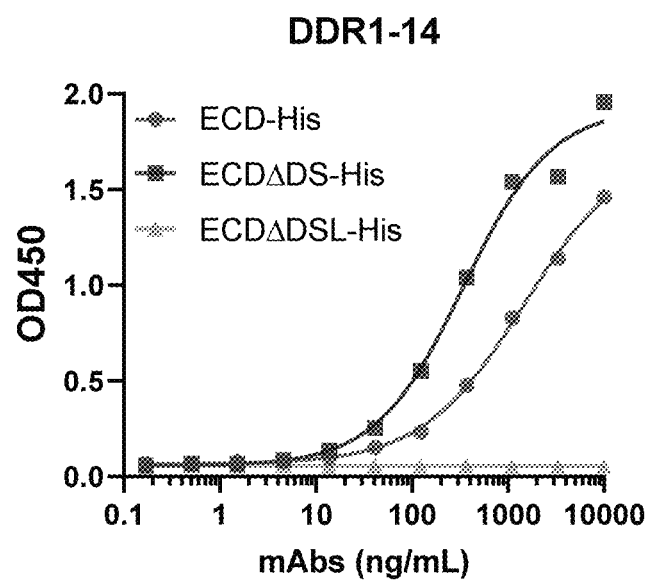

Antibody binding domain determination. To determine the binding of DDR1-9 (FIG. 18B) and DDR1-14 (FIG. 18C), and humanized DDR1-9hu-Abl to ECD and DS or DSL domains an ELISA method was used (FIG. 18A). Recombinant DDR1 extracellular (ECD) protein and domain deletion proteins were coated onto high binding 96-well plates at concentration at 2 μg/ml. DDR1 antibody titration was used to determine binding curves and EC50s shown in FIG. 18ECD and domain proteins were expressed in HEK293 cells and purified using NTA resin to >85% purity. Recombinantly expressed domain proteins were coated on a high-binding 96-well plate (Fisher Scientific) at concentration at 2ug/ml. A series of antibody titrations was used to determine binding EC50. Deletion of DSL domain of DDR1 ECD impaired the bindings of both DDR1-9 and DDR1-14 antibodies. Fragment with deletion of DS domain showed similar or better binding than the ECD protein. Fragment with DSL deletion totally abolished DDR1-9, DDR1-14, and DDR1-9Hu binding.

Deletion of the DS domain of DDR1 ECD did not affect binding of DDR1-9 and DDR1-14 antibody but resulted in a reduced binding by humanized DDR1-9hu antibody. The deletion of DS domain alone reduced binding with an $EC_{50}$ of 168 ng/ml vs 83 ng/ml, while the deletion of the DSL domain alone totally abolished binding of all three DDR1 antibodies.

TABLE 11

Binding affinities determined using BLI based Octet method

| Antibody Name | Heavy/Light chain pairing | KD (nM) | kon (1/Ms) | kdis (1/s) | Full R^2 |
| --- | --- | --- | --- | --- | --- |
| DDR1-9Hu-Ab1 | DDR1-9hu_Hv/ DDR1-9hu_Lv1 | 0.39 ± 0.02 | 1.65E+05 | 6.52E−05 | 0.9967 |
| DDR1-9Hu-Ab2 | DDR1-9hu_Hv/ DDR1-9hu_Lv2 | 0.77 ± 0.02 | 1.46E+05 | 1.13E−04 | 0.9957 |

TABLE 12

$EC_{50}$ of anti-DDR1 monoclonal antibodies

| Mab Name | EC50 (μg/ml) |
| --- | --- |
| DDR1-3 | 0.0598 |
| DDR1-9 | 0.1827 |
| DDR1-14 | 0.0713 |
| DDR1-33 | 0.1482 |

TABLE 13

Binding affinity to human DDR1 determined using Octet (96-Red) instrument

| Antibodies | KD | kon(1/Ms) | kdis(1/s) | Full X^2 | Full R^2 |
| --- | --- | --- | --- | --- | --- |
| DDR1-3 | 1.100 ± 0.038 nM | 1.73E+06 | 1.91E−03 | 6.840 | 0.934 |
| DDR1-9 | 0.236 ± 0.003 nM | 3.11E+05 | 7.35E−05 | 0.368 | 1.000 |
| DDR1-14 | 0.113 ± 0.005 nM | 2.02E+05 | 2.27E−05 | 0.162 | 1.000 |
| DDR1-33 | 0.797 ± 0.005 nM | 6.19E+05 | 4.93E−04 | 2.602 | 0.998 |

TABLE 14

Epitope groups of DDR1 mAbs

| mAb Name | Epitope Bins |
|---|---|
| DDR1-3 | Bin1 |
| DDR1-9 | Bin2 |
| DDR1-33 | |
| DDR1-14 | Bin3 |

Figure 19:
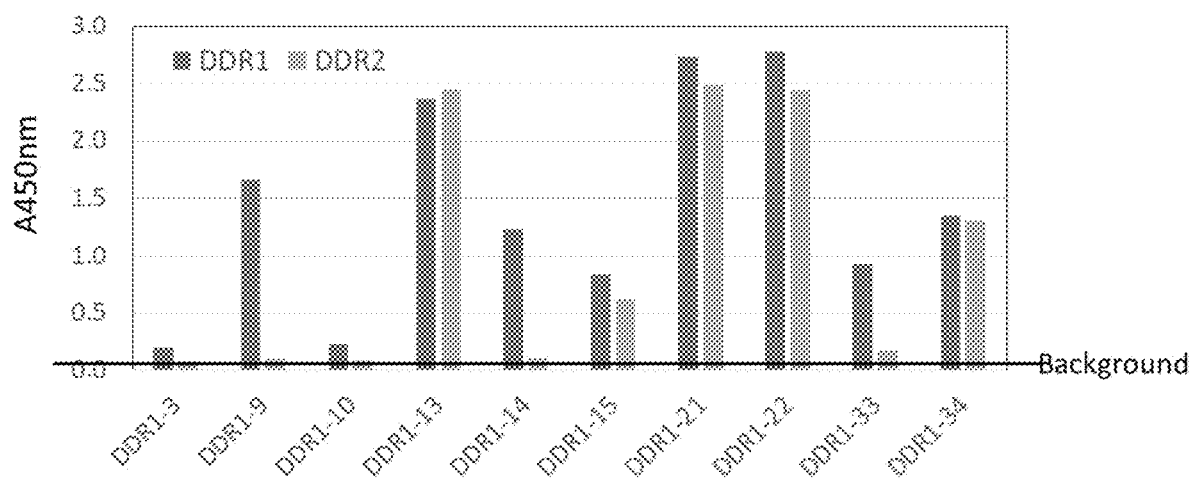
FIG. 19. Determination of cross-reactivity of a panel of monoclonal antibodies to human DDR2 using ELISA method. DDR1 or DDR2 ECD protein was coated on a high binding plate and each of monoclonal antibodies at 1 µg/ml concentration was added for binding detection with HRP conjugated anti-rabbit antibody (Jackson ImmuneResearch, PA).

To determination cross-reactivity of a panel of anti-human DDR1 monoclonal antibodies to human DDR2 ECD, an ELISA method was used. DDR1 ECD or DDR2 ECD protein was coated on a high binding plate and each of monoclonal antibodies was applied at 1ug/ml concentration and binding was detected using HRP conjugated anti-rabbit antibody (Jackson ImmuneResearch, PA). The results are shown in FIG. 19. Monoclonal antibodies DDR1-3; DDR1-9; DDR1-10; DDR1-14 and DDR1-33 were specific for DDR1 epitopes, while clones DDR1-13; DDR1-15; DDR1-21; DDR1-22 and DDR1-34 appear to recognize epitopes present on both DDR1 and DDR2 ECD.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A monoclonal antibody or antigen-binding fragment thereof that specifically binds to discoidin domain receptor 1 (DDR1) protein, comprising:

a light chain variable region comprising an LC-CDR1, an LC-CDR2 and an LC-CDR3, wherein the amino acid sequence of the LC-CDR1 comprises the amino acid sequence of amino acids 24-34 of SEQ ID NO: 150, the amino acid sequence of the LC-CDR2 comprises the amino acid sequence of amino acids 50-56 of SEQ ID NO: 150, the amino acid sequence of the LC-CDR3 comprises the amino acid sequence of amino acids 89-97 of SEQ ID NO: 150, and a heavy chain variable region comprising an HC-CDR1, an HC-CDR2, and an HC-CDR3, wherein the amino acid sequence of the HC-CDR1 comprises the amino acid sequence of amino acids 31-35 of SEQ ID NO: 152, the amino acid sequence of the HC-CDR2 comprises the amino acid sequence of amino acids 50-65 of SEQ ID NO: 152, and the amino acid sequence of the HC-CDR3 comprises the amino acid sequence of amino acids 98-110 of SEQ ID NO: 152, and wherein the monoclonal antibody is a rabbit, a chimeric or a humanized antibody, and wherein the monoclonal antibody is not a bispecific antibody.

2. An antibody-drug conjugate, comprising the monoclonal antibody or antigen-binding fragment thereof of claim 1, and an anti-tumor drug, wherein the anti-tumor drug is linked to the monoclonal antibody or antigen-binding fragment thereof.

3. A pharmaceutical composition comprising the monoclonal antibody or antigen-binding fragment thereof of claim 1, and a pharmaceutically acceptable carrier.

4. The monoclonal antibody or antigen-binding fragment thereof of claim 1, wherein the amino acid sequence of the light chain variable region comprises the amino acid sequence of SEQ ID NO: 150 and the amino acid sequence of the heavy chain variable region comprises the amino acid sequence of SEQ ID NO: 152.

5. The monoclonal antibody or antigen-binding fragment thereof of claim 1, which is a humanized antibody.

6. The monoclonal antibody or antigen-binding fragment thereof of claim 1, which comprises a heavy chain of $IgG_1$, $IgG_2$, $IgG_3$, or $IgG_4$ subtype.

7. The monoclonal antibody or antigen-binding fragment thereof of claim 1, which comprises a heavy chain of $IgG_1$ subtype.

8. The monoclonal antibody or antigen-binding fragment thereof of claim 1, wherein the antigen-binding fragment is a ScFv (single chain fragment variable) antibody, Fab fragment, $F(ab')_2$ fragment, or Fv fragment.

9. A pharmaceutical composition comprising the monoclonal antibody or antigen-binding fragment thereof of claim 4, and a pharmaceutically acceptable carrier.

10. The monoclonal antibody or antigen-binding fragment thereof of claim 1, which is a humanized antibody comprising two $IgG_1$ heavy chains and two kappa light chains.

11. The monoclonal antibody or antigen-binding fragment thereof of claim 4, which is a humanized antibody comprising two $IgG_1$ heavy chains and two kappa light chains.

12. A pharmaceutical composition comprising the monoclonal antibody or antigen-binding fragment thereof of claim 10, and a pharmaceutically acceptable carrier.

13. A pharmaceutical composition comprising the monoclonal antibody or antigen-binding fragment thereof of claim 11, and a pharmaceutically acceptable carrier.

\* \* \* \* \*

```
SEQUENCE LISTING

Sequence total quantity: 316
SEQ ID NO: 1            moltype = DNA  length = 3304
FEATURE                 Location/Qualifiers
source                  1..3304
                        mol_type = other DNA
                        organism = Homo sapiens
SEQUENCE: 1
agatgctgcc cccaccccct taggcccgag ggatcaggag ctatgggacc agaggccctg   60
tcatctttac tgctgctgct cttggtggca agtggagatg ctgacatgaa gggacattt   120
gatcctgcca agtgccgcta tgccctgggc atgcaggacc ggaccatccc agacagtgac  180
atctctgctt ccagctcctg gtcagattcc actgccgccc gccacagcag gttggagagc  240
agtgacgggg atgggcctg gtgccccgca gggtcggtgt ttcccaagga ggaggagtac   300
ttgcaggtgg atctacaacg actgcacctg gtggctctgg tgggcaccca gggacggcat  360
gccgggggcc tgggcaagga gttctcccgg agctaccggc tgcgttactc ccgggatggt  420
cgccgctgga tgggctggaa ggaccgctgg ggtcaggagg tgatctcagg caatgaggac  480
cctgagggag tggtgctgaa ggaccttggg ccccccatgg ttgcccgact ggttcgcttc  540
taccccgggc ctgaccgggt catgagcgtc tgtctgcggg tagagctcta tggctgcctc  600
tggagggatg gactcctgtc ttacaccgcc cctgtgcggg agacaatgta tttatctgag  660
gccgtgtacc tcaacgactc cacctatgac ggacataccg tgggcggact gcagtatggg  720
ggtctgggcc agctggcaga tggtgtggtg gggctggatg actttaggaa gagtcaggag  780
ctgcgggtct ggccaggcta tgactatgtg ggatggagca accagcagtt ctccagtggc  840
tatgtggaga tggagtttga gtttgaccgg ctgagggcct tccaggctat gcaggtccac  900
tgtaacaaca tgcacacgct gggagcccgt ctgcctgcgg gggtggaatg tcgcttccgg  960
cgtggccctg ccatggcctg ggaggggag cccatgcgcc acaacctagg gggcaacctg  1020
ggggacccca gagcccgggc tgtctcagtg ccccttggcg gccgtgtggc tcgctttctg  1080
cagtgccgct tcctcttttgc ggggcccctgg ttactcttca gcgaaaatctc cttcatctct  1140
gatgtggtga acaattcctc tccggcactg ggaggcacct tcccgccagc ccctggtgg  1200
ccgcctggcc cacctcccac caacttcagc agcttggagc tggagcccag aggccagcag  1260
cccgtggcca aggccgaggg gagcccgacc gccatcctca tcggctgcct ggtggccatc  1320
atcctgctcc tgctgctcat cattgccctc atgctctggc ggctgcactg gcgcaggctc  1380
ctcagcaagg ctgaacggag ggtgttggaa gaggagctga cggttcacct ctctgtccct  1440
ggggacacta tcctcatcaa caaccgccca ggtcctagag agccaccccc gtaccaggag  1500
ccccggcctc gtgggaatcc gccccactcc gctccctgtg tccccaatgg ctctggtgca  1560
cctgtgtgag gtcgacagcc ctcaagatct ggttagtctt gatttccccc ttaatgtgcg  1620
taagggacac cctttgctgg tagctgtcaa gatcttacgg ccagatgcca ccaagaatgc  1680
caggaatgat ttcctgaaag aggtgaagat catgtcgagg ctcaaggacc caaacatcat  1740
tcggctgctg ggcgtgtgtg tgcaggacga ccccctctgc atgattactg actacatgga  1800
gaacggcgac ctcaaccagt tcctcagtgc ccaccagctg gaggacaagg cagccgaggg  1860
ggccctggg gacgggcagg ctgcgcaggg gcccaccatc agctacccaa tgctgctgca  1920
tgtggcagcc cagatcgcct ccggcatgcg ctatctggcc acactcaact ttgtacatcg  1980
ggacctggcc acgcggaact gcctagttgg ggaaaatttc accatcaaaa tcgcagactt  2040
tggcatgagc cggaacctct atgctgggga ctattaccgt gtgcagggcc gggcagtgct  2100
gcccatccgc tggatggcct gggagtgcat cctcatgggg aagttcacga ctgcgagtga  2160
cgtgtggcc tttggtgtga ccctgtggga ggtgctgatg ctctgtaggg cccagccctt  2220
tgggcagctc accgacgagc aggtcatcga gaacgcgggg gagttcttcc gggaccaggg  2280
ccggcaggtg tacctgtccc ggccgcctgc ctgcccgcag ggctatatg agctgatgct  2340
tcggtgctgg agcgggagt ctgagcagcg accaccttt tcccagctgc atcggttcct  2400
ggcagaggat gcactcaaca cggtgtgaat cacacatcca gctgccctc cctcagggag  2460
cgatccaggg gaagccagtg acactaaaac aagaggacac aatgccacct ctgcccttcc  2520
cctcccgaca gccatcacc tctaatagag gcagtgagac tgcaggtggg ctgggccac  2580
ccagggagct gatgcccctt ctcccttcc tggacacact ctcatgtccc cttcctgttc  2640
ttccttccta gaagccctg tcgcccaccc agctggtcct gtggatggga tcctctccac  2700
cctcctctag ccatcccttg gggaagggtg gggagaaata taggatagac actggacatg  2760
```

-continued

```
gcccattgga gcacctgggc cccactggac aacactgatt cctggagagg tggctgcgcc    2820
cccagcttct ctctccctgt cacacactgg accccactgg ctgagaatct ggggtgagg    2880
aggacaagaa ggagaggaaa atgtttcctt gtgcctgctc ctgtacttgt cctcagcttg    2940
ggcttcttcc tcctccatca cctgaaacac tggacctggg ggtagccccg ccccagccct    3000
cagtcacccc cacttcccac ttgcagtctt gtagctgaaa cttctctaag cctatacgtt    3060
tctgtggagt aaatattggg attgggggga aagagggagc aacggcccat agccttgggg    3120
ttggacatct ctagtgtagc tgccacattg attttctat aatcacttgg ggtttgtaca    3180
tttttgggg gagagacaca gattttaca ctaatatatg gacctagctt gaggcaattt    3240
taatcccctg cactaggcag gtaataataa aggttgagtt ttccacaaaa aaaaaaaaaa    3300
aaaa                                                                 3304

SEQ ID NO: 2              moltype = AA  length = 508
FEATURE                   Location/Qualifiers
source                    1..508
                          mol_type = protein
                          organism = Homo sapiens
SEQUENCE: 2
MGPEALSSLL LLLLVASGDA DMKGHFDPAK CRYALGMQDR TIPDSDISAS SSWSDSTAAR    60
HSRLESSDGD GAWCPAGSVF PKEEEYLQVD LQRLHLVALV GTQGRHAGGL GKEFSRSYRL    120
RYSRDGRRWM GWKDRWGQEV ISGNEDPEGV VLKDLGPPMV ARLVRFYPRA DRVMSVCLRV    180
ELYGCLWRDG LLSYTAPVGQ TMYLSEAVYL NDSTYDGHTV GGLQYGGLGQ LADGVVGLDD    240
FRKSQELRVW PGYDYVGWSN HSFSSGYVEM EFEFDRLRAF QAMQVHCNNM HTLGARLPGG    300
VECRFRRGPA MAWEGEPMRH NLGGNLGDPR ARAVSPLGG RVARFLQCRF LFAGPWLLFS    360
EISFISDVVN NSSPALGGTF PPAPWWPPGP PPTNFSSLEL EPRGQQPVAK AEGSPTAILI    420
GCLVAIILLL LLIIALMLWR LHWRRLLSKA ERRVLEEELT VHLSVPGDTI LINNRPGPRE    480
PPPYQEPRPR GNPPHSAPCV PNGSGAPV                                      508

SEQ ID NO: 3              moltype = AA  length = 6
FEATURE                   Location/Qualifiers
REGION                    1..6
                          note = Synthetic sequence
source                    1..6
                          mol_type = protein
                          organism = synthetic construct
SEQUENCE: 3
QNIYSN                                                               6

SEQ ID NO: 4              moltype = AA  length = 12
FEATURE                   Location/Qualifiers
REGION                    1..12
                          note = Synthetic sequence
source                    1..12
                          mol_type = protein
                          organism = synthetic construct
SEQUENCE: 4
QSGYYSSSTD IA                                                        12

SEQ ID NO: 5              moltype = AA  length = 6
FEATURE                   Location/Qualifiers
REGION                    1..6
                          note = Synthetic sequence
source                    1..6
                          mol_type = protein
                          organism = synthetic construct
SEQUENCE: 5
QTISSW                                                               6

SEQ ID NO: 6              moltype = AA  length = 12
FEATURE                   Location/Qualifiers
REGION                    1..12
                          note = Synthetic sequence
source                    1..12
                          mol_type = protein
                          organism = synthetic construct
SEQUENCE: 6
QQGISSSNVD NV                                                        12

SEQ ID NO: 7              moltype = AA  length = 6
FEATURE                   Location/Qualifiers
REGION                    1..6
                          note = Synthetic sequence
source                    1..6
                          mol_type = protein
                          organism = synthetic construct
SEQUENCE: 7
QTISSW                                                               6

SEQ ID NO: 8              moltype = AA  length = 15
FEATURE                   Location/Qualifiers
```

```
REGION                  1..15
                        note = Synthetic sequence
source                  1..15
                        mol_type = protein
                        organism = synthetic construct
SEQUENCE: 8
QCTYGSGSSS SYGCA                                                             15

SEQ ID NO: 9            moltype = AA  length = 7
FEATURE                 Location/Qualifiers
REGION                  1..7
                        note = Synthetic sequence
source                  1..7
                        mol_type = protein
                        organism = synthetic construct
SEQUENCE: 9
QSVYSNY                                                                       7

SEQ ID NO: 10           moltype = AA  length = 11
FEATURE                 Location/Qualifiers
REGION                  1..11
                        note = Synthetic sequence
source                  1..11
                        mol_type = protein
                        organism = synthetic construct
SEQUENCE: 10
QGGYSEIIEN T                                                                 11

SEQ ID NO: 11           moltype = AA  length = 6
FEATURE                 Location/Qualifiers
REGION                  1..6
                        note = Synthetic sequence
source                  1..6
                        mol_type = protein
                        organism = synthetic construct
SEQUENCE: 11
QSIGSV                                                                        6

SEQ ID NO: 12           moltype = AA  length = 9
FEATURE                 Location/Qualifiers
REGION                  1..9
                        note = Synthetic sequence
source                  1..9
                        mol_type = protein
                        organism = synthetic construct
SEQUENCE: 12
QYIPYGSSP                                                                     9

SEQ ID NO: 13           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 13
QSIGSTY                                                                       7

SEQ ID NO: 14           moltype = AA  length = 12
FEATURE                 Location/Qualifiers
REGION                  1..12
                        note = Synthetic sequence
source                  1..12
                        mol_type = protein
                        organism = synthetic construct
SEQUENCE: 14
LYGGFGSSTG DA                                                                12

SEQ ID NO: 15           moltype = AA  length = 6
FEATURE                 Location/Qualifiers
REGION                  1..6
                        note = Synthetic sequence
source                  1..6
                        mol_type = protein
                        organism = synthetic construct
SEQUENCE: 15
QTIYSN                                                                        6

SEQ ID NO: 16           moltype = AA  length = 10
```

```
                                      -continued

FEATURE                 Location/Qualifiers
REGION                  1..10
                        note = Synthetic sequence
source                  1..10
                        mol_type = protein
                        organism = synthetic construct
SEQUENCE: 16
QSYYGADDYT                                                                  10

SEQ ID NO: 17           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 17
KSVYNNNA                                                                    8

SEQ ID NO: 18           moltype = AA  length = 11
FEATURE                 Location/Qualifiers
REGION                  1..11
                        note = Synthetic sequence
source                  1..11
                        mol_type = protein
                        organism = synthetic construct
SEQUENCE: 18
AGDYSDISDN N                                                                11

SEQ ID NO: 19           moltype = AA  length = 6
FEATURE                 Location/Qualifiers
REGION                  1..6
                        note = Synthetic sequence
source                  1..6
                        mol_type = protein
                        organism = synthetic construct
SEQUENCE: 19
QSISSY                                                                      6

SEQ ID NO: 20           moltype = AA  length = 13
FEATURE                 Location/Qualifiers
REGION                  1..13
                        note = Synthetic sequence
source                  1..13
                        mol_type = protein
                        organism = synthetic construct
SEQUENCE: 20
QNNNGFSGSN FNN                                                              13

SEQ ID NO: 21           moltype = AA  length = 6
FEATURE                 Location/Qualifiers
REGION                  1..6
                        note = Synthetic sequence
source                  1..6
                        mol_type = protein
                        organism = synthetic construct
SEQUENCE: 21
QTIYSS                                                                      6

SEQ ID NO: 22           moltype = AA  length = 13
FEATURE                 Location/Qualifiers
REGION                  1..13
                        note = Synthetic sequence
source                  1..13
                        mol_type = protein
                        organism = synthetic construct
SEQUENCE: 22
QQGSSISNVD KNA                                                              13

SEQ ID NO: 23           moltype = AA  length = 6
FEATURE                 Location/Qualifiers
REGION                  1..6
                        note = Synthetic sequence
source                  1..6
                        mol_type = protein
                        organism = synthetic construct
SEQUENCE: 23
QSIGSY                                                                      6
```

```
SEQ ID NO: 24           moltype = AA   length = 13
FEATURE                 Location/Qualifiers
REGION                  1..13
                        note = Synthetic sequence
source                  1..13
                        mol_type = protein
                        organism = synthetic construct
SEQUENCE: 24
QNNNGMTVSD FNA                                                               13

SEQ ID NO: 25           moltype = AA   length = 7
FEATURE                 Location/Qualifiers
REGION                  1..7
                        note = Synthetic sequence
source                  1..7
                        mol_type = protein
                        organism = synthetic construct
SEQUENCE: 25
QIIDHDH                                                                       7

SEQ ID NO: 26           moltype = AA   length = 13
FEATURE                 Location/Qualifiers
REGION                  1..13
                        note = Synthetic sequence
source                  1..13
                        mol_type = protein
                        organism = synthetic construct
SEQUENCE: 26
QNNNGMTVSD FNA                                                               13

SEQ ID NO: 27           moltype = AA   length = 8
FEATURE                 Location/Qualifiers
REGION                  1..8
                        note = Synthetic sequence
source                  1..8
                        mol_type = protein
                        organism = synthetic construct
SEQUENCE: 27
QSVVDKNW                                                                      8

SEQ ID NO: 28           moltype = AA   length = 10
FEATURE                 Location/Qualifiers
REGION                  1..10
                        note = Synthetic sequence
source                  1..10
                        mol_type = protein
                        organism = synthetic construct
SEQUENCE: 28
AGDFESGVSG                                                                   10

SEQ ID NO: 29           moltype = AA   length = 8
FEATURE                 Location/Qualifiers
REGION                  1..8
                        note = Synthetic sequence
source                  1..8
                        mol_type = protein
                        organism = synthetic construct
SEQUENCE: 29
KNIYNNNA                                                                      8

SEQ ID NO: 30           moltype = AA   length = 11
FEATURE                 Location/Qualifiers
REGION                  1..11
                        note = Synthetic sequence
source                  1..11
                        mol_type = protein
                        organism = synthetic construct
SEQUENCE: 30
AADYSDISDN N                                                                 11

SEQ ID NO: 31           moltype = AA   length = 8
FEATURE                 Location/Qualifiers
REGION                  1..8
                        note = Synthetic sequence
source                  1..8
                        mol_type = protein
                        organism = synthetic construct
SEQUENCE: 31
QSVYSNNY                                                                      8
```

```
SEQ ID NO: 32          moltype = AA   length = 9
FEATURE                Location/Qualifiers
REGION                 1..9
                       note = Synthetic sequence
source                 1..9
                       mol_type = protein
                       organism = synthetic construct
SEQUENCE: 32
LGGYNDDAN                                                                    9

SEQ ID NO: 33          moltype = AA   length = 8
FEATURE                Location/Qualifiers
REGION                 1..8
                       note = Synthetic sequence
source                 1..8
                       mol_type = protein
                       organism = synthetic construct
SEQUENCE: 33
ESVYSNNH                                                                     8

SEQ ID NO: 34          moltype = AA   length = 9
FEATURE                Location/Qualifiers
REGION                 1..9
                       note = Synthetic sequence
source                 1..9
                       mol_type = protein
                       organism = synthetic construct
SEQUENCE: 34
LGGYNDDAN                                                                    9

SEQ ID NO: 35          moltype = AA   length = 7
FEATURE                Location/Qualifiers
REGION                 1..7
                       note = Synthetic sequence
source                 1..7
                       mol_type = protein
                       organism = synthetic construct
SEQUENCE: 35
QSIDNND                                                                      7

SEQ ID NO: 36          moltype = AA   length = 11
FEATURE                Location/Qualifiers
REGION                 1..11
                       note = Synthetic sequence
source                 1..11
                       mol_type = protein
                       organism = synthetic construct
SEQUENCE: 36
QSYCVNTYGY T                                                                11

SEQ ID NO: 37          moltype = AA   length = 6
FEATURE                Location/Qualifiers
REGION                 1..6
                       note = Synthetic sequence
source                 1..6
                       mol_type = protein
                       organism = synthetic construct
SEQUENCE: 37
QSISNH                                                                       6

SEQ ID NO: 38          moltype = AA   length = 14
FEATURE                Location/Qualifiers
REGION                 1..14
                       note = Synthetic sequence
source                 1..14
                       mol_type = protein
                       organism = synthetic construct
SEQUENCE: 38
QSYYIINRSN YANS                                                             14

SEQ ID NO: 39          moltype = AA   length = 6
FEATURE                Location/Qualifiers
REGION                 1..6
                       note = Synthetic sequence
source                 1..6
                       mol_type = protein
                       organism = synthetic construct
SEQUENCE: 39
```

```
ESINSW                                                                    6

SEQ ID NO: 41          moltype = AA  length = 6
FEATURE                Location/Qualifiers
REGION                 1..6
                       note = Synthetic sequence
source                 1..6
                       mol_type = protein
                       organism = synthetic construct
SEQUENCE: 40
QSYYIINRSN YGNS                                                          14

SEQ ID NO: 41          moltype = AA  length = 6
FEATURE                Location/Qualifiers
REGION                 1..6
                       note = Synthetic sequence
source                 1..6
                       mol_type = protein
                       organism = synthetic construct
SEQUENCE: 41
ETISSR                                                                    6

SEQ ID NO: 42          moltype = AA  length = 14
FEATURE                Location/Qualifiers
REGION                 1..14
                       note = Synthetic sequence
source                 1..14
                       mol_type = protein
                       organism = synthetic construct
SEQUENCE: 42
QGCYYGGGSF YDSA                                                          14

SEQ ID NO: 43          moltype = AA  length = 8
FEATURE                Location/Qualifiers
REGION                 1..8
                       note = Synthetic sequence
source                 1..8
                       mol_type = protein
                       organism = synthetic construct
SEQUENCE: 43
ENLYKDNY                                                                  8

SEQ ID NO: 44          moltype = AA  length = 9
FEATURE                Location/Qualifiers
REGION                 1..9
                       note = Synthetic sequence
source                 1..9
                       mol_type = protein
                       organism = synthetic construct
SEQUENCE: 44
AGGYDSVVD                                                                 9

SEQ ID NO: 45          moltype = AA  length = 8
FEATURE                Location/Qualifiers
REGION                 1..8
                       note = Synthetic sequence
source                 1..8
                       mol_type = protein
                       organism = synthetic construct
SEQUENCE: 45
GFSLSRYA                                                                  8

SEQ ID NO: 46          moltype = AA  length = 7
FEATURE                Location/Qualifiers
REGION                 1..7
                       note = Synthetic sequence
source                 1..7
                       mol_type = protein
                       organism = synthetic construct
SEQUENCE: 46
IGSSGLT                                                                   7

SEQ ID NO: 47          moltype = AA  length = 18
FEATURE                Location/Qualifiers
REGION                 1..18
                       note = Synthetic sequence
source                 1..18
                       mol_type = protein
                       organism = synthetic construct
```

```
SEQUENCE: 47
ARGMWYDDSD DYEDYFNL                                                   18

SEQ ID NO: 48           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 48
GIDLSSYA                                                              8

SEQ ID NO: 49           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 49
INIGGGT                                                               7

SEQ ID NO: 50           moltype = AA  length = 14
FEATURE                 Location/Qualifiers
REGION                  1..14
                        note = Synthetic sequence
source                  1..14
                        mol_type = protein
                        organism = synthetic construct
SEQUENCE: 50
ARDVDAHTLT YFTL                                                       14

SEQ ID NO: 51           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 51
GFTLSNNA                                                              8

SEQ ID NO: 52           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 52
IYASGRT                                                               7

SEQ ID NO: 53           moltype = AA  length = 16
FEATURE                 Location/Qualifiers
REGION                  1..16
                        note = Synthetic sequence
source                  1..16
                        mol_type = protein
                        organism = synthetic construct
SEQUENCE: 53
ARGDTETDYG IPYFDL                                                     16

SEQ ID NO: 54           moltype = AA  length = 9
FEATURE                 Location/Qualifiers
REGION                  1..9
                        note = Synthetic sequence
source                  1..9
                        mol_type = protein
                        organism = synthetic construct
SEQUENCE: 54
GFSFSSSYY                                                             9

SEQ ID NO: 55           moltype = AA  length = 8
FEATURE                 Location/Qualifiers
REGION                  1..8
                        note = Synthetic sequence
source                  1..8
                        mol_type = protein
```

```
                              organism = synthetic construct
SEQUENCE: 55
IYASSGST                                                                       8

SEQ ID NO: 56         moltype = AA   length = 14
FEATURE               Location/Qualifiers
REGION                1..14
                      note = Synthetic sequence
source                1..14
                      mol_type = protein
                      organism = synthetic construct
SEQUENCE: 56
AILGADYRLT RLDL                                                               14

SEQ ID NO: 57         moltype = AA   length = 8
FEATURE               Location/Qualifiers
REGION                1..8
                      note = Synthetic sequence
source                1..8
                      mol_type = protein
                      organism = synthetic construct
SEQUENCE: 57
GFSLNRYY                                                                       8

SEQ ID NO: 58         moltype = AA   length = 7
FEATURE               Location/Qualifiers
REGION                1..7
                      note = Synthetic sequence
source                1..7
                      mol_type = protein
                      organism = synthetic construct
SEQUENCE: 58
ISYGDTT                                                                        7

SEQ ID NO: 59         moltype = AA   length = 15
FEATURE               Location/Qualifiers
REGION                1..15
                      note = Synthetic sequence
source                1..15
                      mol_type = protein
                      organism = synthetic construct
SEQUENCE: 59
ARADTGDNGY LGLQL                                                              15

SEQ ID NO: 60         moltype = AA   length = 9
FEATURE               Location/Qualifiers
REGION                1..9
                      note = Synthetid sequence
source                1..9
                      mol_type = protein
                      organism = synthetic construct
SEQUENCE: 60
GFSFSSGYY                                                                      9

SEQ ID NO: 61         moltype = AA   length = 9
FEATURE               Location/Qualifiers
REGION                1..9
                      note = Synthetic sequence
source                1..9
                      mol_type = protein
                      organism = synthetic construct
SEQUENCE: 61
IYTGRTDFT                                                                      9

SEQ ID NO: 62         moltype = AA   length = 17
FEATURE               Location/Qualifiers
REGION                1..17
                      note = Synthetic sequence
source                1..17
                      mol_type = protein
                      organism = synthetic construct
SEQUENCE: 62
ARGDYSGGVG GNYWLDL                                                            17

SEQ ID NO: 63         moltype = AA   length = 8
FEATURE               Location/Qualifiers
REGION                1..8
                      note = Synthetic sequence
source                1..8
```

-continued

```
                       mol_type = protein
                       organism = synthetic construct
SEQUENCE: 63
GIDLSNTW                                                                    8

SEQ ID NO: 64          moltype = AA  length = 7
FEATURE                Location/Qualifiers
REGION                 1..7
                       note = Synthetic sequence
source                 1..7
                       mol_type = protein
                       organism = synthetic construct
SEQUENCE: 64
ITDSGTT                                                                     7

SEQ ID NO: 65          moltype = AA  length = 14
FEATURE                Location/Qualifiers
REGION                 1..14
                       note = Synthetic sequence
source                 1..14
                       mol_type = protein
                       organism = synthetic construct
SEQUENCE: 65
GRDPGDITSG TNDL                                                            14

SEQ ID NO: 66          moltype = AA  length = 8
FEATURE                Location/Qualifiers
REGION                 1..8
                       note = Synthetic sequence
source                 1..8
                       mol_type = protein
                       organism = synthetic construct
SEQUENCE: 66
SGFSLNNY                                                                    8

SEQ ID NO: 67          moltype = AA  length = 7
FEATURE                Location/Qualifiers
REGION                 1..7
                       note = Synthetic sequence
source                 1..7
                       mol_type = protein
                       organism = synthetic construct
SEQUENCE: 67
IFNNGDI                                                                     7

SEQ ID NO: 68          moltype = AA  length = 11
FEATURE                Location/Qualifiers
REGION                 1..11
                       note = Synthetic sequence
source                 1..11
                       mol_type = protein
                       organism = synthetic construct
SEQUENCE: 68
ARTGYRTGGW L                                                               11

SEQ ID NO: 69          moltype = AA  length = 8
FEATURE                Location/Qualifiers
REGION                 1..8
                       note = Synthetic sequence
source                 1..8
                       mol_type = protein
                       organism = synthetic construct
SEQUENCE: 69
GIDLSYYA                                                                    8

SEQ ID NO: 70          moltype = AA  length = 7
FEATURE                Location/Qualifiers
REGION                 1..7
                       note = Synthetic sequence
source                 1..7
                       mol_type = protein
                       organism = synthetic construct
SEQUENCE: 70
INGRGDT                                                                     7

SEQ ID NO: 71          moltype = AA  length = 19
FEATURE                Location/Qualifiers
REGION                 1..19
                       note = Synthetic sequence
```

```
source                  1..19
                        mol_type = protein
                        organism = synthetic construct
SEQUENCE: 71
AREDSAIPFI VGNYYGMDL                                              19

SEQ ID NO: 72           moltype = AA  length = 9
FEATURE                 Location/Qualifiers
REGION                  1..9
                        note = Synthetic sequence
source                  1..9
                        mol_type = protein
                        organism = synthetic construct
SEQUENCE: 72
TFSFNSRYW                                                          9

SEQ ID NO: 73           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 73
INNGDIS                                                            7

SEQ ID NO: 74           moltype = AA  length = 13
FEATURE                 Location/Qualifiers
REGION                  1..13
                        note = Synthetic sequence
source                  1..13
                        mol_type = protein
                        organism = synthetic construct
SEQUENCE: 74
AKGGNLAGDC YGL                                                    13

SEQ ID NO: 75           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 75
GFSLNRYA                                                           8

SEQ ID NO: 76           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 76
IGSSGST                                                            7

SEQ ID NO: 77           moltype = AA  length = 22
FEATURE                 Location/Qualifiers
REGION                  1..22
                        note = Synthetic sequence
source                  1..22
                        mol_type = protein
                        organism = synthetic construct
SEQUENCE: 77
ARDLDDSYGY TYATGMDIRL DL                                          22

SEQ ID NO: 78           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 78
GFSLSDYA                                                           8

SEQ ID NO: 79           moltype = AA  length = 7
FEATURE                 Location/Qualifiers
REGION                  1..7
```

```
                        note = Synthetic sequence
source                  1..7
                        mol_type = protein
                        organism = synthetic construct
SEQUENCE: 79
INSRDDT                                                                 7

SEQ ID NO: 80           moltype = AA  length = 19
FEATURE                 Location/Qualifiers
REGION                  1..19
                        note = Synthetic sequence
source                  1..19
                        mol_type = protein
                        organism = synthetic construct
SEQUENCE: 80
AREDSSIPFI VGNYYGMDL                                                   19

SEQ ID NO: 81           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 81
GFSLSSYG                                                                8

SEQ ID NO: 82           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 82
IYPSGSI                                                                 7

SEQ ID NO: 83           moltype = AA  length = 12
FEATURE                 Location/Qualifiers
REGION                  1..12
                        note = Synthetic sequence
source                  1..12
                        mol_type = protein
                        organism = synthetic construct
SEQUENCE: 83
VRYLTGSSDL HL                                                          12

SEQ ID NO: 84           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 84
GFSLSDYA                                                                8

SEQ ID NO: 85           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 85
INNGDIY                                                                 7

SEQ ID NO: 86           moltype = AA  length = 11
FEATURE                 Location/Qualifiers
REGION                  1..11
                        note = Synthetic sequence
source                  1..11
                        mol_type = protein
                        organism = synthetic construct
SEQUENCE: 86
ARPGYRTGIW L                                                           11

SEQ ID NO: 87           moltype = AA  length = 9
FEATURE                 Location/Qualifiers
```

```
REGION                  1..9
                        note = Synthetic sequence'
source                  1..9
                        mol_type = protein
                        organism = synthetic construct
SEQUENCE: 87
GFDLRSYYY                                                                     9

SEQ ID NO: 88           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 88
IHGGEGNT                                                                      8

SEQ ID NO: 89           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 89
RGGWTNYF                                                                      8

SEQ ID NO: 90           moltype = AA  length = 9
FEATURE                 Location/Qualifiers
REGION                  1..9
                        note = Synthetic sequence
source                  1..9
                        mol_type = protein
                        organism = synthetic construct
SEQUENCE: 90
GFDLSSNYY                                                                     9

SEQ ID NO: 91           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 91
IYSSNTRT                                                                      8

SEQ ID NO: 92           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 92
RGGWTNYL                                                                      8

SEQ ID NO: 93           moltype = AA  length = 8
FEATURE                 Location/Qualifiers
REGION                  1..8
                        note = Synthetic sequence
source                  1..8
                        mol_type = protein
                        organism = synthetic construct
SEQUENCE: 93
GFSLSSHD                                                                      8

SEQ ID NO: 94           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 94
IISSGNT                                                                       7

SEQ ID NO: 95           moltype = AA  length = 10
```

```
FEATURE              Location/Qualifiers
REGION               1..10
                     note = Synthetic sequence
source               1..10
                     mol_type = protein
                     organism = synthetic construct
SEQUENCE: 95
ARDVYSGASP                                                          10

SEQ ID NO: 96        moltype = AA  length = 9
FEATURE              Location/Qualifiers
REGION               1..9
                     note = Synthetic sequence
source               1..9
                     mol_type = protein
                     organism = synthetic construct
SEQUENCE: 96
TFSFNSRYW                                                            9

SEQ ID NO: 97        moltype = AA  length = 7
FEATURE              Location/Qualifiers
REGION               1..7
                     note = Synthetic sequence
source               1..7
                     mol_type = protein
                     organism = synthetic construct
SEQUENCE: 97
INNGDIT                                                              7

SEQ ID NO: 98        moltype = AA  length = 13
FEATURE              Location/Qualifiers
REGION               1..13
                     note = Synthetic sequence
source               1..13
                     mol_type = protein
                     organism = synthetic construct
SEQUENCE: 98
AKGGNLAGDC YGL                                                      13

SEQ ID NO: 99        moltype = AA  length = 8
FEATURE              Location/Qualifiers
REGION               1..8
                     note = Synthetic sequence
source               1..8
                     mol_type = protein
                     organism = synthetic construct
SEQUENCE: 99
GFSLSSYY                                                             8

SEQ ID NO: 100       moltype = AA  length = 7
FEATURE              Location/Qualifiers
REGION               1..7
                     note = Synthetic sequence
source               1..7
                     mol_type = protein
                     organism = synthetic construct
SEQUENCE: 100
ITTAGPL                                                              7

SEQ ID NO: 101       moltype = AA  length = 15
FEATURE              Location/Qualifiers
REGION               1..15
                     note = Synthetic sequence
source               1..15
                     mol_type = protein
                     organism = synthetic construct
SEQUENCE: 101
ARGHAGSIYY SYFDL                                                    15

SEQ ID NO: 102       moltype = AA  length = 8
FEATURE              Location/Qualifiers
REGION               1..8
                     note = Synthetic sequence
source               1..8
                     mol_type = protein
                     organism = synthetic construct
SEQUENCE: 102
GFSLSSYD                                                             8
```

```
SEQ ID NO: 103           moltype = AA  length = 7
FEATURE                  Location/Qualifiers
REGION                   1..7
                         note = Synthetic sequence
source                   1..7
                         mol_type = protein
                         organism = synthetic construct
SEQUENCE: 103
SWNSGFV                                                                  7

SEQ ID NO: 104           moltype = AA  length = 13
FEATURE                  Location/Qualifiers
REGION                   1..13
                         note = Synthetic sequence
source                   1..13
                         mol_type = protein
                         organism = synthetic construct
SEQUENCE: 104
ARLGADDIYY FNL                                                          13

SEQ ID NO: 105           moltype = AA  length = 9
FEATURE                  Location/Qualifiers
REGION                   1..9
                         note = Synthetic sequence
source                   1..9
                         mol_type = protein
                         organism = synthetic construct
SEQUENCE: 105
GFDLSSYYY                                                                9

SEQ ID NO: 106           moltype = AA  length = 8
FEATURE                  Location/Qualifiers
REGION                   1..8
                         note = Synthetic sequence
source                   1..8
                         mol_type = protein
                         organism = synthetic construct
SEQUENCE: 106
IYTSSGAT                                                                 8

SEQ ID NO: 107           moltype = AA  length = 9
FEATURE                  Location/Qualifiers
REGION                   1..9
                         note = Synthetic sequence
source                   1..9
                         mol_type = protein
                         organism = synthetic construct
SEQUENCE: 107
RGGWCDFNL                                                                9

SEQ ID NO: 108           moltype = AA  length = 110
FEATURE                  Location/Qualifiers
REGION                   1..110
                         note = Synthetic sequence
source                   1..110
                         mol_type = protein
                         organism = synthetic construct
SEQUENCE: 108
ELVLTQTPAS VSAAVGGTVT INCQASQNIY SNLAWYQQKP GQPPKLLIYG ASNLESGVPS        60
RFKGSGSGTQ FTLTISDLEC DDAATYYCQS GYYSSSTDIA FGGGTEVVVK                  110

SEQ ID NO: 109           moltype = AA  length = 110
FEATURE                  Location/Qualifiers
REGION                   1..110
                         note = Synthetic sequence
source                   1..110
                         mol_type = protein
                         organism = synthetic construct
SEQUENCE: 109
ELVLTQTPAS VSEPVGGTVT IKCQASQTIS SWLSWYQQKP GQPPKLLIYY AFNLASGVPS        60
RFKGSGSGTE FTLTISDLEC ADAATYYCQQ GISSSNVDNV FGGGTEVVVK                  110

SEQ ID NO: 110           moltype = AA  length = 113
FEATURE                  Location/Qualifiers
REGION                   1..113
                         note = Synthetic sequence
source                   1..113
                         mol_type = protein
                         organism = synthetic construct
```

```
SEQUENCE: 110
ELVLTQTPAS VSEPVGGTVT IKCQASQTIS SWLSWYQQKP GQPPKLLIYY AFNLASGVPS    60
RFKGSGSGTE YTLTISDLEC ADAATYYCQC TYGSGSSSSY GCAFGGGTEL EIK          113

SEQ ID NO: 111          moltype = AA  length = 110
FEATURE                 Location/Qualifiers
REGION                  1..110
                        note = Synthetic sequence
source                  1..110
                        mol_type = protein
                        organism = synthetic construct
SEQUENCE: 111
ELVMTQTPSP VSAAVGGTVT ISCQSSQSVY SNYLSWYQQK PGQPPKLLIY ETSTLASGVP    60
SRFKGSGSGT QFTLTISDVQ CDDAATYYCQ GGYSEIIENT FGGGTEVEIK              110

SEQ ID NO: 112          moltype = AA  length = 107
FEATURE                 Location/Qualifiers
REGION                  1..107
                        note = Synthetic sequence
source                  1..107
                        mol_type = protein
                        organism = synthetic construct
SEQUENCE: 112
ELVMTQTPAS VEAAVGGTVT IKCQASQSIG SVLAWYQQKP GQRPKLLISG VFDLASGVPS    60
RFKGSGSGTE FTLTISDLEC ADAATYYCQY IPYGSSPFGG GTEVVVK                 107

SEQ ID NO: 113          moltype = AA  length = 111
FEATURE                 Location/Qualifiers
REGION                  1..111
                        note = Synthetic sequence
source                  1..111
                        mol_type = protein
                        organism = synthetic construct
SEQUENCE: 113
ELVMTQTASP VSAAVGGTVT INCQASQSIG STYLSWYQQK PGQPPKLLIY KASILASGVP    60
SRFSGSGSGT EYTLTISGVQ CDDAATYYCL YGGFGSSTGD AFGGGTVLVV K            111

SEQ ID NO: 114          moltype = AA  length = 108
FEATURE                 Location/Qualifiers
REGION                  1..108
                        note = Synthetic sequence
source                  1..108
                        mol_type = protein
                        organism = synthetic construct
SEQUENCE: 114
ELVLTQTPAS VSEPVGGTVT IKCQASQTIY SNLAWYQQKP GQRPKLLIYQ ASKLASGVPS    60
RFKGSGSGTE YTLTISDLEC ADAATYYCQS YYGADDYTFG GGTEVVVK                108

SEQ ID NO: 115          moltype = AA  length = 111
FEATURE                 Location/Qualifiers
REGION                  1..111
                        note = Synthetic sequence
source                  1..111
                        mol_type = protein
                        organism = synthetic construct
SEQUENCE: 115
ELVMTQTPSP VSAAVGGTVS ISCQSSKSVY NNNALSWFQQ KPGQPPKVLI YGVSTLDSGV    60
SSRFSGSGYG TEFTLTISDV QCDDAATYYC AGDYSDISDN NFGGGTELEI K            111

SEQ ID NO: 116          moltype = AA  length = 111
FEATURE                 Location/Qualifiers
REGION                  1..111
                        note = Synthetic sequence
source                  1..111
                        mol_type = protein
                        organism = synthetic construct
SEQUENCE: 116
ELDMTQTPAS VSEPVGGTVT IKCQASQSIS SYLAWYQQKP GQPPKRLIFE ASTLASGVPS    60
RFSGSGSGTD FTLTISDLEC ADAATYYCQN NNGFSGSNFN NFGGGTEVEI K            111

SEQ ID NO: 117          moltype = AA  length = 111
FEATURE                 Location/Qualifiers
REGION                  1..111
                        note = Synthetic sequence
source                  1..111
                        mol_type = protein
                        organism = synthetic construct
SEQUENCE: 117
ELVMTQTPAS VEVAVGGTVT IKCQASQTIY SSLAWYQQKP GQPPKLLIYK ASTLASGVPS    60
```

```
RFKGSGSGTQ FTLTISGVQC DDAATYYCQQ GSSISNVDKN AFGGGTEVEI K            111

SEQ ID NO: 118          moltype = AA   length = 111
FEATURE                 Location/Qualifiers
REGION                  1..111
                        note = Synthetic sequence
source                  1..111
                        mol_type = protein
                        organism = synthetic construct
SEQUENCE: 118
ELVLTQTPAS VSEPVGGTVT IKCQASQSIG SYLSWYQQKA GQPPKRLIYE ASTLASGVPS   60
RFSGSGSGTD FTLTISDLEC ADVATYYCQN NNGMTVSDFN AFGGGTEVEI K            111

SEQ ID NO: 119          moltype = AA   length = 112
FEATURE                 Location/Qualifiers
REGION                  1..112
                        note = Synthetic sequence
source                  1..112
                        mol_type = protein
                        organism = synthetic construct
SEQUENCE: 119
ELDLTQTPAS VSAAVGGTVT INCQSSQIID HDHLSWYQQK PGQRPKLLIY RASTLTSGVP   60
SRFKGSGSGT DFTLTISDLE CADVATYYCQ NNNGMTVSDF NAFGGGTEVE IK           112

SEQ ID NO: 120          moltype = AA   length = 110
FEATURE                 Location/Qualifiers
REGION                  1..110
                        note = Synthetic sequencce
source                  1..110
                        mol_type = protein
                        organism = synthetic construct
SEQUENCE: 120
ELVLTQTPSS TSAAVGGTVT ISCQSSQSVV DKNWLAWYQQ KPGQPPKLLI YEASKLASGV   60
PPRFSGSGSG TQFTLTISGV QCDDAATYYC AGDFESGVSG FGGGTEVEIK              110

SEQ ID NO: 121          moltype = AA   length = 111
FEATURE                 Location/Qualifiers
REGION                  1..111
                        note = Synthetic sequence
source                  1..111
                        mol_type = protein
                        organism = synthetic construct
SEQUENCE: 121
ELVLTQTPSP VSAAVGGTVT INCQSSKNIY NNNALSWFQQ KPGQPPKLLI YGASTLASGV   60
PSRFKGSGSG TQFTLTISDV QCDDAATYYC AADYSDISDN NFGGGTEVVV K            111

SEQ ID NO: 122          moltype = AA   length = 109
FEATURE                 Location/Qualifiers
REGION                  1..109
                        note = Synthetic sequence
source                  1..109
                        mol_type = protein
                        organism = synthetic construct
SEQUENCE: 122
ELVLTQTPSS VSAAVGGTVT ISCQSSQSVY SNNYLAWYQQ KPGQPPKLLI YAASTLASGV   60
PSRFKGSGSG TQFTLTISGV QCDDAVYYC LGGYNDDANF GGGTEVEIK                109

SEQ ID NO: 123          moltype = AA   length = 109
FEATURE                 Location/Qualifiers
REGION                  1..109
                        note = Synthetic sequence
source                  1..109
                        mol_type = protein
                        organism = synthetic construct
SEQUENCE: 123
ELDLTQTPSS VSAAVGGTVT ISCQSSESVY SNNHLAWYQQ KPGQPPKLLI YAASTLASGV   60
PSRFSGSGSG TQFTLTISGV QCDDAVYYC LGGYNDDANF GGGTEVVVK                109

SEQ ID NO: 124          moltype = AA   length = 110
FEATURE                 Location/Qualifiers
REGION                  1..110
                        note = Synthetic sequence
source                  1..110
                        mol_type = protein
                        organism = synthetic construct
SEQUENCE: 124
ELDLTQTPAS VEAAVGGTVT IKCQASQSID NNDLAWYQQK PGQPPNLLIS RTSTLASGVS   60
SRFKGSGSGT EFTLTISDLE CADAATYYCQ SYCVNTYGYT FGGGTEVVVK              110
```

```
SEQ ID NO: 125          moltype = AA  length = 112
FEATURE                 Location/Qualifiers
REGION                  1..112
                        note = Synthetic sequence
source                  1..112
                        mol_type = protein
                        organism = synthetic construct
SEQUENCE: 125
ELVMTQTPAS VEAAVGGTVT IKCQASQSIS NHLGWYQQKP GQPPKLLIYR ASTLESGVSS    60
RFKGSGSGSE FTLTISDLEC ADAATYYCQS YYIINRSNYA NSFGGGTEVE IK           112

SEQ ID NO: 126          moltype = AA  length = 112
FEATURE                 Location/Qualifiers
REGION                  1..112
                        note = Synthetic sequence
source                  1..112
                        mol_type = protein
                        organism = synthetic construct
SEQUENCE: 126
ELVMTQTPAS VEAAVGGTVT IKCQASESIN SWLAWYQQKP GQRPKLLIYD ASKLASGVPS    60
RFKGSGSGTQ FTLTISDLEC ADAATYYCQS YYIINRSNYG NSFGGGTEVE IK           112

SEQ ID NO: 127          moltype = AA  length = 112
FEATURE                 Location/Qualifiers
REGION                  1..112
                        note = Synthetic sequence
source                  1..112
                        mol_type = protein
                        organism = synthetic construct
SEQUENCE: 127
ELVMTQTPAS VEAAVGGTVT IKCQASETIS SRLAWYQQKP GQPPKLLIYQ ASKLPSGVPS    60
RFKGTGSGTE YTLTISDLEC ADAATYYCQG CYYGGGSFYD SAFGGGTEVV VK           112

SEQ ID NO: 128          moltype = AA  length = 109
FEATURE                 Location/Qualifiers
REGION                  1..109
                        note = Synthetic sequence
source                  1..109
                        mol_type = protein
                        organism = synthetic construct
SEQUENCE: 128
ELDLTQTPAS VSAAVGGTVT ISCQSSENLY KDNYLAWYQQ KPGQPPKLLI YGASNLASGV    60
PSRFKGSGSG TQFTLTISDL ECDDAATYYC AGGYDSVVDF GGGTEVVVK               109

SEQ ID NO: 129          moltype = AA  length = 121
FEATURE                 Location/Qualifiers
REGION                  1..121
                        note = Synthetic sequence
source                  1..121
                        mol_type = protein
                        organism = synthetic construct
SEQUENCE: 129
QSVEESGGRL VTPGTPLTLT CTVSGFSLSR YAMTWVRQAP GKGLEWIGII GSSGLTYFAT    60
WAKGRFTISK TSTTVDLKIT SPTTEDTATY FCARGMWYDD SDDYEDYFNL WGPGTLVTIS   120
S                                                                   121

SEQ ID NO: 130          moltype = AA  length = 117
FEATURE                 Location/Qualifiers
REGION                  1..117
                        note = Synthetic sequence
source                  1..117
                        mol_type = protein
                        organism = synthetic construct
SEQUENCE: 130
QSVKESGGRL VTPGTPLTLT CTVSGIDLSS YAMSWVRQAP GKGLEWIGTI NIGGGTWDAT    60
WARGRFTISR TSTTVDLKIT SPTIGDTATY FCARDVDAHT LTYFTLWGPG TLVTISS      117

SEQ ID NO: 131          moltype = AA  length = 119
FEATURE                 Location/Qualifiers
REGION                  1..119
                        note = Synthetic sequence
source                  1..119
                        mol_type = protein
                        organism = synthetic construct
SEQUENCE: 131
QSVKESGGRL VTPGTPLTLT CTVSGFTLSN NAISWVRQAP GKGLEWIGII YASGRTYYAT    60
WAKGRFTISK TSTTVDLKMT SPTTEDTATY FCARGDTETD YGIPYFDLWG PGTLVTISS    119

SEQ ID NO: 132          moltype = AA  length = 122
```

```
FEATURE                 Location/Qualifiers
REGION                  1..122
                        note = Synthetic sequence
source                  1..122
                        mol_type = protein
                        organism = synthetic construct
SEQUENCE: 132
SQSLKESGGD LVKPGASRTL TCIAPGFSFS SSYYMCWVRQ APGKGLEWIA CIYASSGSTY    60
YASWAKGRFT ISKTSSTTVT LQMTTLTAAD TATYFCAAIL GADYRLTRLD LWGQGTLVTV   120
SS                                                                 122

SEQ ID NO: 133          moltype = AA  length = 118
FEATURE                 Location/Qualifiers
REGION                  1..118
                        note = Synthetic sequence
source                  1..118
                        mol_type = protein
                        organism = synthetic construct
SEQUENCE: 133
QSLEESGGRL VTPGTPLTLT CTASGFSLNR YYMLWVRQAP GEGLEWIGTI SYGDTTYYAS    60
WAKGRFTISK TSTTVDLKMT SPTTEDTATY FCARADTGDN GYLGLQLWGP GTLVTVSS    118

SEQ ID NO: 134          moltype = AA  length = 124
FEATURE                 Location/Qualifiers
REGION                  1..124
                        note = Synthetic sequence
source                  1..124
                        mol_type = protein
                        organism = synthetic construct
SEQUENCE: 134
QSLEESGGDL VKPGASLTLT CTASGFSFSS GYYMCWVRQA PGKGLEWIAC IYTGRTDFTD    60
YASWAKGRFT ISKTSSTTVT LQLTTLTAAD TATYFCARGD YSGGVGGNYW LDLWGQGTLV   120
TISS                                                               124

SEQ ID NO: 135          moltype = AA  length = 117
FEATURE                 Location/Qualifiers
REGION                  1..117
                        note = Synthetic sequence
source                  1..117
                        mol_type = protein
                        organism = synthetic construct
SEQUENCE: 135
QSLEESGGRL VTPGTPLTLT CTVSGIDLSN TWMNWVRQAP GKGLEWIGVI TDSGTTYYAN    60
WAKGRFTISR TSTTVDLKMP SLTTEDTATY FCGRDPGDIT SGTNDLWGPG TLVTISS     117

SEQ ID NO: 136          moltype = AA  length = 114
FEATURE                 Location/Qualifiers
REGION                  1..114
                        note = Synthetic sequence
source                  1..114
                        mol_type = protein
                        organism = synthetic construct
SEQUENCE: 136
EQSVEESGGR LVTPGGSLTL TCTASGFSLN NYAIIWVRQA PGKGLEYIGI FNNGDIYYAN    60
WAKGRFTISK TSTTVGLKIV SPTTEDTATY FCARTGYRTG GWLWGPGTLV TISS        114

SEQ ID NO: 137          moltype = AA  length = 122
FEATURE                 Location/Qualifiers
REGION                  1..122
                        note = Synthetic sequence
source                  1..122
                        mol_type = protein
                        organism = synthetic construct
SEQUENCE: 137
QSVKESGGRL VTPGTPLTLT CTVSGIDLSY YAMSWVRQAP GKGLEYIGII NGRGDTGYAT    60
WAKGRFTISK TSTTVDLRIT SPTIEDTATY FCAREDSAIP FIVGNYYGMD LWGPGTLVTV   120
SS                                                                 122

SEQ ID NO: 138          moltype = AA  length = 120
FEATURE                 Location/Qualifiers
REGION                  1..120
                        note = Synthetic sequence
source                  1..120
                        mol_type = protein
                        organism = synthetic construct
SEQUENCE: 138
SQSLEESGGD LVKPGASLTL TCTASTFSFN SRYWTCWVRQ APGKGLEWIG CINNGDISTY    60
YASWATGRFT ISKSSSTTVT LHMTSLTAAD TATYFCAKGG NLAGDCYGLW GPGTLVTISS   120
```

```
SEQ ID NO: 139           moltype = AA   length = 125
FEATURE                  Location/Qualifiers
REGION                   1..125
                         note = Synthetic sequence
source                   1..125
                         mol_type = protein
                         organism = synthetic construct
SEQUENCE: 139
SSVEESGGRL VAPGTPLTLT CTVSGFSLNR YAMSWVRQAP GKGLEWIGII GSSGSTYYAS     60
WAKGRFTISK TSTTVDLKIT SPTTEDTATY FCARDLDDSY GYTYATGMDI RLDLWGQGTL    120
VTVSS                                                                125

SEQ ID NO: 140           moltype = AA   length = 123
FEATURE                  Location/Qualifiers
REGION                   1..123
                         note = Synthetic sequence
source                   1..123
                         mol_type = protein
                         organism = synthetic construct
SEQUENCE: 140
QSVKESGGGL FKPMDTLTLT CTVSGFSLSD YAMSWVRQAP GKGLEWIGII NSRDDTGYAS     60
WAKGRFTISK TSSTTVDLRI TSPTTEDTAT YFCAREDSSI PFIVGNYYGM DLWGPGTLVT    120
VSS                                                                  123

SEQ ID NO: 141           moltype = AA   length = 115
FEATURE                  Location/Qualifiers
REGION                   1..115
                         note = Synthetic sequence
source                   1..115
                         mol_type = protein
                         organism = synthetic construct
SEQUENCE: 141
QSLEESGGRL VTPGTPLTLT CTVSGFSLSS YGVHWVRQAP GKGLDWIGKI YPSGSIYYSS     60
WAKGRFTISK TSTTVDLKMT SLTTEDTATY FCVRYLTGSS DLHLWGPGTL VTISS         115

SEQ ID NO: 142           moltype = AA   length = 114
FEATURE                  Location/Qualifiers
REGION                   1..114
                         note = Synthetic sequence
source                   1..114
                         mol_type = protein
                         organism = synthetic construct
SEQUENCE: 142
QSVKESGGRL VTPGGSLTLT CTVSGFSLSD YAMIWVRQAP GKGLEYIGII NNGDIYYATW     60
AKGRFTISET SSTTMGLNII SPTTEDTATY FCARPGYRTG IWLWGPGTLV TISS          114

SEQ ID NO: 143           moltype = AA   length = 116
FEATURE                  Location/Qualifiers
REGION                   1..116
                         note = Synthetic sequence
source                   1..116
                         mol_type = protein
                         organism = synthetic construct
SEQUENCE: 143
SQSVKESGGD LVKPGASLTL TCKASGFDLR SYYYMCWVRQ APGKGLEWIA CIHGGEGNTY     60
YASWAKGRFT ISKTSSTAVT LQMTSLTAAD TATYFCARGG WTNYFWGPGT LVTVSS        116

SEQ ID NO: 144           moltype = AA   length = 116
FEATURE                  Location/Qualifiers
REGION                   1..116
                         note = Synthetic sequence
source                   1..116
                         mol_type = protein
                         organism = synthetic construct
SEQUENCE: 144
EQSLKESGGD LVKPGASLTL TCTASGFDLS SNYYMCWVRQ APGKGPEWIA CIYSSNTRTW     60
YARWAKGRFT ISKTSSTAVT LQMTSLTAAD TATYFCARGG WTNYLWGPGT LVTISS        116

SEQ ID NO: 145           moltype = AA   length = 113
FEATURE                  Location/Qualifiers
REGION                   1..113
                         note = Synthetic sequence
source                   1..113
                         mol_type = protein
                         organism = synthetic construct
SEQUENCE: 145
QSVEESGGRL VTPGTPLTLT CTVSGFSLSS HDMIWVRQAA GKGLEWIGLI ISSGNTWYAS     60
WAKGRFTISK TSTTVDLKMT SLTTEDTATY FCARDVYSGA SPWGPGTLVT ISS           113
```

```
SEQ ID NO: 146          moltype = AA   length = 118
FEATURE                 Location/Qualifiers
REGION                  1..118
                        note = Synthetic sequence
source                  1..118
                        mol_type = protein
                        organism = synthetic construct
SEQUENCE: 146
QSVKSGGGLV KPGASLTLTC KASTFSFNSR YWTCWVRQAP GKGLEWIGCI NNGDITTYYT   60
NWATGRFTIS KSSSTTVTLQ MTSLTAADTA TYFCAKGGNL AGDCYGLWGP GTLVTISG    118

SEQ ID NO: 147          moltype = AA   length = 118
FEATURE                 Location/Qualifiers
REGION                  1..118
                        note = Synthetic sequence
source                  1..118
                        mol_type = protein
                        organism = synthetic construct
SEQUENCE: 147
QSLEESGGRL VTPGTPLTLT CTASGFSLSS YYMSWVRQAP GEGLEWIGTI TTAGPLYYAT   60
WAKGRFTISK TSTTVDLKMT GPTTEDTATY FCARGHAGSI YYSYFDLWGP GTLVTVSS    118

SEQ ID NO: 148          moltype = AA   length = 116
FEATURE                 Location/Qualifiers
REGION                  1..116
                        note = Synthetic sequence
source                  1..116
                        mol_type = protein
                        organism = synthetic construct
SEQUENCE: 148
QSVEESGGRL VTPGGSLTLT CTVSGFSLSS YDMSWVRQAP GKGLEWIGIS WNSGFVDYAS   60
WAKGRFSISK TSTTVDLKIT SPTTEDTATY FCARLGADDI YYFNLWGPGT LVTISS      116

SEQ ID NO: 149          moltype = AA   length = 116
FEATURE                 Location/Qualifiers
REGION                  1..116
                        note = Synthetic sequence
source                  1..116
                        mol_type = protein
                        organism = synthetic construct
SEQUENCE: 149
QSVKESGGGL VKPEGSLTLT CKASGFDLSS YYYMCWVRQA PGKGLEWIAC IYTSSGATWY   60
ANWAKGRFTI SKTSSTTVTL QMTALTAADT ATYFCARGGW CDFNLWGPGT LVTISS      116

SEQ ID NO: 150          moltype = AA   length = 107
FEATURE                 Location/Qualifiers
REGION                  1..107
                        note = Synthetic sequence
source                  1..107
                        mol_type = protein
                        organism = synthetic construct
SEQUENCE: 150
DIQMTQSPSS VSASVGDRVT ITCQASQSIG SVLAWYQQKP GKAPKLLISG VFDLASGVPS   60
RFSGSGSGTD FTLTISSLQP EDFATYYCQY IPYGSSPFGG GTKVEIK                107

SEQ ID NO: 151          moltype = AA   length = 107
FEATURE                 Location/Qualifiers
REGION                  1..107
                        note = Synthetic sequence
source                  1..107
                        mol_type = protein
                        organism = synthetic construct
SEQUENCE: 151
DIQMTQSPSS VSASVGDRVT ITCRASQSIG SVLAWYQQKP GKAPKLLIYG VFSLQSGVPS   60
RFSGSGSGTD FTLTISSLQP EDFATYYCQY IPYGSSPFGG GTKVEIK                107

SEQ ID NO: 152          moltype = AA   length = 121
FEATURE                 Location/Qualifiers
REGION                  1..121
                        note = Synthetic sequence
source                  1..121
                        mol_type = protein
                        organism = synthetic construct
SEQUENCE: 152
QVQLVESGGR VVQPGRSLRL SCTASGFSLN RYYMLWVRQA PGKGLEWIGT ISYGDTTYYA   60
SWAKGRFTIS RDNSKNTLYL QMNSLRAEDT AVYYCARADT GDNGYLGLQL WGQGTLVTVS  120
S                                                                 121

SEQ ID NO: 153          moltype = DNA  length = 18
```

```
FEATURE              Location/Qualifiers
misc_feature         1..18
                     note = Synthetic sequence
source               1..18
                     mol_type = other DNA
                     organism = synthetic construct
SEQUENCE: 153
cagaacattt acagcaat                                                        18

SEQ ID NO: 154       moltype = DNA   length = 36
FEATURE              Location/Qualifiers
misc_feature         1..36
                     note = Synthetic sequence
source               1..36
                     mol_type = other DNA
                     organism = synthetic construct
SEQUENCE: 154
caaagtggtt attatagtag tagtactgat attgct                                    36

SEQ ID NO: 155       moltype = DNA   length = 18
FEATURE              Location/Qualifiers
misc_feature         1..18
                     note = Synthetic sequence
source               1..18
                     mol_type = other DNA
                     organism = synthetic construct
SEQUENCE: 155
cagaccatta gcagttgg                                                        18

SEQ ID NO: 156       moltype = DNA   length = 36
FEATURE              Location/Qualifiers
misc_feature         1..36
                     note = Synthetic sequence
source               1..36
                     mol_type = other DNA
                     organism = synthetic construct
SEQUENCE: 156
caacagggta ttagtagtag taatgttgat aatgtt                                    36

SEQ ID NO: 157       moltype = DNA   length = 18
FEATURE              Location/Qualifiers
misc_feature         1..18
                     note = Synthetic sequence
source               1..18
                     mol_type = other DNA
                     organism = synthetic construct
SEQUENCE: 157
cagaccatta gcagttgg                                                        18

SEQ ID NO: 158       moltype = DNA   length = 45
FEATURE              Location/Qualifiers
misc_feature         1..45
                     note = Synthetic sequence
source               1..45
                     mol_type = other DNA
                     organism = synthetic construct
SEQUENCE: 158
caatgcactt atggtagtgg tagtagtagt agtt atggtt gtgct                         45

SEQ ID NO: 159       moltype = DNA   length = 21
FEATURE              Location/Qualifiers
misc_feature         1..21
                     note = Synthetic sequence
source               1..21
                     mol_type = other DNA
                     organism = synthetic construct
SEQUENCE: 159
cagagtgttt atagtaacta c                                                    21

SEQ ID NO: 160       moltype = DNA   length = 33
FEATURE              Location/Qualifiers
misc_feature         1..33
                     note = Synthetic sequence
source               1..33
                     mol_type = other DNA
                     organism = synthetic construct
SEQUENCE: 160
caaggcggtt atagtgagat tattgaaaat act                                       33
```

```
SEQ ID NO: 161            moltype = DNA   length = 18
FEATURE                   Location/Qualifiers
misc_feature              1..18
                          note = Synthetic sequence
source                    1..18
                          mol_type = other DNA
                          organism = synthetic construct
SEQUENCE: 161
cagagcattg gtagtgtt                                                      18

SEQ ID NO: 162            moltype = DNA   length = 27
FEATURE                   Location/Qualifiers
misc_feature              1..27
                          note = Synthetic sequence
source                    1..27
                          mol_type = other DNA
                          organism = synthetic construct
SEQUENCE: 162
caatatattc cttatggtag tagtcct                                            27

SEQ ID NO: 163            moltype = DNA   length = 21
FEATURE                   Location/Qualifiers
misc_feature              1..21
                          note = Synthetic sequence
source                    1..21
                          mol_type = other DNA
                          organism = synthetic construct
SEQUENCE: 163
cagagtattg gtagtaccta c                                                  21

SEQ ID NO: 164            moltype = DNA   length = 36
FEATURE                   Location/Qualifiers
misc_feature              1..36
                          note = Synthetic sequence
source                    1..36
                          mol_type = other DNA
                          organism = synthetic construct
SEQUENCE: 164
ctatacggtg gttttggtag tagtactggt gatgct                                  36

SEQ ID NO: 165            moltype = DNA   length = 18
FEATURE                   Location/Qualifiers
misc_feature              1..18
                          note = Synthetic sequence
source                    1..18
                          mol_type = other DNA
                          organism = synthetic construct
SEQUENCE: 165
cagaccattt atagtaat                                                      18

SEQ ID NO: 166            moltype = DNA   length = 30
FEATURE                   Location/Qualifiers
misc_feature              1..30
                          note = Synthetic sequence
source                    1..30
                          mol_type = other DNA
                          organism = synthetic construct
SEQUENCE: 166
caaagctatt atggtgctga tgattatact                                         30

SEQ ID NO: 167            moltype = DNA   length = 24
FEATURE                   Location/Qualifiers
misc_feature              1..24
                          note = Synthetic sequence
source                    1..24
                          mol_type = other DNA
                          organism = synthetic construct
SEQUENCE: 167
aagagtgttt ataataacaa tgcc                                               24

SEQ ID NO: 168            moltype = DNA   length = 33
FEATURE                   Location/Qualifiers
misc_feature              1..33
                          note = Synthetic sequence
source                    1..33
                          mol_type = other DNA
                          organism = synthetic construct
SEQUENCE: 168
gcaggcgatt atagtgatat tagtgataat aat                                     33
```

```
SEQ ID NO: 169          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 169
cagagcatta gtagctac                                                     18

SEQ ID NO: 170          moltype = DNA  length = 39
FEATURE                 Location/Qualifiers
misc_feature            1..39
                        note = Synthetic sequence
source                  1..39
                        mol_type = other DNA
                        organism = synthetic construct
SEQUENCE: 170
caaaacaata atggttttag tggtagtaat ttcaataat                              39

SEQ ID NO: 171          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 171
cagaccattt acagctct                                                     18

SEQ ID NO: 172          moltype = DNA  length = 39
FEATURE                 Location/Qualifiers
misc_feature            1..39
                        note = Synthetic sequence
source                  1..39
                        mol_type = other DNA
                        organism = synthetic construct
SEQUENCE: 172
caacagggtt ccagtattag taatgttgat aaaaatgct                              39

SEQ ID NO: 173          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 173
cagagcattg gtagttac                                                     18

SEQ ID NO: 174          moltype = DNA  length = 39
FEATURE                 Location/Qualifiers
misc_feature            1..39
                        note = Synthetic sequence
source                  1..39
                        mol_type = other DNA
                        organism = synthetic construct
SEQUENCE: 174
caaaataata atggtatgac tgtcagcgat ttcaatgct                              39

SEQ ID NO: 175          moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 175
cagattattg atcacgacca c                                                 21

SEQ ID NO: 176          moltype = DNA  length = 39
FEATURE                 Location/Qualifiers
misc_feature            1..39
                        note = Synthetic sequence
source                  1..39
                        mol_type = other DNA
                        organism = synthetic construct
SEQUENCE: 176
```
caaaataata atggtatgac tgtcagcgat ttcaatgct                                      39

SEQ ID NO: 177          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 177
cagagtgttg ttgataagaa ctgg                                                      24

SEQ ID NO: 178          moltype = DNA   length = 30
FEATURE                 Location/Qualifiers
misc_feature            1..30
                        note = Synthetic sequence
source                  1..30
                        mol_type = other DNA
                        organism = synthetic construct
SEQUENCE: 178
gcaggcgatt ttgagagtgg tgttagtggt                                                30

SEQ ID NO: 179          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 179
aagaatattt ataataataa tgcc                                                      24

SEQ ID NO: 180          moltype = DNA   length = 33
FEATURE                 Location/Qualifiers
misc_feature            1..33
                        note = Synthetic sequence
source                  1..33
                        mol_type = other DNA
                        organism = synthetic construct
SEQUENCE: 180
gcagcagatt atagtgatat tagtgataat aat                                            33

SEQ ID NO: 181          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 181
cagagtgttt atagtaacaa ctac                                                      24

SEQ ID NO: 182          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 182
ctaggcgggt ataatgatga tgctaat                                                   27

SEQ ID NO: 183          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 183
gagagtgttt atagtaacaa ccac                                                      24

SEQ ID NO: 184          moltype = DNA   length = 27
FEATURE                 Location/Qualifiers
misc_feature            1..27
                        note = Synthetic sequence
source                  1..27
                        mol_type = other DNA
                        organism = synthetic construct

```
SEQUENCE: 184
ctaggcggtt ataatgatga tgctaat                                           27

SEQ ID NO: 185          moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 185
cagagtattg ataacaacga c                                                 21

SEQ ID NO: 186          moltype = DNA  length = 33
FEATURE                 Location/Qualifiers
misc_feature            1..33
                        note = Synthetic sequence
source                  1..33
                        mol_type = other DNA
                        organism = synthetic construct
SEQUENCE: 186
caaagctatt gcgttaatac ttatggttat act                                    33

SEQ ID NO: 187          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 187
cagagcatta gtaatcac                                                     18

SEQ ID NO: 188          moltype = DNA  length = 42
FEATURE                 Location/Qualifiers
misc_feature            1..42
                        note = Synthetic sequence
source                  1..42
                        mol_type = other DNA
                        organism = synthetic construct
SEQUENCE: 188
caaagctatt atattattaa taggagtaat tatgctaatt ct                          42

SEQ ID NO: 189          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 189
gagagcatta atagttgg                                                     18

SEQ ID NO: 190          moltype = DNA  length = 42
FEATURE                 Location/Qualifiers
misc_feature            1..42
                        note = Synthetic sequence
source                  1..42
                        mol_type = other DNA
                        organism = synthetic construct
SEQUENCE: 190
caaagctatt atattattaa taggagtaat tatggtaatt ct                          42

SEQ ID NO: 191          moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 191
gagaccatta gtagtaga                                                     18

SEQ ID NO: 192          moltype = DNA  length = 42
FEATURE                 Location/Qualifiers
misc_feature            1..42
                        note = Synthetic sequence
source                  1..42
                        mol_type = other DNA
```

```
                        organism = synthetic construct
SEQUENCE: 192
caaggctgtt attatggtgg gggtagtttt tatgattctg ct                    42

SEQ ID NO: 193          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 193
gagaatcttt ataaggacaa ctac                                        24

SEQ ID NO: 194          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 194
gcaggcggtt atgatagtgt tgttgat                                     27

SEQ ID NO: 195          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 195
ggattctccc tcagtagata tgca                                        24

SEQ ID NO: 196          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 196
attggtagta gtggtctcac a                                           21

SEQ ID NO: 197          moltype = DNA   length = 54
FEATURE                 Location/Qualifiers
misc_feature            1..54
                        note = Synthetic sequence
source                  1..54
                        mol_type = other DNA
                        organism = synthetic construct
SEQUENCE: 197
gccagaggga tgtggtacga tgactccgat gattacgagg actactttaa cttg       54

SEQ ID NO: 198          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 198
ggaatcgacc tcagtagcta tgca                                        24

SEQ ID NO: 199          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 199
attaatattg gtggtggcac a                                           21

SEQ ID NO: 200          moltype = DNA   length = 42
FEATURE                 Location/Qualifiers
misc_feature            1..42
                        note = Synthetic sequence
source                  1..42
```

```
                        mol_type = other DNA
                        organism = synthetic construct
SEQUENCE: 200
gccagagatg ttgatgccca taccctcaca tactttacct tg                              42

SEQ ID NO: 201          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 201
ggattcaccc tcagtaataa tgca                                                  24

SEQ ID NO: 202          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 202
atttatgcta gtggtaggac a                                                     21

SEQ ID NO: 203          moltype = DNA   length = 48
FEATURE                 Location/Qualifiers
misc_feature            1..48
                        note = Synthetic sequence
source                  1..48
                        mol_type = other DNA
                        organism = synthetic construct
SEQUENCE: 203
gccagaggag atactgagac tgattatggt attccttact tgacttg                         48

SEQ ID NO: 204          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 204
ggattctcct tcagtagcag ttactac                                               27

SEQ ID NO: 205          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 205
atttatgcta gtagtggtag cact                                                  24

SEQ ID NO: 206          moltype = DNA   length = 42
FEATURE                 Location/Qualifiers
misc_feature            1..42
                        note = Synthetic sequence
source                  1..42
                        mol_type = other DNA
                        organism = synthetic construct
SEQUENCE: 206
gcaattcttg gtgctgatta taggttgact cgattggatc tc                              42

SEQ ID NO: 207          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 207
ggattctccc tcaatcgcta ctac                                                  24

SEQ ID NO: 208          moltype = DNA   length = 21
FEATURE                 Location/Qualifiers
misc_feature            1..21
                        note = Synthetic sequence
```

```
                        source          1..21
                                        mol_type = other DNA
                                        organism = synthetic construct
SEQUENCE: 208
attagttatg gtgataccac a                                              21

SEQ ID NO: 209          moltype = DNA   length = 45
FEATURE                 Location/Qualifiers
misc_feature            1..45
                        note = Synthetic sequence
source                  1..45
                        mol_type = other DNA
                        organism = synthetic construct
SEQUENCE: 209
gccagagcag atactggtga taatggttat ttaggccttc agttg                    45

SEQ ID NO: 210          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 210
ggattctcct tcagtagcgg ctactac                                        27

SEQ ID NO: 211          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 211
atttatactg gtcgcactga tttcact                                        27

SEQ ID NO: 212          moltype = DNA   length = 51
FEATURE                 Location/Qualifiers
misc_feature            1..51
                        note = Synthetic sequence
source                  1..51
                        mol_type = other DNA
                        organism = synthetic construct
SEQUENCE: 212
gcgagagggg attattctgg tggtgttggt ggtaattatt ggttggatct c             51

SEQ ID NO: 213          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 213
ggaatcgacc tcagtaacac ctgg                                           24

SEQ ID NO: 214          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 214
attactgata gtggtaccac a                                              21

SEQ ID NO: 215          moltype = DNA   length = 42
FEATURE                 Location/Qualifiers
misc_feature            1..42
                        note = Synthetic sequence
source                  1..42
                        mol_type = other DNA
                        organism = synthetic construct
SEQUENCE: 215
ggccgagatc ctggtgatat tactagtggt acgaatgatt tg                       42

SEQ ID NO: 216          moltype = DNA   length = 24
FEATURE                 Location/Qualifiers
misc_feature            1..24
```

```
                        note = Synthetic sequence
source                  1..24
                        mol_type = other DNA
                        organism = synthetic construct
SEQUENCE: 216
tctggattct ccctcaataa ctat                                          24

SEQ ID NO: 217          moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 217
atttttaata atggtgatat a                                             21

SEQ ID NO: 218          moltype = DNA  length = 33
FEATURE                 Location/Qualifiers
misc_feature            1..33
                        note = Synthetic sequence
source                  1..33
                        mol_type = other DNA
                        organism = synthetic construct
SEQUENCE: 218
gccagaactg gctataggac tggtggctgg ttg                                33

SEQ ID NO: 219          moltype = DNA  length = 24
FEATURE                 Location/Qualifiers
misc_feature            1..24
                        note = Synthetic sequence
source                  1..24
                        mol_type = other DNA
                        organism = synthetic construct
SEQUENCE: 219
ggaatcgacc tcagttacta tgca                                          24

SEQ ID NO: 220          moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 220
attaatggtc gtggtgacac a                                             21

SEQ ID NO: 221          moltype = DNA  length = 57
FEATURE                 Location/Qualifiers
misc_feature            1..57
                        note = Synthetic sequence
source                  1..57
                        mol_type = other DNA
                        organism = synthetic construct
SEQUENCE: 221
gcccgagaag acagtgctat tcctttcata gtaggaaact attacggcat ggacctc      57

SEQ ID NO: 222          moltype = DNA  length = 27
FEATURE                 Location/Qualifiers
misc_feature            1..27
                        note = Synthetic sequence
source                  1..27
                        mol_type = other DNA
                        organism = synthetic construct
SEQUENCE: 222
acattctcct tcaatagccg ctactgg                                       27

SEQ ID NO: 223          moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 223
attaataacg gtgacattag c                                             21

SEQ ID NO: 224          moltype = DNA  length = 39
FEATURE                 Location/Qualifiers
```

```
misc_feature           1..39
                       note = Synthetic sequence
source                 1..39
                       mol_type = other DNA
                       organism = synthetic construct
SEQUENCE: 224
gcgaaagggg gtaatcttgc tggtgattgt tatgggttg                        39

SEQ ID NO: 225         moltype = DNA  length = 24
FEATURE                Location/Qualifiers
misc_feature           1..24
                       note = Synthetic sequence
source                 1..24
                       mol_type = other DNA
                       organism = synthetic construct
SEQUENCE: 225
ggattctccc tcaatcgcta tgca                                        24

SEQ ID NO: 226         moltype = DNA  length = 21
FEATURE                Location/Qualifiers
misc_feature           1..21
                       note = Synthetic sequence
source                 1..21
                       mol_type = other DNA
                       organism = synthetic construct
SEQUENCE: 226
attggtagta gtggtagtac a                                           21

SEQ ID NO: 227         moltype = DNA  length = 66
FEATURE                Location/Qualifiers
misc_feature           1..66
                       note = Synthetic sequence
source                 1..66
                       mol_type = other DNA
                       organism = synthetic construct
SEQUENCE: 227
gccagagatt tggacgatag ttatggttat acttatgcta cggggatgga cattcggttg 60
gatctc                                                            66

SEQ ID NO: 228         moltype = DNA  length = 24
FEATURE                Location/Qualifiers
misc_feature           1..24
                       note = Synthetic sequence
source                 1..24
                       mol_type = other DNA
                       organism = synthetic construct
SEQUENCE: 228
ggattctccc tcagtgacta tgca                                        24

SEQ ID NO: 229         moltype = DNA  length = 21
FEATURE                Location/Qualifiers
misc_feature           1..21
                       note = Synthetic sequence
source                 1..21
                       mol_type = other DNA
                       organism = synthetic construct
SEQUENCE: 229
attaatagtc gtgatgacac a                                           21

SEQ ID NO: 230         moltype = DNA  length = 57
FEATURE                Location/Qualifiers
misc_feature           1..57
                       note = Synthetic sequence
source                 1..57
                       mol_type = other DNA
                       organism = synthetic construct
SEQUENCE: 230
gccagagaag acagtagtat tccttttata gtaggaaatt actacggcat ggacctc    57

SEQ ID NO: 231         moltype = DNA  length = 24
FEATURE                Location/Qualifiers
misc_feature           1..24
                       note = Synthetic sequence
source                 1..24
                       mol_type = other DNA
                       organism = synthetic construct
SEQUENCE: 231
ggattctccc tcagtagtta tgga                                        24
```

```
SEQ ID NO: 232          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 232
atttatccta gtggtagtat a                                             21

SEQ ID NO: 233          moltype = DNA   length = 36
FEATURE                 Location/Qualifiers
misc_feature            1..36
                        note = Synthetic sequence
source                  1..36
                        mol_type = other DNA
                        organism = synthetic construct
SEQUENCE: 233
gtcagatatc ttactggtag cagtgatttg catttg                             36

SEQ ID NO: 234          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 234
ggattctccc tcagtgacta tgca                                          24

SEQ ID NO: 235          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 235
atcaataatg gtgatatata c                                             21

SEQ ID NO: 236          moltype = DNA   length = 33
FEATURE                 Location/Qualifiers
misc_feature            1..33
                        note = Synthetic sequence
source                  1..33
                        mol_type = other DNA
                        organism = synthetic construct
SEQUENCE: 236
gccagacctg gttataggac tggtatatgg ttg                                33

SEQ ID NO: 237          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 237
ggattcgacc tcaggagcta ctactac                                       27

SEQ ID NO: 238          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 238
attcatggtg gtgagggtaa cact                                          24

SEQ ID NO: 239          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 239
agaggtggct ggactaatta cttt                                          24
```

```
SEQ ID NO: 240          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 240
ggattcgacc tcagtagcaa ctactac                                        27

SEQ ID NO: 241          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 241
atttatagta gtaatactag aaca                                           24

SEQ ID NO: 242          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 242
agaggtggct ggactaatta cttg                                           24

SEQ ID NO: 243          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 243
ggattctccc tcagtagcca cgac                                           24

SEQ ID NO: 244          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 244
attattagta gtggtaacac a                                              21

SEQ ID NO: 245          moltype = DNA   length = 30
FEATURE                 Location/Qualifiers
misc_feature            1..30
                        note = Synthetic sequence
source                  1..30
                        mol_type = other DNA
                        organism = synthetic construct
SEQUENCE: 245
gccagagatg tttatagtgg tgcgagtcct                                     30

SEQ ID NO: 246          moltype = DNA   length = 27
FEATURE                 Location/Qualifiers
misc_feature            1..27
                        note = Synthetic sequence
source                  1..27
                        mol_type = other DNA
                        organism = synthetic construct
SEQUENCE: 246
acattctcct tcaatagccg ctactgg                                        27

SEQ ID NO: 247          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 247
```
attaataacg gtgacattac c                                          21

SEQ ID NO: 248          moltype = DNA   length = 39
FEATURE                 Location/Qualifiers
misc_feature            1..39
                        note = Synthetic sequence
source                  1..39
                        mol_type = other DNA
                        organism = synthetic construct
SEQUENCE: 248
gcgaaagggg gtaatcttgc tggtgattgt tatgggttg                       39

SEQ ID NO: 249          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 249
ggattctccc tcagtagtta ctac                                       24

SEQ ID NO: 250          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 250
attactactg ctggtccact a                                          21

SEQ ID NO: 251          moltype = DNA   length = 45
FEATURE                 Location/Qualifiers
misc_feature            1..45
                        note = Synthetic sequence
source                  1..45
                        mol_type = other DNA
                        organism = synthetic construct
SEQUENCE: 251
gccagagggc atgctggtag tatttattat tcatactttg acttg                45

SEQ ID NO: 252          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 252
ggattctccc tcagcagcta cgac                                       24

SEQ ID NO: 253          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 253
agttggaata gtggctttgt t                                          21

SEQ ID NO: 254          moltype = DNA   length = 39
FEATURE                 Location/Qualifiers
misc_feature            1..39
                        note = Synthetic sequence
source                  1..39
                        mol_type = other DNA
                        organism = synthetic construct
SEQUENCE: 254
gccagacttg gtgctgatga catctactat tttaacttg                       39

SEQ ID NO: 255          moltype = DNA   length = 27
FEATURE                 Location/Qualifiers
misc_feature            1..27
                        note = Synthetic sequence
source                  1..27
                        mol_type = other DNA
                        organism = synthetic construct

```
SEQUENCE: 255
ggattcgacc tcagtagcta ctactac                                                27

SEQ ID NO: 256          moltype = DNA  length = 24
FEATURE                 Location/Qualifiers
misc_feature            1..24
                        note = Synthetic sequence
source                  1..24
                        mol_type = other DNA
                        organism = synthetic construct
SEQUENCE: 256
atttatacta gtagtggtgc caca                                                   24

SEQ ID NO: 257          moltype = DNA  length = 27
FEATURE                 Location/Qualifiers
misc_feature            1..27
                        note = Synthetic sequence
source                  1..27
                        mol_type = other DNA
                        organism = synthetic construct
SEQUENCE: 257
agaggaggtt ggtgcgactt taacttg                                                27

SEQ ID NO: 258          moltype = DNA  length = 330
FEATURE                 Location/Qualifiers
misc_feature            1..330
                        note = Synthetic sequence
source                  1..330
                        mol_type = other DNA
                        organism = synthetic construct
SEQUENCE: 258
gagctcgtgc tgacccagac accagcctcc gtgtctgcag ctgtgggagg cacagtcacc            60
atcaattgcc aggccagtca gaacatttac agcaatttag cctggtatca gcagaaacca          120
ggacagcctc ccaagctcct gatctatggt gcatccaatc tggaatctgg ggtcccatcg          180
cggttcaaag gcagtggatc tgggacacag ttcactctca ccatcagcag cctggagtgt          240
gacgatgctg ccacttacta ctgtcaaagt ggttattata gtagtagtac tgatattgct          300
ttcggcggag ggaccgaggt ggtggtcaaa                                           330

SEQ ID NO: 259          moltype = DNA  length = 330
FEATURE                 Location/Qualifiers
misc_feature            1..330
                        note = Synthetic sequence
source                  1..330
                        mol_type = other DNA
                        organism = synthetic construct
SEQUENCE: 259
gagctcgtgc tgacccagac accagcctcc gtgtctgaac ctgtgggagg cacagtcacc            60
atcaagtgtc aggccagtca gaccattagc agttggttat cctggtatca gcagaaacca          120
gggcagcctc ccaagctcct gatctattat gcattcaatc tggcatctgg ggtcccatcg          180
cggttcaaag gcagtggatc tgggacagag ttcactctca ccatcagcga cctggagtgt          240
gccgatgctg ccacttacta ctgtcaacag ggtattagta gtagtaatgt tgataatgtt          300
ttcggcggag ggaccgaggt ggtggtcaaa                                           330

SEQ ID NO: 260          moltype = DNA  length = 339
FEATURE                 Location/Qualifiers
misc_feature            1..339
                        note = Synthetic sequence
source                  1..339
                        mol_type = other DNA
                        organism = synthetic construct
SEQUENCE: 260
gagctcgtgc tgacccagac accagcctcc gtgtctgaac ctgtgggagg cacagtcacc            60
atcaagtgtc aggccagtca gaccattagc agttggttat cctggtatca gcagaaacca          120
gggcagcctc ccaagctcct gatctattat gcattcaatc tggcatctgg ggtcccatcg          180
cggttcaaag gcagtggatc tgggacagag tacactctca ccatcagcga cctggagtgt          240
gccgatgctg ccacttatta ttgtcaatgc acttatggta gtggtagtag tagtagttat          300
ggttgtgctt tcggcggagg gaccgagctg gaaatcaaa                                 339

SEQ ID NO: 261          moltype = DNA  length = 330
FEATURE                 Location/Qualifiers
misc_feature            1..330
                        note = Synthetic sequence
source                  1..330
                        mol_type = other DNA
                        organism = synthetic construct
SEQUENCE: 261
gagctcgtga tgacccagac accatctccc gtgtctgcag ctgtgggagg cacagtcacc            60
atcagttgcc agtccagtca gagtgtttat agtaactact tatcctggta tcagcagaaa          120
ccaggggcagc tcccaagct cctgatctac gaaacatcca ctctgcatc tgggtcccca          180
```

```
tcgcggttca aaggcagtgg atcggggaca cagttcactc tcaccatcag cgacgtgcag    240
tgtgacgatg ctgccactta ctactgtcaa ggcggttata gtgagattat tgaaaatact    300
ttcggcggag ggaccgaggt ggaaatcaaa                                      330

SEQ ID NO: 262          moltype = DNA   length = 321
FEATURE                 Location/Qualifiers
misc_feature            1..321
                        note = Synthetic sequence
source                  1..321
                        mol_type = other DNA
                        organism = synthetic construct
SEQUENCE: 262
gagctcgtga tgacccagac accagcctcc gtggaggcag ctgtgggagg cacagtcacc    60
atcaagtgcc aggccagtca gagcattggt agtgttttgg cctgggtatca gcagaaacca   120
gggcagcgtc ccaagctcct gatctctggt gtatttgatc tggcatctgg ggtcccgtcg   180
cggttcaaag gcagtggatc tgggacagag ttcactctca ccatcagcga cctggagtgt    240
gccgatgctg ccacttacta ctgtcaatat attccttatg gtagtagtcc tttcggcgga    300
gggaccgagg tggtggtcaa a                                               321

SEQ ID NO: 263          moltype = DNA   length = 333
FEATURE                 Location/Qualifiers
misc_feature            1..333
                        note = Synthetic sequence
source                  1..333
                        mol_type = other DNA
                        organism = synthetic construct
SEQUENCE: 263
gagctcgtga tgacccagac tgcatccccc gtgtctgcag ctgtgggagg cacagtcacc    60
atcaattgcc aggccagtca gagtattggt agtacctact tatcctggta tcagcagaaa   120
ccagggcagc ctcccaaaact cctgatctac aaggcttcca ttctgcgtc tggggtccca   180
tcgcggttca gcggcagtgg atctgggaca gagtacactc tcaccatcag cggcgtgcag   240
tgtgacgatg ctgccactta ttactgtcta tacggtggtt ttggtagtag tactggtgat    300
gctttcggcg agggaccgt gctggtggtc aaa                                 333

SEQ ID NO: 264          moltype = DNA   length = 324
FEATURE                 Location/Qualifiers
misc_feature            1..324
                        note = Synthetic sequence
source                  1..324
                        mol_type = other DNA
                        organism = synthetic construct
SEQUENCE: 264
gagctcgtgc tgacccagac accagcctcc gtgtctgaac ctgtgggagg cacagtcacc    60
atcaagtgcc aggccagtca gaccatttat agtaatttag cctggtatca gcagaaacca   120
gggcagcgtc ccaagctcct gatctaccag gcatccaaac tggcatctgg ggtcccatcg   180
cggttcaaag gcagtggatc tgggacagag tatactctca ccatcagcga cctggagtgt   240
gccgatgctg ccacttacta ctgtcaaagc tattatggtg ctgatgatta ctttcggc    300
ggagggaccg aggtggtggt caaa                                            324

SEQ ID NO: 265          moltype = DNA   length = 333
FEATURE                 Location/Qualifiers
misc_feature            1..333
                        note = Synthetic sequence
source                  1..333
                        mol_type = other DNA
                        organism = synthetic construct
SEQUENCE: 265
gagctcgtga tgacccagac accatctccc gtgtctgcag ctgtgggagg cacagtcagc    60
atcagttgcc agtccagtaa gagtgttat aataacaatg ccttatcgt gtttcaacag   120
aaaccagggc agcctcccaa ggtcctgatc tatggtgtat ccactctgga ttctggggtc    180
tcatcgcggt tcagcggcag tggatatggg acagagttca ctctcaccat cagcgacgtg    240
cagtgtgacg atgctgccac ttactactgt gcaggcgatt atagtgatat tagtgataat    300
aatttcggcg agggaccga gctggaaatc aaa                                 333

SEQ ID NO: 266          moltype = DNA   length = 333
FEATURE                 Location/Qualifiers
misc_feature            1..333
                        note = Synthetic sequence
source                  1..333
                        mol_type = other DNA
                        organism = synthetic construct
SEQUENCE: 266
gagctcgata tgacccagac accagcctcc gtgtctgaac ctgtgggagg cacagtcacc    60
atcaagtgcc aggccagtca gagcattagt agctacttag cctggtatca gcagaaacca   120
gggcagcctc ccaagcgcct gatctttgag gcatccactc tggcctctgg ggtcccctcg    180
cggttcagcg gcagtggatc tgggacagat ttcactctca ccatcagcga cctggagtgt    240
gccgatgctg ccacttacta ctgtcaaaac aataatggtt ttagtggtag taatttcaat   300
aatttcggcg agggaccga ggtggaaatc aaa                                  333
```

```
SEQ ID NO: 267         moltype = DNA  length = 333
FEATURE                Location/Qualifiers
misc_feature           1..333
                       note = Synthetic sequence
source                 1..333
                       mol_type = other DNA
                       organism = synthetic construct
SEQUENCE: 267
gagctcgtga tgacccagac accagcctct gtggaggtag ctgtgggagg cacagtcacc   60
atcaagtgcc aggccagtca gaccatttac agctctttag cctggtatca gcagaaacca  120
gggcagcctc ccaagctcct gatctacaag gcttccactc tggcatctgg ggtcccatcg  180
cggttcaaag gcagtggatc tgggacacag ttcactctca ccatcagtgg cgtgcagtgt  240
gacgatgctg ccacttacta ctgtcaacag ggttccagta ttagtaatgt tgataaaaat  300
gctttcggcg gagggaccga ggtggaaatc aaa                               333

SEQ ID NO: 268         moltype = DNA  length = 333
FEATURE                Location/Qualifiers
misc_feature           1..333
                       note = Synthetic sequence
source                 1..333
                       mol_type = other DNA
                       organism = synthetic construct
SEQUENCE: 268
gagctcgtgc tgacccagac accagcctcc gtgtctgaac ctgtgggagg cacagtcacc   60
atcaagtgcc aggccagtca gagcattggt agttacttat cctggtatca acagaaagca  120
gggcagcctc ccaagcgcct gatctatgag gcatccactc tggcctctgg ggtcccatcg  180
cggttcagcg gcagtggatc tgggacagat ttcactctca ccatcagcgg cctggagtgt  240
gccgatgttg ccacttatta ctgtcaaaat aataatggta tgactgtcag cgatttcaat  300
gctttcggcg gagggaccga ggtggaaatc aaa                               333

SEQ ID NO: 269         moltype = DNA  length = 336
FEATURE                Location/Qualifiers
misc_feature           1..336
                       note = Synthetic sequence
source                 1..336
                       mol_type = other DNA
                       organism = synthetic construct
SEQUENCE: 269
gagctcgatc tgacccagac accagcctcc gtgtctgcag ctgtaggagg cacagtcacc   60
atcaattgcc agtccagtca gattattgat cacgaccact atcctggta tcagcagaaa   120
ccagggcagc gtcccaagct cctaatctac cgggcatcca ctctgacatc tggggtcccc  180
tcgcggttca aggcagtgg atctgggaca gatttcactc tcaccatcag cgacctggag  240
tgtgccgatg ttgccactta ttactgtcaa aataataatg gtatgactgt cagcgatttc  300
aatgctttcg gcggagggac cgaggtggaa atcaaa                            336

SEQ ID NO: 270         moltype = DNA  length = 330
FEATURE                Location/Qualifiers
misc_feature           1..330
                       note = Synthetic sequence
source                 1..330
                       mol_type = other DNA
                       organism = synthetic construct
SEQUENCE: 270
gagctcgtgc tgacccagac accatcttcc acgtctgcag ctgtgggagg cacagtcacc   60
atcagttgcc agtccagtca gagtgttgtt gataagaact ggttagcctg gtatcagcag  120
aaaccagggc agcctcccaa gctcttgatc tacgaagcat ccaaactggc atctggggtc  180
ccgccgcggt tcagcggcag tggatctggg acacagttca ctctcaccat cagcggcgtg  240
cagtgtgacg atgctgccac ttactactgt gcaggcgatt ttgagagtgg tgttagtggt  300
ttcggcggag ggaccgaggt ggaaatcaaa                                   330

SEQ ID NO: 271         moltype = DNA  length = 333
FEATURE                Location/Qualifiers
misc_feature           1..333
                       note = Synthetic sequence
source                 1..333
                       mol_type = other DNA
                       organism = synthetic construct
SEQUENCE: 271
gagctcgtgc tgacccagac accatcaccc gtgtctgcag ctgtgggagg cacagtcacc   60
atcaattgcc agtccagtaa gaatatttat aataataatg ccttatcctg gtttcaacag  120
aaaccagggc agcctcccaa gctcctgatc tatggtgcat ccactctggc atctggggtc  180
ccatcgcggt tcaaaggcag tggatctggg acacagttca ctctcaccat cagcgacgtg  240
cagtgtgacg atgctgccac ttactactgt gcagcagatt atagtgatat tagtgataat  300
aatttcggcg gagggaccga ggtggtggtc aaa                               333

SEQ ID NO: 272         moltype = DNA  length = 327
FEATURE                Location/Qualifiers
misc_feature           1..327
                       note = Synthetic sequence
```

```
source                          1..327
                                mol_type = other DNA
                                organism = synthetic construct
SEQUENCE: 272
gagctcgtgc tgacccagac accatcctcc gtgtctgcag ctgtgggagg cacagtcacc    60
atcagttgcc agtccagtca gagtgtttat agtaacaact acttagcctg gtatcagcag   120
aaaccagggc agcctcccaa gctcctgatc tatgctgcat ccactctggc atctggggtc   180
ccatcgcggt tcaaaggcag tggatctggg acacagttca ctctcaccat cagcggcgtg   240
cagtgtgacg atgctgccgt ttactactgt ctaggcgggt ataatgatga tgctaatttc   300
ggcggaggga ccgaggtgga aatcaaa                                       327

SEQ ID NO: 273                  moltype = DNA   length = 327
FEATURE                         Location/Qualifiers
misc_feature                    1..327
                                note = Synthetic sequence
source                          1..327
                                mol_type = other DNA
                                organism = synthetic construct
SEQUENCE: 273
gagctcgatc tgacccagac accatcctcc gtgtctgcag ctgtgggagg cacagtcacc    60
atcagttgcc agtccagtga gagtgtttat agtaacaacc acttagcctg gtatcagcag   120
aaaccagggc agcctcccaa gctcctgatc tatgctgcat ccactctggc atctggggtc   180
ccatcgcggt tcagtggcag tggatctggg acacagttca ctctcaccat cagcggcgtg   240
cagtgtgacg atgctgccgt ttactactgt ctaggcggtt ataatgatga tgctaatttc   300
ggcggaggga ccgaggtggt ggtcaaa                                       327

SEQ ID NO: 274                  moltype = DNA   length = 330
FEATURE                         Location/Qualifiers
misc_feature                    1..330
                                note = Synthetic sequence
source                          1..330
                                mol_type = other DNA
                                organism = synthetic construct
SEQUENCE: 274
gagctcgatc tgacccagac accagcctcc gtggaggcag ctgtgggagg cacagtcacc    60
atcaagtgcc aggccagtca gagtattgat aacaacgact agcctggta tcagcagaaa   120
ccagggcagc ctcccaacct cctgatctcc aggacatcca ctctggcatc tggggtctca   180
tcgcggttca aaggcagtgg atctgggaca gagttcactc tcaccatcag cgacctggag   240
tgtgccgatg ctgccactta ctactgtcaa agctattgcg ttaatactta tggttatact   300
ttcggcggag ggaccgaggt ggtggtcaaa                                    330

SEQ ID NO: 275                  moltype = DNA   length = 336
FEATURE                         Location/Qualifiers
misc_feature                    1..336
                                note = Synthetic sequence
source                          1..336
                                mol_type = other DNA
                                organism = synthetic construct
SEQUENCE: 275
gagctcgtga tgacccagac accagcctcc gtggaggcag ctgtgggagg cacagtcacc    60
atcaagtgcc aggccagtca gagcattagt aatcacttag gctggtatca gcagaaacca   120
gggcagcctc ccaagctcct gatctacagg gcatccactc tggaatctgg ggtctcatcg   180
cggttcaaag gcagtggatc tgggtcagag ttcactctca ccatcagcga cctggagtgt   240
gccgatgctg ccacttacta ctgtcaaagc tattatatta ttaataggag taattatgct   300
aattctttcg gcggagggac cgaggtggaa atcaaa                             336

SEQ ID NO: 276                  moltype = DNA   length = 335
FEATURE                         Location/Qualifiers
misc_feature                    1..335
                                note = Synthetic sequence
source                          1..335
                                mol_type = other DNA
                                organism = synthetic construct
SEQUENCE: 276
gagctcgtga tgacccagac accagcctcc gtggaggcag ctgtgggagg cacagtcacc    60
atcaagtgcc aagccagtga gagcattaat agttggttag cctggtatca gcagaaacca   120
gggcagcgtc ccaagctcct gatctatgat gcatccaaac tggcatctgg ggtcccatcg   180
cggttcaaag gcagtggatc tgggacacag ttcactctca ccatcagcga cctggagtgt   240
gccgatgctg ccacttacta ctgtcaaagc tattatatta ttaataggag taattatggt   300
aattctttcg gcggagggac cgaggtggaa atcaa                              335

SEQ ID NO: 277                  moltype = DNA   length = 336
FEATURE                         Location/Qualifiers
misc_feature                    1..336
                                note = Synthetic sequence
source                          1..336
                                mol_type = other DNA
                                organism = synthetic construct
SEQUENCE: 277
```

```
gagctcgtga tgacccagac accagcctcc gtggaggcag ctgtgggagg cacagtcacc    60
atcaagtgcc aggccagtga gaccattagt agtagattag cctggtatca gcagaaacca   120
gggcagcctc ccaagctcct gatctaccag gcatccaaac tgccatctgg ggtcccatcg   180
cggttcaaag gcactggatc tgggacagag tacactctca ccatcagcga cctggagtgt   240
gccgatgctg ccacttacta ctgtcaaggc tgttattatg gtgggggtag tttttatgat   300
tctgctttcg gcggagggac cgaggtggtg gtcaaa                              336
```

```
SEQ ID NO: 278         moltype = DNA   length = 327
FEATURE                Location/Qualifiers
misc_feature           1..327
                       note = Synthetic sequence
source                 1..327
                       mol_type = other DNA
                       organism = synthetic construct
SEQUENCE: 278
gagctcgatc tgacccagac accagcctcc gtgtctgcag ctgtgggagg cacagtcacc    60
atcagttgcc agtccagtga gaatctttat aaggacaact acttagcctg gtatcagcag   120
aaaccagggc agcctcccaa gctcctgatc tatggtgcat ccaatctggc atctgggtc   180
ccatcgcggt tcaaaggcag tggatctggg acacagttca ctctcaccat cagcgacctg   240
gagtgtgacg atgctgccac ttactactgc gcaggcggtt atgatagtgt tgttgatttc   300
ggcggaggga ccgaggtggt ggtcaaa                                        327
```

```
SEQ ID NO: 279         moltype = DNA   length = 363
FEATURE                Location/Qualifiers
misc_feature           1..363
                       note = Synthetic sequence
source                 1..363
                       mol_type = other DNA
                       organism = synthetic construct
SEQUENCE: 279
cagtcggtgg aggagtccgg gggtcgcctg gtcacgcctg gacacccct gacactcacc    60
tgcacagtct ctggattctc cctcagtaga tatgcaatga cctgggtccg ccaggctcca   120
gggaagggc tggaatggat cggaatcatt ggtagtagtg gtctcacata cttcgcgacc   180
tgggcgaaag gccgattcac catctccaaa acctcgacca cggtagatct gaaaatcacc   240
agtccgacaa ccgaggacac ggccacctac ttctgtgcca gagggatgtg gtacgatgac   300
tccgatgatt acgaggacta ctttaacttg tggggccag gcaccctggt caccatctct   360
tca                                                                  363
```

```
SEQ ID NO: 280         moltype = DNA   length = 351
FEATURE                Location/Qualifiers
misc_feature           1..351
                       note = Synthetic sequence
source                 1..351
                       mol_type = other DNA
                       organism = synthetic construct
SEQUENCE: 280
cagtcggtga aggagtccgg gggtcgcctg gtcacgcctg gacacccct gacactcacc    60
tgcacagtct ctggaatcga cctcagtagc tatgcaatga gctgggtccg ccaggctcca   120
gggaagggc tggaatggat cggaaccatt aatattggtg gtggcacatg ggacgcgacc   180
tgggcgagag gccgattcac catctccaga acctcgacca cggtggatct gaaaatcacc   240
agtccgacaa tcggggacac ggccacctat ttctgtgcca gagatgttga tgcccatacc   300
ctcacatact ttaccttgtg ggggccaggc accctggtca ccatctcctc a            351
```

```
SEQ ID NO: 281         moltype = DNA   length = 357
FEATURE                Location/Qualifiers
misc_feature           1..357
                       note = Synthetic sequence
source                 1..357
                       mol_type = other DNA
                       organism = synthetic construct
SEQUENCE: 281
cagtcggtga aggagtccgg gggtcgcctg gtcacgcctg gacacccct gacactcacc    60
tgcaccgtct ctggattcac cctcagtaat aatgcaataa gctgggtccg ccaggctcca   120
gggaagggc tggaatggat cggaatcatt tatgctagtg gtaggacata ctacgcgacc   180
tgggcgaaag gccgattcac catctccaaa acctcgacca cggtggatct gaaaatgacc   240
agtccgacaa ccgaggacac ggccacctat ttctgtgcca gaggagatac tgagactgat   300
tatggtattc cttactttga cttgtggggc caggcaccc tggtcaccat ctcctca       357
```

```
SEQ ID NO: 282         moltype = DNA   length = 366
FEATURE                Location/Qualifiers
misc_feature           1..366
                       note = Synthetic sequence
source                 1..366
                       mol_type = other DNA
                       organism = synthetic construct
SEQUENCE: 282
tcgcagtcgt tgaaggagtc cgggggagac ctggtcaagc ctgggcatc ccggacactc    60
acctgtatag cccctggatt ctccttcagt agcagttact acatgtgctg ggtccgccag   120
gctccaggga aggggctgga gtggatcgca tgcatttatg ctagtagtgg tagcacttac   180
```

```
tacgcgagct gggcgaaagg ccgattcacc atctccaaaa cctcgtcgac cacggtgact    240
ctgcaaatga ccactctgac agccgcggac acggccacct atttctgtgc ggcaattctt    300
ggtgctgatt ataggttgac tcgattggat ctctggggcc agggcaccct ggtcaccgtc    360
tcctca                                                               366

SEQ ID NO: 283            moltype = DNA  length = 354
FEATURE                   Location/Qualifiers
misc_feature              1..354
                          note = Synthetic sequence
source                    1..354
                          mol_type = other DNA
                          organism = synthetic construct
SEQUENCE: 283
cagtcgttgg aggagtccgg gggtcgcctg gtcacgcctg gacacccct gacactcacc     60
tgcacagcct ctggattctc cctcaatcgc tactacatgc tctgggtccg ccaggctcca    120
ggggagggcc tggaatggat cggaaccatt agttatggtg ataccacata ctacgcgagc    180
tgggcgaaag gccgattcac catctccaaa acctcgacca cggtggatct gaaaatgacc    240
agtccgacaa ccgaggacac ggccacttat tctgtgtccg agcagatac tggtgataat     300
ggttatttag gccttcagtt gtgggccca ggcaccctgg tcaccgtctc ttca           354

SEQ ID NO: 284            moltype = DNA  length = 372
FEATURE                   Location/Qualifiers
misc_feature              1..372
                          note = Synthetic sequence
source                    1..372
                          mol_type = other DNA
                          organism = synthetic construct
SEQUENCE: 284
cagtcgttgg aggagtccgg gggagacctg gtcaagcctg ggcatccct gacactcacc     60
tgcacagcct ctggattctc cttcagtagc ggctactaca tgtgctgggt ccgccaggct    120
ccagggaagg ggctggagtg gatcgcatgc atttatactg gtcgcactga tttcactgat    180
tacgcgagct gggcgaaagg ccgattcacc atctccaaaa cctcgtcgac cacggtgact    240
ctgcaactga ccactctgac agccgcggac acggccacct atttctgtgc gagagggat    300
tattctggtg gtgttggtgg taattattgg ttggatctct ggggccaggg caccctggtc    360
accatctcct ca                                                        372

SEQ ID NO: 285            moltype = DNA  length = 351
FEATURE                   Location/Qualifiers
misc_feature              1..351
                          note = Synthetic sequence
source                    1..351
                          mol_type = other DNA
                          organism = synthetic construct
SEQUENCE: 285
cagtcgttgg aggagtccgg gggtcgcctg gtcacgcctg gacacccct gacactcacc     60
tgcacagtct ctggaatcga cctcagtaac cctggatga actgggtccg ccaggctcca    120
gggaagggcc tggaatggat cggagtcatt actgatagtg gtaccacata ctacgcgaac    180
tgggcgaaag gccgattcac catctccaga acctcgacca cggtggatct gaaaatgccc    240
agtctgacaa ccgaggacac ggccacctat ttctgtggcc gagatcctgg tgatattact    300
agtggtacga atgatttgtg ggggcccagge acctggtca ccatctcctc a             351

SEQ ID NO: 286            moltype = DNA  length = 342
FEATURE                   Location/Qualifiers
misc_feature              1..342
                          note = Synthetic sequence
source                    1..342
                          mol_type = other DNA
                          organism = synthetic construct
SEQUENCE: 286
gagcagtcgg tggaggagtc cggcggtcgc ctggtcacgc ctggaggatc cctgacactc     60
acctgcacag cctctggatt ctccctcaat aactatgcaa tcatctgggt ccgccaggct    120
ccagggaagg gtctggaata tatcggaatt tttaataatg gtgatatata ctatgcgaac    180
tgggcgaaag gccgattcac catctccaaa acctcgacca cggtgggtct gaaaatcgtc    240
agtccgacaa ccgaggacac ggccacctat ttctgtgcca gaactggcta taggactggt    300
ggctggttgt ggggcccagg caccctggtc accatctcct ca                       342

SEQ ID NO: 287            moltype = DNA  length = 366
FEATURE                   Location/Qualifiers
misc_feature              1..366
                          note = Synthetic sequence
source                    1..366
                          mol_type = other DNA
                          organism = synthetic construct
SEQUENCE: 287
cagtcggtga aggagtccgg gggtcgcctg gtcacgcctg gacacccct gacactcacc     60
tgcacagtct ctggaatcga cctcagttac tatgcaatga ctgggtccg ccaggctcca    120
gggaagggc tggaatacat cggaatcatt aatggtcgtg gtgacacagg ctacgcgacc    180
tgggcgaaag gccgcttcac tatctccaaa acctcgacca cggtggatct gaggatcacc    240
agtccgacaa tcgaggacac ggccacctat ttctgtgccc gagaagacag tgctattcct    300
```

```
ttcatagtag gaaactatta cggcatggac ctctggggcc cagggaccct cgtcaccgtc    360
tcctca                                                               366

SEQ ID NO: 288          moltype = DNA   length = 360
FEATURE                 Location/Qualifiers
misc_feature            1..360
                        note = Synthetic sequence
source                  1..360
                        mol_type = other DNA
                        organism = synthetic construct
SEQUENCE: 288
tcgcagtcgt tggaggagtc cggggggagac ctggtcaagc ctggggcatc cctgacactc    60
acctgcacag cctctacatt ctccttcaat agccgctact ggacatgctg ggtccgccag   120
gctccaggga agggactgga gtggatcgga tgtattaata acggtgacat tagcacttac   180
tacgcgagct gggcgaccgg ccgattcacc atctccaagt cctcgtcgac cacggtgact   240
ctgcatatga ccagtctgac agccgcggac acggccacct atttctgtgc gaaaggggt    300
aatcttgctg gtgattgtta tggggttgtgg ggcccaggca ccctggtcac catctcttca   360

SEQ ID NO: 289          moltype = DNA   length = 375
FEATURE                 Location/Qualifiers
misc_feature            1..375
                        note = Synthetic sequence
source                  1..375
                        mol_type = other DNA
                        organism = synthetic construct
SEQUENCE: 289
agttcggtgg aggagtccgg gggtcgcctg gtcgcgcctg gacacccct gacactcacc     60
tgcacagtct ctggattctc cctcaatcgc tatgcaatga gctgggtccg ccaggctcca   120
gggaaggggc tggagtggat cggaatcatt ggtagtagtg gtagtacata ctacgcgagc   180
tgggcgaaag gccgattcac catctccaaa acctcgtcga cggtggatc gaaaatcacc    240
agtccgacaa ccgaggacac ggccaccttat ttctgtgcca gagatttgga cgatagttat   300
ggttatactt atgctacggg gatggacatt cggttggatc tctggggcca gggcaccctg   360
gtcaccgtct cctca                                                    375

SEQ ID NO: 290          moltype = DNA   length = 369
FEATURE                 Location/Qualifiers
misc_feature            1..369
                        note = Synthetic sequence
source                  1..369
                        mol_type = other DNA
                        organism = synthetic construct
SEQUENCE: 290
cagtcggtga aggagtccgg gggaggcctc ttcaagccaa tggataccct gacactcacc     60
tgcaccgtct ctggattctc cctcagtgac tatgcaatga gctgggtccg ccaggctcca   120
gggaaggggc tggagtggat cggaatcatt aatagtcgtg atgacacagg ctacgcgagc   180
tgggcgaaag gccgattcac catctccaaa acctcgtcga ccacggtgga tctgaggatc   240
accagtccga caaccgagga cacggccacc tatttctgtg ccagagaaga cagtagtatt   300
cctttatag taggaaatta ctacggcatg gacctctggg gcccagggac cctcgtcacc   360
gtctcctca                                                           369

SEQ ID NO: 291          moltype = DNA   length = 345
FEATURE                 Location/Qualifiers
misc_feature            1..345
                        note = Synthetic sequence
source                  1..345
                        mol_type = other DNA
                        organism = synthetic construct
SEQUENCE: 291
cagtcgttgg aggagtccgg gggtcgcctg gtcacgcctg gacacccct gacactcacc      60
tgcacagtct ctggattctc cctcagtagt tatggagtgc actgggtccg ccaggctcca   120
gggaaggggc tggactggat cggaaagatt tatcctagtg gtagtatata ctactcgagc   180
tgggcgaaag gccgattcac catctccaaa acctcgacca cggtggatct gaaaatgacc   240
agtctgacaa ccgaggacac ggccacctat ttctgtgtca gatatcttac tggtagcagt   300
gatttgcatt tgtggggccc aggcacccctg gtcaccatct cctca                  345

SEQ ID NO: 292          moltype = DNA   length = 342
FEATURE                 Location/Qualifiers
misc_feature            1..342
                        note = Synthetic sequence
source                  1..342
                        mol_type = other DNA
                        organism = synthetic construct
SEQUENCE: 292
cagtcggtga aggagtccgg gggtcgcctg gtaacgcctg gaggatccct gacactcacc     60
tgcacagtct ctggattctc cctcagtgac tatgcaatga tctgggtccg ccaggctcca   120
gggaaggggc tggaatatat cggcattatc aataatggtg atatatacta cgcaacctgg   180
gcgaaaggcc gattcaccat ctccgaaacc tcgtcgacca cgatgggtct caatatcatc   240
agtccgacga ccgaggacac ggccacctat ttctgtgcca gacctggtta taggactggt   300
atatggttgt ggggcccagg caccctggtc accatctcct ca                      342
```

```
SEQ ID NO: 293           moltype = DNA  length = 348
FEATURE                  Location/Qualifiers
misc_feature             1..348
                         note = Synthetic sequence
source                   1..348
                         mol_type = other DNA
                         organism = synthetic construct
SEQUENCE: 293
tcgcagtcgg tgaaggagtc cgggggagac ctggtcaagc ctggggcatc cctgacactc    60
acctgcaaag cctctggatt cgacctcagg agctactact acatgtgctg ggtccgccag   120
gctccaggga aggggctgga gtggatcgca tgcattcatg gtggtgaggg taacacttac   180
tacgcgagct gggcgaaagg ccgattcacc atctccaaga cctcgtcgac cgcggtgact   240
ctacaaatga ccagtctgac agccgcggac acggccacct atttctgtgc gagaggtggc   300
tggactaatt acttttgggg cccaggcacc ctggtcaccg tctcttca               348

SEQ ID NO: 294           moltype = DNA  length = 348
FEATURE                  Location/Qualifiers
misc_feature             1..348
                         note = Synthetic sequence
source                   1..348
                         mol_type = other DNA
                         organism = synthetic construct
SEQUENCE: 294
gagcagtcgt tgaaggagtc cgggggagac ctggtcaagc ctggggcatc cctgacactc    60
acctgcacag cctctggatt cgacctcagt agcaactact acatgtgctg ggtccgccag   120
gctccaggga aggggcctga gtggatcgca tgcatttata gtagtaatac tagaacatgg   180
tacgcgcgct gggcgaaagg ccgattcacc atctccaaga cctcgtcgac cgcggtgact   240
ctacaaatga ccagtctgac agccgcggac acggccacct atttctgtgc gagaggtggc   300
tggactaatt acttgtgggg cccaggcacc ctagtcacca tctcctca               348

SEQ ID NO: 295           moltype = DNA  length = 339
FEATURE                  Location/Qualifiers
misc_feature             1..339
                         note = Synthetic sequence
source                   1..339
                         mol_type = other DNA
                         organism = synthetic construct
SEQUENCE: 295
cagtcggtgg aggagtccgg gggtcgcctg gtcacgcctg gacacccct gacactcacc     60
tgcacagtct ctggattctc cctcagtagc cacgacatga tctgggtccg ccaggctgca   120
gggaaggggc tggaatggat cggacttatt attagtagtg gtaacacatg gtacgcgagc   180
tgggcgaaag gccgattcac catctccaaa acctcggatct gaaaatgacc               240
agtctgacaa ccgaggacac ggccacctat ttctgtgcca gagatgttta tagtggtcg    300
agtccttggg gcccaggcac cctggtcacc atctcctca                         339

SEQ ID NO: 296           moltype = DNA  length = 351
FEATURE                  Location/Qualifiers
misc_feature             1..351
                         note = Synthetic sequence
source                   1..351
                         mol_type = other DNA
                         organism = synthetic construct
SEQUENCE: 296
cagtcggtga agtccggggg aggcctggtc aagcctgggg catccctgac actcacctgc    60
aaagcctcta cattctcctt caatagccgc tactggacat gctgggtccg ccaggctcca   120
gggaagggac tggagtggat cggatgtatt aataacggtg acattaccac ttactacacg   180
aactgggcga ccggccgatt caccatctcc agtcctcgt cgaccacggt gactctgcaa    240
atgaccagtc tgacagccgc ggacacggcc acctatttct gtgcgaaagg gggtaatctt   300
gctggtgatt gttatgggtt gtggggccca ggcaccctgt caccatctca              351

SEQ ID NO: 297           moltype = DNA  length = 354
FEATURE                  Location/Qualifiers
misc_feature             1..354
                         note = Synthetic sequence
source                   1..354
                         mol_type = other DNA
                         organism = synthetic construct
SEQUENCE: 297
cagtcgttgg aggagtccgg gggtcgcctg gtcacgcctg gacacccct gacactcacc     60
tgcacagcct ctggattctc cctcagtagt tactacatga gctgggtccg ccaggctcca   120
gggaggggc tggaatggat cggaaccatt actactgctg gtccactata ttacgcgacc    180
tgggcgaaag gccgattcac catctccaaa acctcgacca cggtggatct gaaaatgacc   240
agtccgacaa ccgaggacac ggccacctat ttctgtgcca gagggcatgc tggtagtatt   300
tattattcat actttgactt gtggggccca ggcaccctgt caccgtctc ttca           354

SEQ ID NO: 298           moltype = DNA  length = 348
FEATURE                  Location/Qualifiers
misc_feature             1..348
```

```
                            note = Synthetic sequence
source                      1..348
                            mol_type = other DNA
                            organism = synthetic construct
SEQUENCE: 298
cagtcggtgg aggagtccgg gggtcgcctg gtcacgcctg gaggatccct gacactcacc    60
tgcacagtct ctggattctc cctcagcagc tacgacatga gctgggtccg ccaggctcca   120
gggaaggggc tggagtggat cggaatcagt tggaatagtg gctttgttga ctacgcgagc   180
tgggcgaaag gccgattcag catctccaaa acctcgacca cggtggatct gaaaatcacc   240
agtccgacaa ccgaggacac ggccacctat ttctgtgcca cgacttggtgc tgatgacatc   300
tactatttta acttgtgggg cccaggcacc ctggtcacca tctcctca              348

SEQ ID NO: 299              moltype = DNA  length = 348
FEATURE                     Location/Qualifiers
misc_feature                1..348
                            note = Synthetic sequence
source                      1..348
                            mol_type = other DNA
                            organism = synthetic construct
SEQUENCE: 299
cagtcggtga aggagtccgg gggaggcctg gtcaagcctg agggatccct gacactcacc    60
tgcaaagcct ctggattcga cctcagtagc tactactaca tgtgctgggt ccgccaggct   120
ccagggaagg ggctggagtg gatcgcatgc atttatacta gtagtggtgc cacatgtac   180
gcgaactggg cgaaaggccg attcaccatt tccaaaacct cgtcgaccac ggtgactctg   240
cagatgaccc tctctgacag cgcggacacg gccaccattt tctgtgcgag aggaggttgg   300
tgcgacttta acttgtgggg cccaggcacc ctggtcacca tctcctca              348

SEQ ID NO: 300              moltype = DNA  length = 363
FEATURE                     Location/Qualifiers
misc_feature                1..363
                            note = Synthetic sequence
source                      1..363
                            mol_type = other DNA
                            organism = synthetic construct
SEQUENCE: 300
caagtgcagc tggtggagag cggaggcaga gtggtgcagc ccggcagatc tctgagactg    60
agctgtaccg ccagcggctt ctctctgaat agatactaca tgctgtgggt gagacaagcc   120
cccggcaagg gactggagtg gatcggcacc atcagctacg gcgataccac ctactacgcc   180
agctgcaagg agggaagatt caccatctct agagacaact ccaagaacac actgtatctg   240
cagatgaact ctctgagagc cgaggacacc gccgtgtact actgcgccag agccgatacc   300
ggcgacaacg gctatctggg actgcagctg tggggacaag gcacactggt gaccgtgagc   360
agc                                                                363

SEQ ID NO: 301              moltype = DNA  length = 321
FEATURE                     Location/Qualifiers
misc_feature                1..321
                            note = Synthetic sequence
source                      1..321
                            mol_type = other DNA
                            organism = synthetic construct
SEQUENCE: 301
gacatccaga tgacccagag ccctagcagc gtgagcgcta gcgtgggaga cagagtgacc    60
atcacatgcc aagccagcca gagcattggc agcgtgctgg cttggtacca gcagaagccc   120
ggcaaggccc ccaagctgct gatcagcggc gtgtttgatc tggccagcgg cgtgccctcc   180
agatttagcg gcagcggcag cggaaccgat ttcactcgga ccatcagctc tctgcagccc   240
gaggacttcg ccacctacta ctgccagtac atcccttacg gcagctcccc ctttggcgga   300
ggcaccaagg tggaaatcaa g                                             321

SEQ ID NO: 302              moltype = DNA  length = 321
FEATURE                     Location/Qualifiers
misc_feature                1..321
                            note = Synthetic sequence
source                      1..321
                            mol_type = other DNA
                            organism = synthetic construct
SEQUENCE: 302
gatatccaga tgacccagag ccctagcagc gtgagcgcta gcgtgggaga cagagtgacc    60
atcacatgca gagcctccca gagcattggc agcgtgctgg cttggtacca gcagaagccc   120
ggcaaggccc ccaagctgct gatctacgga gtgttctctc tgcagagcgg cgtgccctcc   180
agatttccg gcagcggctc cggcacagac ttcactgac catcagctc tctgcagccc      240
gaggacttcg ccacctacta ctgccagtac atcccttacg gcagctcccc ctttggaggc   300
ggcaccaaag tggagatcaa g                                             321

SEQ ID NO: 303              moltype = DNA  length = 17
FEATURE                     Location/Qualifiers
misc_feature                1..17
                            note = Synthetic sequence
source                      1..17
                            mol_type = other DNA
```

```
                        organism = synthetic construct
SEQUENCE: 303
aagcagtgat ggagatg                                                      17

SEQ ID NO: 304          moltype = DNA   length = 17
FEATURE                 Location/Qualifiers
misc_feature            1..17
                        note = Synthetic sequence
source                  1..17
                        mol_type = other DNA
                        organism = synthetic construct
SEQUENCE: 304
tgtgttcccc aaagaag                                                      17

SEQ ID NO: 305          moltype = DNA   length = 16
FEATURE                 Location/Qualifiers
misc_feature            1..16
                        note = Synthetic sequence
source                  1..16
                        mol_type = other DNA
                        organism = synthetic construct
SEQUENCE: 305
gaccatgcag ttatct                                                       16

SEQ ID NO: 306          moltype = DNA   length = 19
FEATURE                 Location/Qualifiers
misc_feature            1..19
                        note = Synthetic sequence
source                  1..19
                        mol_type = other DNA
                        organism = synthetic construct
SEQUENCE: 306
ggtgagcctg gtcaaacgg                                                    19

SEQ ID NO: 307          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 307
actgtgtcct ttcacgcctt t                                                 21

SEQ ID NO: 308          moltype = DNA   length = 20
FEATURE                 Location/Qualifiers
misc_feature            1..20
                        note = Synthetic sequence
source                  1..20
                        mol_type = other DNA
                        organism = synthetic construct
SEQUENCE: 308
aggcagaagt tgacccacct                                                   20

SEQ ID NO: 309          moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 309
cagtggtact agctgcaagg g                                                 21

SEQ ID NO: 310          moltype = DNA   length = 18
FEATURE                 Location/Qualifiers
misc_feature            1..18
                        note = Synthetic sequence
source                  1..18
                        mol_type = other DNA
                        organism = synthetic construct
SEQUENCE: 310
caacgagcgg ttccgatg                                                     18

SEQ ID NO: 311          moltype = DNA   length = 20
FEATURE                 Location/Qualifiers
misc_feature            1..20
                        note = Synthetic sequence
source                  1..20
```

```
                        mol_type = other DNA
                        organism = synthetic construct
SEQUENCE: 311
gccacaggat tccataccca                                                   20

SEQ ID NO: 312          moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 312
cagaccatgc agttatctga ggtg                                              24

SEQ ID NO: 313          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 313
cagaccatgc agttattctg aggtg                                             25

SEQ ID NO: 314          moltype = DNA   length = 25
FEATURE                 Location/Qualifiers
misc_feature            1..25
                        note = Synthetic sequence
source                  1..25
                        mol_type = other DNA
                        organism = synthetic construct
SEQUENCE: 314
cagaccatgc agttattctg aggtg                                             25

SEQ ID NO: 315          moltype = DNA   length = 30
FEATURE                 Location/Qualifiers
misc_feature            1..30
                        note = Synthetic sequence
source                  1..30
                        mol_type = other DNA
                        organism = synthetic construct
SEQUENCE: 315
cctgtgttcc ccaaagaaga ggagtacttg                                        30

SEQ ID NO: 316          moltype = DNA   length = 19
FEATURE                 Location/Qualifiers
misc_feature            1..19
                        note = Synthetic sequence
source                  1..19
                        mol_type = other DNA
                        organism = synthetic construct
SEQUENCE: 316
cctgtgttcc ccaaagtac                                                    19
```